(12) United States Patent
Singh et al.

(10) Patent No.: US 10,696,693 B2
(45) Date of Patent: Jun. 30, 2020

(54) FUSED IMIDAZOLE DERIVATIVES AS TGF-BETA INHIBITORS

(71) Applicant: Rigel Pharmaceuticals, Inc., South San Francisco, CA (US)

(72) Inventors: Rajinder Singh, Belmont, CA (US); Todd Kinsella, Redwood City, CA (US); Jiaxin Yu, Foster City, CA (US); Marina Gelman, San Francisco, CA (US); Ihab S. Darwish, San Carlos, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/527,908

(22) PCT Filed: Nov. 16, 2015

(86) PCT No.: PCT/US2015/060872
§ 371 (c)(1),
(2) Date: May 18, 2017

(87) PCT Pub. No.: WO2016/081364
PCT Pub. Date: May 26, 2016

(65) Prior Publication Data
US 2018/0346487 A1    Dec. 6, 2018

Related U.S. Application Data

(60) Provisional application No. 62/141,509, filed on Apr. 1, 2015, provisional application No. 62/082,959, filed on Nov. 21, 2014.

(51) Int. Cl.
| | |
|---|---|
| *C07D 498/04* | (2006.01) |
| *C07D 487/04* | (2006.01) |
| *C07D 519/00* | (2006.01) |
| *A61K 31/424* | (2006.01) |
| *A61K 31/428* | (2006.01) |
| *A61K 31/498* | (2006.01) |
| *A61P 19/02* | (2006.01) |
| *A61K 31/416* | (2006.01) |
| *A61K 31/4188* | (2006.01) |
| *A61K 31/4365* | (2006.01) |
| *A61K 31/437* | (2006.01) |
| *A61K 31/4709* | (2006.01) |
| *A61K 31/517* | (2006.01) |
| *A61K 31/519* | (2006.01) |
| *A61K 31/5377* | (2006.01) |
| *A61K 45/06* | (2006.01) |

(52) U.S. Cl.
CPC .......... *C07D 519/00* (2013.01); *A61K 31/416* (2013.01); *A61K 31/4188* (2013.01); *A61K 31/428* (2013.01); *A61K 31/437* (2013.01); *A61K 31/4365* (2013.01); *A61K 31/4709* (2013.01); *A61K 31/498* (2013.01); *A61K 31/517* (2013.01); *A61K 31/519* (2013.01); *A61K 31/5377* (2013.01); *A61K 45/06* (2013.01); *A61P 19/02* (2018.01); *C07D 487/04* (2013.01); *C07D 498/04* (2013.01)

(58) Field of Classification Search
CPC ...... C07D 498/04; A61K 31/424; A61P 19/02
USPC .................. 548/218; 514/375, 376
See application file for complete search history.

(56) References Cited

U.S. PATENT DOCUMENTS

| | | | | |
|---|---|---|---|---|
| 6,610,697 | B1* | 8/2003 | Dodd .................. | C07D 487/04 514/211.01 |
| 2004/0176390 | A1* | 9/2004 | Blumberg ............ | C07D 471/04 514/253.09 |
| 2005/0272791 | A1* | 12/2005 | Bonjouklian ........ | C07D 403/04 514/394 |
| 2008/0161341 | A1* | 7/2008 | Calderwood ........ | C07D 498/04 514/303 |

(Continued)

FOREIGN PATENT DOCUMENTS

| | | |
|---|---|---|
| WO | 2004/050659 | 6/2004 |
| WO | 2007/076086 | 7/2007 |

(Continued)

OTHER PUBLICATIONS

Sun et al., Curr Opin Rheumatol. Jan. 2017; 29(1): 96-102.*

(Continued)

*Primary Examiner* — Venkataraman Balasubramanian
(74) *Attorney, Agent, or Firm* — James J. Diehl

(57) ABSTRACT

Disclosed are imidazole compounds, as well as pharmaceutical compositions and methods of use thereof. One embodiment is a compound having the structure Formula (I) and pharmaceutically acceptable salts, prodrugs and N-oxides thereof (and solvates and hydrates thereof), wherein A, Z, X, $R^1$, $R^2$ m, p and a are as described herein. In certain embodiments, a compound disclosed herein inhibits TGF-β, and can be used to treat disease by blocking TGF-β signaling.

(I)

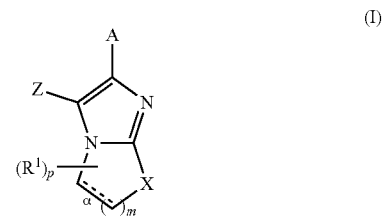

9 Claims, No Drawings

(56) References Cited

U.S. PATENT DOCUMENTS

| | | | | |
|---|---|---|---|---|
| 2009/0270402 A1* | 10/2009 | Calderwood | ........ | C07D 487/04 514/249 |
| 2010/0166819 A1* | 7/2010 | Lee | ...................... | C07D 471/10 424/422 |
| 2013/0018052 A1* | 1/2013 | Lee | ...................... | C07D 519/00 514/249 |
| 2015/0159134 A1* | 6/2015 | Choudhary | .......... | C12N 5/0621 424/93.7 |
| 2015/0344481 A1* | 12/2015 | Velaparthi | ............ | C07D 519/00 514/210.18 |

FOREIGN PATENT DOCUMENTS

| WO | 2008/063287 | 5/2008 |
|---|---|---|
| WO | WO2009005675 | 1/2009 |
| WO | 2013/009140 | 1/2013 |
| WO | WO2014100533 | 6/2014 |
| WO | WO2015087231 | 6/2015 |

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dernneret al., Bio/Technology, 1994, 12:320.*
Golub et al., Science, 286, 531-537, 1999.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Pharmaceutical Chemistry, Jan. 31, 2004, edited by Qidong You, Chemical Industry Press, p. 203, Tables 3-1.

* cited by examiner

US 10,696,693 B2

FUSED IMIDAZOLE DERIVATIVES AS TGF-BETA INHIBITORS

This is the US national phase under 35 U.S.C. § 371 of international application PCT/US2015/060872, filed Nov. 16, 2015, which claims the benefit of priority of U.S. provisional application 62/141,509, filed, Apr. 1, 2015, and U.S. provisional application 62/082,959, filed Nov. 21, 2014.

FIELD OF INVENTION

This invention relates to the field of compounds, pharmaceutical compositions, and methods of using the compounds and compositions containing them. This invention relates more particularly to the field of imidazole compounds and pharmaceutical compositions thereof, methods of inhibiting TGF-β with the compounds, and methods of treating and/or preventing disease with the compounds.

TECHNICAL BACKGROUND

Growth and Differentiation Factor-8 (GDF-8), also known as myostatin, and TGF-β1 are members of the Transforming Growth Factor-beta (TGF-β) superfamily of structurally related growth factors, all of which possess physiologically important growth-regulatory and morphogenetic properties (Kingsley et al. (1994) Genes Dev., 8: 133-46; Hoodless et al. (1998) Curr. Topics Microbiol. Immunol., 228: 235-72). For example, activation of TGF-β1 signaling and expansion of extracellular matrix are early and persistent contributors to the development and progression of fibrotic disorders, such as involved in chronic renal disease and vascular disease. Border W. A., et al, N. Engl. J. Med., 1994; 331(19), 1286-92. GDF-8 is a negative regulator of skeletal muscle mass. For example, GDF-8 is highly expressed in the developing and adult skeletal muscle. The GDF-8 null mutation in transgenic mice is characterized by a marked hypertrophy and hyperplasia of the skeletal muscle (McPherron et al. (1997) Nature, 387: 83-90). Similar increases in skeletal muscle mass are evident in naturally occurring mutations of GDF-8 in cattle (Ashmore et al. (1974) Growth, 38: 501 507; Swatland and Kieffer (1994) J. Anim. Sci., 38: 752-757; McPherron and Lee (1997) Proc. Natl. Acad. Sci. USA, 94: 12457-12461; and Kambadur et al. (1997) Genome Res., 7: 910-915). Because GDF-8 is expressed in both developing and adult muscles, it is not clear whether it regulates muscle mass during development or in adults. Recent studies have also shown that muscle wasting associated with HIV-infection in humans is accompanied by increases in GDF-8 protein expression (Gonzalez-Cadavid et al. (1998) PNAS, 95: 14938-43). In addition, GDF-8 can modulate the production of muscle-specific enzymes (e.g., creatine kinase) and modulate myoblast cell proliferation (WO 00/43781).

A number of human and animal disorders are associated with loss or functional impairment of muscle tissue, including muscular dystrophy, muscle atrophy, congestive obstructive pulmonary disease, muscle wasting syndrome, sarcopenia, and cachexia. To date, very few reliable or effective therapies exist for these disorders. However, the terrible symptoms associated with these disorders may be substantially reduced by employing therapies that increase the amount of muscle tissue in patients suffering from the disorders. While not curing the conditions, such therapies would significantly improve the quality of life for these patients and could ameliorate some of the effects of these diseases.

In addition to its growth-regulatory and morphogenetic properties in skeletal muscle, GDF-8 may also be involved in a number of other physiological processes, including glucose homeostasis in the development of type 2 diabetes and adipose tissue disorders, such as obesity. For example, GDF-8 modulates pre-adipocyte differentiation to adipocytes (Kim et al. (2001) BBRC, 281: 902-906).

There are also a number of conditions associated with a loss of bone, including osteoporosis, especially in the elderly and/or postmenopausal women. Currently available therapies for these conditions work by inhibiting bone resorption.

Like TGF-β-1, -2, and -3, the GDF-8 protein is synthesized as a precursor protein consisting of an amino-terminal propeptide and a carboxy-terminal mature domain (McPherron and Lee, (1997) Proc. Natl. Acad. Sci. USA, 94: 12457-12461). Before cleavage, the precursor GDF-8 protein forms a homodimer. The amino-terminal propeptide is then cleaved from the mature domain. The cleaved propeptide may remain noncovalently bound to the mature domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). It is believed that two GDF-8 propeptides bind to the GDF-8 mature dimer (Thies et al. (2001) Growth Factors, 18: 251-259). Due to this inactivating property, the propeptide is known as the "latency-associated peptide" (LAP), and the complex of mature domain and propeptide is commonly referred to as the "small latent complex" (Gentry and Nash (1990) Biochemistry, 29: 6851-6857; Derynck et al. (1995) Nature, 316: 701-705; and Massague (1990) Ann. Rev. Cell Biol., 12: 597-641). Other proteins are also known to bind to GDF-8 or structurally related proteins and inhibit their biological activity. Such inhibitory proteins include follistatin, and potentially, follistatin-related proteins (Gamer et al. (1999) Dev. Biol., 208: 222-232). The mature domain is believed to be active as a homodimer when the propeptide is removed.

GDF-8 is highly conserved in sequence and in function across species. The amino acid sequence of murine and human GDF-8 is identical, as is the pattern of mRNA expression (McPherron et al. (1997) Nature 387: 83-90; Gonzalez-Cadavid et al. (1998) Proc. Natl. Acad. Sci. USA 95: 14938-14943). This conservation of sequence and function suggests that inhibition of GDF-8 in humans is likely to have a similar effect to inhibition of GDF-8 in mice.

U.S. Pat. No. 7,320,789 shows that GDF-8 antibodies in mouse models can increase muscle strength (e.g., for treating sarcopenia), increase muscle mass and strength in dystrophic muscle (e.g., for treating Duchenne's muscular dystrophy), increase bone mass and bone density (e.g., for prevention and treatment of osteoporosis), augment bone healing (e.g., for treating an established muscle or bone degenerative disease (e.g., fracture repair and spine fusion, preventing the decline in bone mass, microarchitecture and strength associated with estrogen deficiency, increasing trabecular bone density), and are useful for treatment of metabolic disorders such as type 2 diabetes, impaired glucose tolerance, metabolic syndrome (e.g., syndrome X), insulin resistance induced by trauma (e.g., burns), and adipose tissue disorders (e.g., obesity).

SUMMARY

In view of the foregoing, we recognized that new therapeutic agents that inhibit the activity of GDF-8 may useful and therefore desirable for treating human or animal disorders in which an increase in muscle tissue would be therapeutically beneficial, particularly muscle and adipose tissue disorders, bone degenerative diseases, neuromuscular disorders, and diabetes.

Accordingly, the present invention comprises compounds, pharmaceutical compositions and methods of using them to treat and/or prevent disease by inhibiting TGF-β.

Disclosed herein are compounds having structural formula (I)

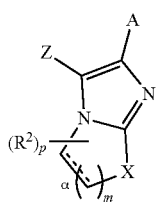
(I)

and pharmaceutically acceptable salts, prodrugs, and N-oxides thereof (and solvates and hydrates thereof), wherein A, Z, $R^1$, X, m and p are as described herein.

Also disclosed herein are pharmaceutical compositions. Examples of such compositions include those having at least one pharmaceutically acceptable carrier, diluent, or excipient; and a compound, pharmaceutically acceptable salt, prodrug, or N-oxide (or solvate or hydrate) as described herein.

Another aspect of the present invention comprises methods for treating and/or preventing disease by blocking TGF-β. Accordingly, the invention also comprises methods for treating disease using the presently disclosed compounds and pharmaceutical compositions.

All publications referenced herein are incorporated by reference in their entirety to the extent they are not inconsistent with the teachings presented herein.

DETAILED DESCRIPTION

In one aspect, the invention comprises compounds that inhibit TGF-β.

In embodiment $I_1$ of this first aspect, the compounds have structural formula (I):

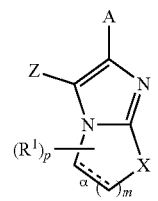
(I)

or a pharmaceutically acceptable salt, prodrug, or N-oxide thereof, or a solvate or hydrate thereof,
wherein
bond α is a single or double bond;
X is —CH$_2$—, —CH(R$^x$)—, —N(R$^a$)— or —O—,
wherein R$^a$ is hydrogen, —C$_1$-C$_6$alkyl, —C$_1$-C$_6$haloalkyl, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R or —N(R)S(O)$_2$R, and
wherein when X is —CH(R$^x$)—, p≥1, and R$^x$ combines with an R$^1$ group bound to the carbon adjacent to X to form a 5- or 6-membered heterocyclyl with an annular —N(R$^a$)—;
m is 1 or 2;
A is phenyl or pyridyl, each optionally substituted with one to five R$^2$ groups, wherein
each R$^2$ is independently halogen, —C$_1$-C$_6$alkyl, —C$_1$-C$_6$haloalkyl, —C$_1$-C$_6$alkoxy, C$_{3-8}$Cak(C$_{0-6}$alkyl), Hca(C$_{0-6}$alkyl), Ar(C$_{0-6}$alkyl), Het(C$_{0-6}$alkyl), —O—(C$_0$-C$_6$alkyl)-Ar, —O—(C$_0$-C$_6$alkyl)-Het, —O—(C$_0$-C$_6$alkyl)-Cak, —O—(C$_0$-C$_6$alkyl)-Hca, —NO$_2$ or —CN, wherein the Ar, Het, Cak, Hca, alkyl, and haloalkyl are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, or C$_1$-C$_6$haloalkyl;
Z is
a fused bicyclic ring of the formula,

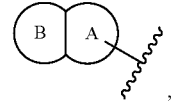

wherein
ring A is Ar or 5- or 6-membered Het,
ring B is 5- or 6-membered Het,
wherein
Z is optionally substituted by one or two —R$^Z$ groups that are each independently C$_{3-8}$Cak(C$_{0-6}$alkyl), Hca(C$_{0-6}$alkyl), Ar(C$_{0-6}$alkyl), Het(C$_{0-6}$alkyl), halogen, cyano, C$_{1-6}$alkyl, C$_{1-6}$haloalkyl, —C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), —O—C$_{1-6}$alkyl-OR, —O—C$_{1-6}$alkyl-SR, —O—C$_{1-6}$alkyl-NR$_2$, —O—C$_{1-6}$alkyl-Hca, wherein each Ar, Het, Cak, Hca, alkyl, and haloalkyl group is optionally substituted by one or two —R$^{ZZ}$ groups;
wherein each —R$^{ZZ}$ is independently halogen, cyano, C$_{1-6}$alkyl, C$_{1-6}$haloalkyl, —C$_1$-C$_6$alkoxy, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR);
each R$^1$ is independently halogen, C$_1$-C$_6$alkyl, C$_1$-C$_6$haloalkyl, —C$_1$-C$_6$alkoxy, C$_{3-8}$Cak(C$_{0-6}$alkyl), Hca(C$_{0-6}$alkyl), Ar(C$_{0-6}$alkyl), Het(C$_{0-6}$alkyl), —O—(C$_0$-C$_6$alkyl)-Ar, —O—(C$_0$-C$_6$alkyl)-Het, —O—(C$_0$-C$_6$alkyl)-Cak, —O—(C$_0$-C$_6$alkyl)-Hca, —C(O)OR, —NO$_2$ or —CN, wherein the Ar, Het, Cak, Hca, alkyl, and haloalkyl are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)

C(O)OR, —N(R)C(O)NR₂, —N(R)S(O)R, —N(R)S(O)₂R, C₁-C₆alkyl, —C₁-C₆alkoxy or C₁-C₆haloalkyl;

or, when α is a single bond and two R¹ groups are attached to the same carbon atom, the two R¹ groups together with the atom to which they are attached form a C₃-C₈Cak or C₃-C₈Hca ring, wherein the Cak and Hca rings are optionally substituted with 1, 2, 3, or 4 groups which are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, C₁-C₆alkyl, —C₁-C₆alkoxy or C₁-C₆haloalkyl;

p is 0, 1, 2, 3, 4, 5 or 6; and each R is independently hydrogen, C₁-C₆alkyl, C₁-C₆haloalkyl, —(C₀-C₆alkyl)-Ar, —(C₀-C₆alkyl)-Het, —(C₀-C₆alkyl)-Cak, or —(C₀-C₆alkyl)-Hca, wherein Ar, Het, Cak, Hca, alkyl, and haloalkyl are optionally substituted with C₁-C₆alkyl, halogen, —OH, —NH₂, C₁-C₆haloalkyl or cyano.

In embodiment I', the compounds are of any embodiment disclosed herein, provided that the compound is not any compound expressly recited in International Publication Nos. WO 2004/014900 A1, WO 2008/063287 A2 or WO 2014/100533, or in Callahan et al., "Identification of Novel Inhibitors of the Transforming Growth Factor β1 (TGF-β1) Type 1 Receptor (ALK5)" *J. Med. Chem.*, 2002, 45 (5), pp 999-1001. Compounds of WO 2004/014900 A1 expressly excluded include (but are not limited to) compounds 103-107:

1-isopropylsulfonyl-2-amino-6-(2-(phenyl)-imidazo[1,2-a]pyridin-3-yl) benzimidazole dimethanesulfonate, 1-isopropylsulfonyl-2-amino-6-(8-(methyl)-2-(phenyl)-imidazo[1,2-a]pyridin-3-yl)-benzimidazole dimethanesulfonate, 1-isopropylsulfonyl-2-amino-6-(2-(phenyl)-6,7-dihydro-5H-pyrrolo[1,2-a]imidazol-3-yl)-benzimidazole dimethanesulfonate, 1-isopropylsulfonyl-2-amino-6-(2-(4-fluorophenyl)-6,7-dihydro-5H-pyrrolo[1,2-a]imidazole-3-yl)benzimidazole methanesulfonate, and 1-isopropylsulfonyl-2-amino-6-(2-(phenyl)-5,6,7,8-tetrahydro-imidazo[1,2-a]pyridin-3-yl)-benzimidazole.

In embodiment I₂, the compounds are of embodiment I₁, provided that the compound is not:

1-isobutyl-6-(2-(4-fluorophenyl)-6,7-dihydro-5H-pyrrolo[1,2-a]imidazol-3-yl)-1H-benzo[d]imidazol-2-amine;

1-isopropylsulfonyl-2-amino-6-(2-(4-fluorophenyl)-6,7-dihydro-5H-pyrrolo[1,2-a]imidazol-3-yl)-benzimidazole methanesulfonate;

1-(isopropylsulfonyl)-6-(2-phenyl-6,7-dihydro-5H-pyrrolo[1,2-a]imidazol-3-yl)-1H-benzo[d]imidazol-2-amine;

1H-Benzotriazole, 6-[6-(4-fluorophenyl)imidazo[2,1-b]oxazol-5-yl];

1H-Indazole, 5-[6-(4-fluorophenyl)imidazo[2,1-b]oxazol-5-yl]-3-methyl;

1H-Benzimidazole, 6-[6-(4-fluorophenyl)imidazo[2,1-b]oxazol-5-yl]-2-(4-pyridinyl);

1H-Benzotriazole, 6-[6-(4-fluorophenyl)imidazo[2,1-b]oxazol-5-yl]-1-methyl;

1H-Benzotriazole, 1-ethyl-6-[6-(4-fluorophenyl)imidazo[2,1-b]oxazol-5-yl];

1H-Benzotriazole, 6-[6-(4-fluorophenyl)imidazo[2,1-b]oxazol-5-yl]-1-(1-methylethyl);

1H-Benzimidazole, 6-[6-(4-fluorophenyl)imidazo[2,1-b]oxazol-5-yl]-2-(4-pyridinyl)-, 3-oxide;

1H-Benzotriazole, 6-[6-(4-fluorophenyl)imidazo[2,1-b]oxazol-5-yl]-1-phenyl;

1H-Benzotriazole, 6-[6-(4-fluorophenyl)imidazo[2,1-b]oxazol-5-yl]-1-(2-methylpropyl);

1H-Benzotriazole, 1-(1,1-dimethylethyl)-6-[6-(4-fluorophenyl)imidazo[2,1-b]oxazol-5-yl];

1H-Benzotriazole, 1-(2,2-dimethylpropyl)-6-[6-(4-fluorophenyl)imidazo[2,1-b]oxazol-5-yl];

1H-Benzotriazole, 6-[6-(4-fluorophenyl)imidazo[2,1-b]oxazol-5-yl]-1-(phenylmethyl);

1H-Benzotriazole, 1-cyclohexyl-6-[6-(4-fluorophenyl)imidazo[2,1-b]oxazol-5-yl];

1H-Benzotriazole, 1-(cyclopropylmethyl)-6-[6-(4-fluorophenyl)imidazo[2,1-b]oxazol-5-yl];

1H-Benzimidazol-2-amine, 6-[6-(4-fluorophenyl)imidazo[2,1-b]oxazol-5-yl]-1-phenyl;

1H-Benzimidazole-1-ethanol, 2-amino-6-[6-(4-fluorophenyl)imidazo[2,1-b]oxazol-5-yl];

1H-Benzimidazol-2-amine, 6-[6-(4-fluorophenyl)imidazo[2,1-b]oxazol-5-yl]-1-(2-methylpropyl);

1H-Benzimidazol-2-amine, 1-(1,1-dimethylethyl)-6-[6-(4-fluorophenyl)imidazo[2,1-b]oxazol-5-yl];

1H-Benzotriazole, 6-[6-(2,4-difluorophenyl)imidazo[2,1-b]oxazol-5-yl]-1-(1-methylethyl);

1,2-Benzisoxazole, 5-[6-(2,4-difluorophenyl)imidazo[2,1-b]oxazol-5-yl]-3-(1-methylethyl);

1H-Benzimidazol-2-amine, 1-(2,2-dimethylpropyl)-6-[6-(4-fluorophenyl)imidazo[2,1-b]oxazol-5-yl];

1H-Benzimidazol-2-amine, 6-[6-(4-fluorophenyl)imidazo[2,1-b]oxazol-5-yl]-1-(phenylmethyl);

1H-Benzotriazole, 4-fluoro-6-[6-(4-fluorophenyl)imidazo[2,1-b]oxazol-5-yl]-1-(2-methylpropyl);

1H-Benzimidazol-2-amine, 4-fluoro-6-[6-(4-fluorophenyl)imidazo[2,1-b]oxazol-5-yl]-1-(2-methylpropyl);

1H-Benzotriazole-1-ethanol, 6-[6-(2,4-difluorophenyl)imidazo[2,1-b]oxazol-5-yl]-a,a-dimethyl;

1H-Benzotriazole, 6-[6-(2,4-difluorophenyl)imidazo[2,1-b]oxazol-5-yl]-1-(1-methylcyclobutyl);

1H-Benzotriazole-1-propanol, 6-[6-(2,4-difluorophenyl)imidazo[2,1-b]oxazol-5-yl]-b,b-dimethyl;

3-(benzo[d][1,3]dioxol-5-yl)-2-(pyridin-2-yl)-6,7-dihydro-5H-pyrrolo[1,2-a]imidazole;

6-(2-(4-fluorophenyl)-6,7-dihydro-5H-pyrrolo[1,2-a]imidazol-3-yl)imidazo[1,2-b]pyridazin-2-amine;

N-(6-(2-(4-fluorophenyl)-6,7-dihydro-5H-pyrrolo[1,2-a]imidazol-3-yl)imidazo[1,2-b]pyridazin-2-yl)acetamide;

N-(6-(2-(4-fluorophenyl)-6,7-dihydro-5H-pyrrolo[1,2-a]imidazol-3-yl)imidazo[1,2-b]pyridazin-2-yl)isonicotinamide;

N-(6-(2-(4-fluorophenyl)-6,7-dihydro-5H-pyrrolo[1,2-a]imidazol-3-yl)imidazo[1,2-b]pyridazin-2-yl)-3-(pyridin-3-yl)benzamide;

2-fluoro-N-(6-(2-(4-fluorophenyl)-6,7-dihydro-5H-pyrrolo[1,2-a]imidazol-3-yl)imidazo[1,2-b]pyridazin-2-yl)isonicotinamide;

2,6-difluoro-N-(6-(2-(4-fluorophenyl)-6,7-dihydro-5H-pyrrolo[1,2-a]imidazol-3-yl)imidazo[1,2-b]pyridazin-2-yl)isonicotinamide; or N-(6-(2-(4-fluorophenyl)-6,7-dihydro-5H-pyrrolo[1,2-a]imidazol-3-yl)imidazo[1,2-b]pyridazin-2-yl)-2-morpholinoisonicotinamide.

In embodiment 1₃, the compounds are of embodiment I₁, provided that (a) when the bond α is a double bond, p is 0, m is 1 and X is —O—, the compound is not (1) one in which Z is benzotriazolyl, or (2) one in which A is p-fluorophenyl;

(b) when the bond α is a single bond, p is 0, m is 1 and X is —CH$_2$—, the compound is not one in which Z is benzoimidazolyl;

(c) when the bond α is a single bond, p is 0, m is 1, X is —CH$_2$—, and A is 2-pyridyl, the compound is not one in which Z is benzo[d][1,3]dioxolyl; and (d) when the bond α is a single bond, p is 0, m is 1, X is —CH$_2$—, and A is p-fluorophenyl, the compound is not one in which Z is

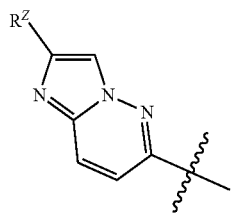

In embodiment I$_4$, the compounds are of embodiment I$_1$, wherein
Z is
(a) a fused bicyclic ring of the formula,

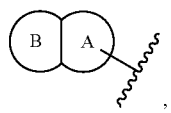

wherein
(1) ring A is —Ar, and
ring B is a 6-membered Het; or
(2) ring A is 6-membered Het, and
ring B is a 5-membered Het; or
(b)

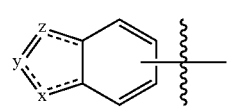

wherein
x is CH, O, or S;
y is CH, CH$_2$, or N; and
z is CH, O, S, N or N(R$^a$);
wherein Z is optionally substituted by one or two —R$^Z$ groups;
provided that the compound is not:
1H-Indazole, 5-[6-(4-fluorophenyl)imidazo[2,1-b]oxazol-5-yl]-3-methyl;
1H-Benzimidazole, 6-[6-(4-fluorophenyl)imidazo[2,1-b]oxazol-5-yl]-2-(4-pyridinyl);
1H-Benzimidazole, 6-[6-(4-fluorophenyl)imidazo[2,1-b]oxazol-5-yl]-2-(4-pyridinyl)-, 3-oxide;
1H-Benzimidazol-2-amine, 6-[6-(4-fluorophenyl)imidazo[2,1-b]oxazol-5-yl]-1-phenyl;
1H-Benzimidazole-1-ethanol, 2-amino-6-[6-(4-fluorophenyl)imidazo[2,1-b]oxazol-5-yl];
1H-Benzimidazol-2-amine, 6-[6-(4-fluorophenyl)imidazo[2,1-b]oxazol-5-yl]-1-(2-methylpropyl);
1H-Benzimidazol-2-amine, 1-(1,1-dimethylethyl)-6-[6-(4-fluorophenyl)imidazo[2,1-b]oxazol-5-yl];
1,2-Benzisoxazole, 5-[6-(2,4-difluorophenyl)imidazo[2,1-b]oxazol-5-yl]-3-(1-methylethyl);
1H-Benzimidazol-2-amine, 1-(2,2-dimethylpropyl)-6-[6-(4-fluorophenyl)imidazo[2,1-b]oxazol-5-yl];
1H-Benzimidazol-2-amine, 6-[6-(4-fluorophenyl)imidazo[2,1-b]oxazol-5-yl]-1-(phenylmethyl);
1H-Benzimidazol-2-amine, 4-fluoro-6-[6-(4-fluorophenyl)imidazo[2,1-b]oxazol-5-yl]-1-(2-methylpropyl);
3-(benzo[d][1,3]dioxol-5-yl)-2-(pyridin-2-yl)-6,7-dihydro-5H-pyrrolo[1,2-a]imidazole;
6-(2-(4-fluorophenyl)-6,7-dihydro-5H-pyrrolo[1,2-a]imidazol-3-yl)imidazo[1,2-b]pyridazin-2-amine;
N-(6-(2-(4-fluorophenyl)-6,7-dihydro-5H-pyrrolo[1,2-a]imidazol-3-yl)imidazo[1,2-b]pyridazin-2-yl)acetamide;
N-(6-(2-(4-fluorophenyl)-6,7-dihydro-5H-pyrrolo[1,2-a]imidazol-3-yl)imidazo[1,2-b]pyridazin-2-yl)isonicotinamide;
N-(6-(2-(4-fluorophenyl)-6,7-dihydro-5H-pyrrolo[1,2-a]imidazol-3-yl)imidazo[1,2-b]pyridazin-2-yl)-3-(pyridin-3-yl)benzamide;
2-fluoro-N-(6-(2-(4-fluorophenyl)-6,7-dihydro-5H-pyrrolo[1,2-a]imidazol-3-yl)imidazo[1,2-b]pyridazin-2-yl)isonicotinamide;
2,6-difluoro-N-(6-(2-(4-fluorophenyl)-6,7-dihydro-5H-pyrrolo[1,2-a]imidazol-3-yl)imidazo[1,2-b]pyridazin-2-yl)isonicotinamide; or
N-(6-(2-(4-fluorophenyl)-6,7-dihydro-5H-pyrrolo[1,2-a]imidazol-3-yl)imidazo[1,2-b]pyridazin-2-yl)-2-morpholinoisonicotinamide.

In embodiment I$_5$, the compounds are of embodiment I$_1$, wherein
Z is
(a) a fused bicyclic ring of the formula,

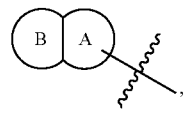

wherein
(1) ring A is —Ar, and
ring B is a 6-membered Het; or
(2) ring A is 6-membered Het, and
ring B is a 5-membered Het; or
(b)

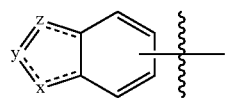

wherein
x is CH, O, or S;
y is CH, CH$_2$, or N; and
z is CH, O, S, N or N(R$^a$);
wherein Z is optionally substituted by one or two —R$^Z$ groups.

In embodiment I₆, the compounds are of embodiment I₁, wherein

Z is (a) a fused bicyclic ring of the formula,

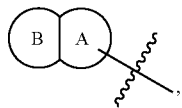

wherein
(1) ring A is —Ar, and
ring B is a 6-membered Het; or
(2) ring A is 6-membered Het, and
ring B is a 5-membered Het; or (b)

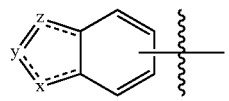

wherein
x is CH, or S;
y is CH, CH₂, or N; and
z is CH, O, S, N or N(Rᵃ);
wherein Z is optionally substituted by one or two —R$^Z$ groups that are each independently C₃₋₈Cak(C₀₋₆alkyl), Hca(C₀₋₆alkyl), Ar(C₀₋₆alkyl), Het(C₀₋₆alkyl), halogen, cyano, C₁₋₆haloalkyl, —C₁-C₆alkoxy, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂, —CH₂—OP(O)(OR), —O—C₁₋₆alkyl-OR, —O—C₁₋₆alkyl-SR, —O—C₁₋₆alkyl-NR₂, —O—C₁₋₆alkyl-Hca, wherein each Ar, Het, Cak, Hca, and haloalkyl group is optionally substituted by one or two —R$^{Z2}$ groups;
wherein each —R$^{Z2}$ is independently halogen, cyano, C₁₋₆alkyl, C₁₋₆haloalkyl, —C₁-C₆alkoxy, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR).

In embodiment I₇, the compounds are of embodiment I₁, wherein

Z is (a) a fused bicyclic ring of the formula,

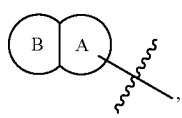

wherein
ring A is —Ar, and
ring B is a 6-membered Het; or (b)

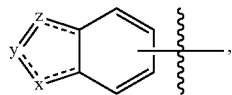

wherein
x is CH, or S;
y is CH, CH₂, or N; and
z is CH, O, S, N or N(Rᵃ); or

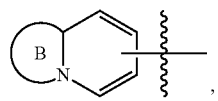

(c)
wherein
ring B is a 5-membered Het;
wherein

Z is optionally substituted by one or two —R$^Z$ groups that are each independently C₃₋₈Cak(C₀₋₆alkyl), Hca(C₀₋₆alkyl), Ar(C₀₋₆alkyl), Het(C₀₋₆alkyl), halogen, cyano, C₁₋₆haloalkyl, —C₁-C₆alkoxy, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂, —CH₂—OP(O)(OR), —O—C₁₋₆alkyl-OR, —O—C₁₋₆alkyl-SR, —O—C₁₋₆alkyl-NR₂, —O—C₁₋₆alkyl-Hca, wherein each Ar, Het, Cak, Hca, and haloalkyl group is optionally substituted by one or two —R$^{Z2}$ groups;
wherein each —R$^{Z2}$ is independently halogen, cyano, C₁₋₆alkyl, C₁₋₆haloalkyl, —C₁-C₆alkoxy, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR).

In embodiment I₈, the compounds are of embodiment I₁, wherein the compounds have structural formula (I), or a pharmaceutically acceptable salt, prodrug, or N-oxide thereof, or a solvate or hydrate thereof, wherein A is phenyl or pyridyl, each optionally substituted with one to five R² groups, wherein
each R² is independently halogen, —C₁-C₆alkyl, —C₁-C₆haloalkyl, —C₁-C₆alkoxy, —NO₂ or —CN, wherein the alkyl, haloalkyl and alkoxy are optionally substituted with 1, 2, 3, or 4 groups that are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, C₁-C₆alkyl, or C₁-C₆haloalkyl;

Z is a fused bicyclic ring of the formula,

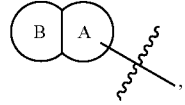

wherein
ring A is Ar or 5- or 6-membered Het,
ring B is 5- or 6-membered Het,
wherein
Z is optionally substituted by one or two —$R^Z$ groups that are each independently halogen, cyano, $C_{1-6}$alkyl, $C_{1-6}$haloalkyl, $C_{1-6}$alkoxy —O—$C_{1-6}$alkyl-OR, —O—$C_{1-6}$alkyl-SR, —O—$C_{1-6}$alkyl-NR$_2$, —O—$C_{1-6}$alkyl-Hca or Het($C_{0-6}$alkyl), wherein each alkyl, haloalkyl alkoxy, Hca and Het group is optionally substituted by one or two —$R^{Z2}$ groups;
wherein each —$R^{Z2}$ is independently halogen, cyano, $C_{1-6}$alkyl, $C_{1-6}$haloalkyl, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

each $R^1$ is independently halogen, $C_1$-$C_6$alkyl, $C_1$-$C_6$haloalkyl, $C_1$-$C_6$alkoxy, —C(O)OR, —NO$_2$ or —CN, wherein the alkyl, haloalkyl and alkoxy are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R or —N(R)S(O)$_2$R;

or, when α is a single bond and two $R^1$ groups are attached to the same carbon atom, the two $R^1$ groups together with the atom to which they are attached form a $C_3$-$C_8$Cak, or $C_3$-$C_8$Hca ring, wherein the Cak and Hca rings are optionally substituted with 1, 2, 3, or 4 groups which are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$alkyl, —$C_1$-$C_6$alkoxy or $C_1$-$C_6$haloalkyl;

p is 0, 1, 2, 3, 4, 5 or 6; and
each R is independently hydrogen, $C_1$-$C_6$alkyl, $C_1$-$C_6$haloalkyl or $C_1$-$C$alkoxy, wherein each alkyl, haloalkyl and alkoxy are optionally substituted with halogen, —OH, —NH$_2$, or cyano.

In embodiment $I_9$, the compounds are of any of embodiments $I_1$-$I_8$ or I', or a pharmaceutically acceptable salt, prodrug, or N-oxide thereof, or a solvate or hydrate thereof, wherein
X is —CH$_2$—, —N($R^a$)— or —O—.

The invention further comprises subgenera of formula (I) in which structural formula (I), A, Z, $R^1$ and p are any group or combinations of groups as defined hereinbelow (e.g., wherein the compound is of structural formula (I) as defined in any of the above embodiments and A is phenyl optionally substituted with one $R^2$ group, wherein $R^2$ is halogen; or the compound is formula (Ib), A is group (1k), Z is group (2g), $R^1$ is group (3d) and p is group (4f)):

Structural Formula (I) is One of Formulae (Ia)-(Ig):

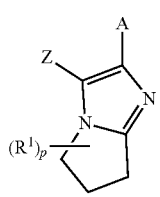
(Ia)

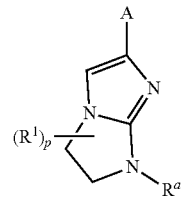
(Ib)

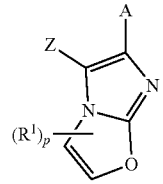
(Ic)

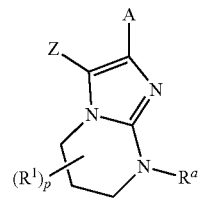
(Id)

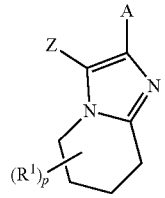
(Ie)

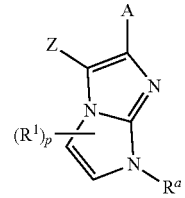
(If)

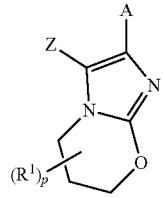
(Ig)

A is Selected from One of the Following Groups (1a)-(1zz):

(1a) A is phenyl or pyridyl, each optionally substituted with one to five $R^2$ groups, wherein $R^2$ is independently halogen, —$C_1$-$C_6$alkyl, —$C_1$-$C_6$haloalkyl, —$C_1$-$C_6$alkoxy, $C_{3-8}$Cak($C_{0-6}$alkyl), Hca($C_{0-6}$alkyl), Ar($C_{0-6}$alkyl), Het($C_{0-6}$alkyl), —O—($C_0$-$C_6$alkyl) —Ar, —O—($C_0$-$C_6$alkyl)-Het, —O—($C_0$-$C_6$alkyl)-Cak, —O—($C_0$-$C_6$alkyl)-Hca, —NO$_2$ or —CN, wherein the Ar, Het, Cak, Hca, alkyl, and haloalkyl are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, or C$_1$-C$_6$haloalkyl.

(1b) A is phenyl optionally substituted with one to five R$^2$ groups, wherein R$^2$ is independently halogen, —C$_1$-C$_6$alkyl, —C$_1$-C$_6$haloalkyl, —C$_1$-C$_6$alkoxy, C$_{3-8}$Cak(C$_{0-6}$alkyl), Hca(C$_{0-6}$alkyl), Ar(C$_{0-6}$alkyl), Het(C$_{0-6}$alkyl), —O—(C$_0$-C$_6$alkyl)—Ar, —O—(C$_0$-C$_6$alkyl)-Het, —O—(C$_0$-C$_6$alkyl)-Cak, —O—(C$_0$-C$_6$alkyl)-Hca, —NO$_2$ or —CN, wherein the Ar, Het, Cak, Hca, alkyl, and haloalkyl are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, or C$_1$-C$_6$haloalkyl.

(1c) A is pyridyl optionally substituted with one to five R$^2$ groups, wherein R$^2$ is independently halogen, —C$_1$-C$_6$alkyl, —C$_1$-C$_6$haloalkyl, —C$_1$-C$_6$alkoxy, C$_{3-8}$Cak(C$_{0-6}$alkyl), Hca(C$_{0-6}$alkyl), Ar(C$_{0-6}$alkyl), Het(C$_{0-6}$alkyl), —O—(C$_0$-C$_6$alkyl)—Ar, —O—(C$_0$-C$_6$alkyl)-Het, —O—(C$_0$-C$_6$alkyl)-Cak, —O—(C$_0$-C$_6$alkyl)-Hca, —NO$_2$ or —CN, wherein the Ar, Het, Cak, Hca, alkyl, and haloalkyl are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, or C$_1$-C$_6$haloalkyl.

(1d) A is phenyl optionally substituted with one to five R$^2$ groups, wherein R$^2$ is independently halogen, —C$_1$-C$_6$alkyl, —C$_1$-C$_6$haloalkyl, —C$_1$-C$_6$alkoxy, C$_{3-8}$Cak(C$_{0-6}$alkyl), Hca(C$_{0-6}$alkyl), Ar(C$_{0-6}$alkyl), Het(C$_{0-6}$alkyl), —O—(C$_0$-C$_6$alkyl)—Ar, —O—(C$_0$-C$_6$alkyl)-Het, —O—(C$_0$-C$_6$alkyl)-Cak, —O—(C$_0$-C$_6$ alkyl)-Hca, —NO$_2$ or —CN.

(1e) A is phenyl optionally substituted with one to five R$^2$ groups, wherein R$^2$ is independently halogen, —C$_1$-C$_6$alkyl, —C$_1$-C$_6$haloalkyl, —C$_1$-C$_6$alkoxy, C$_{3-8}$Cak(C$_{0-6}$alkyl), Hca(C$_{0-6}$alkyl), Ar(C$_{0-6}$alkyl), Het(C$_{0-6}$alkyl), —NO$_2$ or —CN.

(1f) A is phenyl optionally substituted with one to five R$^2$ groups, wherein R$^2$ is independently halogen, —C$_1$-C$_6$alkyl, —C$_1$-C$_6$haloalkyl, —C$_1$-C$_6$alkoxy, C$_{3-8}$Cak(C$_{0-6}$alkyl), Hca(C$_{0-6}$alkyl), Ar(C$_{0-6}$alkyl), Het(C$_{0-6}$alkyl), —NO$_2$ or —CN.

(1g) A is phenyl optionally substituted with one to five R$^2$ groups, wherein R$^2$ is independently halogen, —C$_1$-C$_6$alkyl, —C$_1$-C$_6$haloalkyl, —C$_1$-C$_6$alkoxy, —NO$_2$ or —CN.

(1h) A is phenyl optionally substituted with one to five R$^2$ groups, wherein R$^2$ is independently halogen, —C$_1$-C$_6$alkyl, —C$_1$-C$_6$haloalkyl or —C$_1$-C$_6$alkoxy, (1i) A is phenyl optionally substituted with one to five R$^2$ groups, wherein R$^2$ is independently halogen, —C$_1$-C$_6$alkyl or —C$_1$-C$_6$haloalkyl.

(1j) A is phenyl substituted with one to five R$^2$ groups, wherein R$^2$ is independently halogen or —C$_1$-C$_6$alkyl.

(1k) A is phenyl substituted with one to five R$^2$ groups, wherein R$^2$ is independently halogen.

(1l) A is phenyl substituted with one to five R$^2$ groups, wherein R$^2$ is independently —C$_1$-C$_6$alkyl or —C$_1$-C$_6$alkoxy.

(1m) A is phenyl substituted with one to three R$^2$ groups, wherein R$^2$ is independently halogen or —C$_1$-C$_6$alkyl.

(1n) A is phenyl substituted with three R$^2$ groups, wherein R$^2$ is independently halogen, —C$_1$-C$_6$alkyl, —C$_1$-Chalo$_6$alkyl or —C$_1$-C$_6$alkoxy.

(1o) A is phenyl substituted with three R$^2$ groups, wherein R$^2$ is independently halogen or —C$_1$-C$_6$alkyl.

(1p) A is phenyl substituted with one or two R$^2$ groups, wherein R$^2$ is independently halogen or —C$_1$-C$_6$alkyl.

(1q) A is phenyl substituted with two R$^2$ groups, wherein R$^2$ is independently halogen, —C$_1$-C$_6$alkyl or —C$_1$-C$_6$alkoxy.

(1r) A is phenyl substituted with two R$^2$ groups, wherein R$^2$ is independently halogen or —C$_1$-C$_6$alkyl.

(1s) A is phenyl substituted with one R$^2$ group, wherein R$^2$ is independently halogen or —C$_1$-C$_6$alkyl.

(1t) A is phenyl.

(1u) A is phenyl substituted with one R$^2$ group, wherein R$^2$ is halogen.

(1v) A is phenyl substituted with one R$^2$ group, wherein R$^2$ is —C$_1$-C$_6$alkyl.

(1w) A is phenyl substituted with one R$^2$ group, wherein R$^2$ is —C$_1$-C$_6$alkoxy.

(1x) A is phenyl substituted with one to five R$^2$ groups, wherein R$^2$ is independently halogen, —C$_1$-C$_6$alkyl, —C$_1$-C$_6$haloalkyl, —C$_1$-C$_6$alkoxy, —O—(C$_0$-C$_6$alkyl)-Ar, —O—(C$_0$-C$_6$alkyl)-Het, —O—(C$_0$-C$_6$alkyl)-Cak, —O—(C$_0$-C$_6$alkyl)-Hca, —NO$_2$ or —CN, wherein the Ar, Het, Cak, Hca, alkyl, and haloalkyl are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, —C$_1$-C$_6$alkoxy or C$_1$-C$_6$haloalkyl.

(1y) A is phenyl substituted with one to five R$^2$ groups, wherein R$^2$ is independently C$_{3-8}$Cak(C$_{0-6}$alkyl), Hca(C$_{0-6}$alkyl), Ar(C$_{0-6}$alkyl), Het(C$_{0-6}$alkyl), —O—(C$_0$-C$_6$alkyl)—Ar, —O—(C$_0$-C$_6$alkyl)-Het, —O—(C$_0$-C$_6$alkyl)-Cak, —O—(C$_0$-C$_6$alkyl)-Hca, wherein the Ar, Het, Cak, Hca and alkyl are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, —C$_1$-C$_6$alkoxy or C$_1$-C$_6$haloalkyl.

(1z) A is phenyl substituted with one to five R$^2$ groups, wherein R$^2$ is independently —O—(C$_0$-C$_6$alkyl)-Ar, —O—(C$_0$-C$_6$alkyl)-Het, —O—(C$_0$-C$_6$alkyl)-Cak, —O—(C$_0$-C$_6$alkyl)-Hca, wherein the Ar, Het, Cak, Hca and alkyl are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, —C$_1$-C$_6$alkoxy or C$_1$-C$_6$haloalkyl.

(1aa) A is phenyl substituted with one to five R$^2$ groups, wherein R$^2$ is independently C$_{3-8}$Cak(C$_{0-6}$alkyl), Hca(C$_{0-6}$alkyl), Ar(C$_{0-6}$alkyl), Het(C$_{0-6}$alkyl), wherein the Ar, Het, Cak, Hca and alkyl are optionally substituted with 1, 2, 3, or 4 groups that are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, —C$_1$-C$_6$alkoxy or C$_1$-C$_6$haloalkyl.

(1bb) A is phenyl substituted with one to five R$^2$ groups, wherein R$^2$ is independently C$_{3-8}$Cak(C$_{0-6}$alkyl), Hca(C$_{0-6}$alkyl), Ar(C$_{0-6}$alkyl), Het(C$_{0-6}$alkyl), —O—(C$_0$-C$_6$alkyl)—Ar, —O—(C$_0$-C$_6$alkyl)-Het, —O—(C$_0$-C$_6$alkyl)-Cak, or —O—(C$_0$-C$_6$alkyl)-Hca.

(1cc) A is phenyl substituted with one to five R$^2$ groups, wherein R$^2$ is independently —O—(C$_0$-C$_6$alkyl)-Ar, —O—(C$_0$-C$_6$alkyl)-Het, —O—(C$_0$-C$_6$alkyl)-Cak or —O—(C$_0$-C$_6$alkyl)-Hca.

(1dd) A is phenyl substituted with one to five R$^2$ groups, wherein R$^2$ is independently C$_{3-8}$Cak(C$_{0-6}$alkyl), Hca(C$_{0-6}$alkyl), Ar(C$_{0-6}$alkyl) or Het(C$_{0-6}$alkyl).

(1ee) A is phenyl substituted with one to five R$^2$ groups, wherein R$^2$ is independently halogen, —C$_1$-C$_6$alkyl, —C$_1$-C$_6$haloalkyl, C$_{3-8}$Cak(C$_{0-6}$alkyl), Hca(C$_{0-6}$alkyl), Ar (C$_{0-6}$alkyl), Het(C$_{0-6}$alkyl), —O—(C$_0$-C$_6$alkyl)-Ar, —O—(C$_0$-C$_6$alkyl)-Het, —O—(C$_0$-C$_6$alkyl)-Cak, —O—(C$_0$-C$_6$alkyl)-Hca, —NO$_2$ or —CN, wherein the Ar, Het, Cak, Hca, alkyl, and haloalkyl are optionally substituted with 1, 2, 3, or 4 groups that are each independently halogen, cyano, nitro, —OR, —SR, —NR$_2$, —C(O)OR, —C(O)NR$_2$, —C(O)R.

(1ff) A is pyridyl optionally substituted with one to five R$^2$ groups, wherein R$^2$ is independently halogen, —C$_1$-C$_6$alkyl, —C$_1$-C$_6$haloalkyl or —C$_1$-C$_6$alkoxy.

(1gg) A is pyridyl optionally substituted with one to five R$^2$ groups, wherein R$^2$ is independently halogen, —C$_1$-C$_6$alkyl or —C$_1$-C$_6$haloalkyl.

(1hh) A is pyridyl substituted with one to five R$^2$ groups, wherein R$^2$ is independently halogen or —C$_1$-C$_6$alkyl.

(1ii) A is pyridyl substituted with one to five R$^2$ groups, wherein R$^2$ is independently halogen.

(1jj) A is pyridyl substituted with one to five R$^2$ groups, wherein R$^2$ is independently —C$_1$-C$_6$alkyl or —C$_1$-C$_6$alkoxy.

(1kk) A is pyridyl substituted with one to three R$^2$ groups, wherein R$^2$ is independently halogen or —C$_1$-C$_6$alkyl.

(1ll) A is pyridyl substituted with three R$^2$ groups, wherein R$^2$ is independently halogen, —C$_1$-C$_6$alkyl, —C$_1$-Chalo$_6$alkyl or —C$_1$-C$_6$alkoxy.

(1mm) A is pyridyl substituted with three R$^2$ groups, wherein R$^2$ is independently halogen or —C$_1$-C$_6$alkyl.

(1nn) A is pyridyl substituted with one or two R$^2$ groups, wherein R$^2$ is independently halogen or —C$_1$-C$_6$alkyl.

(1oo) A is pyridyl substituted with two R$^2$ groups, wherein R$^2$ is independently halogen, —C$_1$-C$_6$alkyl or —C$_1$-C$_6$alkoxy.

(1pp) A is pyridyl substituted with two R$^2$ groups, wherein R$^2$ is independently halogen or —C$_1$-C$_6$alkyl.

(1qq) A is pyridyl substituted with one R$^2$ group, wherein R$^2$ is independently halogen or —C$_1$-C$_6$alkyl.

(1rr) A is pyridyl.

(1ss) A is pyridyl substituted with one R$^2$ group, wherein R$^2$ is halogen.

(1tt) A is pyridyl substituted with one R$^2$ group, wherein R$^2$ is —C$_1$-C$_6$alkyl.

(1uu) A is pyridyl substituted with one R$^2$ group, wherein R$^2$ is methyl.

(1vv) A is pyridyl substituted with one R$^2$ group, wherein R$^2$ is ethyl.

(1ww) A is pyridyl substituted with one R$^2$ group, wherein R$^2$ is —C$_1$-C$_6$alkoxy.

(1xx) Any one of groups (1a), (1c) or (1ff)-(1uu), wherein pyridyl is 2-pyridyl.

(1yy) Any one of groups (1a), (1c) or (1ff)-(1uu), wherein pyridyl is 3-pyridyl.

(1zz) Any one of groups (1a), (1c) or (1ff)-(1uu), wherein pyridyl is 4-pyridyl.

Z is Selected from One of the Following Groups (2a)-(2aaa):

(2a) Z is
a fused bicyclic ring of the formula,

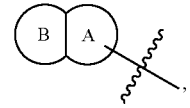

wherein
ring A is Ar or 5- or 6-membered Het,
ring B is 5- or 6-membered Het,
wherein
Z is optionally substituted by one or two —R$^Z$ groups that are each independently C$_{3-8}$Cak(C$_{0-6}$alkyl), Hca(C$_{0-6}$alkyl), Ar(C$_{0-6}$alkyl), Het(C$_{0-6}$alkyl), halogen, cyano, C$_{1-6}$alkyl, C$_{1-6}$haloalkyl, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), —O—C$_{1-6}$alkyl-OR, —O—C$_{1-6}$alkyl-SR, —O—C$_{1-6}$alkyl-NR$_2$ or —O—C$_{1-6}$alkyl-Hca, wherein each Ar, Het, Cak, Hca, alkyl, and haloalkyl group is optionally substituted by one or two —R$^{Z2}$ groups;
wherein each —R$^{Z2}$ is independently halogen, cyano, C$_{1-6}$alkyl, C$_{1-6}$haloalkyl, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(2b) Z is as described in (2a), provided that Z is not

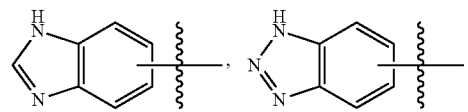

or a substituted analog thereof.

(2c) Z is as described in (2a), provided that Z is not

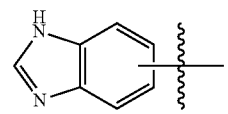

or a substituted analog thereof.

(2d) Z is as described in (2a), provided that Z is not

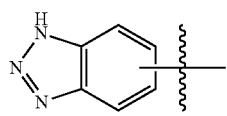

or a substituted analog thereof.

(2e) Z is a fused bicyclic ring of the formula,

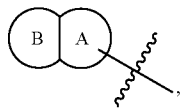

wherein
ring A is Ar or 5- or 6-membered Het; and
ring B is 5- or 6-membered Het; wherein
optionally substituted as described in (2a) above.

(2f) Z is a fused bicyclic ring of the formula,

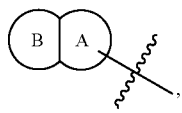

wherein
ring A is Ar; and
ring B is 5- or 6-membered Het; wherein
optionally substituted as described in (2a) above.

(2g) Z is a fused bicyclic ring of the formula,

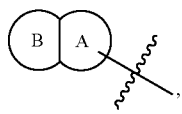

wherein
ring A is Ar; and
ring B is 5-membered Het; wherein
optionally substituted as described in (2a) above.

(2h) Z is a fused bicyclic ring of the formula,

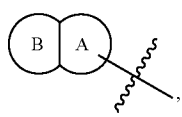

wherein
ring A is Ar; and
ring B is 6-membered Het; wherein
optionally substituted as described in (2a) above.

(2i) Z is a fused bicyclic ring of the formula,

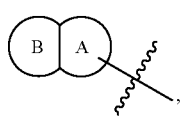

wherein
ring A is 5-membered Het; and
ring B is 5- or 6-membered Het; wherein
optionally substituted as described in (2a) above.

(2j) Z is a fused bicyclic ring of the formula,

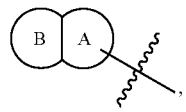

wherein
ring A is 5-membered Het; and
ring B is 5-membered Het; wherein
optionally substituted as described in (2a) above.

(2k) Z is a fused bicyclic ring of the formula,

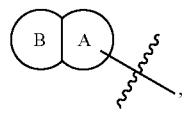

wherein
ring A is 5-membered Het; and
ring B is 6-membered Het; wherein
optionally substituted as described in (2a) above.

(2l) Z is a fused bicyclic ring of the formula,

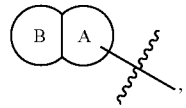

wherein
ring A is 6-membered Het; and
ring B is 5- or 6-membered Het; wherein
optionally substituted as described in (2a) above.

(2m) Z is a fused bicyclic ring of the formula,

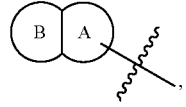

wherein
ring A is 6-membered Het; and
ring B is 5-membered Het; wherein
optionally substituted as described in (2a) above.

(2n) Z is a fused bicyclic ring of the formula,

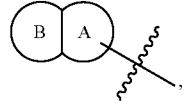

wherein
ring A is 6-membered Het; and
ring B is 6-membered Het; wherein
optionally substituted as described in (2a) above.

(2o) Z is

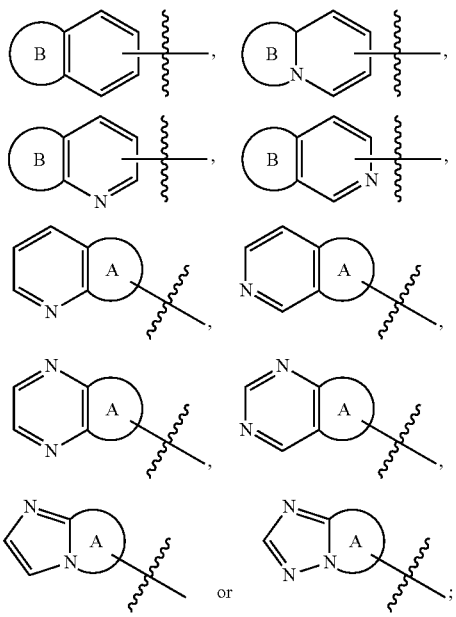

wherein ring A and B are as described in (2a), and Z is optionally substituted as described in (2a) above.

(2p) Z is

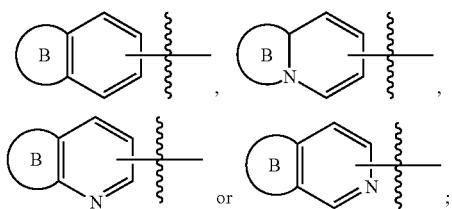

wherein ring B is as described in (2a), and Z is optionally substituted as described in (2a) above.

(2q) Z is

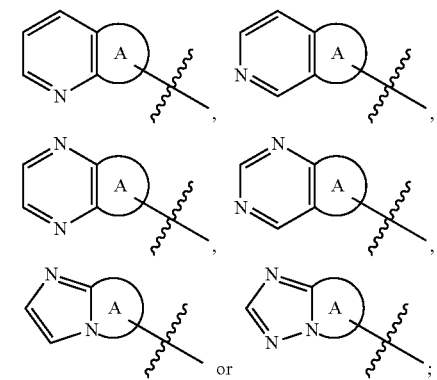

wherein ring A is as described in (2a), and Z is optionally substituted as described in (2a) above.

(2r) Z is

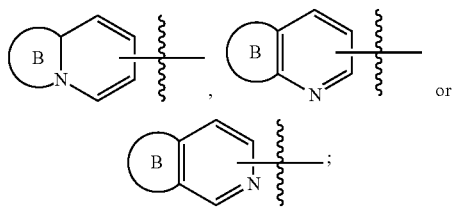

wherein ring B is as described in (2a), and Z is optionally substituted as described in (2a) above.

(2s) Z is

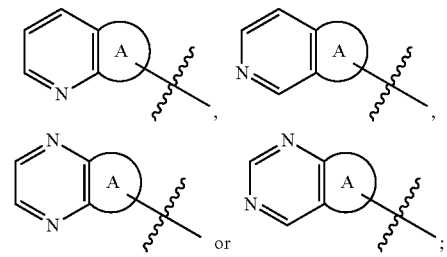

wherein ring A is as described in (2a), and Z is optionally substituted as described in (2a) above.

(2t) Z is

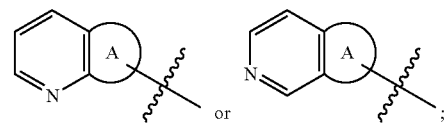

wherein ring A is as described in (2a), and Z is optionally substituted as described in (2a) above.

(2u) Z is

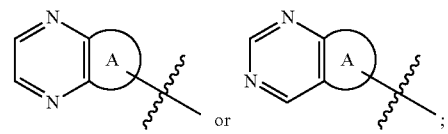

wherein ring A is as described in (2a), and Z is optionally substituted as described in (2a) above.

(2v) Z is

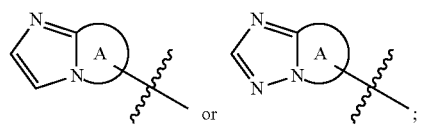

wherein ring A is as described in (2a), and Z is optionally substituted as described in (2a) above.

(2w) Z is
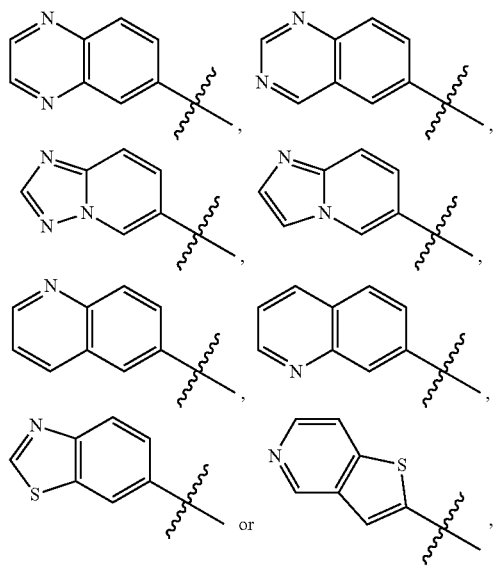
each optionally substituted as described in (2a) above, or
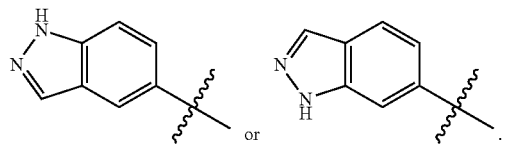 [SMILES: *c1ccc2[nH]ncc2c1 ; *c1ccc2cn[nH]c2c1]
(2x) Z is
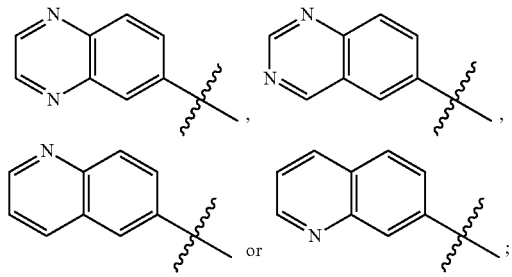
each optionally substituted as described in (2a) above.
(2y) Z is
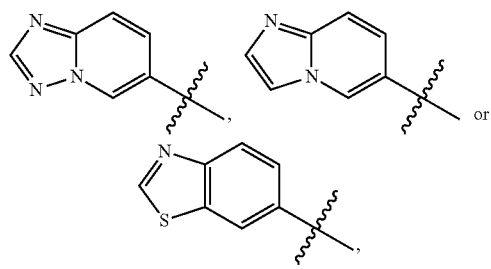
each optionally substituted as described in (2a) above, or
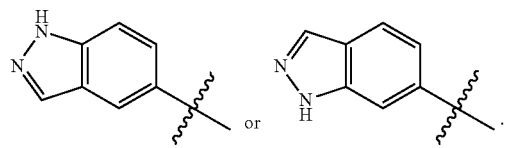 [SMILES: *c1ccc2[nH]ncc2c1 ; *c1ccc2cn[nH]c2c1]
(2z) Z is
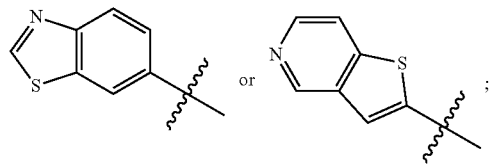 [SMILES: *c1ccc2ncsc2c1 ; *c1cc2cnccc2s1]
each optionally substituted as described in (2a) above.
(2aa) Z is
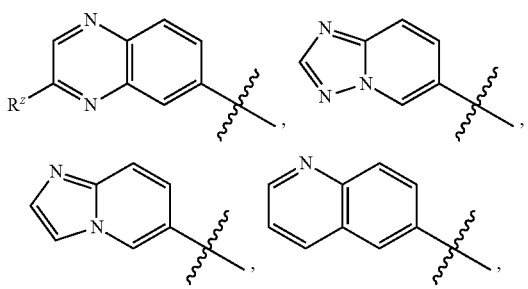
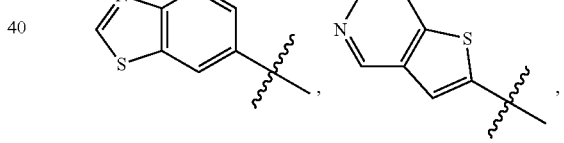
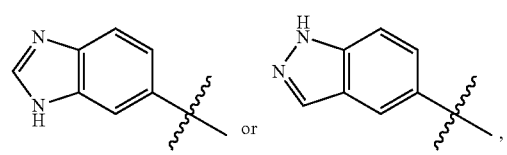
wherein each $R^Z$ is independently hydrogen or —O—$C_{1-6}$alkyl-$NR_2$.
(2bb) Z is
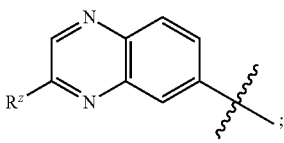
wherein $R^Z$ is as described in (2a).

(2cc) Z is

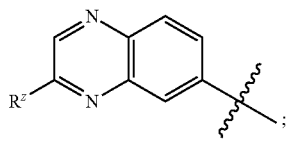

wherein $R^Z$ is independently hydrogen or —O—$C_{1-6}$alkyl-$NR_2$.

(2dd) Z is

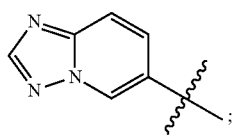 [SMILES: *c1ccc2ncnn2c1]

optionally substituted as described in (2a) above.

(2ee) Z is

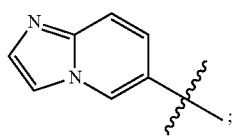 [SMILES: *c1ccc2nccn2c1]

optionally substituted as described in (2a) above.

(2ff) Z is

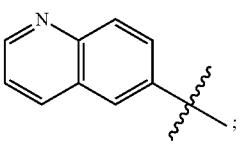 [SMILES: *c1ccc2ncccc2c1]

optionally substituted as described in (2a) above.

(2gg) Z is

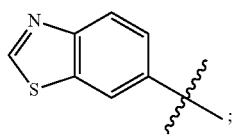 [SMILES: *c1ccc2ncsc2c1]

optionally substituted as described in (2a) above.

(2hh) Z is

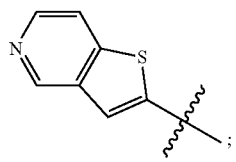

optionally substituted as described in (2a) above.

(2ii) Z is

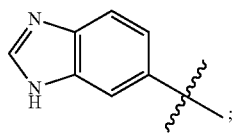

optionally substituted as described in (2a) above.

(2jj) Z is

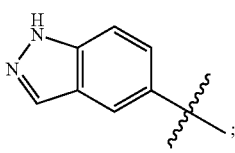 [SMILES: *c1ccc2[nH]ncc2c1]

optionally substituted as described in (2a) above.

(2kk) Z is

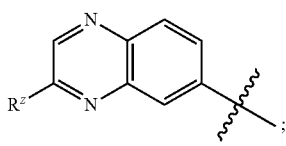

wherein $R^Z$ is as described in (2a).

(2ll) Z is

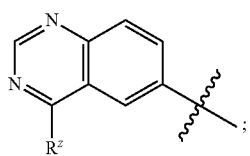

wherein $R^Z$ is as described in (2a).

(2mm) Z is

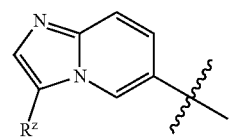

wherein $R^Z$ is as described in (2a).

(2nn) Z is

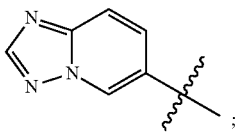 [SMILES: *c1ccc2ncnn2c1]

optionally substituted with one or two $R^Z$ groups as described in (2a).

(2oo) Z is

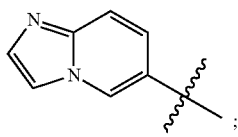 [SMILES: *c1ccc2nccn2c1]

optionally substituted with one or two $R^Z$ groups as described in (2a).

(2pp) Z is

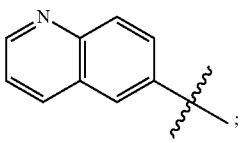 [SMILES: *c1ccc2ncccc2c1]

optionally substituted with one or two $R^Z$ groups as described in (2a).

(2qq) Z is

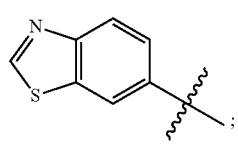 [SMILES: *c1ccc2ncsc2c1]

optionally substituted with one or two $R^Z$ groups as described in (2a).

(2rr) Z is

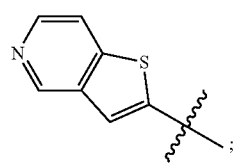

optionally substituted with one or two $R^Z$ groups as described in (2a).

(2ss) Z is

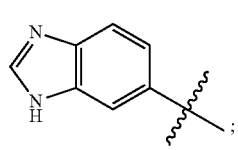 [SMILES: *c1ccc2nc[nH]c2c1]

optionally substituted with one or two $R^Z$ groups as described in (2a).

(2tt) Z is

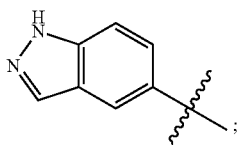 [SMILES: *c1ccc2[nH]ncc2c1]

optionally substituted with one or two $R^Z$ groups as described in (2a).

(2uu) Z is

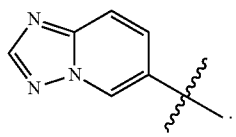 [SMILES: *c1ccc2ncnn2c1]

(2vv) Z is

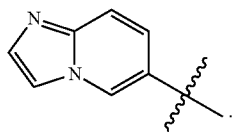 [SMILES: *c1ccc2nccn2c1]

(2ww) Z is

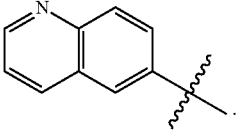 [SMILES: *c1ccc2ncccc2c1]

(2xx) Z is

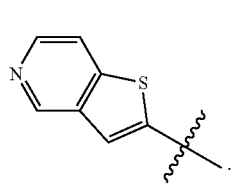 [SMILES: *c1cc2cnccc2s1]

(2yy) Z is

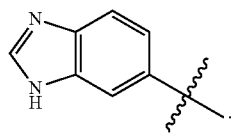 [SMILES: *c1ccc2nc[nH]c2c1]

(2zz) Z is

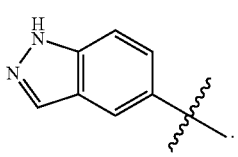

(2aaa) Z is

R¹ is Selected from One of the Following Groups (3a)-(3mm):

(3a) each $R^1$ is independently hydrogen, halogen, $C_1$-$C_6$alkyl, $C_1$-$C_6$haloalkyl, $C_{3-8}$Cak($C_{0-6}$alkyl), Hca($C_{0-6}$alkyl), Ar($C_{0-6}$alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, —C(O)OR, —NO₂ or —CN, wherein the Ar, Het, Cak, Hca, alkyl, and haloalkyl are optionally substituted with 1, 2, 3, or 4 groups that are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl or, when α is a single bond, two $R^1$ groups taken together, when attached to the same carbon atom, form a spirocycle, wherein the spirocycle is $C_3$-$C_8$Cak, or $C_3$-$C_8$Hca, and the Cak and Hca are optionally substituted with 1, 2, 3, or 4 groups which are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3b) each $R^1$ is independently hydrogen, halogen, $C_1$-$C_6$alkyl, $C_1$-$C_6$haloalkyl, $C_{3-8}$Cak($C_{0-6}$alkyl), Hca($C_{0-6}$alkyl), Ar($C_{0-6}$alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, —C(O)OR, —NO₂ or —CN, wherein the Ar, Het, Cak, Hca, alkyl, and haloalkyl are optionally substituted with 1, 2, 3, or 4 groups that are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3c) when α is a single bond, two $R^1$ groups taken together, when attached to the same carbon atom, form a spirocycle, wherein the spirocycle is $C_3$-$C_8$Cak, or $C_3$-$C_8$Hca, and the Cak and Hca are optionally substituted with 1, 2, 3, or 4 groups which are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3d) when α is a single bond, two $R^1$ groups taken together, when attached to the same carbon atom, form a spirocycle, wherein the spirocycle is $C_3$-$C_8$Cak, and the Cak is optionally substituted with 1, 2, 3, or 4 groups which are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3e) when α is a single bond, two $R^1$ groups taken together, when attached to the same carbon atom, form a spirocycle, wherein the spirocycle is $C_3$-$C_8$Hca, and the Hca is optionally substituted with 1, 2, 3, or 4 groups which are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3f) each $R^1$ is independently hydrogen, halogen, $C_1$-$C_6$alkyl, $C_1$-$C_6$haloalkyl, $C_{3-8}$Cak($C_{0-6}$alkyl), Hca($C_{0-6}$alkyl), Ar($C_{0-6}$alkyl), Het($C_{0-6}$alkyl), —C(O)OR, —NO₂ or —CN, wherein the Ar, Het, Cak, Hca, alkyl, and haloalkyl are optionally substituted with 1, 2, 3, or 4 groups that are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3g) each $R^1$ is independently hydrogen, halogen, $C_1$-$C_6$alkyl, $C_1$-$C_6$haloalkyl, —C(O)OR, —NO₂ or —CN, wherein the alkyl, and haloalkyl are optionally substituted with 1, 2, 3, or 4 groups that are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3h) each $R^1$ is independently hydrogen, halogen, $C_1$-$C_6$alkyl, $C_1$-$C_6$haloalkyl, wherein the alkyl and haloalkyl are optionally substituted with 1, 2, 3, or 4 groups that are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3i) each $R^1$ is independently hydrogen, halogen, $C_1$-$C_6$alkyl, wherein the alkyl is optionally substituted with 1, 2, 3, or 4 groups that are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3j) each $R^1$ is independently hydrogen, halogen, $C_1$-$C_6$alkyl, wherein the alkyl is optionally substituted with 1, 2, 3, or 4 groups that are each independently halogen, cyano, nitro, —OR, —SR, —NR₂, —C(O)OR, —C(O)NR₂, —C(O)R.

(3k) each $R^1$ is independently hydrogen, $C_{3-8}$Cak($C_{0-6}$alkyl), Hca($C_{0-6}$alkyl), Ar($C_{0-6}$alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, wherein the Ar, Het, Cak, Hca, alkyl, and haloalkyl are optionally substituted with 1, 2, 3, or 4 groups that are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, $C_1$-$C_6$alkyl, or $C_1$-$C_6$haloalkyl.

(3l) each $R^1$ is independently hydrogen, halogen, —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, wherein the Ar, Het, Cak, Hca, alkyl, and haloalkyl are optionally substituted with 1, 2, 3, or 4 groups that are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, or $C_1$-$C_6$haloalkyl.

(3m) each $R^1$ is independently hydrogen, $C_{3-8}$Cak($C_{0-6}$alkyl), Hca($C_{0-6}$alkyl), Ar ($C_{0-6}$alkyl), Het($C_{0-6}$alkyl), wherein the Ar, Het, Cak, Hca, alkyl, and haloalkyl are optionally substituted with 1, 2, 3, or 4 groups that are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, or $C_1$-$C_6$haloalkyl.

(3n) each $R^1$ is independently hydrogen, $C_1$-$C_6$alkyl, $C_1$-$C_6$haloalkyl, $C_{3-8}$Cak($C_{0-6}$alkyl), Hca($C_{0-6}$alkyl), Ar($C_{0-6}$alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, —C(O)OR, —$NO_2$ or —CN.

(3o) each $R^1$ is independently hydrogen, $C_1$-$C_6$alkyl, $C_1$-$C_6$haloalkyl, —$NO_2$ or —CN.

(3p) each $R^1$ is independently hydrogen, $C_1$-$C_6$haloalkyl, —$NO_2$ or —CN.

(3q) each $R^1$ is independently hydrogen, or C(O)OR.

(3r) each $R^1$ is independently hydrogen, $C_1$-$C_6$alkyl or C(O)OR.

(3s) each $R^1$ is independently hydrogen or $C_1$-$C_6$alkyl.

(3t) each $R^1$ is independently hydrogen or halogen.

(3u) each $R^1$ is independently $C_1$-$C_6$alkyl, $C_1$-$C_6$haloalkyl, —$NO_2$ or —CN.

(3v) each $R^1$ is independently $C_1$-$C_6$haloalkyl, —$NO_2$ or —CN.

(3w) each $R^1$ is independently —$NO_2$ or —CN.

(3x) each $R^1$ is $C_1$-$C_6$alkyl.

(3y) each $R^1$ is C(O)OR.

(3z) each $R^1$ is hydrogen.

(3aa) each $R^1$ is independently hydrogen, $C_{3-8}$Cak($C_{0-6}$alkyl), Hca($C_{0-6}$alkyl), Ar ($C_{0-6}$alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak or —O—($C_0$-$C_6$alkyl)-Hca.

(3bb) each $R^1$ is independently hydrogen, $C_{3-8}$Cak($C_{0-6}$alkyl), Hca($C_{0-6}$alkyl), Ar ($C_{0-6}$alkyl) or Het($C_{0-6}$alkyl).

(3cc) each $R^1$ is independently hydrogen, —O—($C_0$-$C_6$alkyl)-Ar, —O—($C_0$-$C_6$alkyl)-Het, —O—($C_0$-$C_6$alkyl)-Cak or —O—($C_0$-$C_6$alkyl)-Hca.

(3dd) each $R^1$ is independently hydrogen, $C_1$-$C_6$alkyl, $C_1$-$C_6$haloalkyl, —$NO_2$ or —CN.

(3ee) each $R^1$ is independently hydrogen, $C_1$-$C_6$alkyl, $C_1$-$C_6$haloalkyl, $C_{3-8}$Cak($C_{0-6}$alkyl), Hca($C_{0-6}$alkyl), Ar($C_{0-6}$alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, —C(O)OR, —$NO_2$ or —CN.

(3ff) each $R^1$ is independently hydrogen or $C_{3-8}$Cak($C_{0-6}$alkyl).

(3gg) each $R^1$ is independently hydrogen or Hca($C_{0-6}$alkyl).

(3hh) each $R^1$ is independently hydrogen or Ar($C_{0-6}$alkyl).

(3ii) each $R^1$ is independently hydrogen or Het($C_{0-6}$alkyl).

(3jj) each $R^1$ is independently hydrogen or —O—($C_0$-$C_6$alkyl)-Ar.

(3kk) each $R^1$ is independently hydrogen or —O—($C_0$-$C_6$alkyl)-Het.

(3ll) each $R^1$ is independently hydrogen or —O—($C_0$-$C_6$alkyl)-Cak.

(3mm) each $R^1$ is independently hydrogen or —O—($C_0$-$C_6$alkyl)-Hca.

p is Selected from One of the Following Groups (4a)-(4m):

(4a) p is 0, 1, 2, 3, 4, 5 or 6.
(4b) p is 0, 1, 2, 3, 4 or 5.
(4c) p is 0, 1, 2, 3 or 4.
(4d) p is 0, 1, 2 or 3.
(4e) p is 0, 1 or 2.
(4t) p is 0 or 1.
(4g) p is 0.
(4h) p is 1.
(4i) p is 2.
(4j) p is 3.
(4k) p is 4.
(4l) p is 5.
(4m) p is 6.

Particular embodiments of this aspect of the invention comprise compounds of any one of the formulae (I), (I') and (Ia)-(Ig), each as defined in each of the following rows (or a pharmaceutically acceptable salt, prodrug, or N-oxide thereof, or a solvate or hydrate thereof), wherein each entry is a group number as defined above (e.g., (3y) refers to $R^1$ is C(O)OR), and a dash "—" indicates that the variable is as defined in embodiment $I_1$ or defined according to any one of the applicable variable definitions (1a)-(4m) [e.g., when $R^1$ is a dash, it can be either as defined in any of embodiments $I_1$-$I_9$ or any one of definitions (3a)-(3mmm)]:

|        | (I) | A    | Z     | $R^1$ | p    |
|--------|-----|------|-------|-------|------|
| (1)-1  | (I) | (1a) | (2bb) | (3a)  | (4a) |
| (1)-2  | (I) | (1a) | (2f)  | (3b)  | (4b) |
| (1)-3  | (I) | (1b) | (2ff) | (3d)  | (4c) |
| (1)-4  | (I) | (1b) | (2j)  | (3z)  | (4d) |
| (1)-5  | (I) | (1c) | (2k)  | (3r)  | (4e) |
| (1)-6  | (I) | (1c) | (2m)  | (3z)  | (4f) |
| (1)-7  | (I) | (1d) | (2n)  | (3t)  | (4g) |
| (1)-8  | (I) | (1d) | (2ff) | (3u)  | (4h) |
| (1)-9  | (I) | (1e) | (2p)  | (3ee) | (4f) |
| (1)-10 | (I) | (1e) | (2q)  | (3a)  | (4g) |
| (1)-11 | (I) | (1f) | (2w)  | (3a)  | (4i) |
| (1)-12 | (I) | (1f) | (2aa) | (3b)  | (4g) |
| (1)-13 | (I) | (1g) | (2b)  | (3d)  | (4i) |
| (1)-14 | (I) | (1g) | (2ff) | (3o)  | (4a) |
| (1)-15 | (I) | (1h) | (2g)  | (3s)  | (4b) |
| (1)-16 | (I) | (1h) | (2j)  | (3z)  | (4f) |
| (1)-17 | (I) | (1i) | (2k)  | (3u)  | (4g) |
| (1)-18 | (I) | (1i) | (2bb) | (3ee) | (4h) |
| (1)-19 | (I) | (1j) | (2ff) | (3a)  | (4a) |
| (1)-20 | (I) | (1j) | (2cc) | (3b)  | (4b) |
| (1)-21 | (I) | (1k) | (2f)  | (3d)  | (4f) |
| (1)-22 | (I) | (1k) | (2bb) | (3o)  | (4g) |
| (1)-23 | (I) | (1l) | (2j)  | (3a)  | (4h) |
| (1)-24 | (I) | (1l) | (2k)  | (3b)  | (4b) |
| (1)-25 | (I) | (1m) | (2ff) | (3z)  | (4c) |
| (1)-26 | (I) | (1m) | (2n)  | (3o)  | (4d) |
| (1)-27 | (I) | (1n) | (2o)  | (3ee) | (4e) |
| (1)-28 | (I) | (1n) | (2p)  | (3a)  | (4f) |
| (1)-29 | (I) | (1o) | (2q)  | (3z)  | (4g) |
| (1)-30 | (I) | (1o) | (2w)  | (3d)  | (4h) |
| (1)-31 | (I) | (1p) | (2aa) | (3z)  | (4g) |
| (1)-32 | (I) | (1p) | (2cc) | (3a)  | (4a) |
| (1)-33 | (I) | (1q) | (2p)  | (3b)  | (4b) |
| (1)-34 | (I) | (1q) | (2q)  | (3d)  | (4f) |

-continued

| (I) | A | Z | R¹ | p |
|---|---|---|---|---|
| (1)-35 | (I) | (1q) | (2bb) | (3z) | (4g) |
| (1)-36 | (I) | (1r) | (2aa) | (3ee) | (4h) |
| (1)-37 | (I) | (1r) | (2g) | (3a) | (4i) |
| (1)-38 | (I) | (1s) | (2j) | (3b) | (4a) |
| (1)-39 | (I) | (1ww) | (2ff) | (3d) | (4b) |
| (1)-40 | (I) | (1t) | (2m) | (3o) | (4c) |
| (1)-41 | (I) | (1n) | (2n) | (3r) | (4d) |
| (1)-42 | (I) | (1v) | (2b) | (3s) | (4e) |
| (1)-43 | (I) | (1w) | (2bb) | (3t) | (4f) |
| (1)-44 | (I) | (1x) | (2g) | (3z) | (4g) |
| (1)-45 | (I) | (1y) | (2j) | (3ee) | (4h) |
| (1)-46 | (I) | (1z) | (2b) | (3a) | (4a) |
| (1)-47 | (I) | (1aa) | (2f) | (3b) | (4b) |
| (1)-48 | (I) | (1bb) | (2ff) | (3d) | (4c) |
| (1)-49 | (I) | (1cc) | (2j) | (3o) | (4f) |
| (1)-50 | (I) | (1cc) | (2k) | (3r) | (4g) |
| (1)-51 | (Ia) | (1ff) | (2m) | (3s) | (4h) |
| (1)-52 | (Ia) | (1a) | (2n) | (3t) | (4g) |
| (1)-53 | (Ia) | (1b) | (2ff) | (3z) | (4h) |
| (1)-54 | (Ia) | (1b) | (2p) | (3ee) | (4g) |
| (1)-55 | (Ia) | (1c) | (2q) | (3z) | (4a) |
| (1)-56 | (Ia) | (1c) | (2b) | (3b) | (4b) |
| (1)-57 | (Ia) | (1d) | (2ff) | (3z) | (4a) |
| (1)-58 | (Ia) | (1d) | (2g) | (3o) | (4b) |
| (1)-59 | (Ia) | (1e) | (2j) | (3z) | (4c) |
| (1)-60 | (Ia) | (1e) | (2bb) | (3s) | (4d) |
| (1)-61 | (Ia) | (1f) | (2m) | (3t) | (4e) |
| (1)-62 | (Ia) | (1f) | (2ff) | (3u) | (4f) |
| (1)-63 | (Ia) | (1g) | (2o) | (3ee) | (4g) |
| (1)-64 | (Ia) | (1hh) | (2p) | (3z) | (4h) |
| (1)-65 | (Ia) | (1h) | (2q) | (3b) | (4i) |
| (1)-66 | (Ia) | (1h) | (2w) | (3z) | (4a) |
| (1)-67 | (Ia) | (1i) | (2aa) | (3o) | (4b) |
| (1)-68 | (Ia) | (1i) | (2m) | (3r) | (4f) |
| (1)-69 | (Ia) | (1j) | (2bb) | (3z) | (4g) |
| (1)-70 | (Ia) | (1j) | (2o) | (3b) | (4h) |
| (1)-71 | (Ia) | (1k) | (2ff) | (3d) | (4f) |
| (1)-72 | (Ia) | (1ff) | (2q) | (3o) | (4g) |
| (1)-73 | (Ia) | (1l) | (2w) | (3a) | (4h) |
| (1)-74 | (Ia) | (1l) | (2ff) | (3b) | (4i) |
| (1)-75 | (Ia) | (1m) | (2n) | (3d) | (4a) |
| (1)-76 | (Ia) | (1m) | (2o) | (3z) | (4b) |
| (1)-77 | (Ia) | (1n) | (2ff) | (3r) | (4c) |
| (1)-78 | (Ia) | (1ff) | (2bb) | (3s) | (4d) |
| (1)-79 | (Ia) | (1o) | (2cc) | (3t) | (4e) |
| (1)-80 | (Ia) | (1o) | (2aa) | (3z) | (4f) |
| (1)-81 | (Ia) | (1p) | (2cc) | (3ee) | (4g) |
| (1)-82 | (Ia) | (1hh) | (2o) | (3a) | (4h) |
| (1)-83 | (Ia) | (1q) | (2bb) | (3b) | (4g) |
| (1)-84 | (Ia) | (1q) | (2q) | (3z) | (4i) |
| (1)-85 | (Ia) | (1q) | (2m) | (3o) | (4f) |
| (1)-86 | (Ia) | (1r) | (2n) | (3r) | (4g) |
| (1)-87 | (Ia) | (1r) | (2o) | (3z) | (4h) |
| (1)-88 | (Ia) | (1s) | (2cc) | (3a) | (4i) |
| (1)-89 | (Ia) | (1hh) | (2ff) | (3b) | (4a) |
| (1)-90 | (Ia) | (1t) | (2w) | (3z) | (4b) |
| (1)-91 | (Ia) | (1u) | (2aa) | (3o) | (4g) |
| (1)-92 | (Ia) | (1v) | (2k) | (3b) | (4f) |
| (1)-93 | (Ia) | (1w) | (2bb) | (3d) | (4g) |
| (1)-94 | (Ia) | (1x) | (2ff) | (3z) | (4h) |
| (1)-95 | (Ia) | (1ww) | (2o) | (3r) | (4c) |
| (1)-96 | (Ia) | (1z) | (2p) | (3s) | (4d) |
| (1)-97 | (Ia) | (1aa) | (2b) | (3t) | (4e) |
| (1)-98 | (Ia) | (1bb) | (2ff) | (3z) | (4f) |
| (1)-99 | (Ia) | (1cc) | (2g) | (3ee) | (4g) |
| (1)-100 | (Ib) | (1cc) | (2j) | (3a) | (4h) |
| (1)-101 | (Ib) | (1a) | (2k) | (3z) | (4f) |
| (1)-102 | (Ib) | (1a) | (2m) | (3d) | (4g) |
| (1)-103 | (Ib) | (1b) | (2bb) | (3o) | (4h) |
| (1)-104 | (Ib) | (1b) | (2ff) | (3z) | (4a) |
| (1)-105 | (Ib) | (1c) | (2p) | (3s) | (4b) |
| (1)-106 | (Ib) | (1c) | (2q) | (3z) | (4c) |
| (1)-107 | (Ib) | (1d) | (2w) | (3u) | (4d) |
| (1)-108 | (Ib) | (1d) | (2ff) | (3ee) | (4e) |
| (1)-109 | (Ib) | (1e) | (2n) | (3a) | (4f) |
| (1)-110 | (Ib) | (1e) | (2bb) | (3b) | (4g) |
| (1)-111 | (Ib) | (1f) | (2p) | (3z) | (4h) |
| (1)-112 | (Ib) | (1f) | (2q) | (3o) | (4i) |
| (1)-113 | (Ib) | (1g) | (2w) | (3r) | (4g) |
| (1)-114 | (Ib) | (1g) | (2aa) | (3s) | (4a) |
| (1)-115 | (Ib) | (1h) | (2cc) | (3z) | (4b) |
| (1)-116 | (Ib) | (1h) | (2q) | (3u) | (4f) |
| (1)-117 | (Ib) | (1i) | (2bb) | (3ee) | (4g) |
| (1)-118 | (Ib) | (1i) | (2aa) | (3a) | (4h) |
| (1)-119 | (Ib) | (1j) | (2ff) | (3z) | (4a) |
| (1)-120 | (Ib) | (1j) | (2w) | (3d) | (4b) |
| (1)-121 | (Ib) | (1k) | (2m) | (3o) | (4a) |
| (1)-122 | (Ib) | (1k) | (2n) | (3a) | (4b) |
| (1)-123 | (Ib) | (1l) | (2o) | (3b) | (4c) |
| (1)-124 | (Ib) | (1l) | (2p) | (3d) | (4d) |
| (1)-125 | (Ib) | (1m) | (2bb) | (3o) | (4e) |
| (1)-126 | (Ib) | (1m) | (2w) | (3z) | (4f) |
| (1)-127 | (Ib) | (1n) | (2ff) | (3s) | (4g) |
| (1)-128 | (Ib) | (1n) | (2n) | (3t) | (4h) |
| (1)-129 | (Ib) | (1o) | (2o) | (3z) | (4i) |
| (1)-130 | (Ib) | (1o) | (2p) | (3ee) | (4g) |
| (1)-131 | (Ib) | (1p) | (2cc) | (3a) | (4f) |
| (1)-132 | (Ib) | (1p) | (2w) | (3b) | (4g) |
| (1)-133 | (Ib) | (1q) | (2aa) | (3d) | (4h) |
| (1)-134 | (Ib) | (1q) | (2b) | (3z) | (4i) |
| (1)-135 | (Ib) | (1q) | (2f) | (3a) | (4f) |
| (1)-136 | (Ib) | (1r) | (2g) | (3b) | (4g) |
| (1)-137 | (Ib) | (1r) | (2bb) | (3d) | (4h) |
| (1)-138 | (Ib) | (1s) | (2k) | (3z) | (4g) |
| (1)-139 | (Ib) | (1s) | (2m) | (3b) | (4a) |
| (1)-140 | (Ib) | (1t) | (2b) | (3z) | (4b) |
| (1)-141 | (Ib) | (1u) | (2bb) | (3o) | (4c) |
| (1)-142 | (Ib) | (1v) | (2g) | (3r) | (4d) |
| (1)-143 | (Ib) | (1w) | (2j) | (3s) | (4e) |
| (1)-144 | (Ib) | (1x) | (2ff) | (3t) | (4f) |
| (1)-145 | (Ib) | (1y) | (2m) | (3u) | (4g) |
| (1)-146 | (Ib) | (1z) | (2n) | (3ee) | (4h) |
| (1)-147 | (Ib) | (1aa) | (2o) | (3z) | (4g) |
| (1)-148 | (Ib) | (1bb) | (2p) | (3z) | (4i) |
| (1)-149 | (Ib) | (1cc) | (2q) | (3z) | (4a) |
| (1)-150 | (Ib) | (1cc) | (2w) | (3a) | (4b) |
| (1)-151 | (Ic) | (1a) | (2aa) | (3b) | (4c) |
| (1)-152 | (Ic) | (1a) | (2ff) | (3d) | (4d) |
| (1)-153 | (Ic) | (1b) | (2cc) | (3o) | (4e) |
| (1)-154 | (Ic) | (1b) | (2bb) | (3r) | (4f) |
| (1)-155 | (Ic) | (1c) | (2j) | (3s) | (4g) |
| (1)-156 | (Ic) | (1c) | (2k) | (3t) | (4h) |
| (1)-157 | (Ic) | (1d) | (2m) | (3z) | (4f) |
| (1)-158 | (Ic) | (1d) | (2n) | (3ee) | (4g) |
| (1)-159 | (Ic) | (1e) | (2o) | (3z) | (4h) |
| (1)-160 | (Ic) | (1e) | (2cc) | (3z) | (4a) |
| (1)-161 | (Ic) | (1f) | (2q) | (3a) | (4b) |
| (1)-162 | (Ic) | (1f) | (2w) | (3b) | (4c) |
| (1)-163 | (Ic) | (1g) | (2aa) | (3d) | (4d) |
| (1)-164 | (Ic) | (1g) | (2b) | (3o) | (4e) |
| (1)-165 | (Ic) | (1h) | (2bb) | (3z) | (4f) |
| (1)-166 | (Ic) | (1h) | (2g) | (3a) | (4g) |
| (1)-167 | (Ic) | (1i) | (2ff) | (3b) | (4h) |
| (1)-168 | (Ic) | (1i) | (2k) | (3d) | (4g) |
| (1)-169 | (Ic) | (1j) | (2m) | (3o) | (4i) |
| (1)-170 | (Ic) | (1j) | (2bb) | (3r) | (4a) |
| (1)-171 | (Ic) | (1k) | (2o) | (3z) | (4b) |
| (1)-172 | (Ic) | (1k) | (2ff) | (3t) | (4c) |
| (1)-173 | (Ic) | (1l) | (2q) | (3u) | (4d) |
| (1)-174 | (Ic) | (1l) | (2m) | (3ee) | (4e) |
| (1)-175 | (Ic) | (1m) | (2n) | (3b) | (4f) |
| (1)-176 | (Ic) | (1m) | (2o) | (3d) | (4g) |
| (1)-177 | (Ic) | (1n) | (2cc) | (3z) | (4h) |
| (1)-178 | (Ic) | (1n) | (2bb) | (3r) | (4g) |
| (1)-179 | (Ic) | (1o) | (2w) | (3s) | (4i) |
| (1)-180 | (Ic) | (1o) | (2aa) | (3t) | (4g) |
| (1)-181 | (Ic) | (1p) | (2o) | (3u) | (4a) |
| (1)-182 | (Ic) | (1p) | (2p) | (3ee) | (4b) |
| (1)-183 | (Ic) | (1q) | (2q) | (3a) | (4a) |
| (1)-184 | (Ic) | (1q) | (2bb) | (3b) | (4b) |
| (1)-185 | (Ic) | (1q) | (2aa) | (3d) | (4c) |
| (1)-186 | (Ic) | (1r) | (2n) | (3z) | (4d) |
| (1)-187 | (Ic) | (1r) | (2ff) | (3z) | (4e) |
| (1)-188 | (Ic) | (1s) | (2p) | (3a) | (4f) |

-continued

| (I) | A | Z | R¹ | p |
|---|---|---|---|---|
| (1)-189 | (Ic) | (1s) | (2m) | (3b) | (4g) |
| (1)-190 | (Ic) | (1t) | (2n) | (3d) | (4h) |
| (1)-191 | (Ic) | (1u) | (2o) | (3o) | (4g) |
| (1)-192 | (Ic) | (1v) | (2cc) | (3r) | (4f) |
| (1)-193 | (Ic) | (1w) | (2bb) | (3z) | (4g) |
| (1)-194 | (Ic) | (1x) | (2ff) | (3t) | (4h) |
| (1)-195 | (Ic) | (1y) | (2aa) | (3u) | (4a) |
| (1)-196 | (Ic) | (1z) | (2k) | (3ee) | (4b) |
| (1)-197 | (Ic) | (1aa) | (2m) | (3z) | (4c) |
| (1)-198 | (Ic) | (1bb) | (2n) | (3z) | (4d) |
| (1)-199 | (Ic) | (1cc) | (2o) | (3a) | (4e) |
| (1)-200 | (Ic) | (1cc) | (2p) | (3b) | (4f) |
| (1)-201 | (Id) | (1a) | (2q) | (3d) | (4g) |
| (1)-202 | (Id) | (1a) | (2bb) | (3o) | (4h) |
| (1)-203 | (Id) | (1b) | (2aa) | (3r) | (4i) |
| (1)-204 | (Id) | (1b) | (2ff) | (3s) | (4a) |
| (1)-205 | (Id) | (1c) | (2q) | (3t) | (4b) |
| (1)-206 | (Id) | (1c) | (2w) | (3u) | (4b) |
| (1)-207 | (Id) | (1d) | (2aa) | (3ee) | (4g) |
| (1)-208 | (Id) | (1d) | (2cc) | (3z) | (4h) |
| (1)-209 | (Id) | (1e) | (2f) | (3z) | (4g) |
| (1)-210 | (Id) | (1e) | (2g) | (3a) | (4h) |
| (1)-211 | (Id) | (1f) | (2bb) | (3b) | (4a) |
| (1)-212 | (Id) | (1f) | (2ff) | (3d) | (4b) |
| (1)-213 | (Id) | (1g) | (2o) | (3o) | (4c) |
| (1)-214 | (Id) | (1g) | (2p) | (3a) | (4d) |
| (1)-215 | (Id) | (1h) | (2cc) | (3b) | (4e) |
| (1)-216 | (Id) | (1h) | (2w) | (3d) | (4f) |
| (1)-217 | (Id) | (1i) | (2aa) | (3z) | (4g) |
| (1)-218 | (Id) | (1i) | (2w) | (3a) | (4h) |
| (1)-219 | (Id) | (1j) | (2aa) | (3b) | (4i) |
| (1)-220 | (Id) | (1j) | (2b) | (3z) | (4g) |
| (1)-221 | (Id) | (1k) | (2bb) | (3o) | (4f) |
| (1)-222 | (Id) | (1k) | (2ff) | (3r) | (4g) |
| (1)-223 | (Id) | (1l) | (2j) | (3s) | (4h) |
| (1)-224 | (Id) | (1l) | (2k) | (3t) | (4a) |
| (1)-225 | (Id) | (1m) | (2m) | (3u) | (4b) |
| (1)-226 | (Ie) | (1m) | (2n) | (3z) | (4a) |
| (1)-227 | (Ie) | (1n) | (2o) | (3z) | (4b) |
| (1)-228 | (Ie) | (1n) | (2p) | (3z) | (4c) |
| (1)-229 | (Ie) | (1o) | (2cc) | (3a) | (4d) |
| (1)-230 | (Ie) | (1o) | (2bb) | (3b) | (4e) |
| (1)-231 | (Ie) | (1p) | (2aa) | (3d) | (4f) |
| (1)-232 | (Ie) | (1p) | (2cc) | (3z) | (4g) |
| (1)-233 | (Ie) | (1q) | (2ff) | (3d) | (4h) |
| (1)-234 | (Ie) | (1q) | (2o) | (3a) | (4g) |
| (1)-235 | (Ie) | (1q) | (2p) | (3b) | (4i) |
| (1)-236 | (Ie) | (1r) | (2q) | (3d) | (4a) |
| (1)-237 | (Ie) | (1r) | (2cc) | (3o) | (4b) |
| (1)-238 | (Ie) | (1s) | (2aa) | (3z) | (4c) |
| (1)-239 | (Ie) | (1s) | (2ff) | (3ee) | (4d) |
| (1)-240 | (Ie) | (1t) | (2bb) | (3z) | (4e) |
| (1)-241 | (Ie) | (1u) | (2o) | (3a) | (4f) |
| (1)-242 | (Ie) | (1v) | (2p) | (3z) | (4g) |
| (1)-243 | (Ie) | (1w) | (2q) | (3a) | (4h) |
| (1)-244 | (Ie) | (1x) | (2w) | (3b) | (4g) |
| (1)-245 | (Ie) | (1y) | (2aa) | (3d) | (4f) |
| (1)-246 | (Ie) | (1z) | (2ff) | (3o) | (4g) |
| (1)-247 | (Ie) | (1aa) | (2k) | (3r) | (4h) |
| (1)-248 | (Ie) | (1bb) | (2cc) | (3s) | (4b) |
| (1)-249 | (Ie) | (1cc) | (2n) | (3t) | (4c) |
| (1)-250 | (If) | (1cc) | (2o) | (3u) | (4d) |
| (1)-251 | (If) | (1a) | (2p) | (3ee) | (4e) |
| (1)-252 | (If) | (1a) | (2m) | (3z) | (4f) |
| (1)-253 | (If) | (1b) | (2bb) | (3z) | (4g) |
| (1)-254 | (If) | (1b) | (2ff) | (3z) | (4h) |
| (1)-255 | (If) | (1c) | (2ff) | (3z) | (4a) |
| (1)-256 | (If) | (1c) | (2q) | (3z) | (4b) |
| (1)-257 | (If) | (1d) | (2w) | (3a) | (4c) |
| (1)-258 | (If) | (1d) | (2aa) | (3b) | (4d) |
| (1)-259 | (If) | (1e) | (2bb) | (3d) | (4e) |
| (1)-260 | (If) | (1e) | (2g) | (3o) | (4f) |
| (1)-261 | (If) | (1f) | (2ff) | (3z) | (4g) |
| (1)-262 | (If) | (1f) | (2k) | (3a) | (4h) |
| (1)-263 | (If) | (1g) | (2m) | (3b) | (4e) |
| (1)-264 | (If) | (1g) | (2cc) | (3d) | (4f) |
| (1)-265 | (If) | (1h) | (2o) | (3b) | (4g) |
| (1)-266 | (If) | (1h) | (2bb) | (3d) | (4h) |
| (1)-267 | (If) | (1i) | (2q) | (3o) | (4i) |
| (1)-268 | (If) | (1i) | (2ff) | (3r) | (4f) |
| (1)-269 | (If) | (1j) | (2n) | (3s) | (4g) |
| (1)-270 | (If) | (1j) | (2o) | (3t) | (4h) |
| (1)-271 | (If) | (1k) | (2p) | (3u) | (4a) |
| (1)-272 | (If) | (1k) | (2q) | (3ee) | (4b) |
| (1)-273 | (If) | (1l) | (2ff) | (3z) | (4c) |
| (1)-274 | (If) | (1l) | (2aa) | (3z) | (4d) |
| (1)-275 | (Ig) | (1m) | (2f) | (3z) | (4e) |
| (1)-276 | (Ig) | (1m) | (2g) | (3z) | (4f) |
| (1)-277 | (Ig) | (1n) | (2cc) | (3z) | (4g) |
| (1)-278 | (Ig) | (1n) | (2cc) | (3z) | (4h) |
| (1)-279 | (Ig) | (1o) | (2m) | (3a) | (4a) |
| (1)-280 | (Ig) | (1o) | (2n) | (3b) | (4b) |
| (1)-281 | (Ig) | (1p) | (2o) | (3d) | (4i) |
| (1)-282 | (Ig) | (1p) | (2p) | (3a) | (4f) |
| (1)-283 | (Ig) | (1q) | (2cc) | (3b) | (4g) |
| (1)-284 | (Ig) | (1q) | (2w) | (3z) | (4h) |
| (1)-285 | (Ig) | (1q) | (2ff) | (3o) | (4a) |
| (1)-286 | (Ig) | (1r) | (2p) | (3r) | (4b) |
| (1)-287 | (Ig) | (1r) | (2bb) | (3s) | (4c) |
| (1)-288 | (Ig) | (1s) | (2w) | (3t) | (4d) |
| (1)-289 | (Ig) | (1s) | (2aa) | (3a) | (4e) |
| (1)-290 | (Ig) | (1t) | (2ff) | (3b) | (4f) |
| (1)-291 | (Ig) | (1u) | (2m) | (3d) | (4g) |
| (1)-292 | (Ig) | (1v) | (2n) | (3o) | (4h) |
| (1)-293 | (Ig) | (1w) | (2o) | (3d) | (4b) |
| (1)-294 | (Ig) | (1x) | (2p) | (3z) | (4c) |
| (1)-295 | (Ig) | (1y) | (2m) | (3r) | (4d) |
| (1)-296 | (Ig) | (1z) | (2bb) | (3s) | (4e) |
| (1)-297 | (Ig) | (1aa) | (2o) | (3a) | (4f) |
| (1)-298 | (Ig) | (1bb) | (2cc) | (3b) | (4g) |
| (1)-299 | (Ig) | (1cc) | (2q) | (3z) | (4h) |
| (1)-300 | (Ig) | (1cc) | (2ff) | (3o) | (4i) |

In some embodiments, the compound of formulae (I), (Ia)-(Ig), (II) or (IIa)-(IIh) is one of the following compounds (or a pharmaceutically acceptable salt, prodrug, or N-oxide thereof, or a solvate or hydrate thereof):

| No. | Structure | Name |
|---|---|---|
| 1 | 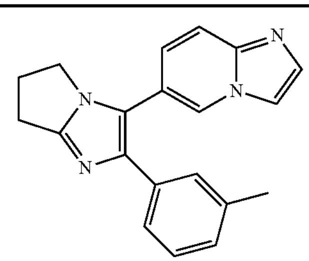 | 6-(2-(m-tolyl)-6,7-dihydro-5H-pyrrolo[1,2-a]imidazol-3-yl)imidazo[1,2-a]pyridine |

-continued

| No. | Structure | Name |
|---|---|---|
| 2 | 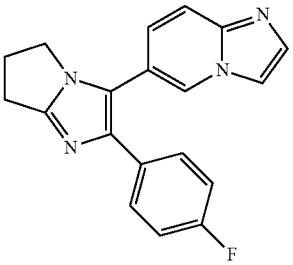 [SMILES: Fc1ccc(-c2nc3n(c2-c2ccc4nccn4c2)CCC3)cc1] | 6-(2-(4-fluorophenyl)-6,7-dihydro-5H-pyrrolo[1,2-a]imidazol-3-yl)imidazo[1,2-a]pyridine |
| 3 | 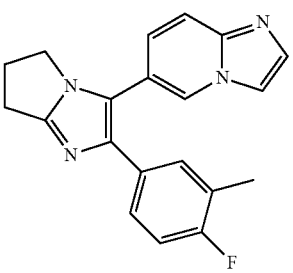 [SMILES: Cc1cc(-c2nc3n(c2-c2ccc4nccn4c2)CCC3)ccc1F] | 6-(2-(4-fluoro-3-methylphenyl)-6,7-dihydro-5H-pyrrolo[1,2-a]imidazol-3-yl)imidazo[1,2-a]pyridine |
| 4 | 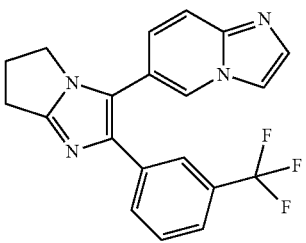 [SMILES: FC(F)(F)c1cccc(-c2nc3n(c2-c2ccc4nccn4c2)CCC3)c1] | 6-(2-(3-(trifluoromethyl)phenyl)-6,7-dihydro-5H-pyrrolo[1,2-a]imidazol-3-yl)imidazo[1,2-a]pyridine |
| 5 | 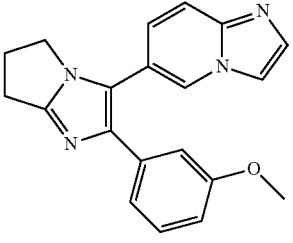 [SMILES: COc1cccc(-c2nc3n(c2-c2ccc4nccn4c2)CCC3)c1] | 6-(2-(3-methoxyphenyl)-6,7-dihydro-5H-pyrrolo[1,2-a]imidazol-3-yl)imidazo[1,2-a]pyridine |
| 6 | 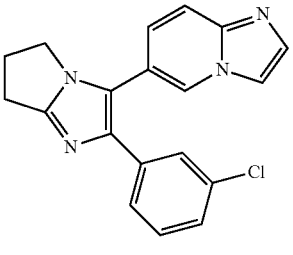 [SMILES: Clc1cccc(-c2nc3n(c2-c2ccc4nccn4c2)CCC3)c1] | 6-(2-(3-chlorophenyl)-6,7-dihydro-5H-pyrrolo[1,2-a]imidazol-3-yl)imidazo[1,2-a]pyridine |
| 7 | 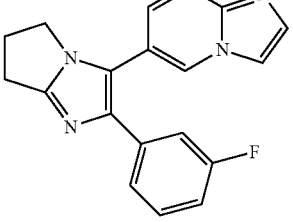 | 6-(2-(3-fluorophenyl)-6,7-dihydro-5H-pyrrolo[1,2-a]imidazol-3-yl)imidazo[1,2-a]pyridine |

| No. | Structure | Name |
|---|---|---|
| 8 | 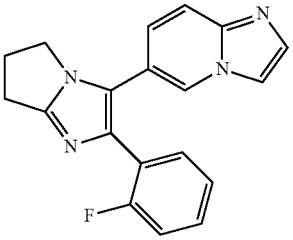 [SMILES: Fc1ccccc1-c1nc2n(c1-c1ccc3nccn3c1)CCC2] | 6-(2-(2-fluorophenyl)-6,7-dihydro-5H-pyrrolo[1,2-a]imidazol-3-yl)imidazo[1,2-a]pyridine |
| 9 | 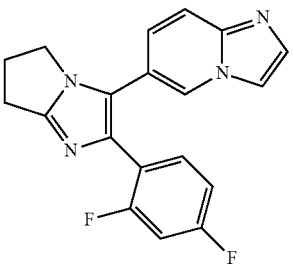 [SMILES: Fc1ccc(-c2nc3n(c2-c2ccc4nccn4c2)CCC3)c(F)c1] | 6-(2-(2,4-difluorophenyl)-6,7-dihydro-5H-pyrrolo[1,2-a]imidazol-3-yl)imidazo[1,2-a]pyridine |
| 10 | 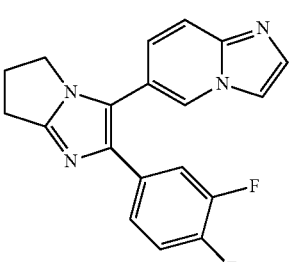 | 6-(2-(3,4-difluorophenyl)-6,7-dihydro-5H-pyrrolo[1,2-a]imidazol-3-yl)imidazo[1,2-a]pyridin |
| 11 | 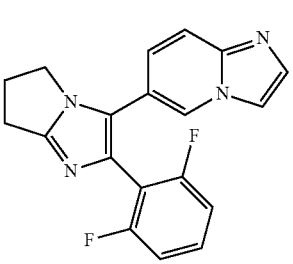 [SMILES: Fc1cccc(F)c1-c1nc2n(c1-c1ccc3nccn3c1)CCC2] | 6-(2-(2,6-difluorophenyl)-6,7-dihydro-5H-pyrrolo[1,2-a]imidazol-3-yl)imidazo[1,2-a]pyridine |
| 12 | 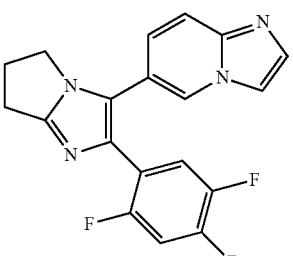 | 6-(2-(2,4,5-trifluorophenyl)-6,7-dihydro-5H-pyrrolo[1,2-a]imidazol-3-yl)imidazo[1,2-a]pyridine |
| 13 | 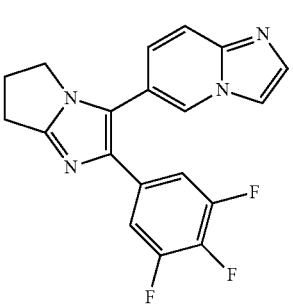 [SMILES: Fc1cc(-c2nc3n(c2-c2ccc4nccn4c2)CCC3)cc(F)c1F] | 6-(2-(3,4,5-trifluorophenyl)-6,7-dihydro-5H-pyrrolo[1,2-a]imidazol-3-yl)imidazo[1,2-a]pyridine |

| No. | Structure | Name |
|---|---|---|
| 14 | 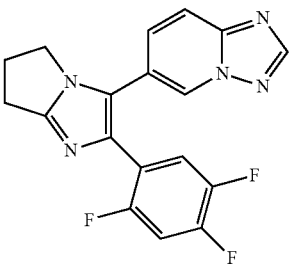 | 6-(2-(2,4,5-trrifluorophenyl)-6,7-dihydro-5H-pyrrolo[1,2-a]imidazol-3-yl)-[1,2,4]triazolo[1,5-a]pyridine |
| 15 | 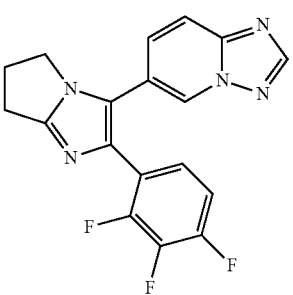 [SMILES: Fc1ccc(-c2nc3n(c2-c2ccc4ncnn4c2)CCC3)c(F)c1F] | 6-(2-(2,3,4-trifluorophenyl)-6,7-dihydro-5H-pyrrolo[1,2-a]imidazol-3-yl)-[1,2,4]triazolo[1,5-a]pyridine |
| 16 | 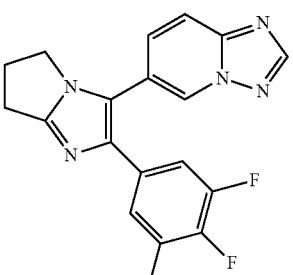 | 6-(2-(3,4,5-trifluorophenyl)-6,7-dihydro-5H-pyrrolo[1,2-a]imidazol-3-yl)-[1,2,4]triazolo[1,5-a]pyridine |
| 17 | 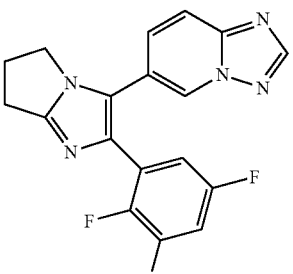 | 6-(2-(2,3,5-trifluorophenyl)-6,7-dihydro-5H-pyrrolo[1,2-a]imidazol-3-yl)-[1,2,4]triazolo[1,5-a]pyridine |
| 18 | 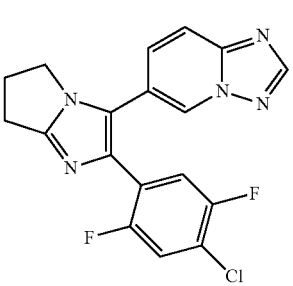 | 6-(2-(4-chloro-2,5-difluorophenyl)-6,7-dihydro-5H-pyrrolo[1,2-a]imidazol-3-yl)-[1,2,4]triazolo[1,5-a]pyridine |

-continued

| No. | Structure | Name |
|---|---|---|
| 19 | 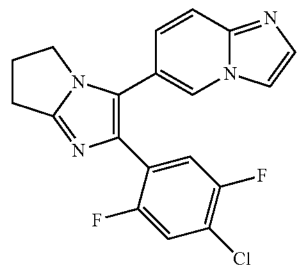 [SMILES: Fc1cc(-c2nc3n(c2-c2ccc4nccn4c2)CCC3)c(F)cc1Cl] | 6-(2-(4-chloro-2,5-difluorophenyl)-6,7-dihydro-5H-pyrrolo[1,2-a]imidazol-3-yl)imidazo[1,2-a]pyridine |
| 20 | 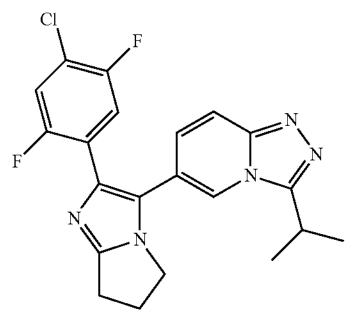 [SMILES: CC(C)c1nnc2ccc(-c3c(-c4cc(F)c(Cl)cc4F)nc4n3CCC4)cn12] | 6-(2-(4-chloro-2,5-difluorophenyl)-6,7-dihydro-5H-pyrrolo[1,2-a]imidazol-3-yl)-3-isopropyl-[1,2,4]triazolo[4,3-a]pyridine |
| 21 | 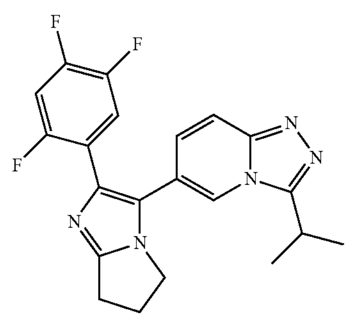 [SMILES: CC(C)c1nnc2ccc(-c3c(-c4cc(F)c(F)cc4F)nc4n3CCC4)cn12] | 3-isopropyl-6-(2-(2,4,5-trifluorophenyl)-6,7-dihydro-5H-pyrrolo[1,2-a]imidazol-3-yl)-[1,2,4]triazolo[4,3-a]pyridine |
| 22 | 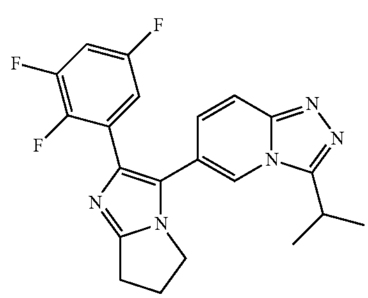 [SMILES: CC(C)c1nnc2ccc(-c3c(-c4cc(F)cc(F)c4F)nc4n3CCC4)cn12] | 3-isopropyl-6-(2-(2,3,5-trifluorophenyl)-6,7-dihydro-5H-pyrrolo[1,2-a]imidazol-3-yl)-[1,2,4]triazolo[4,3-a]pyridine |
| 23 | 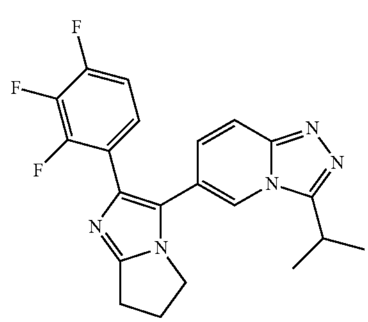 [SMILES: CC(C)c1nnc2ccc(-c3c(-c4ccc(F)c(F)c4F)nc4n3CCC4)cn12] | 3-isopropyl-6-(2-(2,3,4-trifluorophenyl)-6,7-dihydro-5H-pyrrolo[1,2-a]imidazol-3-yl)-[1,2,4]triazolo[4,3-a]pyridine |

| No. | Structure | Name |
|---|---|---|
| 24 | 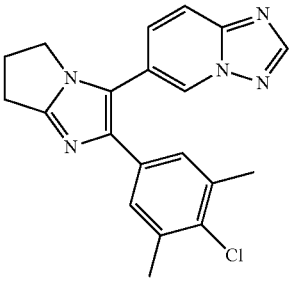 [SMILES: Cc1cc(-c2nc3n(c2-c2ccc4ncnn4c2)CCC3)cc(C)c1Cl] | 6-(2-(4-chloro-3,5-dimethylphenyl)-6,7-dihydro-5H-pyrrolo[1,2-a]imidazol-3-yl)-[1,2,4]triazolo[1,5-a]pyridine |
| 25 | 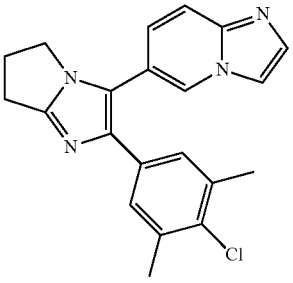 [SMILES: Cc1cc(-c2nc3n(c2-c2ccc4nccn4c2)CCC3)cc(C)c1Cl] | 6-(2-(4-chloro-3,5-dimethylphenyl)-6,7-dihydro-5H-pyrrolo[1,2-a]imidazol-3-yl)imidazo[1,2-a]pyridine |
| 26 | 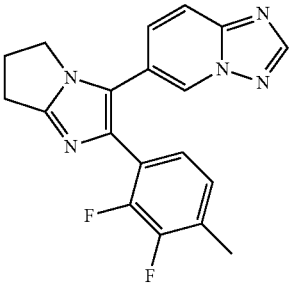 [SMILES: Cc1ccc(-c2nc3n(c2-c2ccc4ncnn4c2)CCC3)c(F)c1F] | 6-(2-(2,3-difluoro-4-methylphenyl)-6,7-dihydro-5H-pyrrolo[1,2-a]imidazol-3-yl)-[1,2,4]triazolo[1,5-a]pyridine |
| 27 | 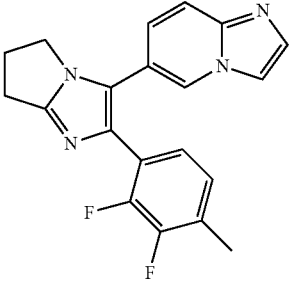 [SMILES: Cc1ccc(-c2nc3n(c2-c2ccc4nccn4c2)CCC3)c(F)c1F] | 6-(2-(2,3-difluoro-4-methylphenyl)-6,7-dihydro-5H-pyrrolo[1,2-a]imidazol-3-yl)imidazo[1,2-a]pyridine |
| 28 | 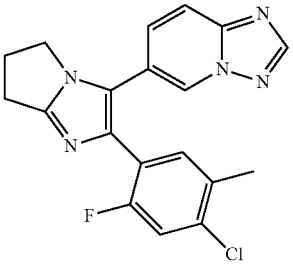 [SMILES: Cc1cc(-c2nc3n(c2-c2ccc4ncnn4c2)CCC3)c(F)cc1Cl] | 6-(2-(4-chloro-2-fluoro-5-methylphenyl)-6,7-dihydro-5H-pyrrolo[1,2-a]imidazol-3-yl)-[1,2,4]triazolo[1,5-a]pyridine |

| No. | Structure | Name |
|---|---|---|
| 29 | 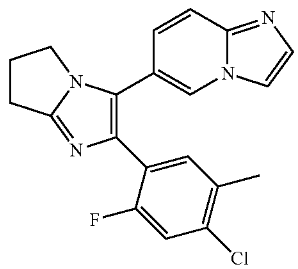 [SMILES: Cc1cc(-c2nc3n(c2-c2ccc4nccn4c2)CCC3)c(F)cc1Cl] | 6-(2-(4-chloro-2-fluoro-5-methylphenyl)-6,7-dihydro-5H-pyrrolo[1,2-a]imidazol-3-yl)imidazo[1,2-a]pyridine |
| 30 | 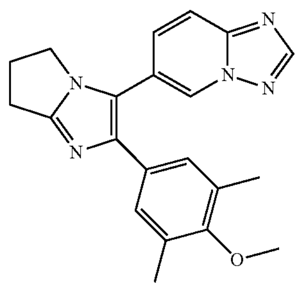 [SMILES: COc1c(C)cc(-c2nc3n(c2-c2ccc4ncnn4c2)CCC3)cc1C] | 6-(2-(4-methoxy-3,5-dimethylphenyl)-6,7-dihydro-5H-pyrrolo[1,2-a]imidazol-3-yl)-[1,2,4]triazolo[1,5-a]pyridine |
| 31 | 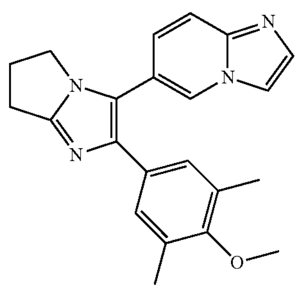 [SMILES: COc1c(C)cc(-c2nc3n(c2-c2ccc4nccn4c2)CCC3)cc1C] | 6-(2-(4-methoxy-3,5-dimethylphenyl)-6,7-dihydro-5H-pyrrolo[1,2-a]imidazol-3-yl)imidazo[1,2-a]pyridine |
| 32 | 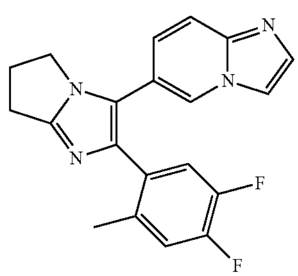 [SMILES: Cc1cc(F)c(F)cc1-c1nc2n(c1-c1ccc3nccn3c1)CCC2] | 6-(2-(4,5-difluoro-2-methylphenyl)-6,7-dihydro-5H-pyrrolo[1,2-a]imidazol-3-yl)imidazo[1,2-a]pyridine |
| 33 | 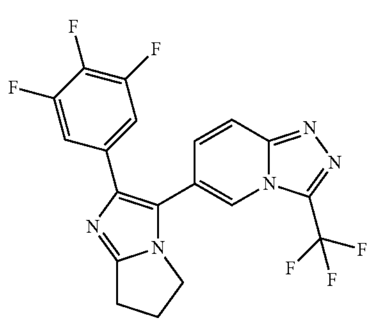 [SMILES: Fc1cc(-c2nc3n(c2-c2ccc4nnc(C(F)(F)F)n4c2)CCC3)cc(F)c1F] | 3-(trifluoromethyl)-6-(2-(3,4,5-trifluorophenyl)-6,7-dihydro-5H-pyrrolo[1,2-a]imidazol-3-yl)-[1,2,4]triazolo[4,3-a]pyridine |

-continued

| No. | Structure | Name |
|---|---|---|
| 34 | 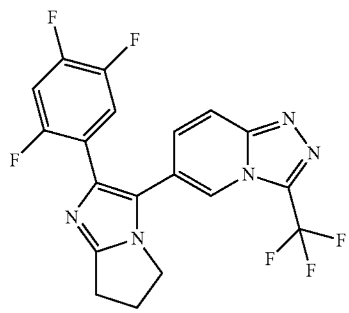 [SMILES: Fc1cc(F)c(-c2nc3n(c2-c2ccc4nnc(C(F)(F)F)n4c2)CCC3)cc1F] | 3-(trifluoromethyl)-6-(2-(2,4,5-trifluorophenyl)-6,7-dihydro-5H-pyrrolo[1,2-a]imidazol-3-yl)-[1,2,4]triazolo[4,3-a]pyridine |
| 35 | 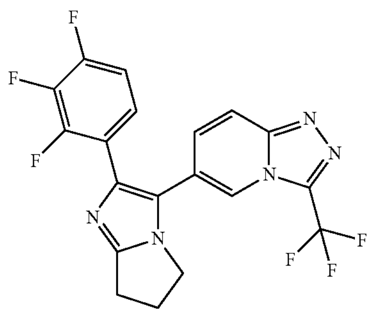 [SMILES: Fc1ccc(-c2nc3n(c2-c2ccc4nnc(C(F)(F)F)n4c2)CCC3)c(F)c1F] | 3-(trifluoromethyl)-6-(2-(2,3,4-trifluorophenyl)-6,7-dihydro-5H-pyrrolo[1,2-a]imidazol-3-yl)-[1,2,4]triaolo[4,3-a]pyridine |
| 36 | 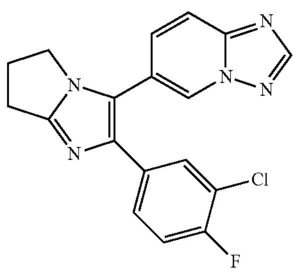 [SMILES: Fc1ccc(-c2nc3n(c2-c2ccc4ncnn4c2)CCC3)cc1Cl] | 6-(2-(3-chloro-4-fluorophenyl)-6,7-dihydro-5H-pyrrolo[1,2-a]imidazol-3-yl)-[1,2,4]triazolo[1,5-a]pyridine |
| 37 | 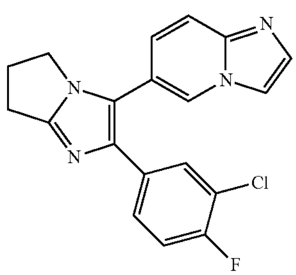 [SMILES: Fc1ccc(-c2nc3n(c2-c2ccc4nccn4c2)CCC3)cc1Cl] | 6-(2-(3-chloro-4-fluorophenyl)-6,7-dihydro-5H-pyrrolo[1,2-a]imidazol-3-yl)imidazo[1,2-a]pyridine |
| 38 | 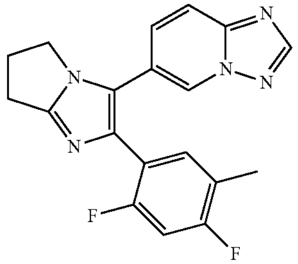 [SMILES: Cc1cc(-c2nc3n(c2-c2ccc4ncnn4c2)CCC3)c(F)cc1F] | 6-(2-(2,4-difluoro-5-methylphenyl)-6,7-dihydro-5H-pyrrolo[1,2-a]imidazol-3-yl)-[1,2,4]triazolo[1,5-a]pyridine |

| No. | Structure | Name |
| --- | --- | --- |
| 39 | 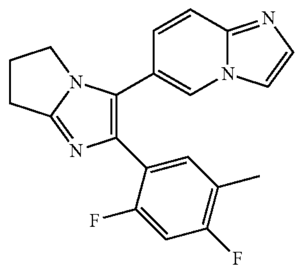 [SMILES: Cc1cc(-c2nc3n(c2-c2ccc4nccn4c2)CCC3)c(F)cc1F] | 6-(2-(2,4-difluoro-5-methylphenyl)-6,7-dihydro-5H-pyrrolo[1,2-a]imidazol-3-yl)imidazo[1,2-a]pyridine |
| 40 | 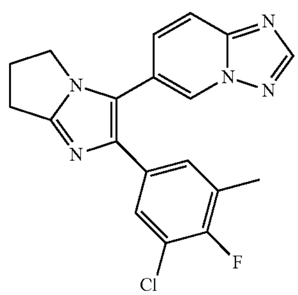 [SMILES: Cc1cc(-c2nc3n(c2-c2ccc4ncnn4c2)CCC3)cc(Cl)c1F] | 6-(2-(3-chloro-4-fluoro-5-methylphenyl)-6,7-dihydro-5H-pyrrolo[1,2-a]imidazol-3-yl)-[1,2,4]triazolo[1,5-a]pyridine |
| 41 | 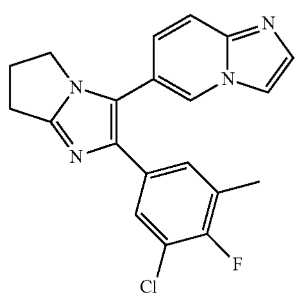 [SMILES: Cc1cc(-c2nc3n(c2-c2ccc4nccn4c2)CCC3)cc(Cl)c1F] | 6-(2-(3-chloro-4-fluoro-5-methylphenyl)-6,7-dihydro-5H-pyrrolo[1,2-a]imidazol-3-yl)imidazo[1,2-a]pyridine |
| 42 | 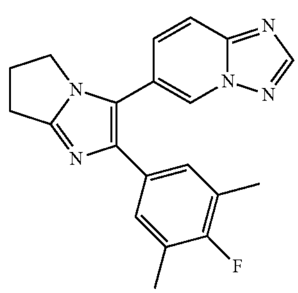 [SMILES: Cc1cc(-c2nc3n(c2-c2ccc4ncnn4c2)CCC3)cc(C)c1F] | 6-(2-(4-fluoro-3,5-dimethylphenyl)-6,7-dihydro-5H-pyrrolo[1,2-a]imidazol-3-yl)-[1,2,4]triazolo[1,5-a]pyridine |
| 43 | 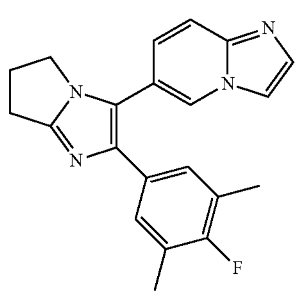 [SMILES: Cc1cc(-c2nc3n(c2-c2ccc4nccn4c2)CCC3)cc(C)c1F] | 6-(2-(4-fluoro-3,5-dimethylphenyl)-6,7-dihydro-5H-pyrrolo[1,2-a]imidazol-3-yl)imidazo[1,2-a]pyridine |

-continued

| No. | Structure | Name |
| --- | --- | --- |
| 44 | 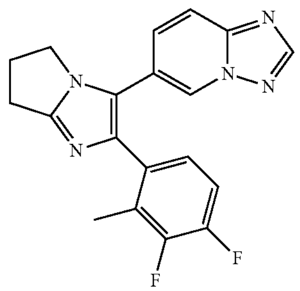 [SMILES: Cc1c(-c2nc3n(c2-c2ccc4ncnn4c2)CCC3)ccc(F)c1F] | 6-(2-(3,4-difluoro-2-methylphenyl)-6,7-dihydro-5H-pyrrolo[1,2-a]imidazol-3-yl)-[1,2,4]triazolo[1,5-a]pyridine |
| 45 | 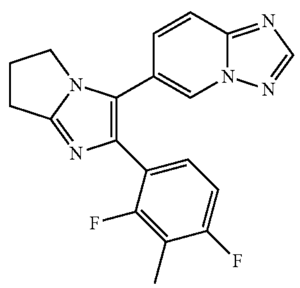 [SMILES: Cc1c(F)ccc(-c2nc3n(c2-c2ccc4ncnn4c2)CCC3)c1F] | 6-(2-(2,4-difluoro-3-methylphenyl)-6,7-dihydro-5H-pyrrolo[1,2-a]imidazol-3-yl)-[1,2,4]triazolo[1,5-a]pyridine |
| 46 | 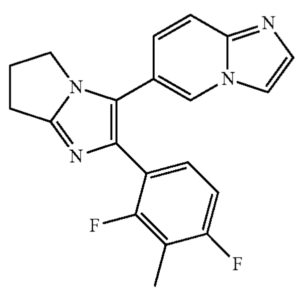 [SMILES: Cc1c(F)ccc(-c2nc3n(c2-c2ccc4nccn4c2)CCC3)c1F] | 6-(2-(2,4-difluoro-3-methylphenyl)-6,7-dihydro-5H-pyrrolo[1,2-a]imidazol-3-yl)imidazo[1,2-a]pyridine |
| 47 | 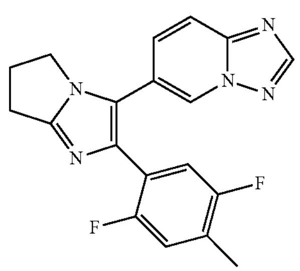 [SMILES: Cc1cc(F)c(-c2nc3n(c2-c2ccc4ncnn4c2)CCC3)cc1F] | 6-(2-(2,5-difluoro-4-methylphenyl)-6,7-dihydro-5H-pyrrolo[1,2-a]imidazol-3-yl)-[1,2,4]triazolo[1,5-a]pyridine |
| 48 | 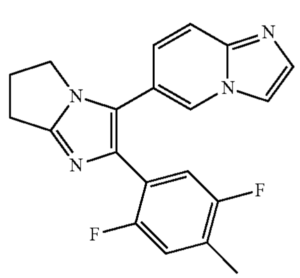 [SMILES: Cc1cc(F)c(-c2nc3n(c2-c2ccc4nccn4c2)CCC3)cc1F] | 6-(2-(2,5-difluoro-4-methylphenyl)-6,7-dihydro-5H-pyrrolo[1,2-a]imidazol-3-yl)imidazo[1,2-a]pyridine |

-continued

| No. | Structure | Name |
|---|---|---|
| 49 | 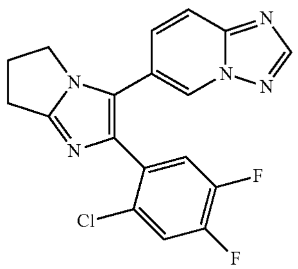 [SMILES: Fc1cc(Cl)c(-c2nc3n(c2-c2ccc4ncnn4c2)CCC3)cc1F] | 6-(2-(2-chloro-4,5-difluorophenyl)-6,7-dihydro-5H-pyrrolo[1,2-a]imidazol-3-yl)-[1,2,4]triazolo[1,5-a]pyridine |
| 50 | 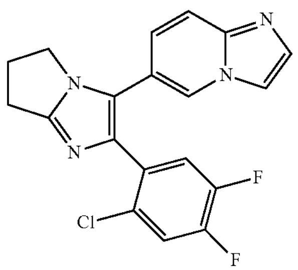 [SMILES: Fc1cc(Cl)c(-c2nc3n(c2-c2ccc4nccn4c2)CCC3)cc1F] | 6-(2-(2-chloro-4,5-difluorophenyl)-6,7-dihydro-5H-pyrrolo[1,2-a]imidazol-3-yl)imidazo[1,2-a]pyridine |
| 51 | 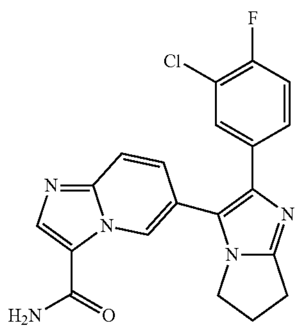 [SMILES: NC(=O)c1cnc2ccc(-c3c(-c4ccc(F)c(Cl)c4)nc4n3CCC4)cn12] | 6-(2-(3-chloro-4-fluorophenyl)-6,7-dihydro-5H-pyrrolo[1,2-a]imidazol-3-yl)imidazo[1,2-a]pyridine-3-carboxamide |
| 52 | 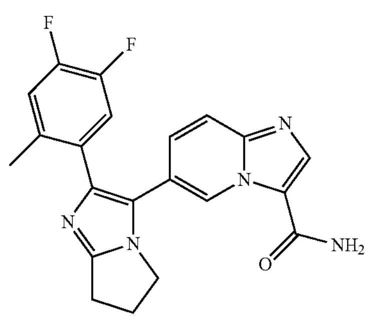 [SMILES: Cc1cc(F)c(F)cc1-c1nc2n(c1-c1ccc3ncc(C(N)=O)n3c1)CCC2] | 6-(2-(4,5-difluoro-2-methylphenyl)-6,7-dihydro-5H-pyrrolo[1,2-a]imidazol-3-yl)imidazo[1,2-a]pyridine-3-carboxamide |
| 53 | 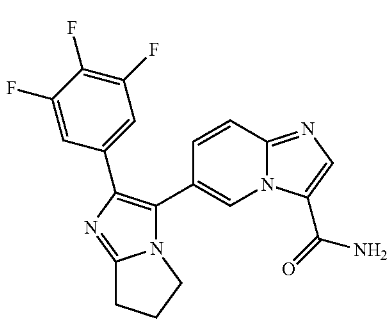 [SMILES: NC(=O)c1cnc2ccc(-c3c(-c4cc(F)c(F)c(F)c4)nc4n3CCC4)cn12] | 6-(2-(3,4,5-trifluorophenyl)-6,7-dihydro-5H-pyrrolo[1,2-a]imidazol-3-yl)imidazo[1,2-a]pyridine-3-carboxamide |

| No. | Structure | Name |
|---|---|---|
| 54 | 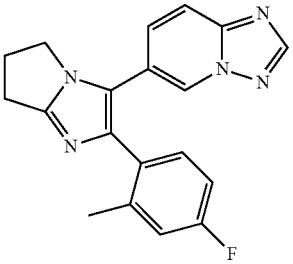 [SMILES: Cc1cc(F)ccc1-c1nc2n(c1-c1ccc3ncnn3c1)CCC2] | 6-(2-(4-fluoro-2-methylphenyl)-6,7-dihydro-5H-pyrrolo[1,2-a]imidazol-3-yl)-[1,2,4]triazolo[1,5-a]pyridine |
| 55 | 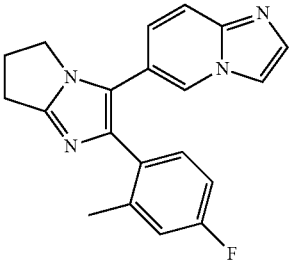 [SMILES: Cc1cc(F)ccc1-c1nc2n(c1-c1ccc3nccn3c1)CCC2] | 6-(2-(4-fluoro-2-methylphenyl)-6,7-dihydro-5H-pyrrolo[1,2-a]imidazol-3-yl)imidazo[1,2-a]pyridine |
| 56 | 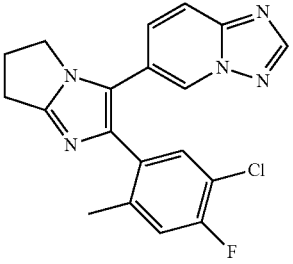 [SMILES: Cc1cc(F)c(Cl)cc1-c1nc2n(c1-c1ccc3ncnn3c1)CCC2] | 6-(2-(5-chloro-4-fluoro-2-methylphenyl)-6,7-dihydro-5H-pyrrolo[1,2-a]imidazol-3-yl)-[1,2,4]triazolo[1,5-a]pyridine |
| 57 | 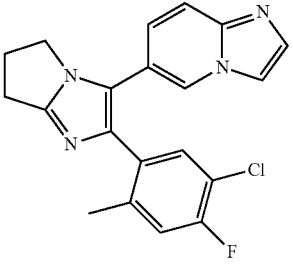 [SMILES: Cc1cc(F)c(Cl)cc1-c1nc2n(c1-c1ccc3nccn3c1)CCC2] | 6-(2-(5-chloro-4-fluoro-2-methylphenyl)-6,7-dihydro-5H-pyrrolo[1,2-a]imidazol-3-yl)imidazo[1,2-a]pyridine |
| 58 | 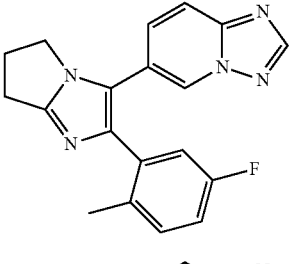 | 6-(2-(5-fluoro-2-methylphenyl)-6,7-dihydro-5H-pyrrolo[1,2-a]imidazol-3-yl)-[1,2,4]triazolo[1,5-a]pyridine |
| 59 | 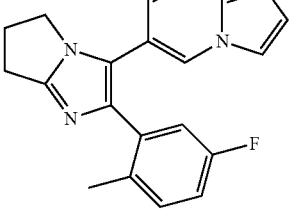 | 6-(2-(5-fluoro-2-methylphenyl)-6,7-dihydro-5H-pyrrolo[1,2-a]imidazol-3-yl)imidazo[1,2-a]pyridine |

| No. | Structure | Name |
|---|---|---|
| 61 | 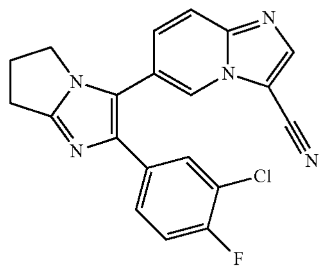 [SMILES: N#Cc1cnc2ccc(-c3c(-c4ccc(F)c(Cl)c4)nc4n3CCC4)cn12] | 6-(2-(3-chloro-4-fluorophenyl)-6,7-dihydro-5H-pyrrolo[1,2-a]imidazol-3-yl)imidazo[1,2-a]pyridine-3-carbonitrile |
| 62 | 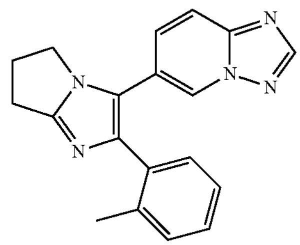 [SMILES: Cc1ccccc1-c1nc2n(c1-c1ccc3ncnn3c1)CCC2] | 6-(2-(2-methylphenyl)-6,7-dihydro-5H-pyrrolo[1,2-a]imidazol-3-yl)-[1,2,4]triazolo[1,5-a]pyridine |
| 63 | 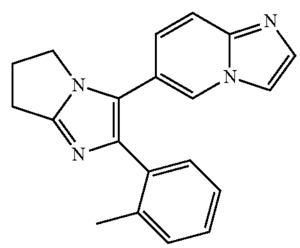 [SMILES: Cc1ccccc1-c1nc2n(c1-c1ccc3nccn3c1)CCC2] | 6-(2-(2-methylphenyl)-6,7-dihydro-5H-pyrrolo[1,2-a]imidazol-3-yl)imidazo[1,2-a]pyridine |
| 64 | 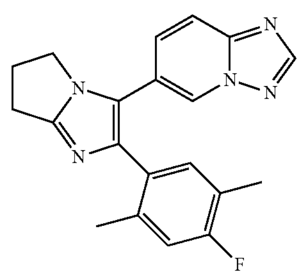 [SMILES: Cc1cc(-c2nc3n(c2-c2ccc4ncnn4c2)CCC3)c(C)cc1F] | 6-(2-(4-fluoro-2,5-dimethylphenyl)-6,7-dihydro-5H-pyrrolo[1,2-a]imidazol-3-yl)-[1,2,4]triazolo[1,5-a]pyridine |
| 65 | 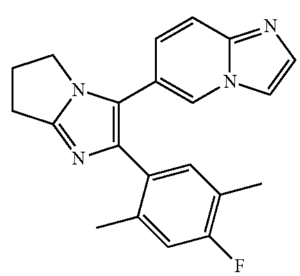 [SMILES: Cc1cc(-c2nc3n(c2-c2ccc4nccn4c2)CCC3)c(C)cc1F] | 6-(2-(4-fluoro-2,5-dimethylphenyl)-6,7-dihydro-5H-pyrrolo[1,2-a]imidazol-3-yl)imidazo[1,2-a]pyridine |
| 66 | 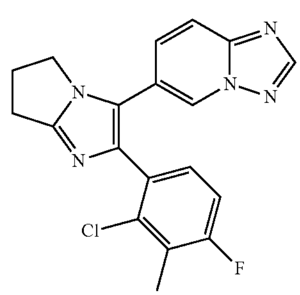 [SMILES: Cc1c(F)ccc(-c2nc3n(c2-c2ccc4ncnn4c2)CCC3)c1Cl] | 6-(2-(2-chloro-4-fluoro-3-methylphenyl)-6,7-dihydro-5H-pyrrolo[1,2-a]imidazol-3-yl)-[1,2,4]triazolo[1,5-a]pyridine |

| No. | Structure | Name |
|---|---|---|
| 67 | 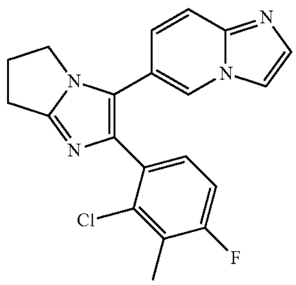 [SMILES: Cc1c(F)ccc(-c2nc3n(c2-c2ccc4nccn4c2)CCC3)c1Cl] | 6-(2-(2-chloro-4-fluoro-3-methylphenyl)-6,7-dihydro-5H-pyrrolo[1,2-a]imidazol-3-yl)imidazo[1,2-a]pyridine |
| 68 | 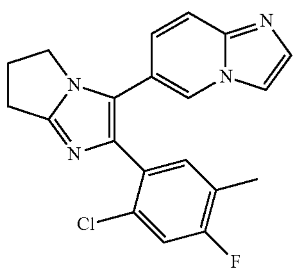 [SMILES: Cc1cc(-c2nc3n(c2-c2ccc4nccn4c2)CCC3)c(Cl)cc1F] | 6-(2-(2-chloro-4-fluoro-5-methylphenyl)-6,7-dihydro-5H-pyrrolo[1,2-a]imidazol-3-yl)imidazo[1,2-a]pyridine |
| 69 | 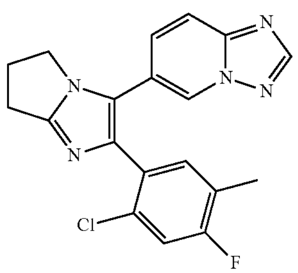 [SMILES: Cc1cc(-c2nc3n(c2-c2ccc4ncnn4c2)CCC3)c(Cl)cc1F] | 6-(2-(2-chloro-4-fluoro-5-methylphenyl)-6,7-dihydro-5H-pyrrolo[1,2-a]imidazol-3-yl)-[1,2,4]triazolo[1,5-a]pyridine |
| 70 | 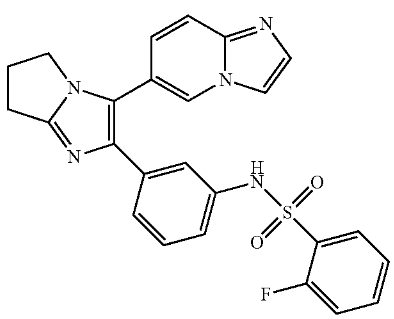 [SMILES: O=S(=O)(Nc1cccc(-c2nc3n(c2-c2ccc4nccn4c2)CCC3)c1)c1ccccc1F] | 2-fluoro-N-(3-(3-(imidazo[1,2-a]pyridin-6-yl)-6,7-dihydro-5H-pyrrolo[1,2-a]imidazol-2-yl)phenyl)benzenesulfonamide |
| 71 | 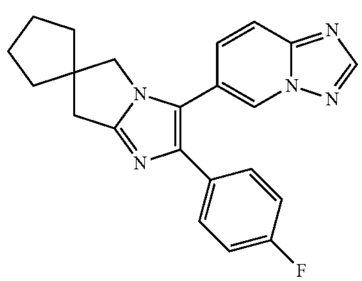 [SMILES: Fc1ccc(-c2nc3n(c2-c2ccc4ncnn4c2)CC2(CCCC2)C3)cc1] | 3'-([1,2,4]triazolo[1,5-a]pyridin-6-yl)-2'-(4-fluorophenyl)-5'H,7'H-spiro[cyclopentane-1,6'-pyrrolo[1,2-a]imidazole] |

-continued

| No. | Structure | Name |
|---|---|---|
| 72 | 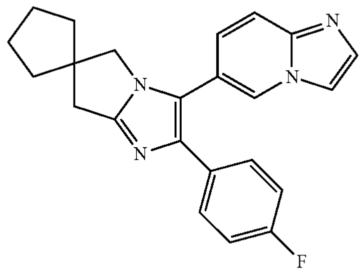 [SMILES: Fc1ccc(-c2nc3n(c2-c2ccc4nccn4c2)CC2(CCCC2)C3)cc1] | 2'-(4-fluorophenyl)-3'-(imidazo[1,2-a]pyridin-6-yl)-5'H,7'H-spiro[cyclopentane-1,6'-pyrrolo[1,2-a]imidazole] |
| 73 | 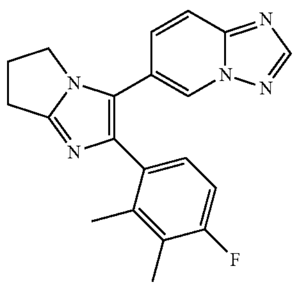 [SMILES: Cc1c(F)ccc(-c2nc3n(c2-c2ccc4ncnn4c2)CCC3)c1C] | 6-(2-(4-fluoro-2,3-dimethylphenyl)-6,7-dihydro-5H-pyrrolo[1,2-a]imidazol-3-yl)-[1,2,4]triazolo[1,5-a]pyridine |
| 74 | 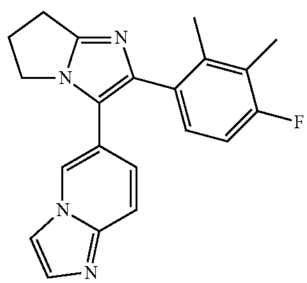 [SMILES: Cc1c(F)ccc(-c2nc3n(c2-c2ccc4nccn4c2)CCC3)c1C] | 6-(2-(4-fluoro-2,3-dimethylphenyl)-6,7-dihydro-5H-pyrrolo[1,2-a]imidazol-3-yl)imidazo[1,2-a]pyridine |
| 75 | 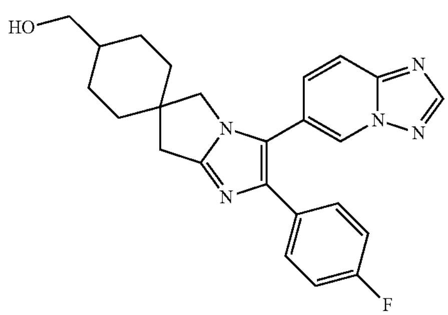 [SMILES: OCC1CCC2(CC1)Cc1nc(-c3ccc(F)cc3)c(-c3ccc4ncnn4c3)n1C2] | (3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)methanol |
| 76 | 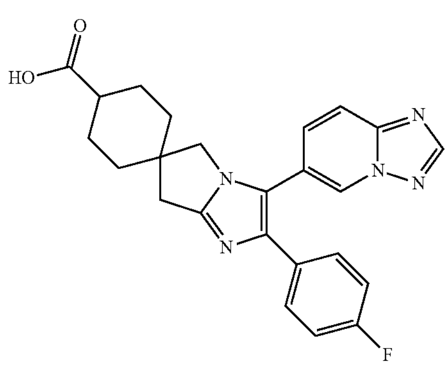 [SMILES: O=C(O)C1CCC2(CC1)Cc1nc(-c3ccc(F)cc3)c(-c3ccc4ncnn4c3)n1C2] | 3'-([1,2,4]triazolo[1,5-a]pyridin-6-yl)-2'-(4-fluorophenyl)-5'H,7'H-spiro[cyclohexane-1,6'-pyrrolo[1,2-a]imidazole]-4-carboxylic acid |

| No. | Structure | Name |
|---|---|---|
| 77 | 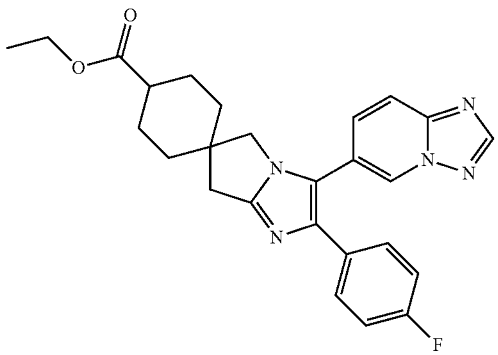 [SMILES: CCOC(=O)C1CCC2(CC1)Cc1nc(-c3ccc(F)cc3)c(-c3ccc4ncnn4c3)n1C2] | ethyl 3'-([1,2,4]triazolo[1,5-a]pyridin-6-yl)-2'-(4-fluorophenyl)-5'H,7'H-spiro[cyclohexane-1,6'-pyrrolo[1,2-a]imidazole]-4-carboxylate |
| 78 | 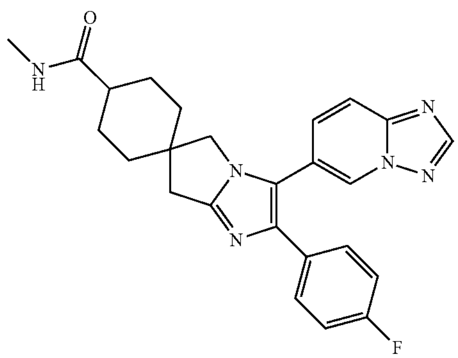 [SMILES: CNC(=O)C1CCC2(CC1)Cc1nc(-c3ccc(F)cc3)c(-c3ccc4ncnn4c3)n1C2] | 3'-([1,2,4]triazolo[1,5-a]pyridin-6-yl)-2'-(4-fluorophenyl)-N-methyl-5'H,7'H-spiro[cyclohexane-1,6'-pyrrolo[1,2-a]imidazole]-4-carboxamide |
| 79 | 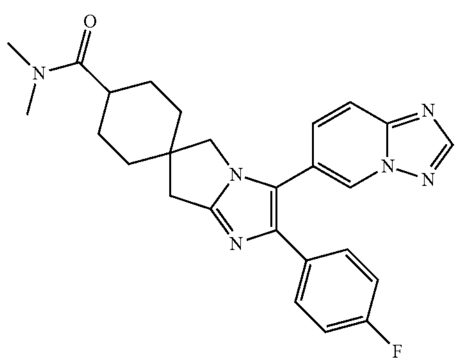 [SMILES: CN(C)C(=O)C1CCC2(CC1)Cc1nc(-c3ccc(F)cc3)c(-c3ccc4ncnn4c3)n1C2] | 3'-([1,2,4]triazolo[1,5-a]pyridin-6-yl)-2'-(4-fluorophenyl)-N,N-dimethyl-5'H,7'H-spiro[cyclohexane-1,6'-pyrrolo[1,2-a]imidazole]-4-carboxamide |
| 80 | 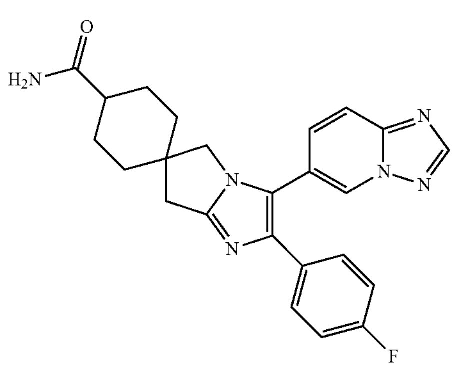 [SMILES: NC(=O)C1CCC2(CC1)Cc1nc(-c3ccc(F)cc3)c(-c3ccc4ncnn4c3)n1C2] | 3'-([1,2,4]triazolo[1,5-a]pyridin-6-yl)-2'-(4-fluorophenyl)-5'H,7'H-spiro[cyclohexane-1,6'-pyrrolo[1,2-a]imidazole]-4-carboxamide |

| No. | Structure | Name |
|---|---|---|
| 81 | 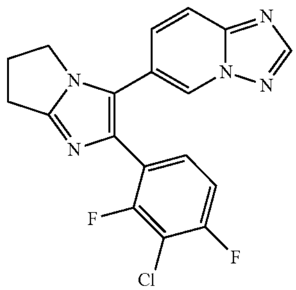 [SMILES: Fc1ccc(-c2nc3n(c2-c2ccc4ncnn4c2)CCC3)c(F)c1Cl] | 6-(2-(3-chloro-2,4-difluorophenyl)-6,7-dihydro-5H-pyrrolo[1,2-a]imidazol-3-yl)-[1,2,4]triazolo[1,5-a]pyridine |
| 82 | 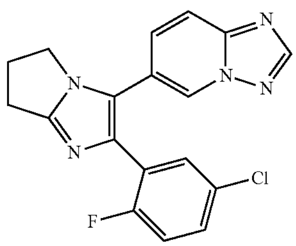 [SMILES: Fc1ccc(Cl)cc1-c1nc2n(c1-c1ccc3ncnn3c1)CCC2] | 6-(2-(5-chloro-2-fluoro)-6,7-dihydro-5H-pyrrolo[1,2-a]imidazol-3-yl)-[1,2,4]triazolo[1,5-a]pyridine |
| 83 | 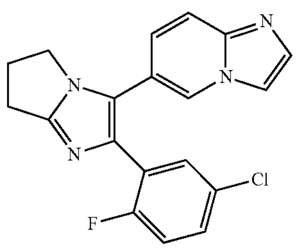 [SMILES: Fc1ccc(Cl)cc1-c1nc2n(c1-c1ccc3nccn3c1)CCC2] | 6-(2-(5-chloro-2-fluoro)-6,7-dihydro-5H-pyrrolo[1,2-a]imidazol-3-yl)imidazo[1,2-a[pyridine |
| 84 | 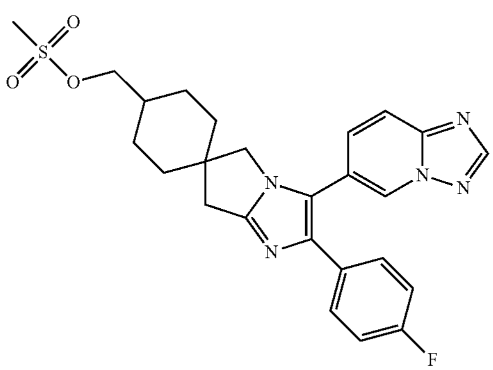 [SMILES: CS(=O)(=O)OCC1CCC2(CC1)Cc1nc(-c3ccc(F)cc3)c(-c3ccc4ncnn4c3)n1C2] | (3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)methyl methanesulfonate |
| 85 | 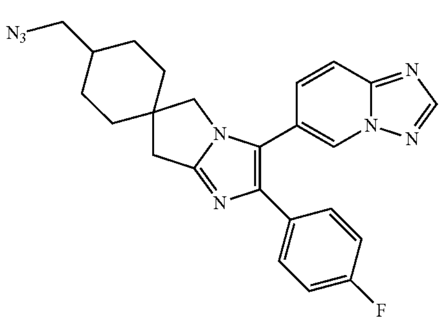 [SMILES: [N-]=[N+]=NCC1CCC2(CC1)Cc1nc(-c3ccc(F)cc3)c(-c3ccc4ncnn4c3)n1C2] | 3'-([1,2,4]triazolo[1,5-a]pyridin-6-yl)-4-(azidomethyl)-2'-(4-fluorophenyl)-5'H,7'H-spiro[cyclohexane-1,6'-pyrrolo[1,2-a]imidazole] |

-continued

| No. | Structure | Name |
|---|---|---|
| 86 | 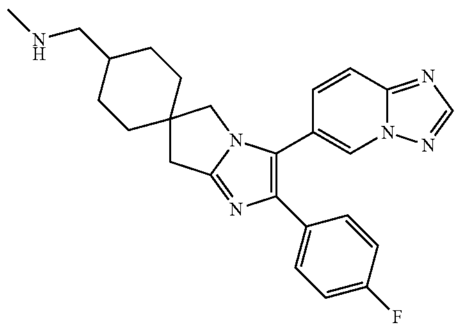 [SMILES: CNCC1CCC2(CC1)Cc1nc(-c3ccc(F)cc3)c(-c3ccc4ncnn4c3)n1C2] | 1-(3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)-N-methylmethanamine |
| 87 | 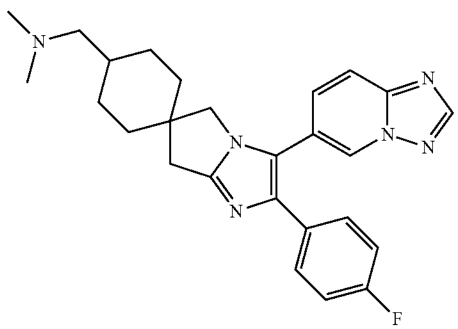 [SMILES: CN(C)CC1CCC2(CC1)Cc1nc(-c3ccc(F)cc3)c(-c3ccc4ncnn4c3)n1C2] | 1-(3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)-N,N-dimethylmethanamine |
| 88 | 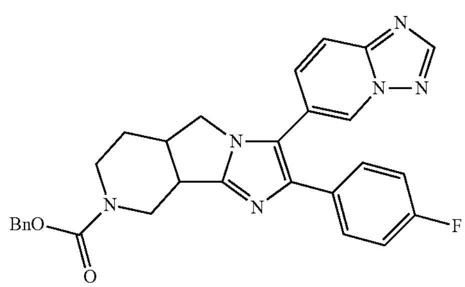 [SMILES: O=C(OCc1ccccc1)N1CCC2Cn3c(nc(-c4ccc(F)cc4)c3-c3ccc4ncnn4c3)C2C1] | benzyl 3-([1,2,4]triazolo[1,5-a]pyridin-6-yl)-2-(4-fluorophenyl)-5,5a,6,7,9,9a-hexahydro-8H-imidazo[1',2':1,2]pyrrolo[3,4-c]pyridine-8-carboxylate |
| 89 | 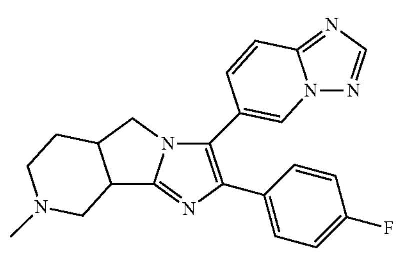 [SMILES: CN1CCC2Cn3c(nc(-c4ccc(F)cc4)c3-c3ccc4ncnn4c3)C2C1] | 3-([1,2,4]triazolo[1,5-a]pyridin-6-yl)-2-(4-fluorophenyl)-8-methyl-5a,6,7,8,9,9a-hexahydro-5H-imidazo[1',2':1,2]pyrrolo[3,4-c]pyridine |
| 90 | 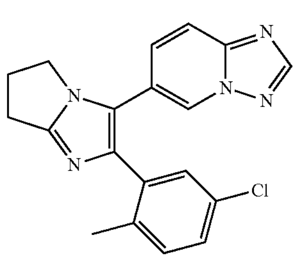 [SMILES: Cc1ccc(Cl)cc1-c1nc2n(c1-c1ccc3ncnn3c1)CCC2] | 6-(2-(5-chloro-2-methyl)-6,7-dihydro-5H-pyrrolo[1,2-a]imidazol-3-yl)-[1,2,4]triaolo[1,5-a]pyridine |

| No. | Structure | Name |
|---|---|---|
| 91 | 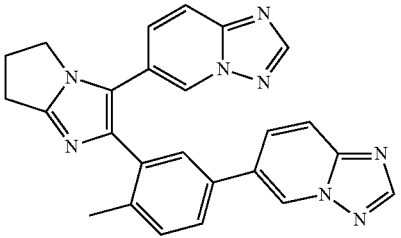 [SMILES: Cc1ccc(-c2ccc3ncnn3c2)cc1-c1nc2n(c1-c1ccc3ncnn3c1)CCC2] | 6-(2-(5-([1,2,4]triazolo[1,5-a]pyridin-6-yl)-2-methylphenyl)-6,7-dihydro-5H-pyrrolo[1,2-a]imidazol-3-yl)-[1,2,4]triazolo[1,5-a]pyridine |
| 92 | 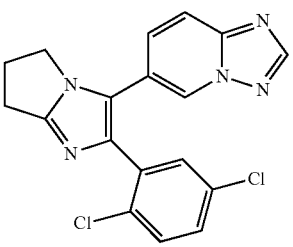 [SMILES: Clc1ccc(Cl)c(-c2nc3n(c2-c2ccc4ncnn4c2)CCC3)c1] | 6-(2-(2,5-dichlorophenyl)-6,7-dihydro-5H-pyrrolo[1,2-a]imidazol-3-yl)-[1,2,4]triazolo[1,5-a]pyridine |
| 93 | 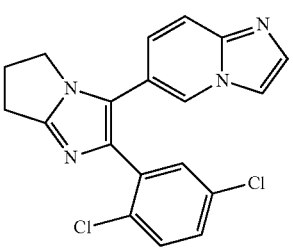 [SMILES: Clc1ccc(Cl)c(-c2nc3n(c2-c2ccc4nccn4c2)CCC3)c1] | 6-(2-(2,5-dichlorophenyl)-6,7-dihydro-5H-pyrrolo[1,2-a]imidazol-3-yl)imidazo[1,2-a]pyridine |
| 94 | 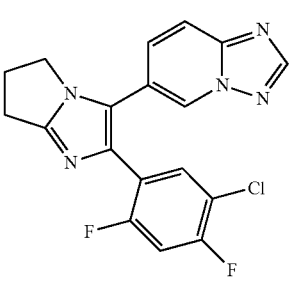 [SMILES: Fc1cc(F)c(-c2nc3n(c2-c2ccc4ncnn4c2)CCC3)cc1Cl] | 6-(2-(5-chloro-2,4-difluoro)-6,7-dihydro-5H-pyrrolo[1,2-a]imidazol-3-yl)-[1,2,4]triazolo[1,5-a]pyridine |
| 95 | 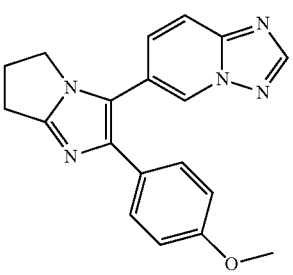 [SMILES: COc1ccc(-c2nc3n(c2-c2ccc4ncnn4c2)CCC3)cc1] | 6-(2-(4-methoxyphenyl)-6,7-dihydro-5H-pyrrolo[1,2-a]imidazol-3-yl)-[1,2,4]triazolo[1,5-a]pyridine |
| 96 | 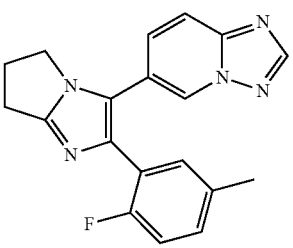 [SMILES: Cc1ccc(F)c(-c2nc3n(c2-c2ccc4ncnn4c2)CCC3)c1] | 6-(2-(2-fluoro-5-methylphenyl)-6,7-dihydro-5H-pyrrolo[1,2-a]imidazol-3-yl)-[1,2,4]triazolo[1,5-a]pyridine |

-continued

| No. | Structure | Name |
|---|---|---|
| 98 | 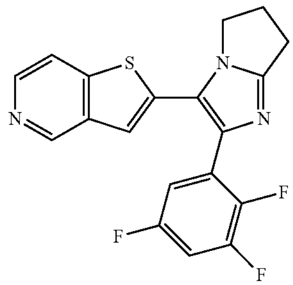 [SMILES: Fc1cc(F)c(F)c(-c2nc3n(c2-c2cc4cnccc4s2)CCC3)c1] | 2-(2-(2,3,5-trifluorophenyl)-6,7-dihydro-5H-pyrrolo[1,2-a]imidazol-3-yl)thieno[3,2-c]pyridine |
| 99 | 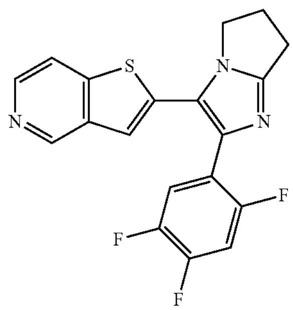 [SMILES: Fc1cc(F)c(-c2nc3n(c2-c2cc4cnccc4s2)CCC3)cc1F] | 2-(2-(2,4,5-trifluorophenyl)-6,7-dihydro-5H-pyrrolo[1,2-a]imidazol-3-yl)thieno[3,2-c]pyridine |
| 100 | 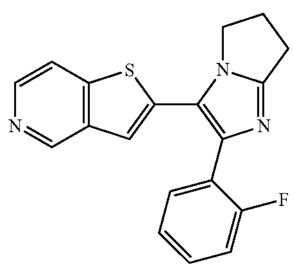 [SMILES: Fc1ccccc1-c1nc2n(c1-c1cc3cnccc3s1)CCC2] | 2-(2-(2-fluorophenyl)-6,7-dihydro-5H-pyrrolo[1,2-a]imidazol-3-yl)thieno[3,2-c]pyridine |
| 101 | 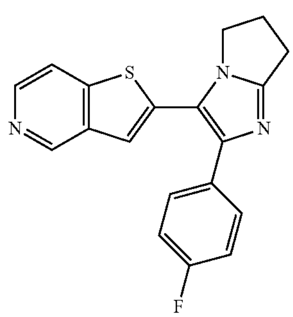 [SMILES: Fc1ccc(-c2nc3n(c2-c2cc4cnccc4s2)CCC3)cc1] | 2-(2-(4-fluorophenyl)-6,7-dihydro-5H-pyrrolo[1,2-a]imidazol-3-yl)thieno[3,2-c]pyridine |
| 102 | 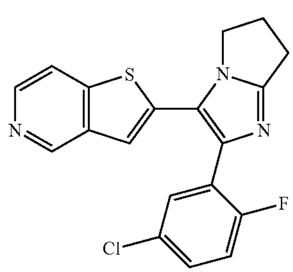 [SMILES: Fc1ccc(Cl)cc1-c1nc2n(c1-c1cc3cnccc3s1)CCC2] | 2-(2-(5-chloro-2-fluorophenyl)-6,7-dihydro-5H-pyrrolo[1,2-a]imidazol-3-yl)thieno[3,2-c]pyridine |

| No. | Structure | Name |
|---|---|---|
| 103 | 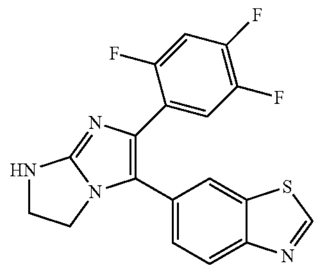 [SMILES: Fc1cc(F)c(-c2nc3n(c2-c2ccc4ncsc4c2)CCN3)cc1F] | 6-(6-(2,4,5-trifluorophenyl)-2,3-dihydro-1H-imidazo[1,2-a]imidazol-5-yl)benzo[d]thiazole |
| 104 | 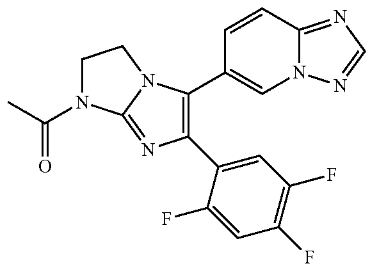 [SMILES: CC(=O)N1CCn2c1nc(-c1cc(F)c(F)cc1F)c2-c1ccc2ncnn2c1] | 1-(5-([1,2,4]triazolo[1,5-a]pyridin-6-yl)-6-(2,4,5-trifluorophenyl)-2,3-dihydro-1H-imidazo[1,2-a]imidazol-1-yl)ethan-1-one |
| 105 | 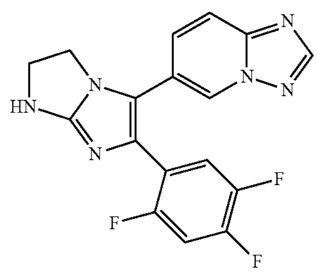 [SMILES: Fc1cc(F)c(-c2nc3n(c2-c2ccc4ncnn4c2)CCN3)cc1F] | 6-(6-(2,4,5-trifluorophenyl)-2,3-dihydro-1H-imidazo[1,2-a]imidazol-5-yl)-[1,2,4]triazolo[1,5-a]pyridine |
| 106 | 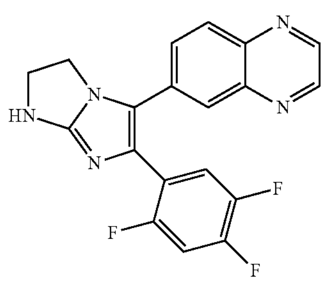 [SMILES: Fc1cc(F)c(-c2nc3n(c2-c2ccc4nccnc4c2)CCN3)cc1F] | 6-(6-(2,4,5-trifluorophenyl)-2,3-dihydro-1H-imidazo[1,2-a]imidazol-5-yl)quinoxaline |
| 107 | 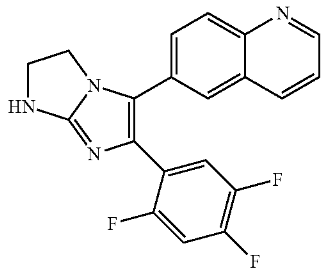 [SMILES: Fc1cc(F)c(-c2nc3n(c2-c2ccc4ncccc4c2)CCN3)cc1F] | 6-(6-(2,4,5-trifluorophenyl)-2,3-dihydro-1H-imidazo[1,2-a]imidazol-5-yl)quinoline |

-continued

| No. | Structure | Name |
|---|---|---|
| 108 | 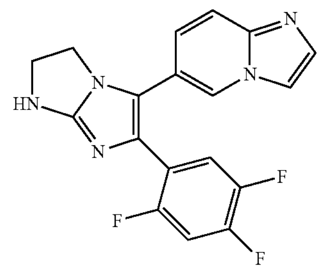 [SMILES: Fc1cc(F)c(-c2nc3n(c2-c2ccc4nccn4c2)CCN3)cc1F] | 6-(6-(2,4,5-trifluorophenyl)-2,3-dihydro-1H-imidazo[1,2-a]imidazol-5-yl)imidazo[1,2-a]pyridine |
| 109 | 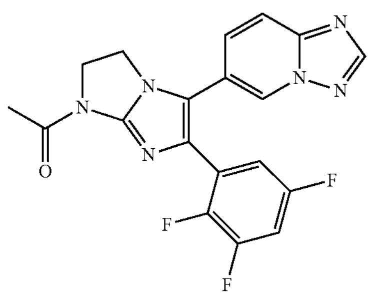 [SMILES: CC(=O)N1CCn2c1nc(-c1cc(F)cc(F)c1F)c2-c1ccc2ncnn2c1] | 1-(5-([1,2,4]triazolo[1,5-a]pyridin-6-yl)-6-(2,3,5-trifluorophenyl)-2,3-dihydro-1H-imidazo[1,2-a]imidazol-1-yl)ethan-1-one |
| 110 | 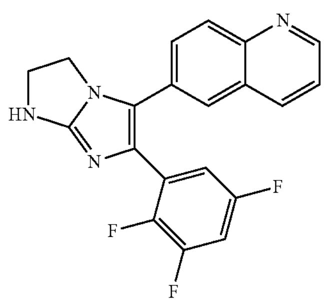 [SMILES: Fc1cc(F)c(F)c(-c2nc3n(c2-c2ccc4ncccc4c2)CCN3)c1] | 6-(6-(2,3,5-trifluorophenyl)-2,3-dihydro-1H-imidazo[1,2-a]imidazol-5-yl)quinoline |
| 111 | 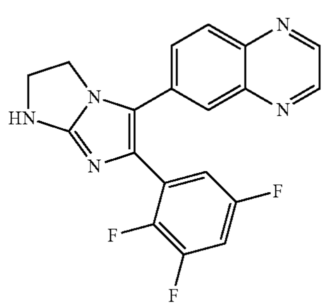 [SMILES: Fc1cc(F)c(F)c(-c2nc3n(c2-c2ccc4nccnc4c2)CCN3)c1] | 6-(6-(2,3,5-trifluorophenyl)-2,3-dihydro-1H-imidazo[1,2-a]imidazol-5-yl)quinoxaline |
| 112 | 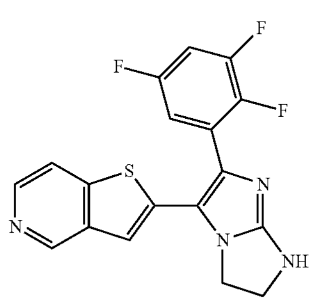 [SMILES: Fc1cc(F)c(F)c(-c2nc3n(c2-c2cc4cnccc4s2)CCN3)c1] | 2-(6-(2,3,5-trifluorophenyl)-2,3-dihydro-1H-imidazo[1,2-a]imidazol-5-yl)thieno[3,2-c]pyridine |

| No. | Structure | Name |
|---|---|---|
| 113 | 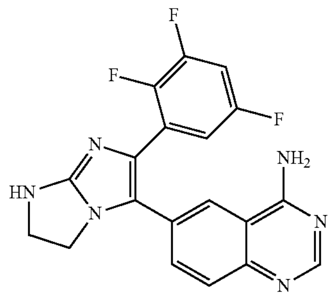 [SMILES: Nc1ncnc2ccc(-c3c(-c4cc(F)cc(F)c4F)nc4n3CCN4)cc12] | 6-(6-(2,3,5-trifluorophenyl)-2,3-dihydro-1H-imidazo[1,2-a]imidazol-5-yl)quinazolin-4-amine |
| 114 | 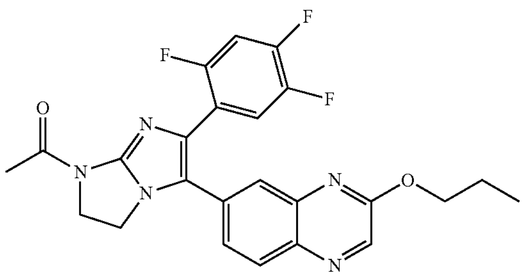 [SMILES: CCCOc1cnc2ccc(-c3c(-c4cc(F)c(F)cc4F)nc4n3CCN4C(C)=O)cc2n1] | 1-(5-(3-(2-methoxyethoxy)quinoxalin-6-yl)-6-(2,4,5-trifluorophenyl)-2,3-dihydro-1H-imidazo[1,2-a]imidazol-1-yl)ethan-1-one |
| 115 | 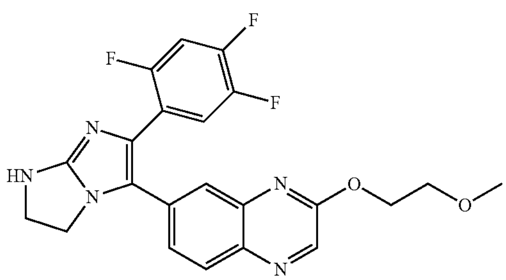 [SMILES: COCCOc1cnc2ccc(-c3c(-c4cc(F)c(F)cc4F)nc4n3CCN4)cc2n1] | 2-(2-methoxyethoxy)-7-(6-(2,4,5-trifluorophenyl)-2,3-dihydro-1H-imidazo[1,2-a]imidazol-5-yl)quinoxaline |
| 116 | 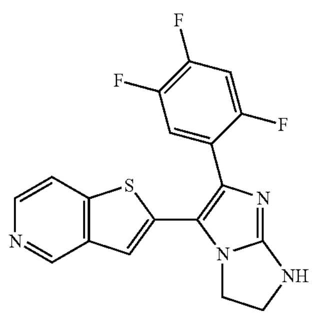 [SMILES: Fc1cc(F)c(-c2nc3n(c2-c2cc4cnccc4s2)CCN3)cc1F] | 2-(6-(2,4,5-trifluorophenyl)-2,3-dihydro-1H-imidazo[1,2-a]imidazol-5-yl)thieno[3,2-c]pyridine |
| 117 | 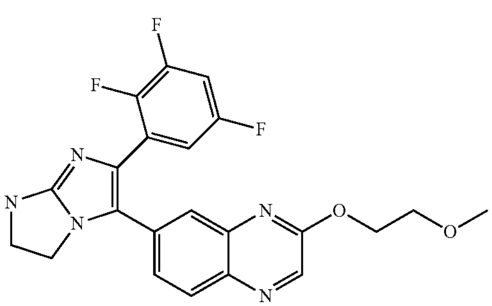 [SMILES: COCCOc1cnc2ccc(-c3c(-c4cc(F)cc(F)c4F)nc4n3CCN4)cc2n1] | 2-(2-methoxyethoxy)-7-(2-(2,3,5-trifluorophenyl)-5,6-dihydro-7$\lambda^2$-imidazo[3,2-a]imidazol-3-yl)quinoxaline |

-continued

| No. | Structure | Name |
|---|---|---|
| 118 | 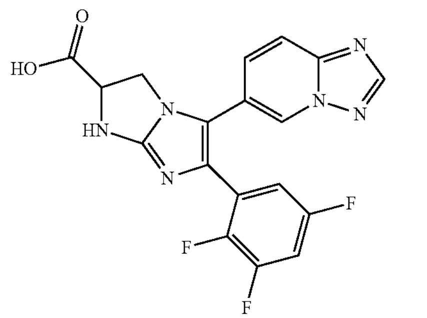 [SMILES: O=C(O)C1Cn2c(nc(-c3cc(F)cc(F)c3F)c2-c2ccc3ncnn3c2)N1] | 5-([1,2,4]triazolo[1,5-a]pyridin-6-yl)-6-(2,3,5-trifluorophenyl)-2,3-dihydro-1H-imidazo[1,2-a]imidazole-2-carboxylic acid |
| 119 | 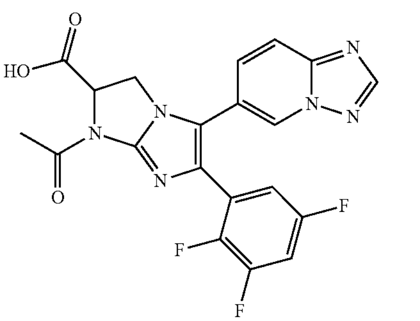 [SMILES: CC(=O)N1c2nc(-c3cc(F)cc(F)c3F)c(-c3ccc4ncnn4c3)n2CC1C(=O)O] | 5-([1,2,4]triazolo[1,5-a]pyridin-6-yl)-1-acetyl-6-(2,3,5-trifluorophenyl)-2,3-dihydro-1H-imidazo[1,2-a]imidazole-2-carboxylic acid |
| 120 | 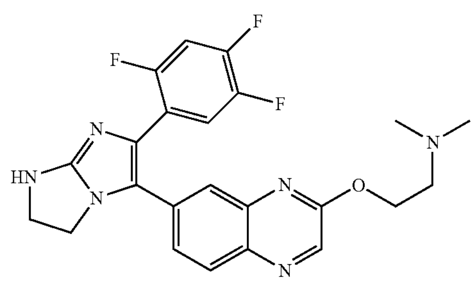 [SMILES: CN(C)CCOc1cnc2ccc(-c3c(-c4cc(F)c(F)cc4F)nc4n3CCN4)cc2n1] | N,N-dimethyl-2-((7-(6-(2,4,5-trifluorophenyl)-2,3-dihydro-1H-imidazo[1,2-a]imidazol-5-yl)quinoxalin-2-yl)oxy)ethan-1-amine |
| 121 | 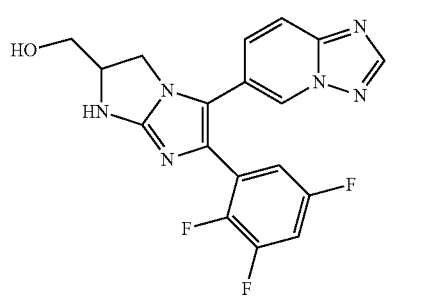 [SMILES: OCC1Cn2c(nc(-c3cc(F)cc(F)c3F)c2-c2ccc3ncnn3c2)N1] | (5-([1,2,4]triazolo[1,5-a]pyridin-6-yl)-6-(2,3,5-trifluorophenyl)-2,3-dihydro-1H-imidazo[1,2-a]imidazol-2-yl)methanol |
| 122 | 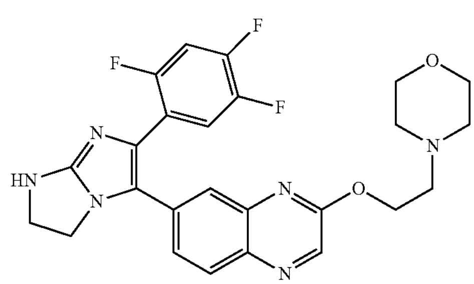 [SMILES: Fc1cc(F)c(-c2nc3n(c2-c2ccc4ncc(OCCN5CCOCC5)nc4c2)CCN3)cc1F] | 4-(2-((7-(6-(2,4,5-trifluorophenyl)-2,3-dihydro-1H-imidazo[1,2-a]imidazol-5-yl)quinoxalin-2-yl)oxy)ethyl)morpholine |

| No. | Structure | Name |
| --- | --- | --- |
| 123 | 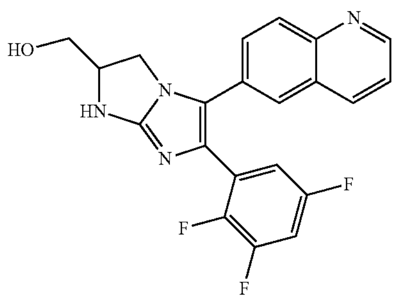 [SMILES: OCC1Cn2c(nc(-c3cc(F)cc(F)c3F)c2-c2ccc3ncccc3c2)N1] | (5-(quinolin-6-yl)-6-(2,3,5-trifluorophenyl)-2,3-dihydro-1H-imidazo[1,2-a]imidazol-2-yl)methanol |
| 124 | 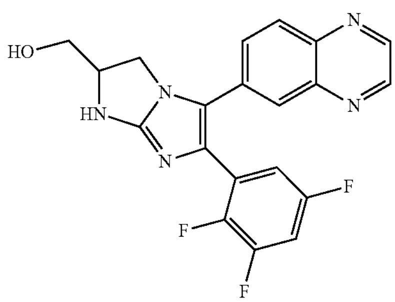 [SMILES: OCC1Cn2c(nc(-c3cc(F)cc(F)c3F)c2-c2ccc3nccnc3c2)N1] | (5-(quinoxalin-6-yl)-6-(2,3,5-trifluorophenyl)-2,3-dihydro-1H-imidazo[1,2-a]imidazol-2-yl)methanol |
| 125 | 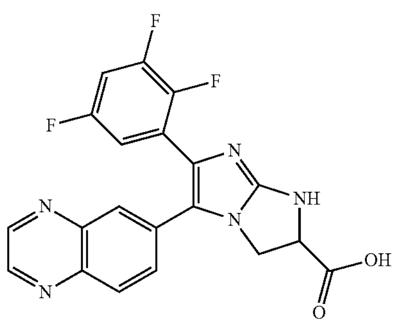 [SMILES: O=C(O)C1Cn2c(nc(-c3cc(F)cc(F)c3F)c2-c2ccc3nccnc3c2)N1] | 5-(quinoxalin-6-yl)-6-(2,3,5-trifluorophenyl)-2,3-dihydro-1H-imidazo[1,2-a]imidazole-2-carboxylic acid |
| 126 | 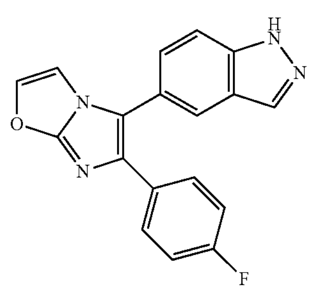 [SMILES: Fc1ccc(-c2nc3occn3c2-c2ccc3[nH]ncc3c2)cc1] | 6-(4-fluorophenyl)-5-(1H-indazol-5-yl)imidazo[2,1-b]oxazole |
| 127 | 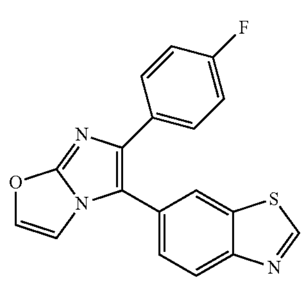 [SMILES: Fc1ccc(-c2nc3occn3c2-c2ccc3ncsc3c2)cc1] | 5-(benzo[d]thiazol-6-yl)-6-(4-fluorophenyl)imidazo[2,1-b]oxazole |

| No. | Structure | Name |
|---|---|---|
| 128 | 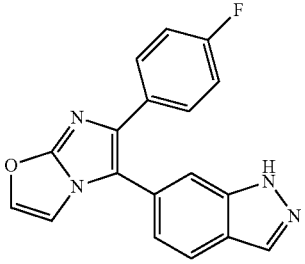 [SMILES: Fc1ccc(-c2nc3occn3c2-c2ccc3cn[nH]c3c2)cc1] | 6-(4-fluorophenyl)-5-(1H-indazol-6-yl)imidazo[1,2-b]oxaozle |
| 129 | 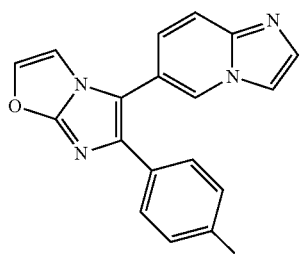 | 6-(4-fluorophenyl)-5-(imidazo[1,2-a]pyridin-6-yl)imidazo[2,1-b]oxazole |
| 130 | 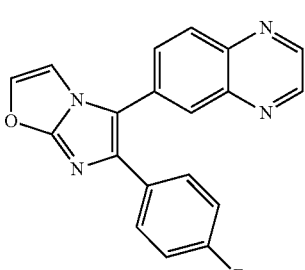 | 6-(4-fluorophenyl)-5-(quinoxalin-6-yl)imidazo[2,1-b]oxazole |
| 131 | 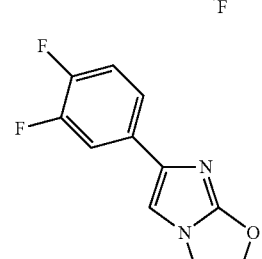 | 6-(3,4-difluorophenyl)imidazo[2,1-b]oxazole |
| 132 | 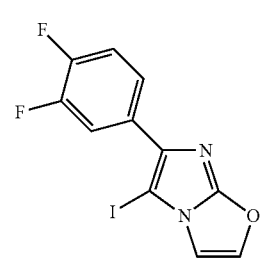 [SMILES: Fc1ccc(-c2nc3occn3c2I)cc1F] | 6-(3,4-difluorophenyl)-5-iodoimidazo[2,1-b]oxazole |
| 133 | 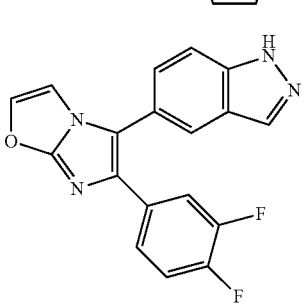 | 6-(3,4-difluorophenyl)-5-(1H-indazol-5-yl)imidazo[2,1-b]oxazole |

-continued

| No. | Structure | Name |
|---|---|---|
| 134 | 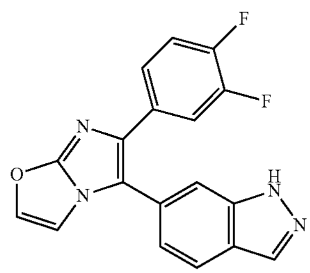 [SMILES: Fc1ccc(-c2nc3occn3c2-c2ccc3cn[nH]c3c2)cc1F] | 6-(3,4-difluorophenyl)-5-(1H-indazol-6-yl)imidazo[2,1-b]oxazole |
| 135 | 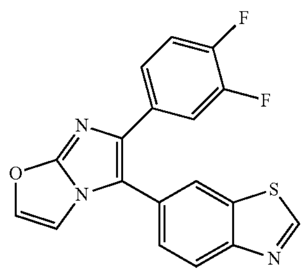 [SMILES: Fc1ccc(-c2nc3occn3c2-c2ccc3ncsc3c2)cc1F] | 5-(benzo[d]thiazol-6-yl)-6-(3,4-difluorophenyl)imidazo[2,1-b]oxazole |
| 136 | 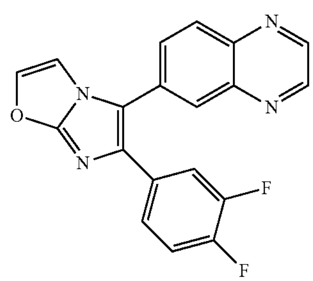 [SMILES: Fc1ccc(-c2nc3occn3c2-c2ccc3nccnc3c2)cc1F] | 6-(3,4-difluorophenyl)-5-(quinoxalin-6-yl)imidazo[2,1-b]oxaole |
| 137 | 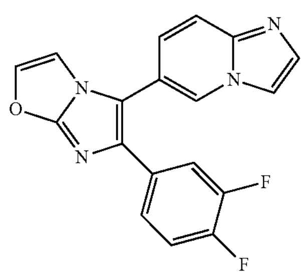 [SMILES: Fc1ccc(-c2nc3occn3c2-c2ccc3nccn3c2)cc1F] | 6-(3,4-difluorophenyl)-5-(imidazo[1,2-a]pyridin-6-yl)imidazo[2,1-b]oxazole |
| 138 | 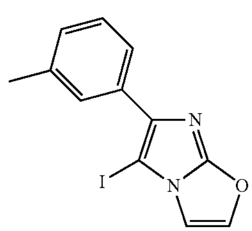 [SMILES: Cc1cccc(-c2nc3occn3c2I)c1] | 5-iodo-6-(m-tolyl)imidazo[2,1-b]oxazole |
| 139 | 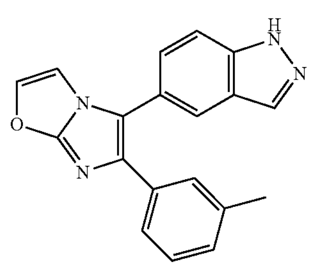 [SMILES: Cc1cccc(-c2nc3occn3c2-c2ccc3[nH]ncc3c2)c1] | 6-(m-tolyl)-5-(1H-indazol-5-yl)imidazo[2,1-b]oxazole |

| No. | Structure | Name |
|---|---|---|
| 140 | 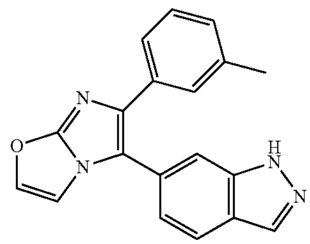 [SMILES: Cc1cccc(-c2nc3occn3c2-c2ccc3cn[nH]c3c2)c1] | 6-(m-tolyl)-5-(1H-indazol-6-yl)imidazo[2,1-b]oxazole |
| 141 | 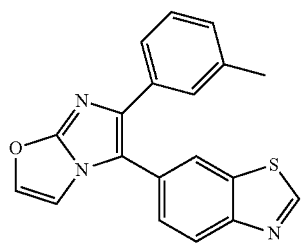 [SMILES: Cc1cccc(-c2nc3occn3c2-c2ccc3ncsc3c2)c1] | 5-(benzo[d]thiazo-6-yl)-6-(m-tolyl)imidazo[2,1-b]oxazole |
| 142 | 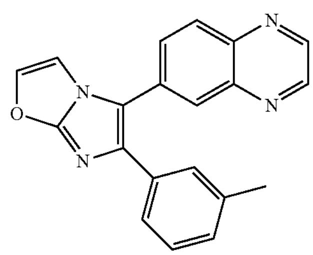 [SMILES: Cc1cccc(-c2nc3occn3c2-c2ccc3nccnc3c2)c1] | 5-(quinoxalin-6-yl)-6-(m-tolyl)imidazo[2,1-b]oxazole |
| 143 | 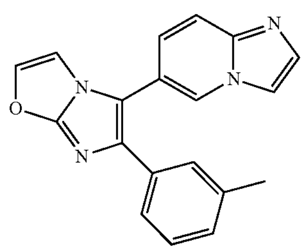 [SMILES: Cc1cccc(-c2nc3occn3c2-c2ccc3nccn3c2)c1] | 6-(m-tolyl)-5-(imidazo[1,2-a]pyridin-6-yl)imidazo[2,1-b]oxazole |
| 144 | 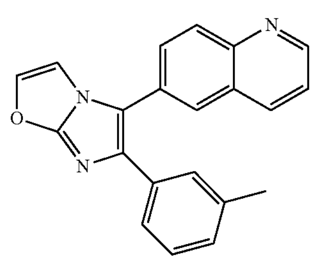 [SMILES: Cc1cccc(-c2nc3occn3c2-c2ccc3ncccc3c2)c1] | 5-(quinolin-6-yl)-6-(m-tolyl)imidazo[2,1-b]oxazole |
| 145 | 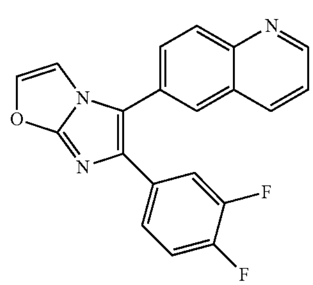 [SMILES: Fc1ccc(-c2nc3occn3c2-c2ccc3ncccc3c2)cc1F] | 5-(quinolin-6-yl)-6-(3,4-difluorophenyl)imidazo[2,1-b]oxazole |

| No. | Structure | Name |
| --- | --- | --- |
| 146 | 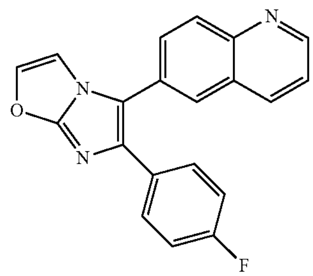 [SMILES: Fc1ccc(-c2nc3occn3c2-c2ccc3ncccc3c2)cc1] | 5-(quinolin-6-yl)-6-(4-fluorophenyl)imidazo[2,1-b]oxazole |
| 147 | 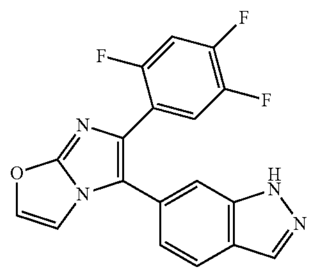 [SMILES: Fc1cc(F)c(-c2nc3occn3c2-c2ccc3cn[nH]c3c2)cc1F] | 6-(2,4,5-trifluorophenyl)-5-(1H-indazol-6-yl)imidazo[2,1-b]oxazole |
| 148 | 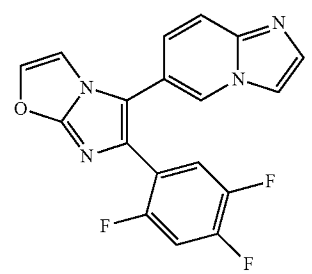 [SMILES: Fc1cc(F)c(-c2nc3occn3c2-c2ccc3nccn3c2)cc1F] | 6-(2,4,5-trifluorophenyl)-5-(imidazo[1,2-a]pyridin-6-yl)imidazo[2,1-b]oxazole |
| 149 | 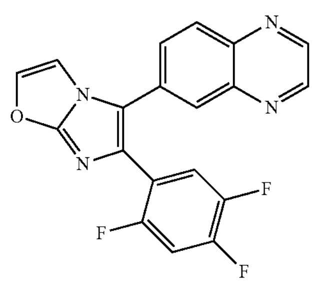 [SMILES: Fc1cc(F)c(-c2nc3occn3c2-c2ccc3nccnc3c2)cc1F] | 5-(quinoxalin-6-yl)-6-(2,4,5-trifluorophenyl)imidazo[2,1-b]oxazole |
| 150 | 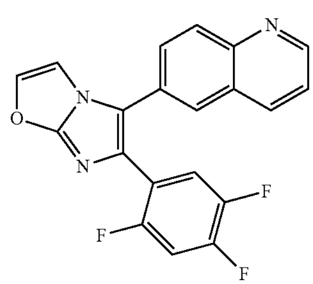 [SMILES: Fc1cc(F)c(-c2nc3occn3c2-c2ccc3ncccc3c2)cc1F] | 5-(quinolin-6-yl)-6-(2,4,5-trifluorophenyl)imidazo[2,1-b]oxazole |

| No. | Structure | Name |
| --- | --- | --- |
| 151 | 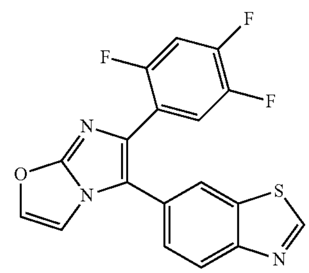 [SMILES: Fc1cc(F)c(-c2nc3occn3c2-c2ccc3ncsc3c2)cc1F] | 5-(benzo[d]thiazol-6-yl)-6-(2,4,5-trifluorophenyl)imidazo[2,1-b]oxazole |
| 152 | 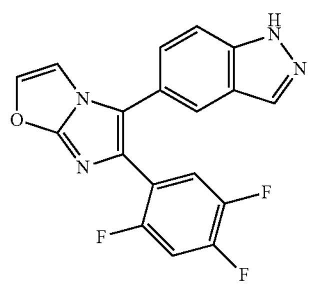 [SMILES: Fc1cc(F)c(-c2nc3occn3c2-c2ccc3[nH]ncc3c2)cc1F] | 6-(2,4,5-trifluorophenyl)-5-(1H-indazol-5-yl)imidazo[2,1-b]oxazole |
| 153 | 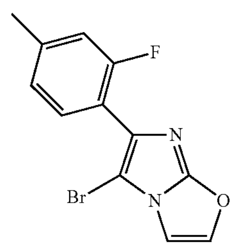 [SMILES: Cc1ccc(-c2nc3occn3c2Br)c(F)c1] | 5-bromo-6-(2-fluoro-4-methylphenyl)imidazo[2,1-b]oxazole |
| 154 | 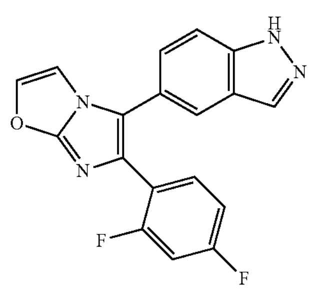 [SMILES: Fc1ccc(-c2nc3occn3c2-c2ccc3[nH]ncc3c2)c(F)c1] | 6-(2,4-difluorophenyl)-5-(1H-indazol-5-yl)imidazo[2,1-b]oxazole |
| 155 | 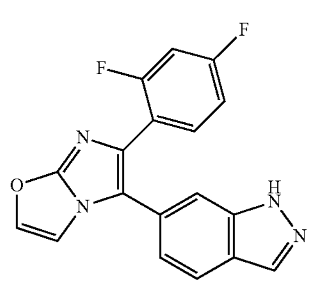 [SMILES: Fc1ccc(-c2nc3occn3c2-c2ccc3cn[nH]c3c2)c(F)c1] | 6-(2,4-difluorophenyl)-5-(1H-indazol-6-yl)imidazo[2,1-b]oxazole |

| No. | Structure | Name |
|---|---|---|
| 156 | 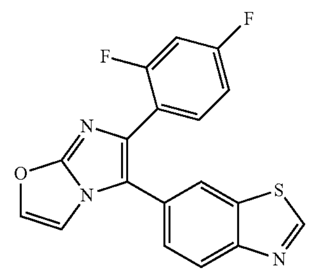 [SMILES: Fc1ccc(-c2nc3occn3c2-c2ccc3ncsc3c2)c(F)c1] | 5-(benzo[d]thiazol-6-yl)-6-(2,4-difluorophenyl)imidazo[2,1-b]oxazole |
| 157 | 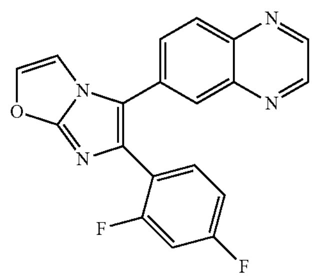 [SMILES: Fc1ccc(-c2nc3occn3c2-c2ccc3nccnc3c2)c(F)c1] | 6-(2,4-difluorophenyl)-5-(quinoxalin-6-yl)imidazo[2,1-b]oxazole |
| 158 | 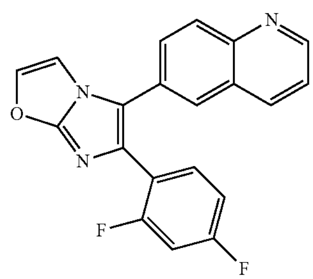 [SMILES: Fc1ccc(-c2nc3occn3c2-c2ccc3ncccc3c2)c(F)c1] | 5-(quinolin-6-yl)-6-(2,4-difluorophenyl)imidazo[2,1-b]oxazole |
| 159 | 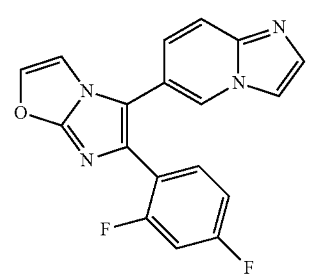 [SMILES: Fc1ccc(-c2nc3occn3c2-c2ccc3nccn3c2)c(F)c1] | 6-(2,4-difluorophenyl)-5-(imidazo[1,2-a]pyridin-6-yl)imidazo[2,1-b]oxazole |
| 160 | 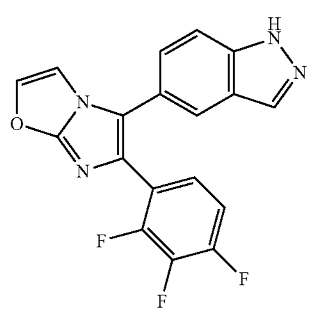 [SMILES: Fc1ccc(-c2nc3occn3c2-c2ccc3[nH]ncc3c2)c(F)c1F] | 6-(2,3,4-trifluorophenyl)-5-(1H-indazol-5-yl)imidazo[2,1-b]oxazole |

-continued

| No. | Structure | Name |
|---|---|---|
| 161 | 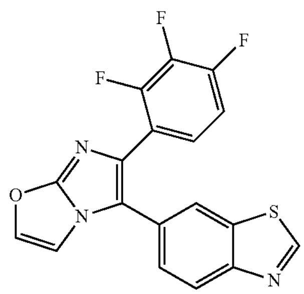 [SMILES: Fc1ccc(-c2nc3occn3c2-c2ccc3ncsc3c2)c(F)c1F] | 5-(benzo[d]thiazol-6-yl)-6-(2,3,4-trifluorophenyl)imidazo[2,1-b]oxazole |
| 162 | 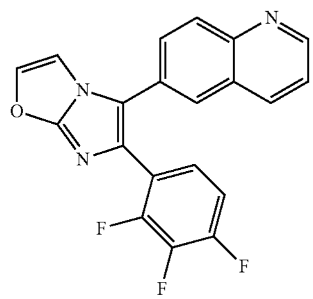 [SMILES: Fc1ccc(-c2nc3occn3c2-c2ccc3ncccc3c2)c(F)c1F] | 5-(quinolin-6-yl)-6-(2,3,4-trifluorophenyl)imidazo[2,1-b]oxazole |
| 163 | 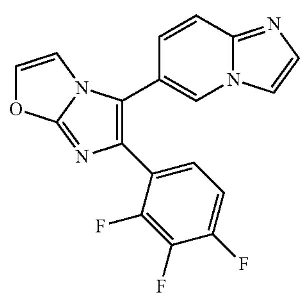 [SMILES: Fc1ccc(-c2nc3occn3c2-c2ccc3nccn3c2)c(F)c1F] | 5-(imidazo[1,2-a]pyridin-6-yl)-6-(2,3,4-trifluorophenyl)imidazo[2,1-b]oxazole |
| 164 | 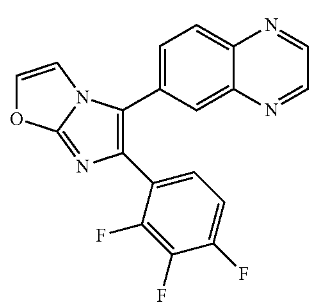 [SMILES: Fc1ccc(-c2nc3occn3c2-c2ccc3nccnc3c2)c(F)c1F] | 5-(quinoxalin-6-yl)-6-(2,3,4-trifluorophenyl)imidazo[2,1-b]oxazole |
| 165 | 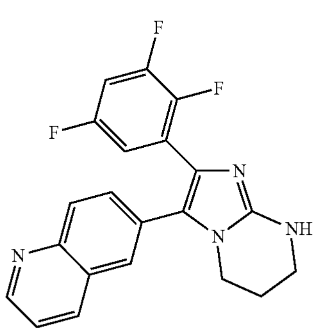 [SMILES: Fc1cc(F)c(F)c(-c2nc3n(c2-c2ccc4ncccc4c2)CCCN3)c1] | 6-(2-(2,3,5-trifluorophenyl)-5,6,7,8-tetrahydroimidazo[1,2-a]pyrimidin-3-yl)quinoline |

-continued

| No. | Structure | Name |
| --- | --- | --- |
| 166 | 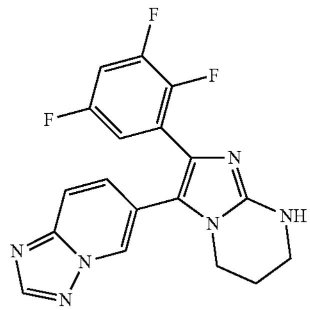 [SMILES: Fc1cc(F)c(F)c(-c2nc3n(c2-c2ccc4ncnn4c2)CCCN3)c1] | 6-(2-(2,3,5-trifluorophenyl)-5,6,7,8-tetrahydroimidazo[1,2-a]pyrimidin-3-yl)-[1,2,4]triazolo[1,5-a]pyridine |
| 167 | 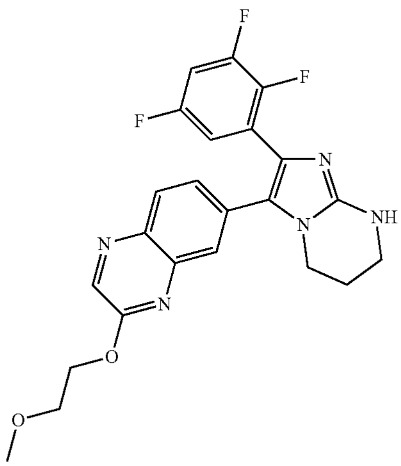 [SMILES: COCCOc1cnc2ccc(-c3c(-c4cc(F)cc(F)c4F)nc4n3CCCN4)cc2n1] | 2-(2-methoxyethoxy)-7-(2-(2,3,5-trifluorophenyl)-5,6,7,8-tetrahydroimidazo[1,2-a]pyrimidin-3-yl)quinoxaline |
| 168 | 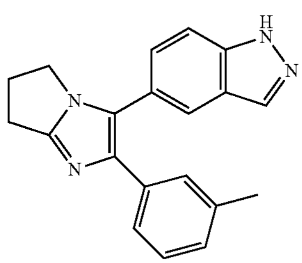 [SMILES: Cc1cccc(-c2nc3n(c2-c2ccc4[nH]ncc4c2)CCC3)c1] | 5-(2-(m-tolyl)-6,7-dihydro-5H-pyrrolo[1,2-a]imidazol-3-yl)-1H-indazole |
| 169 | 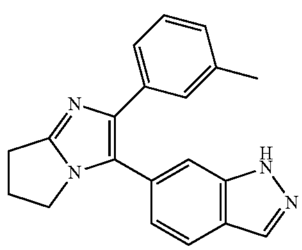 [SMILES: Cc1cccc(-c2nc3n(c2-c2ccc4cn[nH]c4c2)CCC3)c1] | 6-(2-(m-tolyl)-6,7-dihydro-5H-pyrrolo[1,2-a]imidazol-3-yl)-1H-indazole |
| 170 | 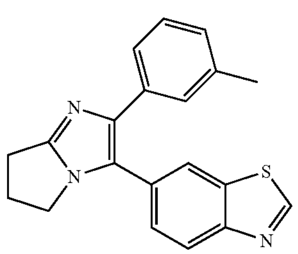 [SMILES: Cc1cccc(-c2nc3n(c2-c2ccc4ncsc4c2)CCC3)c1] | 6-(2-(m-tolyl)-6,7-dihydro-5H-pyrrolo[1,2-a]imidazol-3-yl)benzo[d]thiazole |

| No. | Structure | Name |
|---|---|---|
| 171 | 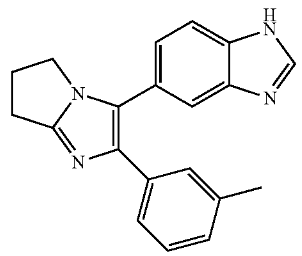 [SMILES: Cc1cccc(-c2nc3n(c2-c2ccc4[nH]cnc4c2)CCC3)c1] | 5-(2-(m-tolyl)-6,7-dihydro-5H-pyrrolo[1,2-a]imidazol-3-yl)-1H-benzo[d]imidazole |
| 172 | 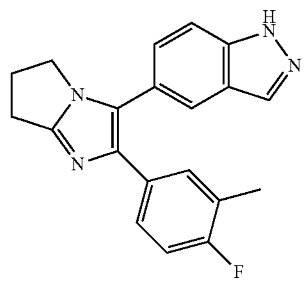 [SMILES: Cc1cc(-c2nc3n(c2-c2ccc4[nH]ncc4c2)CCC3)ccc1F] | 5-(2-(4-fluoro-3-methylphenyl)-6,7-dihydro-5H-pyrrolo[1,2-a]imidazol-3-yl)-1H-indazole |
| 173 | 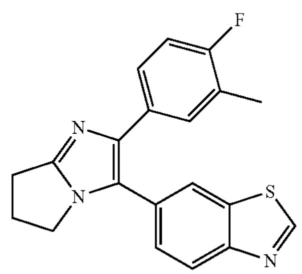 [SMILES: Cc1cc(-c2nc3n(c2-c2ccc4ncsc4c2)CCC3)ccc1F] | 6-(2-(4-fluoro-3-methylphenyl)-6,7-dihydro-5H-pyrrolo[1,2-a]imidazol-3-yl)benzo[d]thiazole |
| 174 | 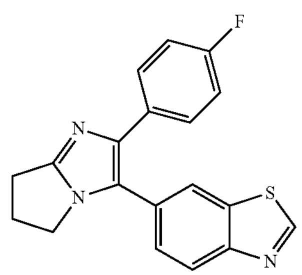 [SMILES: Fc1ccc(-c2nc3n(c2-c2ccc4ncsc4c2)CCC3)cc1] | 6-(2-(4-fluorophenyl)-6,7-dihydro-5H-pyrrolo[1,2-a]imidazol-3-yl)benzo[d]thiazole |
| 175 | 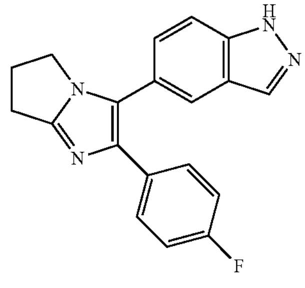 [SMILES: Fc1ccc(-c2nc3n(c2-c2ccc4[nH]ncc4c2)CCC3)cc1] | 5-(2-(4-fluorophenyl)-6,7-dihydro-5H-pyrrolo[1,2-a]imidazol-3-yl)-1H-indazole |

| No. | Structure | Name |
|---|---|---|
| 176 | 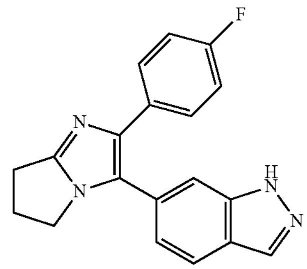 [SMILES: Fc1ccc(-c2nc3n(c2-c2ccc4cn[nH]c4c2)CCC3)cc1] | 6-(2-(4-fluorophenyl)-6,7-dihydro-5H-pyrrolo[1,2-a]imidazol-3-yl)-1H-indazole |
| 177 | 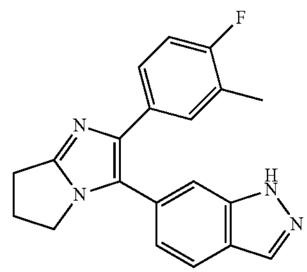 [SMILES: Cc1cc(-c2nc3n(c2-c2ccc4cn[nH]c4c2)CCC3)ccc1F] | 6-(2-(4-fluoro-3-methylphenyl)-6,7-dihydro-5H-pyrrolo[1,2-a]imidazol-3-yl)-1H-indazole |
| 178 | 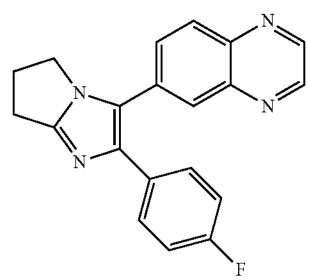 [SMILES: Fc1ccc(-c2nc3n(c2-c2ccc4nccnc4c2)CCC3)cc1] | 6-(2-(4-fluorophenyl)-6,7-dihydro-5H-pyrrolo[1,2-a]imidazol-3-yl)quinoxaline |
| 179 | 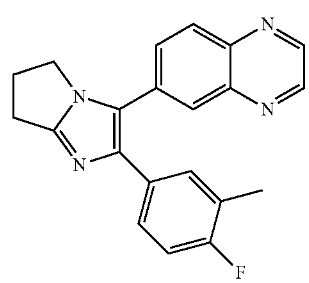 [SMILES: Cc1cc(-c2nc3n(c2-c2ccc4nccnc4c2)CCC3)ccc1F] | 6-(2-(4-fluoro-3-methylphenyl)-6,7-dihydro-5H-pyrrolo[1,2-a]imidazol-3-yl)quinoxaline |
| 180 | 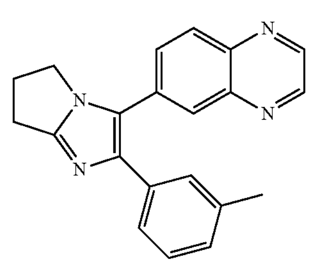 [SMILES: Cc1cccc(-c2nc3n(c2-c2ccc4nccnc4c2)CCC3)c1] | 6-(2-(m-tolyl)-6,7-dihydro-5H-pyrrolo[1,2-a]imidazol-3-yl)quinoxaline |

-continued

| No. | Structure | Name |
|---|---|---|
| 181 | 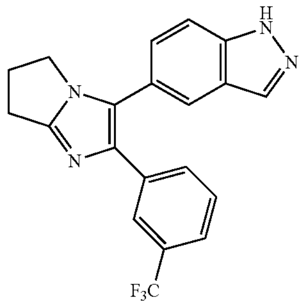 [SMILES: FC(F)(F)c1cccc(-c2nc3n(c2-c2ccc4[nH]ncc4c2)CCC3)c1] | 5-(2-(3-(trifluoromethyl)phenyl)-6,7-dihydro-5H-pyrrolo[1,2-a]imidazol-3-yl)-1H-indazole |
| 182 | 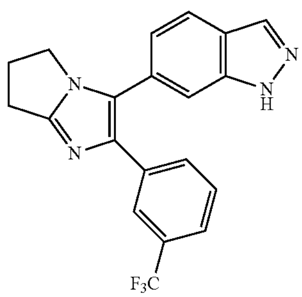 [SMILES: FC(F)(F)c1cccc(-c2nc3n(c2-c2ccc4cn[nH]c4c2)CCC3)c1] | 6-(2-(3-(trifluoromethyl)phenyl)-6,7-dihydro-5H-pyrrolo[1,2-a]imidazol-3-yl)-1H-indazole |
| 183 | 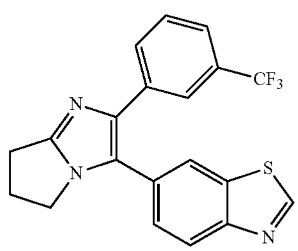 [SMILES: FC(F)(F)c1cccc(-c2nc3n(c2-c2ccc4ncsc4c2)CCC3)c1] | 6-(2-(3-(trifluoromethyl)phenyl)-6,7-dihydro-5H-pyrrolo[1,2-a]imidazol-3-yl)benzo[d]thiazole |
| 184 | 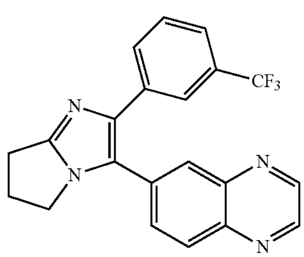 [SMILES: FC(F)(F)c1cccc(-c2nc3n(c2-c2ccc4nccnc4c2)CCC3)c1] | 6-(2-(3-(trifluoromethyl)phenyl)-6,7-dihydro-5H-pyrrolo[1,2-a]imidazol-3-yl)quinoxaline |
| 185 | 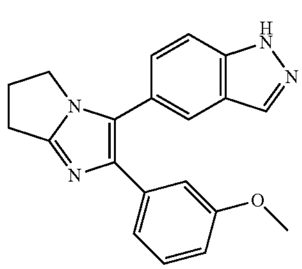 [SMILES: COc1cccc(-c2nc3n(c2-c2ccc4[nH]ncc4c2)CCC3)c1] | 5-(2-(3-methoxyphenyl)-6,7-dihydro-5H-pyrrolo[1,2-a]imidazol-3-yl)-1H-indazole |

| No. | Structure | Name |
|---|---|---|
| 186 | 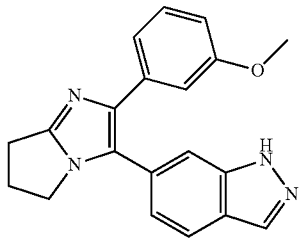 [SMILES: COc1cccc(-c2nc3n(c2-c2ccc4cn[nH]c4c2)CCC3)c1] | 6-(2-(3-methoxyphenyl)-6,7-dihydro-5H-pyrrolo[1,2-a]imidazol-3-yl)-1H-indazole |
| 187 | 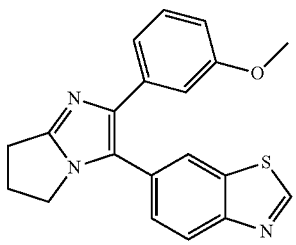 [SMILES: COc1cccc(-c2nc3n(c2-c2ccc4ncsc4c2)CCC3)c1] | 6-(2-(3-methoxyphenyl)-6,7-dihydro-5H-pyrrolo[1,2-a]imidazol-3-yl)benzo[d]thiazole |
| 188 | 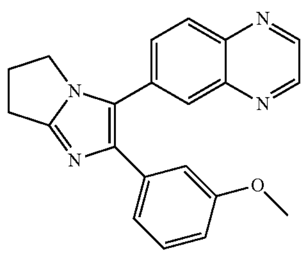 [SMILES: COc1cccc(-c2nc3n(c2-c2ccc4nccnc4c2)CCC3)c1] | 6-(2-(3-methoxyphenyl)-6,7-dihydro-5H-pyrrolo[1,2-a]imidazol-3-yl)quinoxaline |
| 189 | 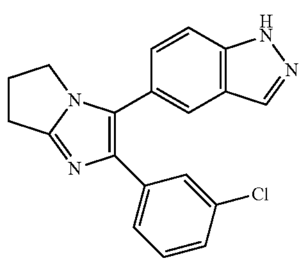 [SMILES: Clc1cccc(-c2nc3n(c2-c2ccc4[nH]ncc4c2)CCC3)c1] | 5-(2-(3-chlorophenyl)-6,7-dihydro-5H-pyrrolo[1,2-a]imidazol-3-yl)-1H-indazole |
| 190 | 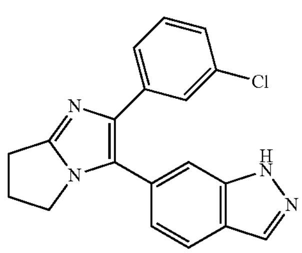 [SMILES: Clc1cccc(-c2nc3n(c2-c2ccc4cn[nH]c4c2)CCC3)c1] | 6-(2-(3-chlorophenyl)-6,7-dihydro-5H-pyrrolo[1,2-a]imidazol-3-yl)-1H-indazole |
| 191 | 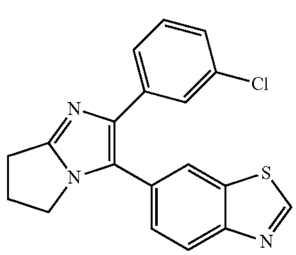 [SMILES: Clc1cccc(-c2nc3n(c2-c2ccc4ncsc4c2)CCC3)c1] | 6-(2-(3-chlorophenyl)-6,7-dihydro-5H-pyrrolo[1,2-a]imidazol-3-yl)benzo[d]thiazole |

-continued

| No. | Structure | Name |
|---|---|---|
| 192 | 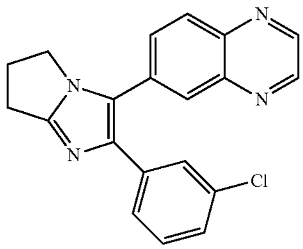 [SMILES: Clc1cccc(-c2nc3n(c2-c2ccc4nccnc4c2)CCC3)c1] | 6-(2-(3-chlorophenyl)-6,7-dihydro-5H-pyrrolo[1,2-a]imidazol-3-yl)quinoxaline |
| 193 | 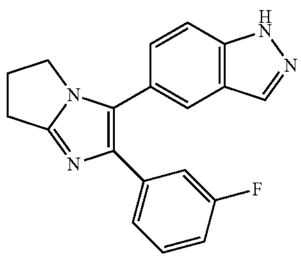 [SMILES: Fc1cccc(-c2nc3n(c2-c2ccc4[nH]ncc4c2)CCC3)c1] | 5-(2-(3-fluorophenyl)-6,7-dihydro-5H-pyrrolo[1,2-a]imidazol-3-yl)-1H-indazole |
| 194 | 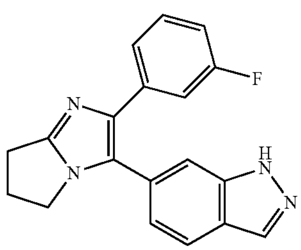 [SMILES: Fc1cccc(-c2nc3n(c2-c2ccc4cn[nH]c4c2)CCC3)c1] | 6-(2-(3-fluorophenyl)-6,7-dihydro-5H-pyrrolo[1,2-a]imidazol-3-yl)-1H-indazole |
| 195 | 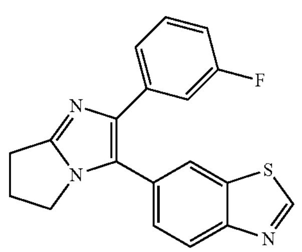 | 6-(2-(3-fluorophenyl)-6,7-dihydro-5H-pyrrolo[1,2-a]imidazol-3-yl)benzo[d]thiazole |
| 196 | 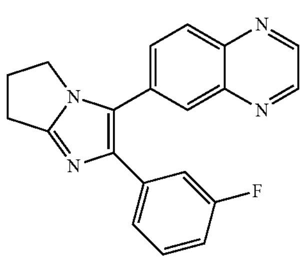 [SMILES: Fc1cccc(-c2nc3n(c2-c2ccc4nccnc4c2)CCC3)c1] | 6-(2-(3-fluorophenyl)-6,7-dihydro-5H-pyrrolo[1,2-a]imidazol-3-yl)quinoxaline |
| 197 | 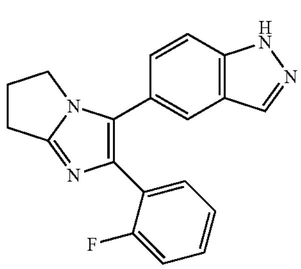 [SMILES: Fc1ccccc1-c1nc2n(c1-c1ccc3[nH]ncc3c1)CCC2] | 5-(2-(2-fluorophenyl)-6,7-dihydro-5H-pyrrolo[1,2-a]imidazol-3-yl)-1H-indazole |

-continued

| No. | Structure | Name |
|---|---|---|
| 198 | 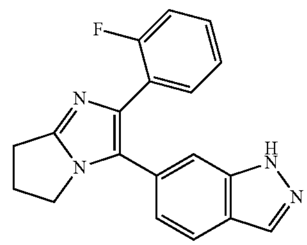 [SMILES: Fc1ccccc1-c1nc2n(c1-c1ccc3cn[nH]c3c1)CCC2] | 6-(2-(2-fluorophenyl)-6,7-dihydro-5H-pyrrolo[1,2-a]imidazol-3-yl)-1H-indazole |
| 199 | 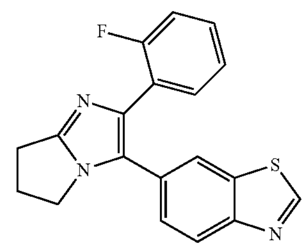 [SMILES: Fc1ccccc1-c1nc2n(c1-c1ccc3ncsc3c1)CCC2] | 6-(2-(2-fluorophenyl)-6,7-dihydro-5H-pyrrolo[1,2-a]imidazol-3-yl)benzo[d]thiazole |
| 200 | 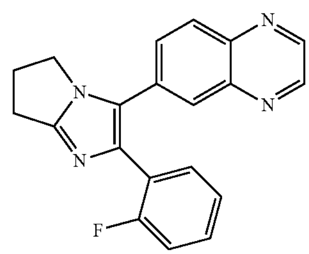 [SMILES: Fc1ccccc1-c1nc2n(c1-c1ccc3nccnc3c1)CCC2] | 6-(2-(2-fluorophenyl)-6,7-dihydro-5H-pyrrolo[1,2-a]imidazol-3-yl)quinoxaline |
| 201 | 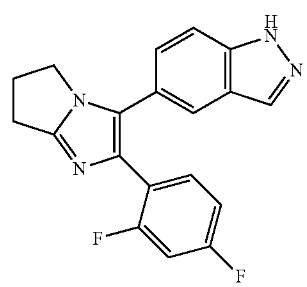 | 5-(2-(2,4-difluorophenyl)-6,7-dihydro-5H-pyrrolo[1,2-a]imidazol-3-yl)-1H-indazole |
| 202 | 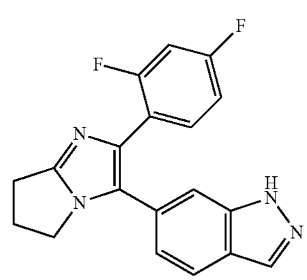 [SMILES: Fc1ccc(-c2nc3n(c2-c2ccc4cn[nH]c4c2)CCC3)c(F)c1] | 6-(2-(2,4-difluorophenyl)-6,7-dihydro-5H-pyrrolo[1,2-a]imidazol-3-yl)-1H-indazole |
| 203 | 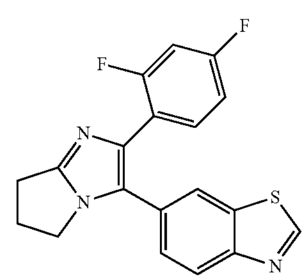 [SMILES: Fc1ccc(-c2nc3n(c2-c2ccc4ncsc4c2)CCC3)c(F)c1] | 6-(2-(2,4-difluorophenyl)-6,7-dihydro-5H-pyrrolo[1,2-a]imidazol-3-yl)benzo[d]thiazole |

| No. | Structure | Name |
|---|---|---|
| 204 | 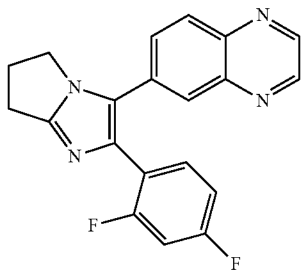 [SMILES: Fc1ccc(-c2nc3n(c2-c2ccc4nccnc4c2)CCC3)c(F)c1] | 6-(2-(2,4-difluorophenyl)-6,7-dihydro-5H-pyrrolo[1,2-a]imidazol-3-yl)quinoxaline |
| 205 | 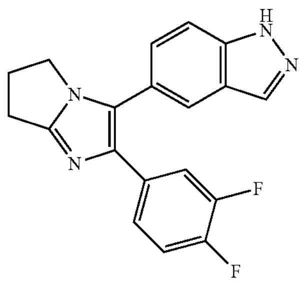 | 5-(2-(3,4-difluorophenyl)-6,7-dihydro-5H-pyrrolo[1,2-a]imidazol-3-yl)-1H-indazole |
| 206 | 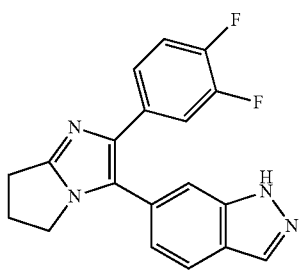 [SMILES: Fc1ccc(-c2nc3n(c2-c2ccc4cn[nH]c4c2)CCC3)cc1F] | 6-(2-(3,4-difluorophenyl)-6,7-dihydro-5H-pyrrolo[1,2-a]imidazol-3-yl)-1H-indazole |
| 207 | 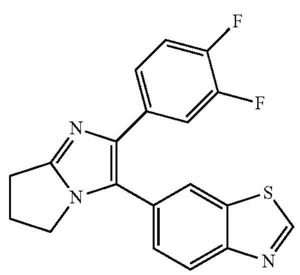 | 6-(2-(3,4-difluorophenyl)-6,7-dihydro-5H-pyrrolo[1,2-a]imidazol-3-yl)benzo[d]thiazole |
| 208 | 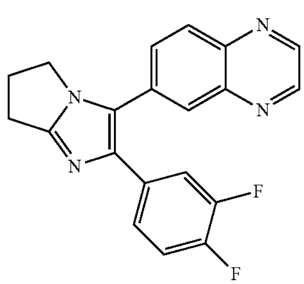 [SMILES: Fc1ccc(-c2nc3n(c2-c2ccc4nccnc4c2)CCC3)cc1F] | 6-(2-(3,4-difluorophenyl)-6,7-dihydro-5H-pyrrolo[1,2-a]imidazol-3-yl)quinoxaline |

| No. | Structure | Name |
|---|---|---|
| 209 | 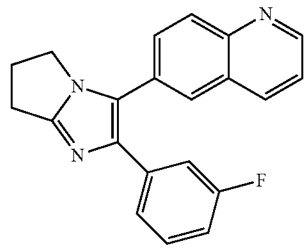 [SMILES: Fc1cccc(-c2nc3n(c2-c2ccc4ncccc4c2)CCC3)c1] | 6-(2-(3-fluorophenyl)-6,7-dihydro-5H-pyrrolo[1,2-a]imidazol-3-yl)quinoline |
| 210 | 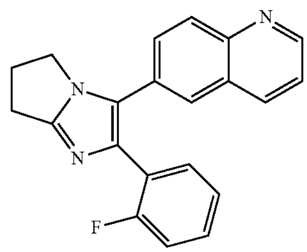 | 6-(2-(2-fluorophenyl)-6,7-dihydro-5H-pyrrolo[1,2-a]imidazol-3-yl)quinoline |
| 211 | 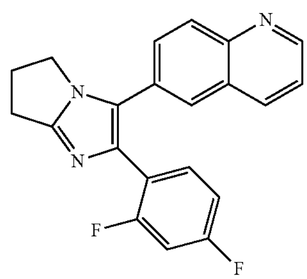 [SMILES: Fc1ccc(-c2nc3n(c2-c2ccc4ncccc4c2)CCC3)c(F)c1] | 6-(2-(2,4-difluorophenyl)-6,7-dihydro-5H-pyrrolo[1,2-a]imidazol-3-yl)quinoline |
| 212 | 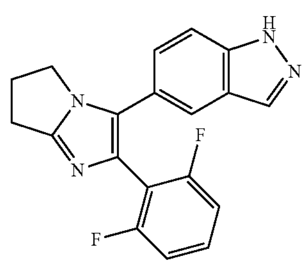 [SMILES: Fc1cccc(F)c1-c1nc2n(c1-c1ccc3[nH]ncc3c1)CCC2] | 5-(2-(2,6-difluorophenyl)-6,7-dihydro-5H-pyrrolo[1,2-a]imidazol-3-yl)-1H-indazole |
| 213 | 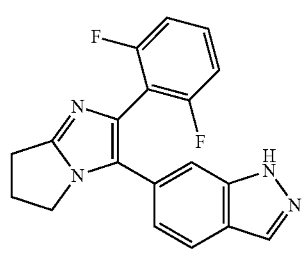 [SMILES: Fc1cccc(F)c1-c1nc2n(c1-c1ccc3cn[nH]c3c1)CCC2] | 6-(2-(2,6-difluorophenyl)-6,7-dihydro-5H-pyrrolo[1,2-a]imidazol-3-yl)-1H-indazole |
| 214 | 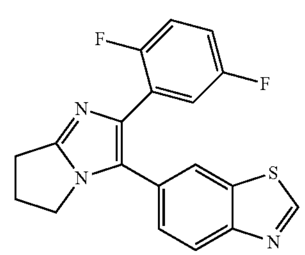 [SMILES: Fc1ccc(F)c(-c2nc3n(c2-c2ccc4ncsc4c2)CCC3)c1] | 6-(2-(2,6-difluorophenyl)-6,7-dihydro-5H-pyrrolo[1,2-a]imidazol-3-yl)benzo[d]thiazole |

-continued

| No. | Structure | Name |
|---|---|---|
| 215 | 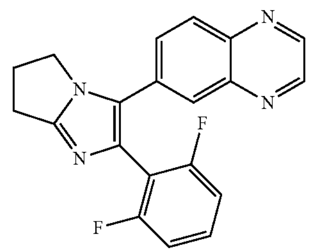 [SMILES: Fc1cccc(F)c1-c1nc2n(c1-c1ccc3nccnc3c1)CCC2] | 6-(2-(2,6-difluorophenyl)-6,7-dihydro-5H-pyrrolo[1,2-a]imidazol-3-yl)quinoxaline |
| 216 | 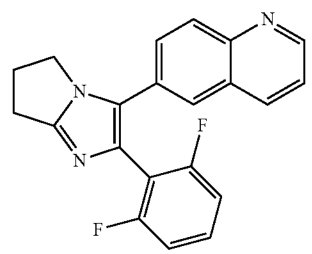 [SMILES: Fc1cccc(F)c1-c1nc2n(c1-c1ccc3ncccc3c1)CCC2] | 6-(2-(2,6-difluorophenyl)-6,7-dihydro-5H-pyrrolo[1,2-a]imidazol-3-yl)quinoline |
| 217 | 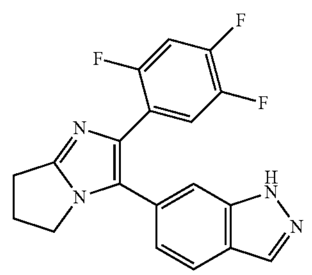 [SMILES: Fc1cc(F)c(-c2nc3n(c2-c2ccc4cn[nH]c4c2)CCC3)cc1F] | 6-(2-(2,4,5-trifluorophenyl)-6,7-dihydro-5H-pyrrolo[1,2-a]imidazol-3-yl)-1H-indazole |
| 218 | 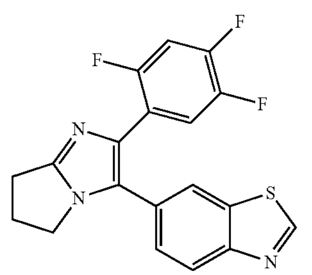 [SMILES: Fc1cc(F)c(-c2nc3n(c2-c2ccc4ncsc4c2)CCC3)cc1F] | 6-(2-(2,4,5-trifluorophenyl)-6,7-dihydro-5H-pyrrolo[1,2-a]imidazol-3-yl)benzo[d]thiazole |
| 219 | 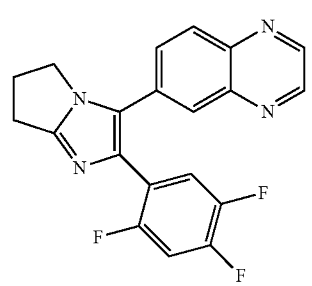 [SMILES: Fc1cc(F)c(-c2nc3n(c2-c2ccc4nccnc4c2)CCC3)cc1F] | 6-(2-(2,4,5-trifluorophenyl)-6,7-dihydro-5H-pyrrolo[1,2-a]imidazol-3-yl)quinoxaline |

-continued

| No. | Structure | Name |
|---|---|---|
| 220 | 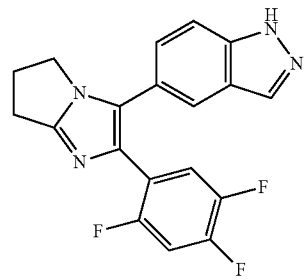 [SMILES: Fc1cc(F)c(-c2nc3n(c2-c2ccc4[nH]ncc4c2)CCC3)cc1F] | 5-(2-(2,4,5-trifluorophenyl)-6,7-dihydro-5H-pyrrolo[1,2-a]imidazol-3-yl)-1H-indazole |
| 221 | 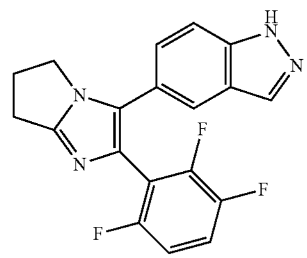 [SMILES: Fc1ccc(F)c(-c2nc3n(c2-c2ccc4[nH]ncc4c2)CCC3)c1F] | 5-(2-(2,3,6-trifluorophenyl)-6,7-dihydro-5H-pyrrolo[1,2-a]imidazol-3-yl)-1H-indazole |
| 222 | 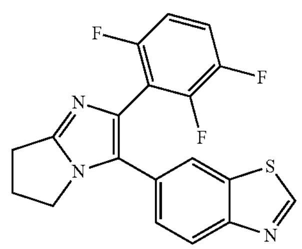 [SMILES: Fc1ccc(F)c(-c2nc3n(c2-c2ccc4ncsc4c2)CCC3)c1F] | 6-(2-(2,3,6-trifluorophenyl)-6,7-dihydro-5H-pyrrolo[1,2-a]imidazol-3-yl)benzo[d]thiazole |
| 223 | 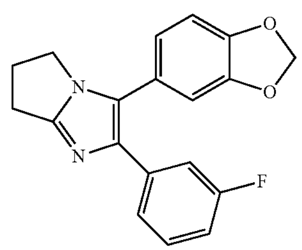 [SMILES: Fc1cccc(-c2nc3n(c2-c2ccc4c(c2)OCO4)CCC3)c1] | 3-(benzo[d][1,3]dioxol-5-yl)-2-(3-fluorophenyl)-6,7-dihydro-5H-pyrrolo[1,2-a]imidazole |
| 224 | 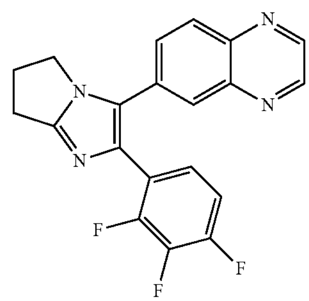 [SMILES: Fc1ccc(-c2nc3n(c2-c2ccc4nccnc4c2)CCC3)c(F)c1F] | 6-(2-(2,3,4-trifluorophenyl)-6,7-dihydro-5H-pyrrolo[1,2-a]imidazol-3-yl)quinoxaline |

| No. | Structure | Name |
| --- | --- | --- |
| 225 | 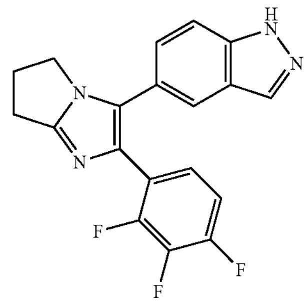 [SMILES: Fc1ccc(-c2nc3n(c2-c2ccc4[nH]ncc4c2)CCC3)c(F)c1F] | 5-(2-(2,3,4-trifluorophenyl)-6,7-dihydro-5H-pyrrolo[1,2-a]imidazol-3-yl)-1H-indazole |
| 226 | 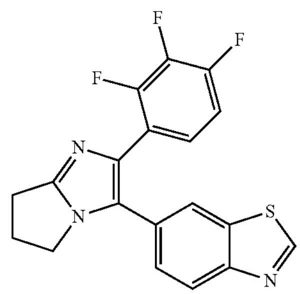 | 6-(2-(2,3,4-trifluorophenyl)-6,7-dihydro-5H-pyrrolo[1,2-a]imidazol-3-yl)benzo[d]thiazole |
| 227 | 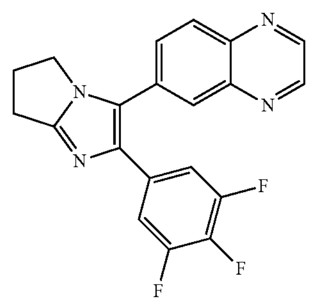 [SMILES: Fc1cc(-c2nc3n(c2-c2ccc4nccnc4c2)CCC3)cc(F)c1F] | 6-(2-(3,4,5-trifluorophenyl)-6,7-dihydro-5H-pyrrolo[1,2-a]imidazol-3-yl)quinoxaline |
| 228 | 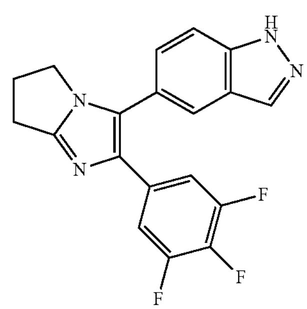 [SMILES: Fc1cc(-c2nc3n(c2-c2ccc4[nH]ncc4c2)CCC3)cc(F)c1F] | 5-(2-(3,4,5-trifluorophenyl)-6,7-dihydro-5H-pyrrolo[1,2-a]imidazol-3-yl)-1H-indazole |
| 229 | 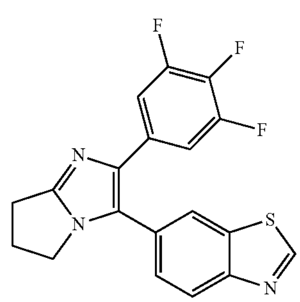 [SMILES: Fc1cc(-c2nc3n(c2-c2ccc4ncsc4c2)CCC3)cc(F)c1F] | 6-(2-(3,4,5-trifluorophenyl)-6,7-dihydro-5H-pyrrolo[1,2-a]imidazol-3-yl)benzo[d]thiazole |

-continued

| No. | Structure | Name |
|---|---|---|
| 230 | 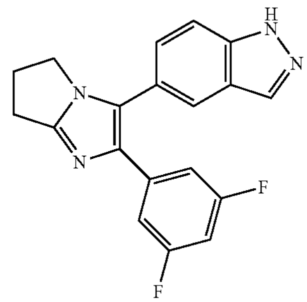 [SMILES: Fc1cc(F)cc(-c2nc3n(c2-c2ccc4[nH]ncc4c2)CCC3)c1] | 5-(2-(3,5-difluorophenyl)-6,7-dihydro-5H-pyrrolo[1,2-a]imidazol-3-yl)-1H-indazole |
| 231 | 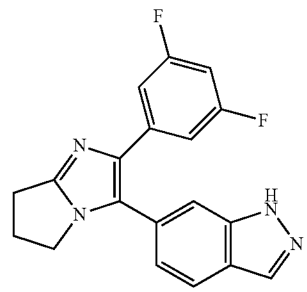 [SMILES: Fc1cc(F)cc(-c2nc3n(c2-c2ccc4cn[nH]c4c2)CCC3)c1] | 6-(2-(3,5-difluorophenyl)-6,7-dihydro-5H-pyrrolo[1,2-a]imidazol-3-yl)-1H-indazole |
| 232 | 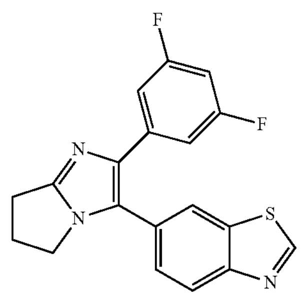 [SMILES: Fc1cc(F)cc(-c2nc3n(c2-c2ccc4ncsc4c2)CCC3)c1] | 6-(2-(3,5-difluorophenyl)-6,7-dihydro-5H-pyrrolo[1,2-a]imidazol-3-yl)benzo[d]thiazole |
| 233 | 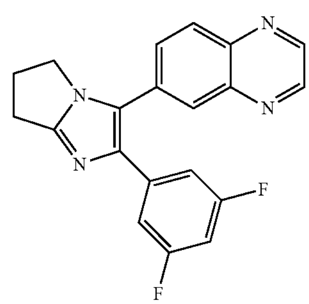 [SMILES: Fc1cc(F)cc(-c2nc3n(c2-c2ccc4nccnc4c2)CCC3)c1] | 6-(2-(3,5-difluorophenyl)-6,7-dihydro-5H-pyrrolo[1,2-a]imidazol-3-yl)quinoxaline |
| 234 | 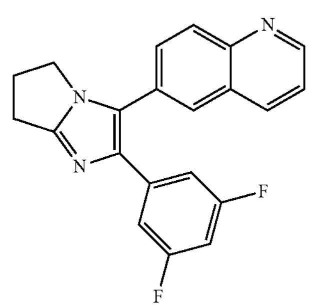 [SMILES: Fc1cc(F)cc(-c2nc3n(c2-c2ccc4ncccc4c2)CCC3)c1] | 6-(2-(3,5-difluorophenyl)-6,7-dihydro-5H-pyrrolo[1,2-a]imidazol-3-yl)quinoline |

| No. | Structure | Name |
|---|---|---|
| 235 | 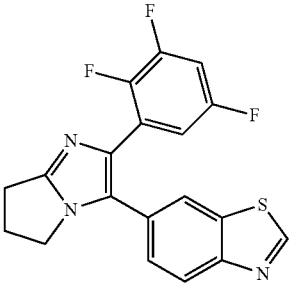 [SMILES: Fc1cc(F)c(F)c(-c2nc3n(c2-c2ccc4ncsc4c2)CCC3)c1] | 6-(2-(2,3,5-trifluorophenyl)-6,7-dihydro-5H-pyrrolo[1,2-a]imidazol-3-yl)benzo[d]thiazole |
| 236 | 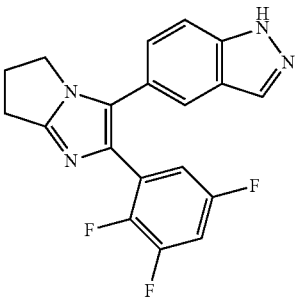 [SMILES: Fc1cc(F)c(F)c(-c2nc3n(c2-c2ccc4[nH]ncc4c2)CCC3)c1] | 5-(2-(2,3,5-trifluorophenyl)-6,7-dihydro-5H-pyrrolo[1,2-a]imidazol-3-yl)-1H-indazole |
| 237 | 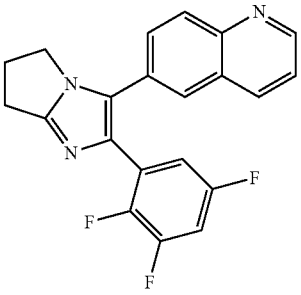 [SMILES: Fc1cc(F)c(F)c(-c2nc3n(c2-c2ccc4ncccc4c2)CCC3)c1] | 6-(2-(2,3,5-trifluorophenyl)-6,7-dihydro-5H-pyrrolo[1,2-a]imidazol-3-yl)quinoline |
| 238 | 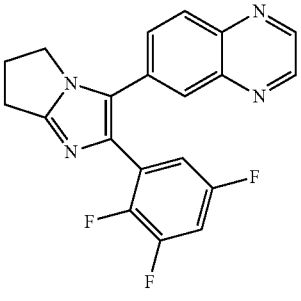 [SMILES: Fc1cc(F)c(F)c(-c2nc3n(c2-c2ccc4nccnc4c2)CCC3)c1] | 6-(2-(2,3,5-trifluorophenyl)-6,7-dihydro-5H-pyrrolo[1,2-a]imidazol-3-yl)quinoxaline |
| 239 | 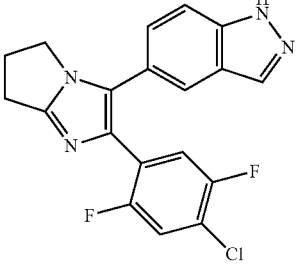 | 5-(2-(4-chloro-2,5-difluorophenyl)-6,7-dihydro-5H-pyrrolo[1,2-a]imidazol-3-yl)-1H-indazole |

-continued

| No. | Structure | Name |
|---|---|---|
| 240 | 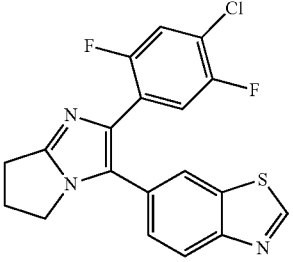 [SMILES: Fc1cc(-c2nc3n(c2-c2ccc4ncsc4c2)CCC3)c(F)cc1Cl] | 6-(2-(4-chloro-2,5-difluorophenyl)-6,7-dihydro-5H-pyrrolo[1,2-a]imidazol-3-yl)benzo[d]thiazole |
| 241 | 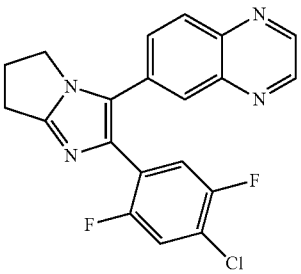 | 6-(2-(4-chloro-2,5-difluorophenyl)-6,7-dihydro-5H-pyrrolo[1,2-a]imidazol-3-yl)quinoxaline |
| 242 | 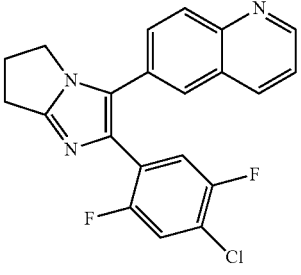 | 6-(2-(4-chloro-2,5-difluorophenyl)-6,7-dihydro-5H-pyrrolo[1,2-a]imidazol-3-yl)quinoline |
| 243 | 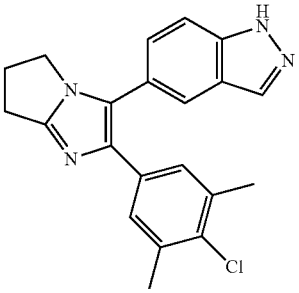 [SMILES: Cc1cc(-c2nc3n(c2-c2ccc4[nH]ncc4c2)CCC3)cc(C)c1Cl] | 5-(2-(4-chloro-3,5-dimethylphenyl)-6,7-dihydro-5H-pyrrolo[1,2-a]imidazol-3-yl)-1H-indazole |
| 244 | 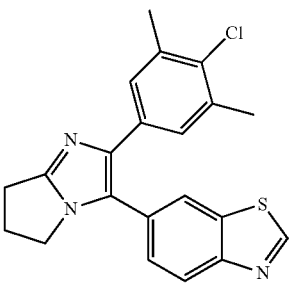 [SMILES: Cc1cc(-c2nc3n(c2-c2ccc4ncsc4c2)CCC3)cc(C)c1Cl] | 6-(2-(4-chloro-3,5-dimethylphenyl)-6,7-dihydro-5H-pyrrolo[1,2-a]imidazol-3-yl)benzo[d]thiazole |

| No. | Structure | Name |
| --- | --- | --- |
| 245 | 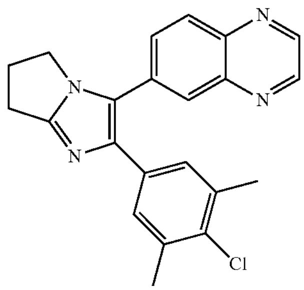 [SMILES: Cc1cc(-c2nc3n(c2-c2ccc4nccnc4c2)CCC3)cc(C)c1Cl] | 6-(2-(4-chloro-3,5-dimethylphenyl)-6,7-dihydro-5H-pyrrolo[1,2-a]imidazol-3-yl)quinoxaline |
| 246 | 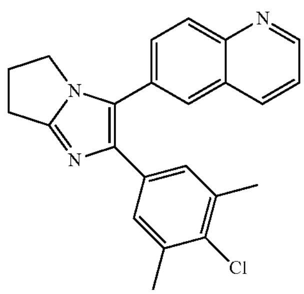 [SMILES: Cc1cc(-c2nc3n(c2-c2ccc4ncccc4c2)CCC3)cc(C)c1Cl] | 6-(2-(4-chloro-3,5-dimethylphenyl)-6,7-dihydro-5H-pyrrolo[1,2-a]imidazol-3-yl)quinoline |
| 247 | 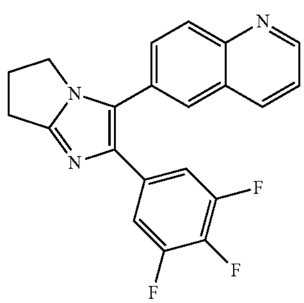 [SMILES: Fc1cc(-c2nc3n(c2-c2ccc4ncccc4c2)CCC3)cc(F)c1F] | 6-(2-(3,4,5-trifluorophenyl)-6,7-dihydro-5H-pyrrolo[1,2-a]imidazol-3-yl)quinoline |
| 248 | 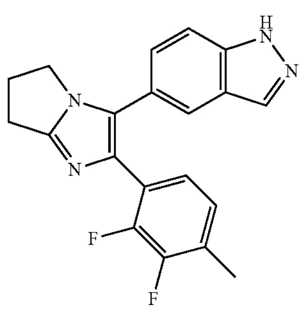 [SMILES: Cc1ccc(-c2nc3n(c2-c2ccc4[nH]ncc4c2)CCC3)c(F)c1F] | 5-(2-(2,3-difluoro-4-methylphenyl)-6,7-dihydro-5H-pyrrolo[1,2-a]imidazol-3-yl)-1H-indazole |
| 249 | 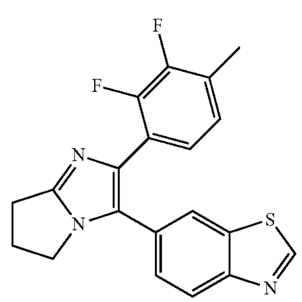 [SMILES: Cc1ccc(-c2nc3n(c2-c2ccc4ncsc4c2)CCC3)c(F)c1F] | 6-(2-(2,3-difluoro-4-methylphenyl)-6,7-dihydro-5H-pyrrolo[1,2-a]imidazol-3-yl)benzo[d]thiazole |

| No. | Structure | Name |
|---|---|---|
| 250 | 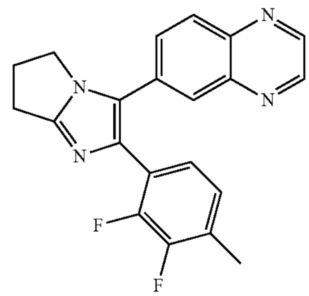 [SMILES: Cc1ccc(-c2nc3n(c2-c2ccc4nccnc4c2)CCC3)c(F)c1F] | 6-(2-(2,3-difluoro-4-methylphenyl)-6,7-dihydro-5H-pyrrolo[1,2-a]imidazol-3-yl)quinoxaline |
| 251 | 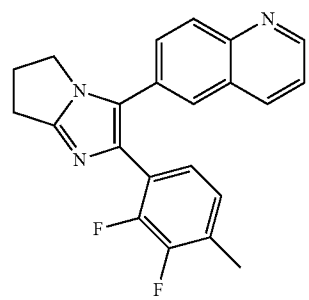 [SMILES: Cc1ccc(-c2nc3n(c2-c2ccc4ncccc4c2)CCC3)c(F)c1F] | 6-(2-(2,3-difluoro-4-methylphenyl)-6,7-dihydro-5H-pyrrolo[1,2-a]imidazol-3-yl)quinoline |
| 252 | 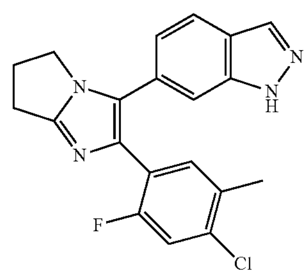 [SMILES: Cc1cc(-c2nc3n(c2-c2ccc4cn[nH]c4c2)CCC3)c(F)cc1Cl] | 6-(2-(4-chloro-2-fluoro-5-methylphenyl)-6,7-dihydro-5H-pyrrolo[1,2-a]imidazol-3-yl)-1H-indazole |
| 253 | 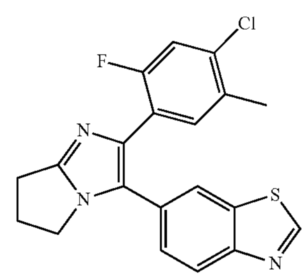 [SMILES: Cc1cc(-c2nc3n(c2-c2ccc4ncsc4c2)CCC3)c(F)cc1Cl] | 6-(2-(4-chloro-2-fluoro-5-methylpheny)-6,7-dihydro-5H-pyrrolo[1,2-a]imidazol-3-yl)benzo[d]thiazole |
| 254 | 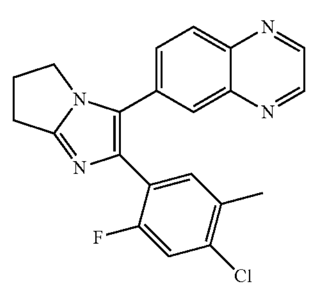 | 6-(2-(4-chloro-2-fluoro-5-methylpheny)-6,7-dihydro-5H-pyrrolo[1,2-a]imidazol-3-yl)quinoxaline |

| No. | Structure | Name |
|---|---|---|
| 255 | 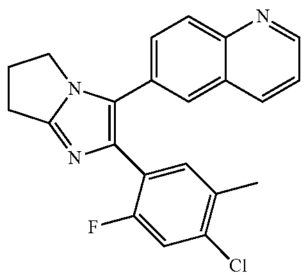 [SMILES: Cc1cc(-c2nc3n(c2-c2ccc4ncccc4c2)CCC3)c(F)cc1Cl] | 6-(2-(4-chloro-2-fluoro-5-methylpheny)-6,7-dihydro-5H-pyrrolo[1,2-a]imidazol-3-yl)quinoline |
| 256 | 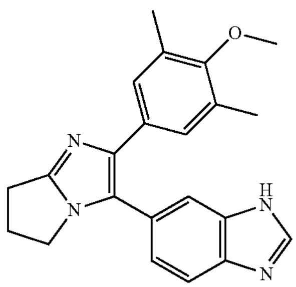 [SMILES: COc1c(C)cc(-c2nc3n(c2-c2ccc4nc[nH]c4c2)CCC3)cc1C] | 6-(2-(4-methoxy-3,5-dimethylphenyl)-6,7-dihydro-5H-pyrrolo[1,2-a]imidazol-3-yl)-1H-indazole |
| 257 | 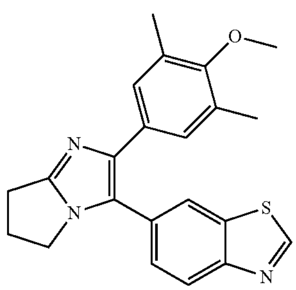 [SMILES: COc1c(C)cc(-c2nc3n(c2-c2ccc4ncsc4c2)CCC3)cc1C] | 6-(2-(4-methoxy-3,5-dimethylphenyl)-6,7-dihydro-5H-pyrrolo[1,2-a]imidazol-3-yl)benzo[d]thiazole |
| 258 | 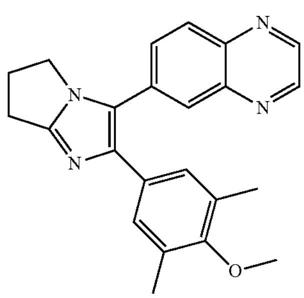 [SMILES: COc1c(C)cc(-c2nc3n(c2-c2ccc4nccnc4c2)CCC3)cc1C] | 6-(2-(4-methoxy-3,5-dimethylphenyl)-6,7-dihydro-5H-pyrrolo[1,2-a]imidaol-3-yl)quinoxaline |
| 259 | 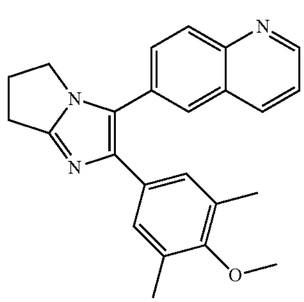 [SMILES: COc1c(C)cc(-c2nc3n(c2-c2ccc4ncccc4c2)CCC3)cc1C] | 6-(2-(4-methoxy-3,5-dimethylphenyl)-6,7-dihydro-5H-pyrrolo[1,2-a]imidazol-3-yl)quinoline |

-continued

| No. | Structure | Name |
|---|---|---|
| 260 | 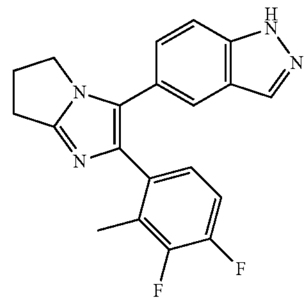 [SMILES: Cc1c(-c2nc3n(c2-c2ccc4[nH]ncc4c2)CCC3)ccc(F)c1F] | 6-(2-(3,4-difluoro-2-methylphenyl)-6,7-dihydro-5H-pyrrolo[1,2-a]imidazol-3-yl)-1H-indazole |
| 261 | 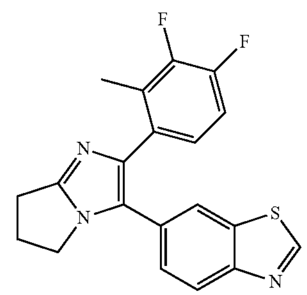 [SMILES: Cc1c(-c2nc3n(c2-c2ccc4ncsc4c2)CCC3)ccc(F)c1F] | 6-(2-(3,4-difluoro-2-methylphenyl)-6,7-dihydro-5H-pyrrolo[1,2-a]imidazol-3-yl)benzo[d]thiazole |
| 262 | 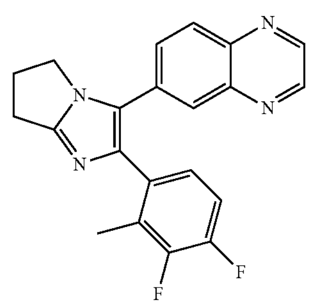 [SMILES: Cc1c(-c2nc3n(c2-c2ccc4nccnc4c2)CCC3)ccc(F)c1F] | 6-(2-(3,4-difluoro-2-methylphenyl)-6,7-dihydro-5H-pyrrolo[1,2-a]imidazol-3-yl)quinoxaline |
| 263 | 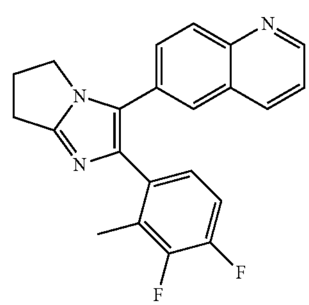 [SMILES: Cc1c(-c2nc3n(c2-c2ccc4ncccc4c2)CCC3)ccc(F)c1F] | 6-(2-(3,4-difluoro-2-methylphenyl)-6,7-dihydro-5H-pyrrolo[1,2-a]imidzaol-3-yl)quinoline |
| 264 | 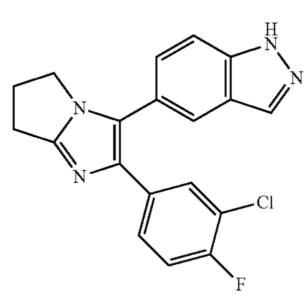 [SMILES: Fc1ccc(-c2nc3n(c2-c2ccc4[nH]ncc4c2)CCC3)cc1Cl] | 5-(2-(3-chloro-4-fluoropheny)-6,7-dihydro-5H-pyrrolo[1,2-a]imidazol-3-yl)-1H-indazole |

| No. | Structure | Name |
|---|---|---|
| 265 | 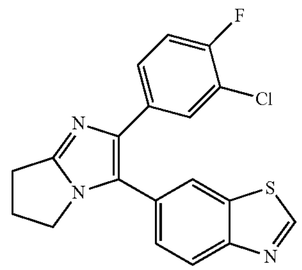 [SMILES: Fc1ccc(-c2nc3n(c2-c2ccc4ncsc4c2)CCC3)cc1Cl] | 6-(2-(3-chloro-4-fluoropheny)-6,7-dihydro-5H-pyrrolo[1,2-a]imidazol-3-yl)benzo[d]thiazole |
| 266 | 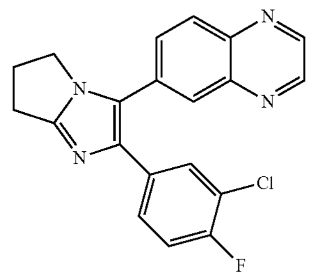 [SMILES: Fc1ccc(-c2nc3n(c2-c2ccc4nccnc4c2)CCC3)cc1Cl] | 6-(2-(3-chloro-4-fluoropheny)-6,7-dihydro-5H-pyrrolo[1,2-a]imidazol-3-yl)quinoxaline |
| 267 | 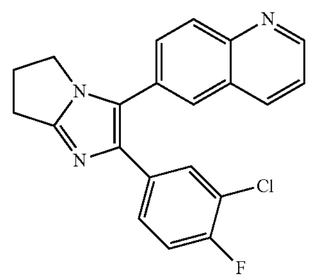 [SMILES: Fc1ccc(-c2nc3n(c2-c2ccc4ncccc4c2)CCC3)cc1Cl] | 6-(2-(3-chloro-4-fluoropheny)-6,7-dihydro-5H-pyrrolo[1,2-a]imidazol-3-yl)quinoline |
| 268 | 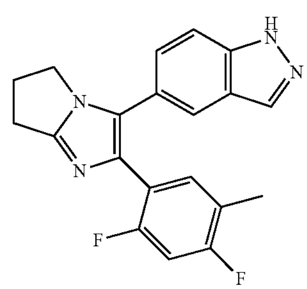 | 5-(2-(2,4-difluoro-5-methylphenyl)-6,7-dihydro-5H-pyrrolo[1,2-a]imidazol-3-yl)-1H-indazole |
| 269 | 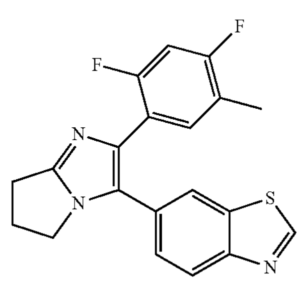 [SMILES: Cc1cc(-c2nc3n(c2-c2ccc4ncsc4c2)CCC3)c(F)cc1F] | 6-(2-(2,4-difluoro-5-methylphenyl)-6,7-dihydro-5H-pyrrolo[1,2-a]imidaozl-3-yl)benzo[d]thiazole |

-continued

| No. | Structure | Name |
|---|---|---|
| 270 | 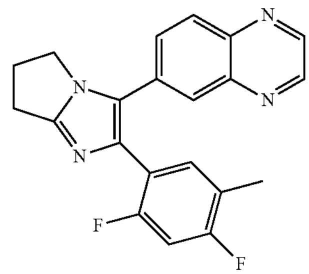 | 6-(2-(2,4-difluoro-5-methylphenyl)-6,7-dihydro-5H-pyrrolo[1,2-a]imidazol-3-yl)quinoxaline |
| 271 | 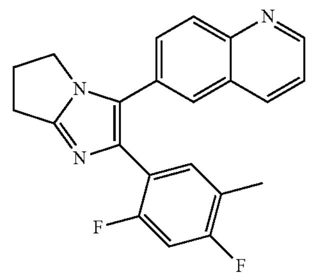 | 6-(2-(2,4-difluoro-5-methylphenyl)-6,7-dihydro-5H-pyrrolo[1,2-a]imidazol-3-yl)quinoline |
| 272 | 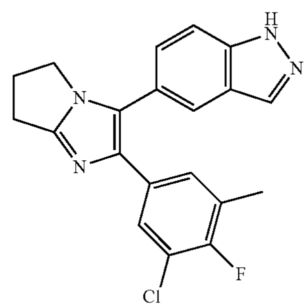 [SMILES: Cc1cc(-c2nc3n(c2-c2ccc4[nH]ncc4c2)CCC3)cc(Cl)c1F] | 5-(2-(3-chloro-4-fluoro-5-methylphenyl)-6,7-dihydro-5H-pyrrolo[1,2-a]imidazol-3-yl)-1H-indazole |
| 273 | 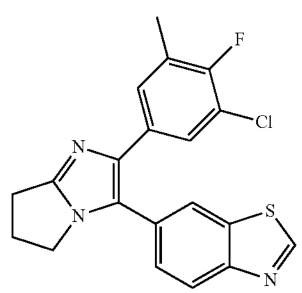 [SMILES: Cc1cc(-c2nc3n(c2-c2ccc4ncsc4c2)CCC3)cc(Cl)c1F] | 6-(2-(3-chloro-4-fluoro-5-methylpheny)-6,7-dihydro-5H-pyrrolo[1,2-a]imidazol-3-yl)benzo[d]thiazole |
| 274 | 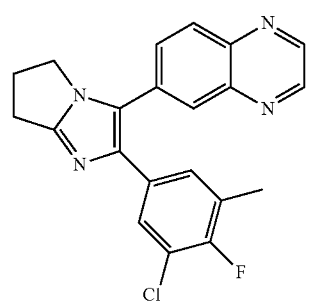 [SMILES: Cc1cc(-c2nc3n(c2-c2ccc4nccnc4c2)CCC3)cc(Cl)c1F] | 6-(2-(3-chloro-4-fluoro-5-methylpheny)-6,7-dihydro-5H-pyrrolo[1,2-a]imidazol-3-yl)quinoxaline |

| No. | Structure | Name |
|---|---|---|
| 275 | 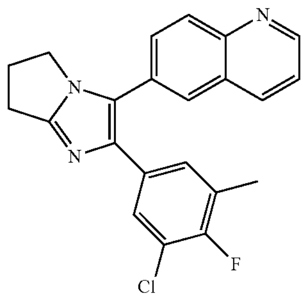 [SMILES: Cc1cc(-c2nc3n(c2-c2ccc4ncccc4c2)CCC3)cc(Cl)c1F] | 6-(2-(3-chloro-4-fluoro-5-methylpheny)-6,7-dihydro-5H-pyrrolo[1,2-a]imidazol-3-yl)quinoline |
| 276 | 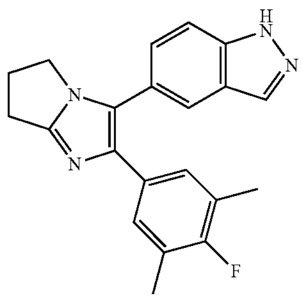 [SMILES: Cc1cc(-c2nc3n(c2-c2ccc4[nH]ncc4c2)CCC3)cc(C)c1F] | 5-(2-(4-fluoro-3,5-dimethylphenyl)-6,7-dihydro-5H-pyrrolo[1,2-a]imidazol-3-yl)-1H-indazole |
| 277 | 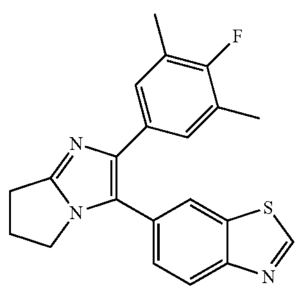 [SMILES: Cc1cc(-c2nc3n(c2-c2ccc4ncsc4c2)CCC3)cc(C)c1F] | 6-(2-(4-fluoro-3,5-dimethylphenyl)-6,7-dihydro-5H-pyrrolo[1,2-a]imidazol-3-yl)benzo[d]thiazole |
| 278 | 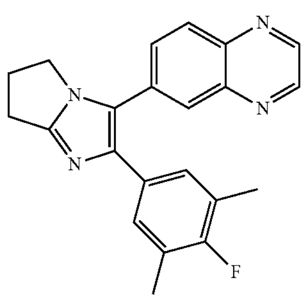 [SMILES: Cc1cc(-c2nc3n(c2-c2ccc4nccnc4c2)CCC3)cc(C)c1F] | 6-(2-(4-fluoro-3,5-dimethylphenyl)-6,7-dihydro-5H-pyrrolo[1,2-a]imidazol-3-yl)quinoxaline |
| 279 | 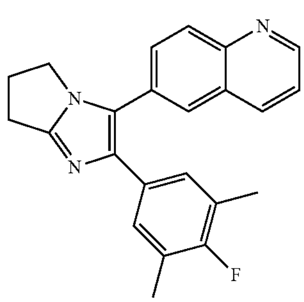 [SMILES: Cc1cc(-c2nc3n(c2-c2ccc4ncccc4c2)CCC3)cc(C)c1F] | 6-(4-fluoro-3,5-dimethylphenyl)-6,7-dihydro-5H-pyrrolo[1,2-a]imidazol-3-yl)quinoline |

| No. | Structure | Name |
|---|---|---|
| 280 | 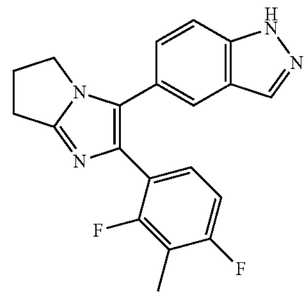 [SMILES: Cc1c(F)ccc(-c2nc3n(c2-c2ccc4[nH]ncc4c2)CCC3)c1F] | 5-(2-(2,4-difluoro-3-methylphenyl)-6,7-dihydro-5H-pyrrolo[1,2-a]imidazol-3-yl)-1H-indazole |
| 281 | 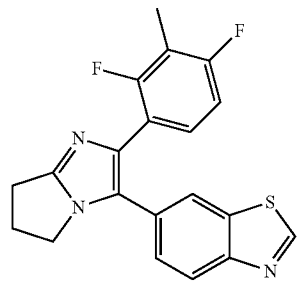 [SMILES: Cc1c(F)ccc(-c2nc3n(c2-c2ccc4ncsc4c2)CCC3)c1F] | 6-(2-(2,4-difluoro-3-methylphenyl)-6,7-dihydro-5H-pyrrolo[1,2-a]imidazol-3-yl)benzo[d]thiazol |
| 282 | 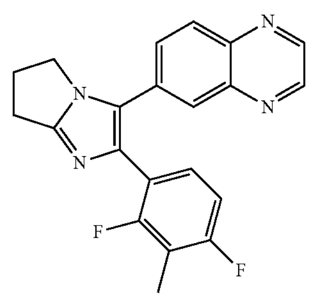 | 6-(2-(2,4-difluoro-3-methylphenyl)-6,7-dihydro-5H-pyrrolo[1,2-a]imidazol-3-yl)quinoxaline |
| 283 | 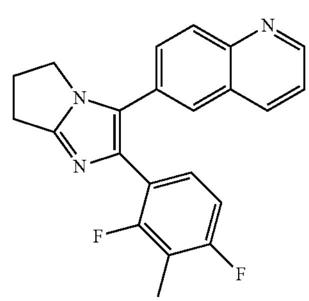 [SMILES: Cc1c(F)ccc(-c2nc3n(c2-c2ccc4ncccc4c2)CCC3)c1F] | 6-(2-(2,4-difluoro-3-methylphenyl)-6,7-dihydro-5H-pyrrolo[1,2-a]imidazol-3-yl)quinoline |
| 284 | 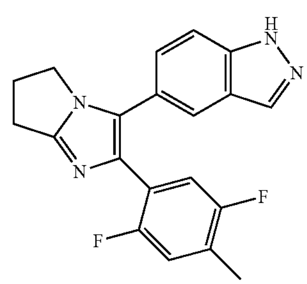 [SMILES: Cc1cc(F)c(-c2nc3n(c2-c2ccc4[nH]ncc4c2)CCC3)cc1F] | 5-(2-(2,5-difluoro-4-methylphenyl)-6,7-dihydro-5H-pyrrolo[1,2-a]imidazol-3-yl)-1H-indazole |

| No. | Structure | Name |
|---|---|---|
| 285 | 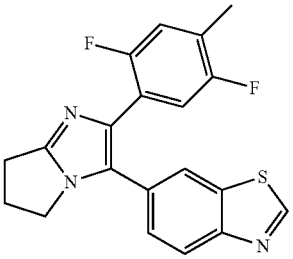 [SMILES: Cc1cc(F)c(-c2nc3n(c2-c2ccc4ncsc4c2)CCC3)cc1F] | 6-(2-(2,5-difluoro-4-methylphenyl)-6,7-dihydro-5H-pyrrolo[1,2-a]imidazol-3-yl)benzo[d]thiazole |
| 286 | 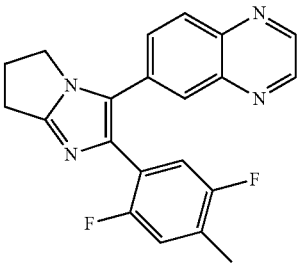 [SMILES: Cc1cc(F)c(-c2nc3n(c2-c2ccc4nccnc4c2)CCC3)cc1F] | 6-(2-(2,5-difluoro-4-methylphenyl)-6,7-dihydro-5H-pyrrolo[1,2-a]imidazol-3-yl)quinoxaline |
| 287 | 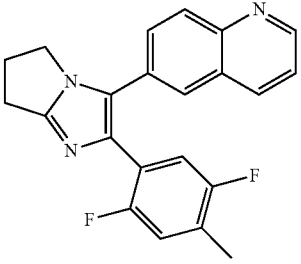 [SMILES: Cc1cc(F)c(-c2nc3n(c2-c2ccc4ncccc4c2)CCC3)cc1F] | 6-(2-(2,5-difluoro-4-methylphenyl)-6,7-dihydro-5H-pyrrolo[1,2-a]imidazol-3-yl)quinoline |
| 288 | 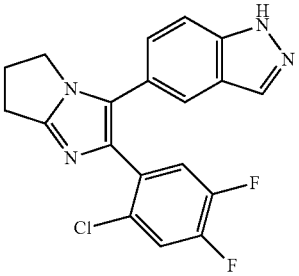 | 5-(2-(2-chloro-4,5-difluorophenyl)-6,7-dihydro-5H-pyrrolo[1,2-a]imidazol-3-yl)-1H-indazole |
| 289 | 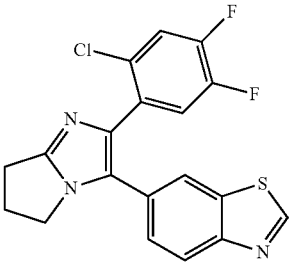 [SMILES: Fc1cc(Cl)c(-c2nc3n(c2-c2ccc4ncsc4c2)CCC3)cc1F] | 6-(2-(2-chloro-4,5-difluorophenyl)-6,7-dihydro-5H-pyrrolo[1,2-a]imidazol-3-yl)benzo[d]thiazole |

-continued

| No. | Structure | Name |
|---|---|---|
| 290 | 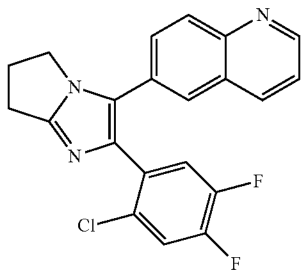 | 6-(2-(2-chloro-4,5-difluorophenyl)-6,7-dihydro-5H-pyrrolo[1,2-a]imidazol-3-yl)quinoline |
| 291 | 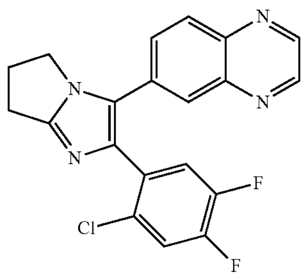 | 6-(2-(2-chloro-4,5-difluorophenyl)-6,7-dihydro-5H-pyrrolo[1,2-a]imidazol-3-yl)quinoxaline |
| 292 | 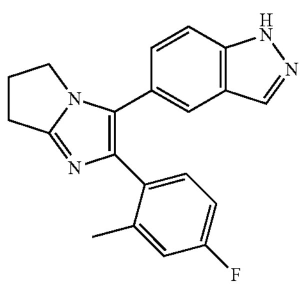 [SMILES: Cc1cc(F)ccc1-c1nc2n(c1-c1ccc3[nH]ncc3c1)CCC2] | 5-(2-(4-fluoro-2-methylphenyl)-6,7-dihydro-5H-pyrrolo[1,2-a]imidazol-3-yl)-1H-indazole |
| 293 | 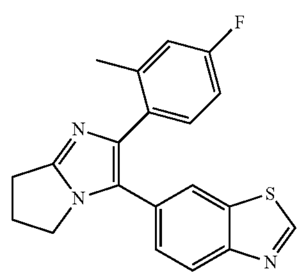 [SMILES: Cc1cc(F)ccc1-c1nc2n(c1-c1ccc3ncsc3c1)CCC2] | 6-(2-(4-fluoro-2-methylphenyl)-6,7-dihydro-5H-pyrrolo[1,2-a]imidazol-3-yl)benzo[d]thiazole |
| 294 | 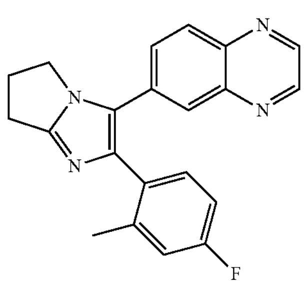 [SMILES: Cc1cc(F)ccc1-c1nc2n(c1-c1ccc3nccnc3c1)CCC2] | 6-(2-(4-fluoro-2-methylphenyl)-6,7-dihydro-5H-pyrrolo[1,2-a]imidazol-3-yl)quinoxaline |

| No. | Structure | Name |
|---|---|---|
| 295 | 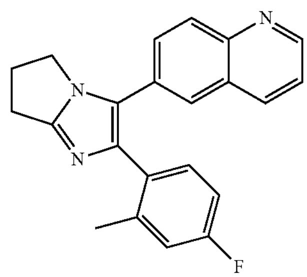 [SMILES: Cc1cc(F)ccc1-c1nc2n(c1-c1ccc3ncccc3c1)CCC2] | 6-(2-(4-fluoro-2-methylphenyl)-6,7-dihydro-5H-pyrrolo[1,2-a]imidazol-3-yl)quinoline |
| 296 | 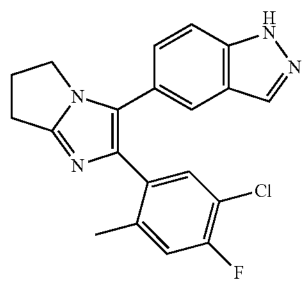 [SMILES: Cc1cc(F)c(Cl)cc1-c1nc2n(c1-c1ccc3[nH]ncc3c1)CCC2] | 5-(2-(5-chloro-4-fluoro-2-methylphenyl)-6,7-dihydro-5H-pyrrolo[1,2-a]imidaol-3-yl)-1H-indazole |
| 297 | 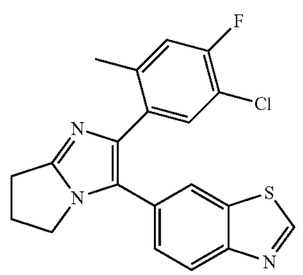 [SMILES: Cc1cc(F)c(Cl)cc1-c1nc2n(c1-c1ccc3ncsc3c1)CCC2] | 6-(2-(5-chloro-4-fluoro-2-methylphenyl)-6,7-dihydro-5H-pyrrolo[1,2-a]imidazol-3-yl)benzo[d]thiazole |
| 298 | 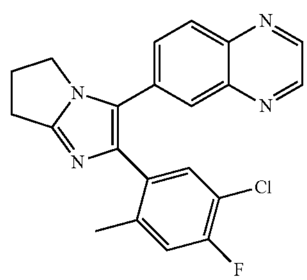 [SMILES: Cc1cc(F)c(Cl)cc1-c1nc2n(c1-c1ccc3nccnc3c1)CCC2] | 6-(2-(5-chloro-4-fluoro-2-methylphenyl)-6,7-dihydro-5H-pyrrolo[1,2-a]imidazol-3-yl)quinoxaline |
| 299 | 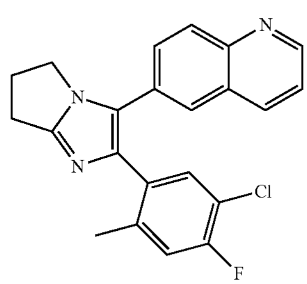 [SMILES: Cc1cc(F)c(Cl)cc1-c1nc2n(c1-c1ccc3ncccc3c1)CCC2] | 6-(2-(5-chloro-4-fluoro-2-methylphenyl)-6,7-dihydro-5H-pyrrolo[1,2-a]imidazol-3-yl)quinoline |

-continued

| No. | Structure | Name |
|---|---|---|
| 300 | 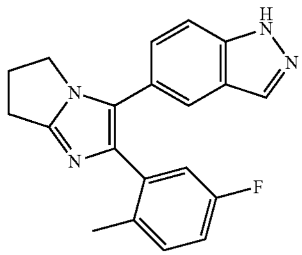 [SMILES: Cc1ccc(F)cc1-c1nc2n(c1-c1ccc3[nH]ncc3c1)CCC2] | 5-(2-(5-fluoro-2-methylphenyl)-6,7-dihydro-5H-pyrrolo[1,2-a]imidazol-3-yl)-1H-indazole |
| 301 | 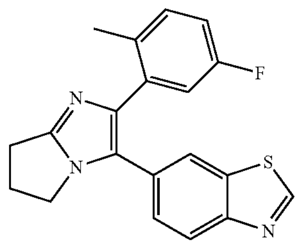 [SMILES: Cc1ccc(F)cc1-c1nc2n(c1-c1ccc3ncsc3c1)CCC2] | 6-(2-(5-fluoro-2-methylphenyl)-6,7-dihydro-5H-pyrrolo[1,2-a]imidazol-3-yl)benzo[d]thiazole |
| 302 | 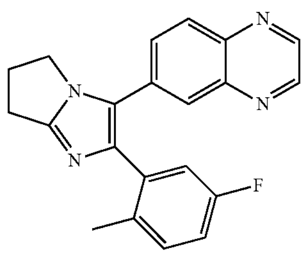 [SMILES: Cc1ccc(F)cc1-c1nc2n(c1-c1ccc3nccnc3c1)CCC2] | 6-(2-(5-fluoro-2-methylphenyl)-6,7-dihydro-5H-pyrrolo[1,2-a]imidazol-3-yl)quinoxaline |
| 303 | 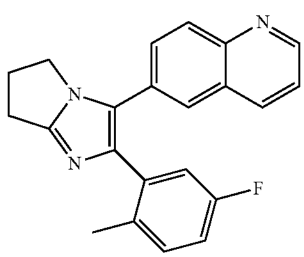 [SMILES: Cc1ccc(F)cc1-c1nc2n(c1-c1ccc3ncccc3c1)CCC2] | 6-(5-fluoro-2-methylphenyl)-6,7-dihydro-5H-pyrrolo[1,2-a]imidazol-3-yl)quinoline |
| 304 | 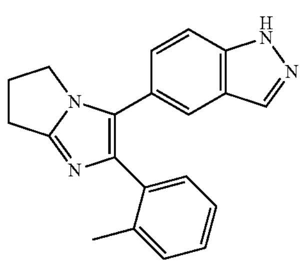 [SMILES: Cc1ccccc1-c1nc2n(c1-c1ccc3[nH]ncc3c1)CCC2] | 5-(2-(o-tolyl)-6,7-dihydro-5H-pyrrolo[1,2-a]imidazol-3-yl)-1H-indazole |
| 305 | 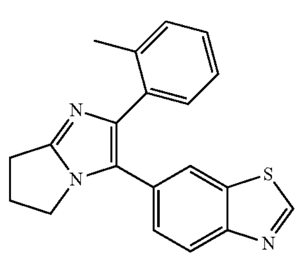 [SMILES: Cc1ccccc1-c1nc2n(c1-c1ccc3ncsc3c1)CCC2] | 6-(2-(o-tolyl)-6,7-dihydro-5H-pyrrolo[1,2-a]imidazol-3-yl)benzo[d]thiazole |

-continued

| No. | Structure | Name |
|---|---|---|
| 306 | 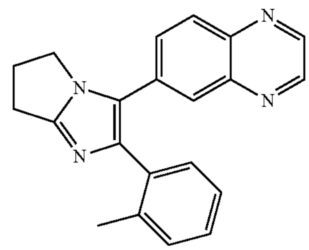 [SMILES: Cc1ccccc1-c1nc2n(c1-c1ccc3nccnc3c1)CCC2] | 6-(2-(o-tolyl)-6,7-dihydro-5H-pyrrolo[1,2-a]imidazol-3-yl)quinoxaline |
| 307 | 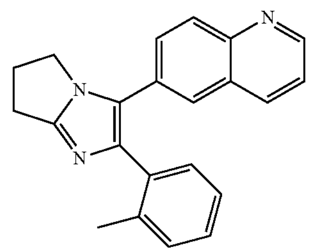 [SMILES: Cc1ccccc1-c1nc2n(c1-c1ccc3ncccc3c1)CCC2] | 6-(2-(o-tolyl)-6,7-dihydro-5H-pyrrolo[1,2-a]imidazol-3-yl)quinoline |
| 308 | 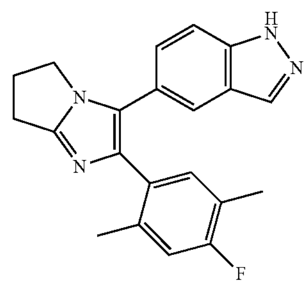 [SMILES: Cc1cc(-c2nc3n(c2-c2ccc4[nH]ncc4c2)CCC3)c(C)cc1F] | 5-(2-(4-fluoro-2,5-dimethylphenyl)-6,7-dihydro-5H-pyrrolo[1,2-a]imidaol-3-yl)-1H-indazole |
| 309 | 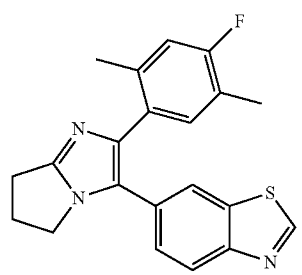 [SMILES: Cc1cc(-c2nc3n(c2-c2ccc4ncsc4c2)CCC3)c(C)cc1F] | 6-(2-(4-fluoro-2,5-dimethylphenyl)-6,7-dihydro-5H-pyrrolo[1,2-a]imidazol-3-yl)benzo[d]thiazole |
| 310 | 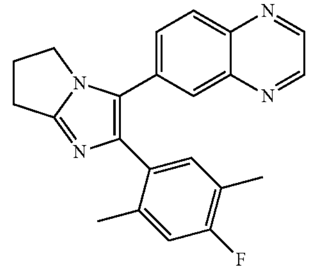 [SMILES: Cc1cc(-c2nc3n(c2-c2ccc4nccnc4c2)CCC3)c(C)cc1F] | 6-(2-(4-fluoro-2,5-dimethylphenyl)-6,7-dihydro-5H-pyrrolo[1,2-a]imidazol-3-yl)quinoxaline |

-continued

| No. | Structure | Name |
|---|---|---|
| 311 | 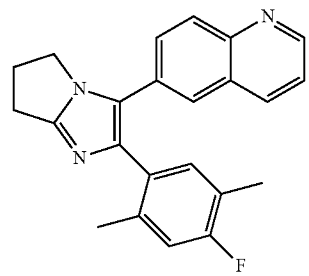 [SMILES: Cc1cc(-c2nc3n(c2-c2ccc4ncccc4c2)CCC3)c(C)cc1F] | 6-(2-(4-fluoro-2,5-dimethylphenyl)-6,7-dihydro-5H-pyrrolo[1,2-a]imidazol-3-yl)quinoline |
| 312 | 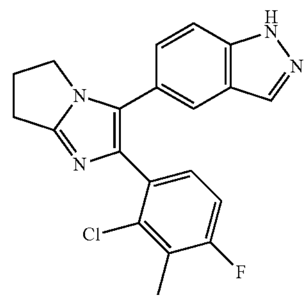 [SMILES: Cc1c(F)ccc(-c2nc3n(c2-c2ccc4[nH]ncc4c2)CCC3)c1Cl] | 5-(2-(2-chloro-4-fluoro-3-methylphenyl)-6,7-dihydro-5H-pyrrolo[1,2-a]imidazol-3-yl)-1H-indazole |
| 313 | 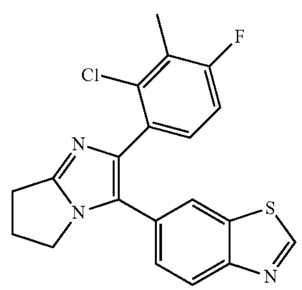 | 6-(2-(2-chloro-4-fluoro-3-methylphenyl)-6,7-dihydro-5H-pyrrolo[1,2-a]imidazol-3-yl)benzo[d]thiazole |
| 314 | 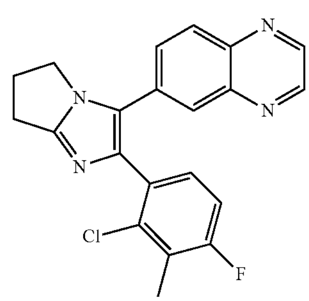 [SMILES: Cc1c(F)ccc(-c2nc3n(c2-c2ccc4nccnc4c2)CCC3)c1Cl] | 6-(2-(2-chloro-4-fluoro-3-methylphenyl)-6,7-dihydro-5H-pyrrolo[1,2-a]imidazol-3-yl)quinoxaline |
| 315 | 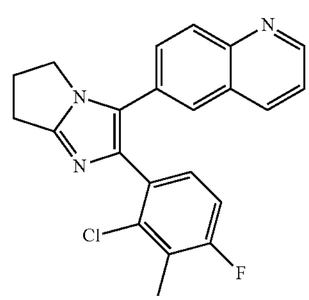 [SMILES: Cc1c(F)ccc(-c2nc3n(c2-c2ccc4ncccc4c2)CCC3)c1Cl] | 6-(2-(2-chloro-4-fluoro-3-methylphenyl)-6,7-dihydro-5H-pyrrolo[1,2-a]imidazol-3-yl)quinoline |

-continued

| No. | Structure | Name |
|---|---|---|
| 316 | 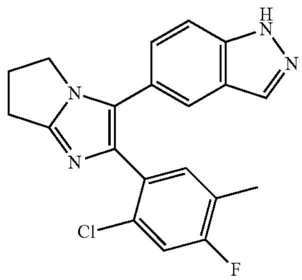 [SMILES: Cc1cc(-c2nc3n(c2-c2ccc4[nH]ncc4c2)CCC3)c(Cl)cc1F] | 5-(2-(2-chloro-4-fluoro-5-methylphenyl)-6,7-dihydro-5H-pyrrolo[1,2-a]imidazol-3-yl)-1H-indazole |
| 317 | 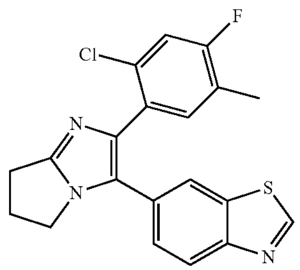 [SMILES: Cc1cc(-c2nc3n(c2-c2ccc4ncsc4c2)CCC3)c(Cl)cc1F] | 6-(2-(2-chloro-4-fluoro-5-methylphenyl)-6,7-dihydro-5H-pyrrolo[1,2-a]imidazol-3-yl)benzo[d]thiazole |
| 318 | 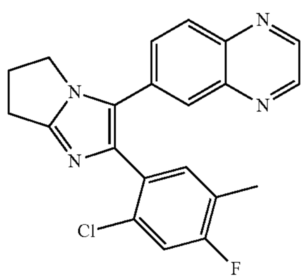 [SMILES: Cc1cc(-c2nc3n(c2-c2ccc4nccnc4c2)CCC3)c(Cl)cc1F] | 6-(2-(2-chloro-4-fluoro-5-methylphenyl)-6,7-dihydro-5H-pyrrolo[1,2-a]imidazol-3-yl)quinoxaline |
| 319 | 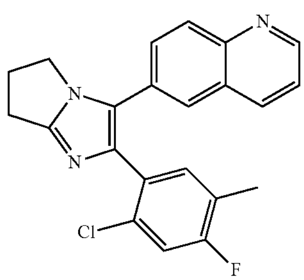 [SMILES: Cc1cc(-c2nc3n(c2-c2ccc4ncccc4c2)CCC3)c(Cl)cc1F] | 6-(2-(2-chloro-4-fluoro-5-methylphenyl)-6,7-dihydro-5H-pyrrolo[1,2-a]imidazol-3-yl)quinoline |
| 320 | 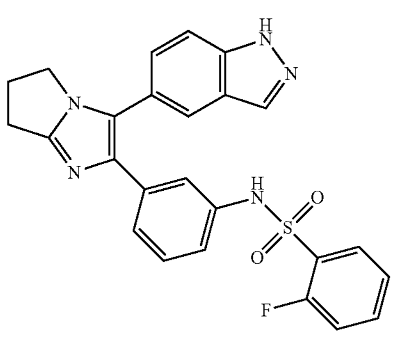 [SMILES: O=S(=O)(Nc1cccc(-c2nc3n(c2-c2ccc4[nH]ncc4c2)CCC3)c1)c1ccccc1F] | N-(3-(3-(1H-indazol-5-yl)-6,7-dihydro-5H-pyrrolo[1,2-a]imidazol-2-yl)phenyl)-2-fluorobenzenesulfonamide |

| No. | Structure | Name |
| --- | --- | --- |
| 321 | 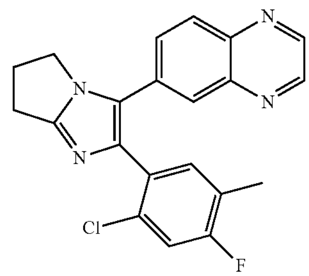 [SMILES: Cc1cc(-c2nc3n(c2-c2ccc4nccnc4c2)CCC3)c(Cl)cc1F] | 6-(2-(2-chloro-4-fluoro-5-methylphenyl)-6,7-dihydro-5H-pyrrolo[1,2-a]imidazol-3-yl)quinoxaline |
| 322 | 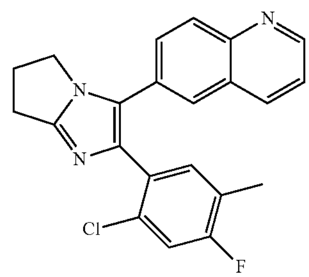 [SMILES: Cc1cc(-c2nc3n(c2-c2ccc4ncccc4c2)CCC3)c(Cl)cc1F] | 6-(2-(2-chloro-4-fluoro-5-methylphenyl)-6,7-dihydro-5H-pyrrolo[1,2-a]imidazol-3-yl)quinoline |
| 323 | 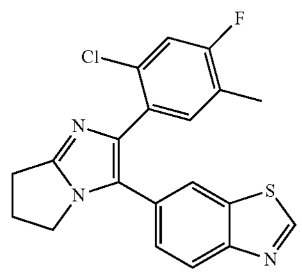 | 6-(2-(2-chloro-4-fluoro-5-methylphenyl)-6,7-dihydro-5H-pyrrolo[1,2-a]imidazol-3-yl)benzo[d]thiazole |
| 324 | 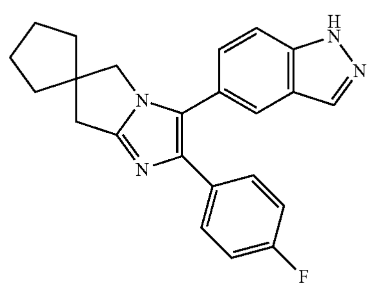 [SMILES: Fc1ccc(-c2nc3n(c2-c2ccc4[nH]ncc4c2)CC2(CCCC2)C3)cc1] | 2'-(4-fluorophenyl)-3'-(1H-indazol-5-yl)-5'H,7'H-spiro[cyclopentane-1,6'-pyrrolo[1,2-a]imidazole] |
| 325 | 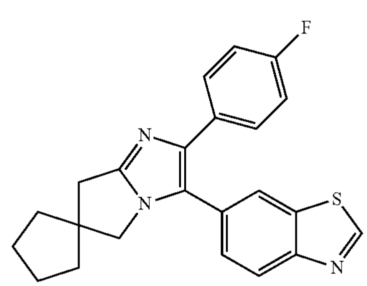 [SMILES: Fc1ccc(-c2nc3n(c2-c2ccc4ncsc4c2)CC2(CCCC2)C3)cc1] | 6-(2'-(4-fluorophenyl)-5'H,7'H-spiro[cyclopentane-1,6'-pyrrolo[1,2-a]imidazol]-3'-yl)benzo[d]thiazole |

| No. | Structure | Name |
|---|---|---|
| 326 | 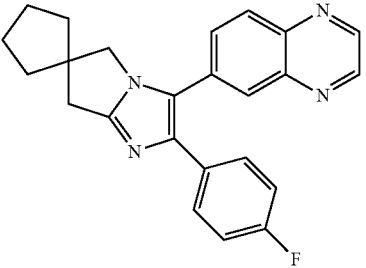 [SMILES: Fc1ccc(-c2nc3n(c2-c2ccc4nccnc4c2)CC2(CCCC2)C3)cc1] | 2'-(4-fluorophenyl)-3'-(quinoxalin-6-yl)-5'H,7'H-spiro[cyclopentane-1,6'-pyrrolo[1,2-a]imidazole] |
| 327 | 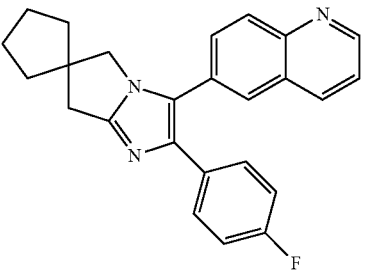 [SMILES: Fc1ccc(-c2nc3n(c2-c2ccc4ncccc4c2)CC2(CCCC2)C3)cc1] | 2'-(4-fluorophenyl)-3'-(quinolin-6-yl)-5'H,7'H-spiro[cyclopentane-1,6'-pyrrolo[1,2-a]imidazole] |
| 328 | 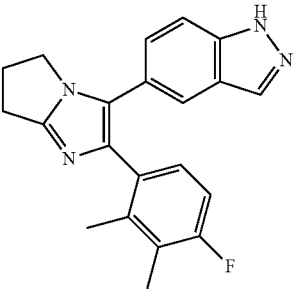 [SMILES: Cc1c(F)ccc(-c2nc3n(c2-c2ccc4[nH]ncc4c2)CCC3)c1C] | 5-(2-(4-fluoro-2,3-dimethylphenyl)-6,7-dihydro-5H-pyrrolo[1,2-a]imidazol-3-yl)-1H-indazole |
| 329 | 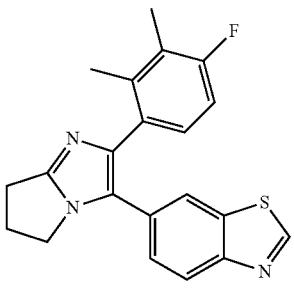 | 6-(2-(4-fluoro-2,3-dimethylphenyl)-6,7-dihydro-5H-pyrrolo[1,2-a]imidazol-3-yl)benzo[d]thiazole |
| 330 | 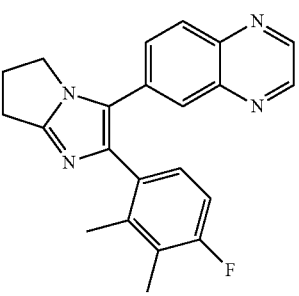 [SMILES: Cc1c(F)ccc(-c2nc3n(c2-c2ccc4nccnc4c2)CCC3)c1C] | 6-(2-(4-fluoro-2,3-dimethylphenyl)-6,7-dihydro-5H-pyrrolo[1,2-a]imidazol-3-yl)quinoxaline |

-continued

| No. | Structure | Name |
|---|---|---|
| 331 | 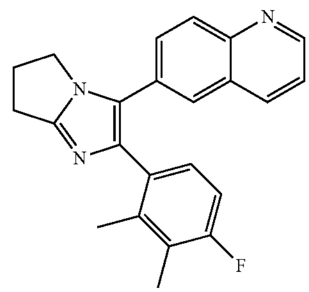 [SMILES: Cc1c(F)ccc(-c2nc3n(c2-c2ccc4ncccc4c2)CCC3)c1C] | 6-(2-(4-fluoro-2,3-dimethylphenyl)-6,7-dihydro-5H-pyrrolo[1,2-a]imidazol-3-yl)quinoline |
| 332 | 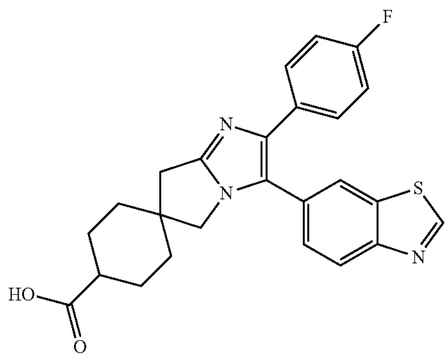 [SMILES: O=C(O)C1CCC2(CC1)Cc1nc(-c3ccc(F)cc3)c(-c3ccc4ncsc4c3)n1C2] | 3'-(benzo[d]thiazol-6-yl)-2'-(4-fluorophenyl)-5'H,7'H-spiro[cyclohexane-1,6'-pyrrolo[1,2-a]imidazole]-4-carboxylic acid |
| 333 | 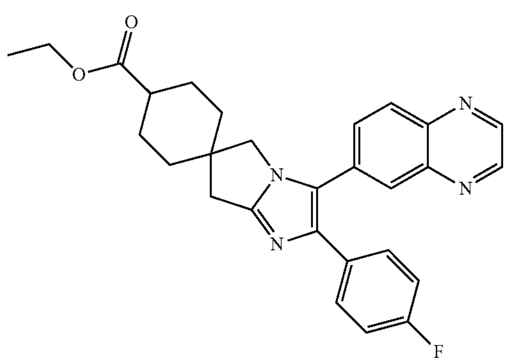 [SMILES: CCOC(=O)C1CCC2(CC1)Cc1nc(-c3ccc(F)cc3)c(-c3ccc4nccnc4c3)n1C2] | Ethyl 2'-(4-fluorophenyl)-3'-(quinoxalin-6-yl)-5'H,7'H-spiro[cyclohexane-1,6'-pyrrolo[1,2-a]imidazole]-4-carboxylate |
| 334 | 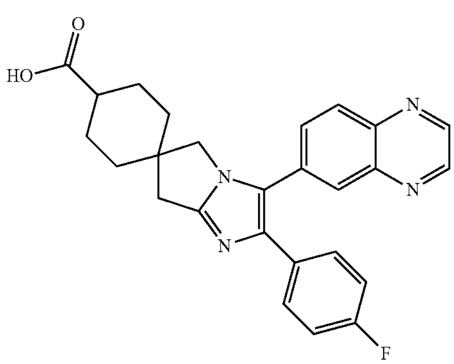 [SMILES: O=C(O)C1CCC2(CC1)Cc1nc(-c3ccc(F)cc3)c(-c3ccc4nccnc4c3)n1C2] | 2'-(4-fluorophenyl)-3'-(quinoxalin-6-yl)-5'H,7'H-spiro[cyclohexane-1,6'-pyrrolo[1,2-a]imidazole]-4-carboxylic acid |

-continued

| No. | Structure | Name |
|---|---|---|
| 335 | 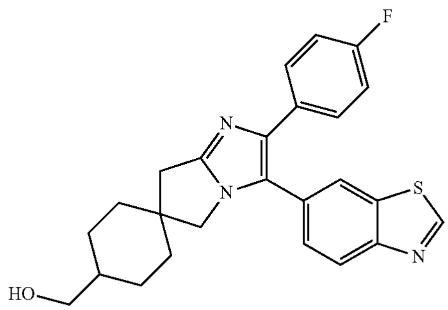 [SMILES: OCC1CCC2(CC1)Cc1nc(-c3ccc(F)cc3)c(-c3ccc4ncsc4c3)n1C2] | (3'-(benzo[d]thiazol-6-yl)-2'-(4-fluorophenyl)-5'H,7'H-spiro[cyclohexane-1,6'-pyrrolo[1,2-a]imidazol]-4-yl)methanol |
| 336 | 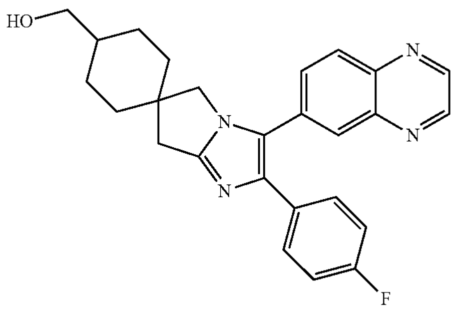 [SMILES: OCC1CCC2(CC1)Cc1nc(-c3ccc(F)cc3)c(-c3ccc4nccnc4c3)n1C2] | (2'-(4-fluorophenyl)-3'-(quinoxalin-6-yl)-5'H,7'H-spiro[cyclohexane-1,6'-pyrrolo[1,2-a]imidazol]-4-yl)methanol |
| 337 | 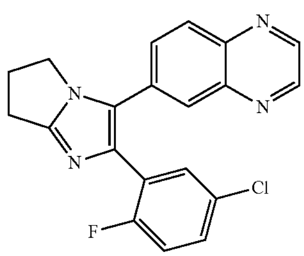 [SMILES: Fc1ccc(Cl)cc1-c1nc2n(c1-c1ccc3nccnc3c1)CCC2] | 6-(2-(5-chloro-2-fluoropheny)-6,7-dihydro-5H-pyrrolo[1,2-a]imidazol-3-yl)quinoxaline |
| 338 | 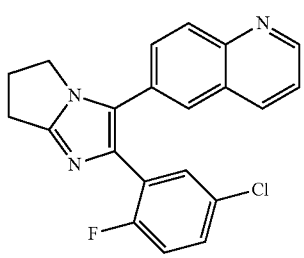 [SMILES: Fc1ccc(Cl)cc1-c1nc2n(c1-c1ccc3ncccc3c1)CCC2] | 6-(2-(5-chloro-2-fluoropheny)-6,7-dihydro-5H-pyrrolo[1,2-a]imidazol-3-yl)quinoline |
| 339 | 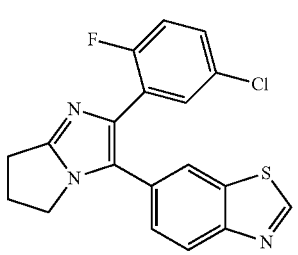 [SMILES: Fc1ccc(Cl)cc1-c1nc2n(c1-c1ccc3ncsc3c1)CCC2] | 6-(2-(5-chloro-2-fluoropheny)-6,7-dihydro-5H-pyrrolo[1,2-a]imidazol-3-yl)benzo[d]thiazole |

| No. | Structure | Name |
|---|---|---|
| 340 | 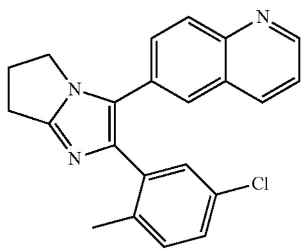 [SMILES: Cc1ccc(Cl)cc1-c1nc2n(c1-c1ccc3ncccc3c1)CCC2] | 6-(2-(5-chloro-2-methylpheny)-6,7-dihydro-5H-pyrrolo[1,2-a]imidazol-3-yl)quinoline |
| 341 | 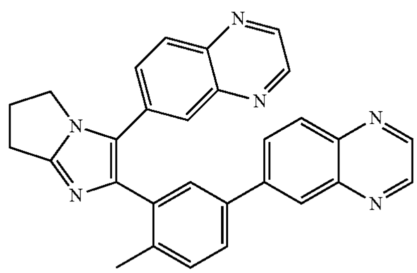 [SMILES: Cc1ccc(-c2ccc3nccnc3c2)cc1-c1nc2n(c1-c1ccc3nccnc3c1)CCC2] | 6-(4-methyl-3-(3-(quinoxalin-6-yl)-6,7-dihydro-5H-pyrrolo[1,2-a]imidazol-2-yl)phenyl)quinoxaline |
| 342 | 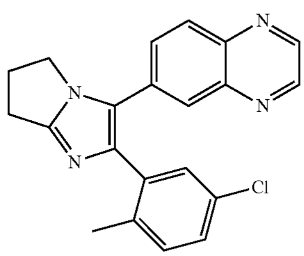 [SMILES: Cc1ccc(Cl)cc1-c1nc2n(c1-c1ccc3nccnc3c1)CCC2] | 6-(2-(5-chloro-2-methylpheny)-6,7-dihydro-5H-pyrrolo[1,2-a]imidazol-3-yl)quinoxaline |
| 343 | 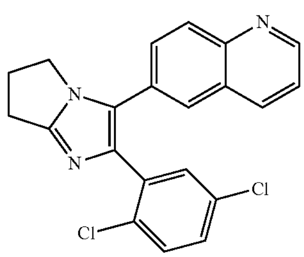 [SMILES: Clc1ccc(Cl)c(-c2nc3n(c2-c2ccc4ncccc4c2)CCC3)c1] | 6-(2-(2,5-dichlorophenyl)-6,7-dihydro-5H-pyrrolo[1,2-a]imidazol-3-yl)quinoline |
| 344 | 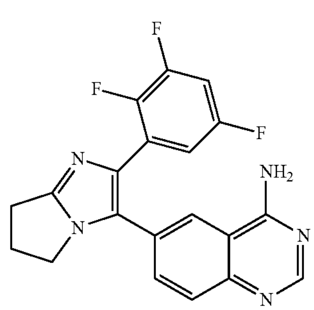 [SMILES: Nc1ncnc2ccc(-c3c(-c4cc(F)cc(F)c4F)nc4n3CCC4)cc12] | 6-(2-(2,3,5-trifluorophenyl)-6,7-dihydro-5H-pyrrolo[1,2-a]imidazol-3-yl)quinazolin-4-amine |

-continued

| No. | Structure | Name |
|---|---|---|
| 345 | 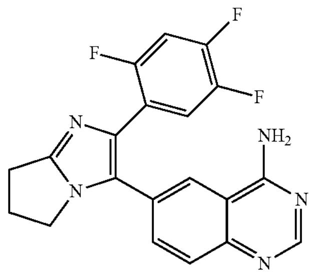 [SMILES: Nc1ncnc2ccc(-c3c(-c4cc(F)c(F)cc4F)nc4n3CCC4)cc12] | 6-(2-(2,4,5-trifluorophenyl)-6,7-dihydro-5H-pyrrolo[1,2-a]imidazol-3-yl)quinazolin-4-amine |
| 346 | 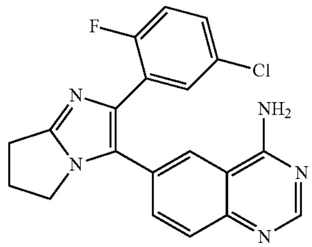 [SMILES: Nc1ncnc2ccc(-c3c(-c4cc(Cl)ccc4F)nc4n3CCC4)cc12] | 6-(2-(5-chloro-2-fluorophenyl)-6,7-dihydro-5H-pyrrolo[1,2-a]imidazol-3-yl)quinazolin-4-amine |
| 347 | 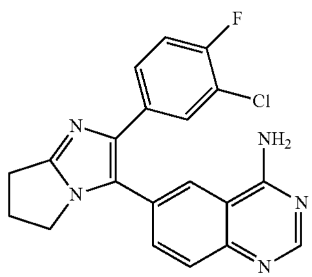 [SMILES: Nc1ncnc2ccc(-c3c(-c4ccc(F)c(Cl)c4)nc4n3CCC4)cc12] | 6-(2-(3-chloro-4-fluorophenyl)-6,7-dihydro-5H-pyrrolo[1,2-a]imidazol-3-yl)quinazolin-4-amine |
| 348 | 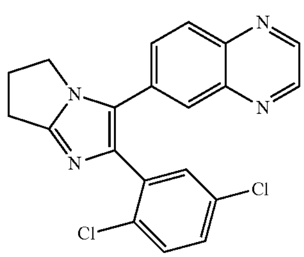 [SMILES: Clc1ccc(Cl)c(-c2nc3n(c2-c2ccc4nccnc4c2)CCC3)c1] | 6-(2-(2,5-dichloropheny)-6,7-dihydro-5H-pyrrolo[1,2-a]imidazol-3-yl)quinoxaline |
| 349 | 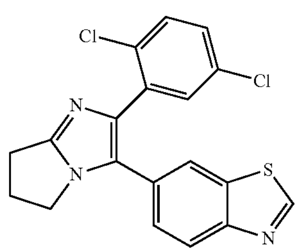 [SMILES: Clc1ccc(Cl)c(-c2nc3n(c2-c2ccc4ncsc4c2)CCC3)c1] | 6-(2-(2,5-dichlorophenyl)-6,7-dihydro-5H-pyrrolo[1,2-a]imidazol-3-yl)benzo[d]thiazole |
| 350 | 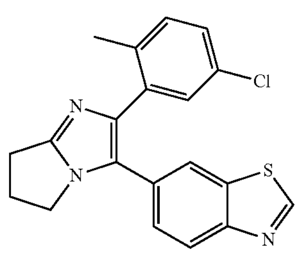 [SMILES: Cc1ccc(Cl)cc1-c1nc2n(c1-c1ccc3ncsc3c1)CCC2] | 6-(2-(5-chloro-2-methylphenyl)-6,7-dihydro-5H-pyrrolo[1,2-a]imidazol-3-yl)benzo[d]thiazole |

US 10,696,693 B2

169 170

-continued

| No. | Structure | Name |
|---|---|---|
| 351 | 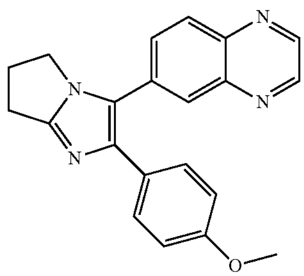 [SMILES: COc1ccc(-c2nc3n(c2-c2ccc4nccnc4c2)CCC3)cc1] | 6-(2-(4-methoxyphenyl)-6,7-dihydro-5H-pyrrolo[1,2-a]imidazol-3-yl)quinoxaline |
| 352 | 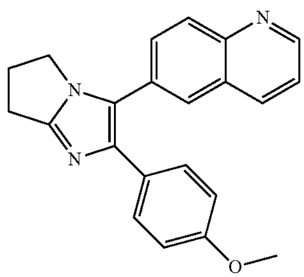 [SMILES: COc1ccc(-c2nc3n(c2-c2ccc4ncccc4c2)CCC3)cc1] | 6-(2-(4-methoxyphenyl)-6,7-dihydro-5H-pyrrolo[1,2-a]imidazol-3-yl)quinoline |
| 353 | 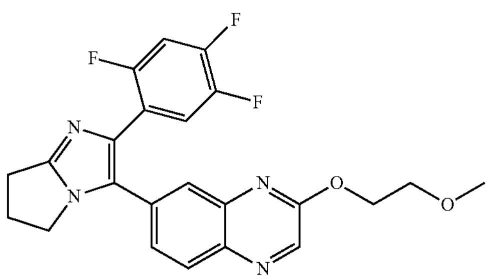 [SMILES: COCCOc1cnc2ccc(-c3c(-c4cc(F)c(F)cc4F)nc4n3CCC4)cc2n1] | 2-(2-methoxyethoxy)-7-(2-(2,4,5-trifluorophenyl)-6,7-dihydro-5H-pyrrolo[1,2-a]imidazol-3-yl)quinoxaline |
| 354 | 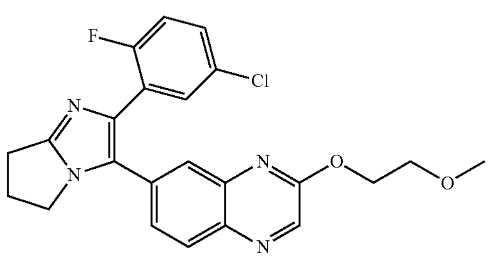 [SMILES: COCCOc1cnc2ccc(-c3c(-c4cc(Cl)ccc4F)nc4n3CCC4)cc2n1] | 7-(2-(5-chloro-2-fluorophenyl)-6,7-dihydro-5H-pyrrolo[1,2-a]imidazol-3-yl)-2-(2-methoxyethoxy)quinoxaline |
| 355 | 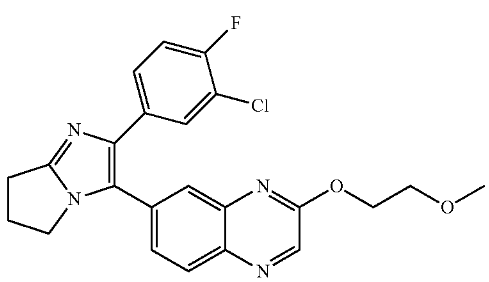 [SMILES: COCCOc1cnc2ccc(-c3c(-c4ccc(F)c(Cl)c4)nc4n3CCC4)cc2n1] | 7-(2-(3-chloro-4-fluorophenyl)-6,7-dihydro-5H-pyrrolo[1,2-a]imidazol-3-yl)-2-(2-methoxyethoxy)quinoxaline |

-continued

| No. | Structure | Name |
|---|---|---|
| 356 | 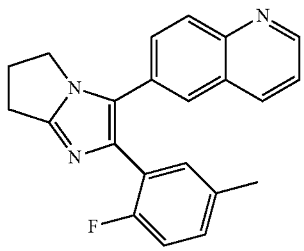 [SMILES: Cc1ccc(F)c(-c2nc3n(c2-c2ccc4ncccc4c2)CCC3)c1] | 6-(2-(2-fluoro-5-methylphenyl)-6,7-dihydro-5H-pyrrolo[1,2-a]imidazol-3-yl)quinoline |
| 357 | 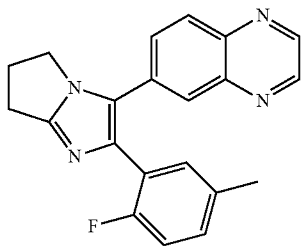 [SMILES: Cc1ccc(F)c(-c2nc3n(c2-c2ccc4nccnc4c2)CCC3)c1] | 6-(2-(2-fluoro-5-methylphenyl)-6,7-dihydro-5H-pyrrolo[1,2-a]imidazol-3-yl)quinoxaline |
| 358 | 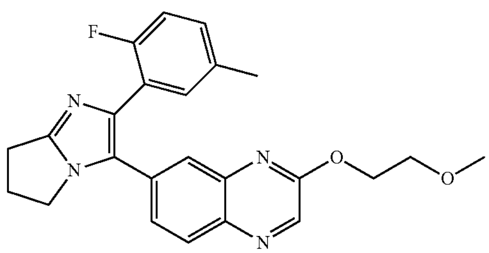 [SMILES: COCCOc1cnc2ccc(-c3c(-c4cc(C)ccc4F)nc4n3CCC4)cc2n1] | 7-(2-(2-fluoro-5-methylphenyl)-6,7-dihydro-5H-pyrrolo[1,2-a]imidazol-3-yl)-2-(2-methoxyethoxy)quinoxaline |
| 359 | 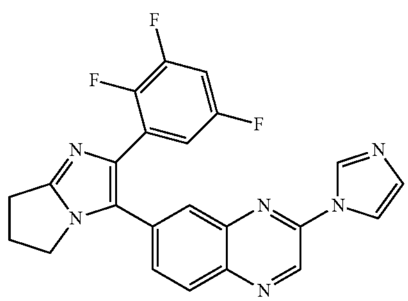 [SMILES: Fc1cc(F)c(F)c(-c2nc3n(c2-c2ccc4ncc(-n5ccnc5)nc4c2)CCC3)c1] | 2-(1H-imidazol-1-yl)-7-(2-(2,3,5-trifluorophenyl)-6,7-dihydro-5H-pyrrolo[1,2-a]imidazol-3-yl)quinoxaline |
| 360 | 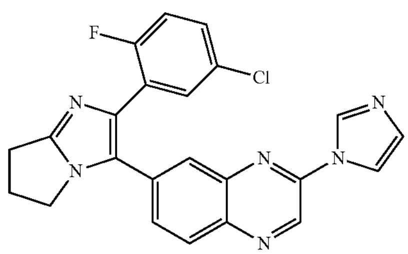 [SMILES: Fc1ccc(Cl)cc1-c1nc2n(c1-c1ccc3ncc(-n4ccnc4)nc3c1)CCC2] | 7-(2-(5-chloro-2-fluorophenyl)-6,7-dihydro-5H-pyrrolo[1,2-a]imidazol-3-yl)-2-(1H-imidazol-1-yl)quinoxaline |

-continued

| No. | Structure | Name |
|---|---|---|
| 361 | 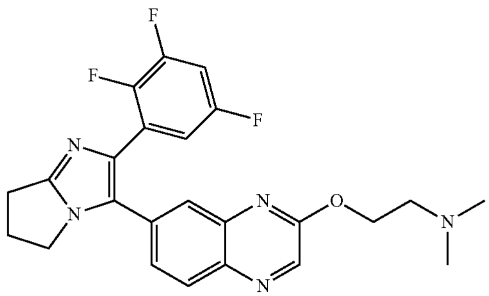 [SMILES: CN(C)CCOc1cnc2ccc(-c3c(-c4cc(F)cc(F)c4F)nc4n3CCC4)cc2n1] | N,N-dimethyl-2-((7-(2-(2,3,5-trifluorophenyl)-6,7-dihydro-5H-pyrrolo[1,2-a]imidazol-3-yl)quinoxalin-2-yl)oxy)ethan-1-amine |
| 362 | 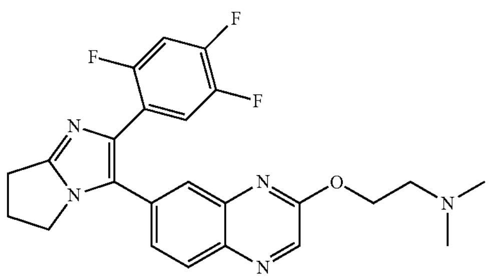 [SMILES: CN(C)CCOc1cnc2ccc(-c3c(-c4cc(F)c(F)cc4F)nc4n3CCC4)cc2n1] | N,N-dimethyl-2-((7-(2-(2,4,5-trifluorophenyl)-6,7-dihydro-5H-pyrrolo[1,2-a]imidazol-3-yl)quinoxalin-2-yl)oxy)ethan-1-amine |
| 363 | 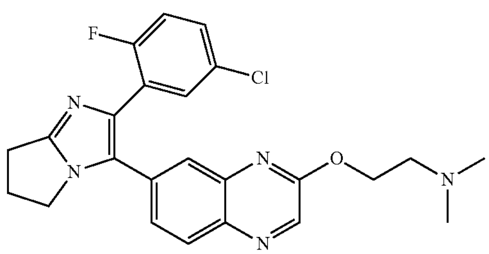 [SMILES: CN(C)CCOc1cnc2ccc(-c3c(-c4cc(Cl)ccc4F)nc4n3CCC4)cc2n1] | 2-((7-(2-(5-chloro-2-fluorophenyl)-6,7-dihydro-5H-pyrrolo[1,2-a]imidazol-3-yl)quinoxalin-2-yl)oxy)-N,N-dimethylethan-1-amine |
| 364 | 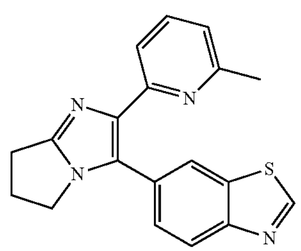 [SMILES: Cc1cccc(-c2nc3n(c2-c2ccc4ncsc4c2)CCC3)n1] | 6-(2-(6-methylpyridin-2-yl)-6,7-dihydro-5H-pyrrolo[1,2-a]imidazol-3-yl)benzo[d]thiazole |
| 365 | 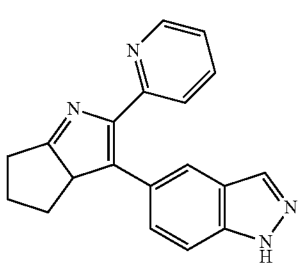 [SMILES: c1ccc(C2=C(c3ccc4[nH]ncc4c3)C3CCCC3=N2)nc1] | 5-(2-(pyridin-2-yl)-3a,4,5,6-tetrahydrocyclopenta[b]pyrrol-3-yl)-1H-indazole |
| 366 | 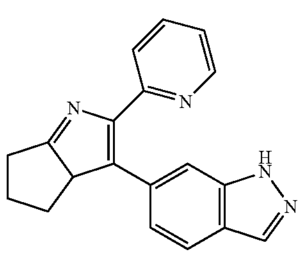 [SMILES: c1ccc(C2=C(c3ccc4cn[nH]c4c3)C3CCCC3=N2)nc1] | 6-(2-(pyridin-2-yl)-3a,4,5,6-tetrahydrocyclopenta[b]pyrrol-3-yl)-1H-indazole |

| No. | Structure | Name |
|---|---|---|
| 367 | 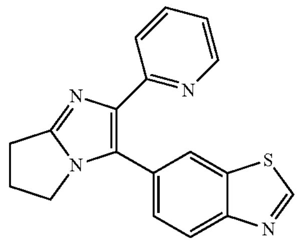 [SMILES: c1ccc(-c2nc3n(c2-c2ccc4ncsc4c2)CCC3)nc1] | 6-(2-(pyridin-2-yl)-6,7-dihydro-5H-pyrrolo[1,2-a]imidazol-3-yl)benzo[d]thiazole |
| 368 | 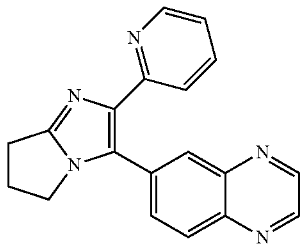 [SMILES: c1ccc(-c2nc3n(c2-c2ccc4nccnc4c2)CCC3)nc1] | 6-(2-(pyridin-2-yl)-6,7-dihydro-5H-pyrrolo[1,2-a]imidazol-3-yl)quinoxaline |
| 369 | 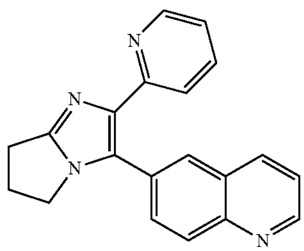 [SMILES: c1ccc(-c2nc3n(c2-c2ccc4ncccc4c2)CCC3)nc1] | 6-(2-(pyridin-2-yl)-6,7-dihydro-5H-pyrrolo[1,2-a]imidazol-3-yl)quinoline |
| 370 | 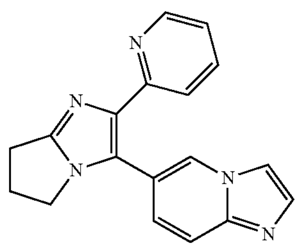 [SMILES: c1ccc(-c2nc3n(c2-c2ccc4nccn4c2)CCC3)nc1] | 6-(2-(pyridin-2-yl)-6,7-dihydro-5H-pyrrolo[1,2-a]imidazol-3-yl)imidazo[1,2-a]pyridine |

In embodiment II₁ of this aspect, the invention comprises compounds having the structure of formula (II):

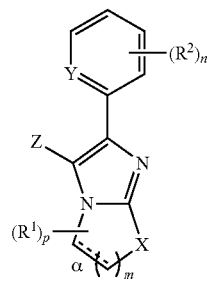
(II)

or a pharmaceutically acceptable salt, prodrug or N-oxide thereof, or solvate or hydrate thereof, wherein
  bond α is a single bond or double bond;
  m is 1 or 2,
  Y is —CH— or —N—;
  X is —CH$_2$—, —O— or —N(R$^a$)—, wherein R$^a$ is hydrogen or —C(O)R;
  p is 0 or 1;
  Z is
  (a)

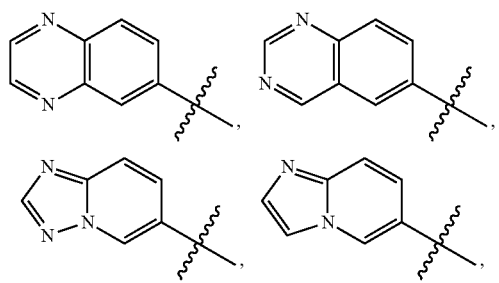

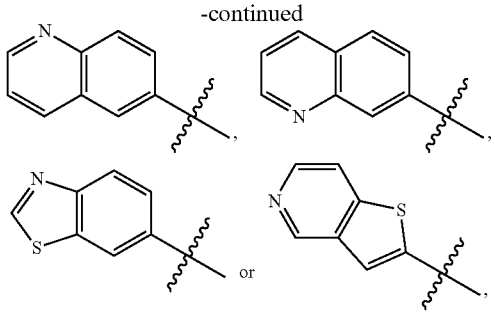

or

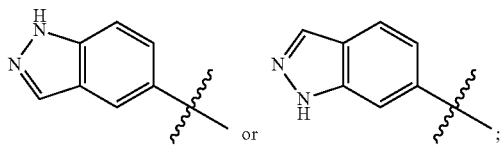 [SMILES: *c1ccc2[nH]ncc2c1 ; *c1ccc2cn[nH]c2c1]

or;

(b)
R¹ is hydrogen, $C_1$-$C_6$alkyl or —C(O)OR,
wherein the alkyl is optionally substituted with 1, 2, 3, or 4 —OR groups;
each R² is independently halogen or —$C_1$-$C_6$alkyl;
n is 0, 1, 2 or 3; and
each R is independently hydrogen or $C_1$-$C_6$alkyl.

In embodiment II₂ of this aspect, the invention comprises compounds of embodiment II₁, wherein
Z is optionally substituted by one or two —$R^Z$ groups that are each independently halogen, cyano, $C_{1-6}$ alkyl, $C_{1-6}$haloalkyl, $C_{1-6}$ alkoxy, —O—$C_{1-6}$ alkyl-OR, —O—$C_{1-6}$ alkyl-SR, —O—$C_{1-6}$ alkyl-NR₂, —O—$C_{1-6}$alkyl-Hca or Het($C_{0-6}$ alkyl), wherein each alkyl, haloalkyl, alkoxy, Hca or Het group is optionally substituted by one or two —$R^{Z2}$ groups;
wherein each —$R^{Z2}$ is independently halogen, cyano, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR).

In embodiment II₃ of this aspect, the invention comprises compounds of embodiment II₁ having the structure of formula (II):

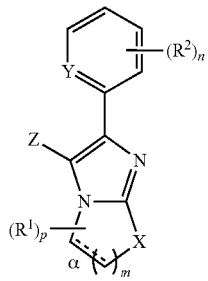

(II)

or a pharmaceutically acceptable salt, prodrug or N-oxide thereof, or solvate or hydrate thereof, wherein
bond α is a single bond, m is 1, X is —CH₂— and p is 0; or
bond α is a single bond, m is 1, X is —N($R^a$)— and p is 1,
wherein $R^a$ is hydrogen or —C(O)R; or
bond α is a double bond, m is 1, X is —O— and p is 0; or
bond α is a single bond, m is 2, X is —NH— and p is 0;
Z is
(a)

optionally substituted by one or two —$R^Z$ groups that are each independently halogen, cyano, $C_{1-6}$alkyl, $C_{1-6}$haloalkyl, $C_{3-8}$Cak($C_{0-6}$alkyl), Hca($C_{0-6}$alkyl), Ar ($C_{0-6}$alkyl), Het($C_{0-6}$alkyl), —O—$C_{1-6}$alkyl-OR, —O—$C_{1-6}$alkyl-SR, —O—$C_{1-6}$alkyl-NR₂ or —O—$C_{1-6}$alkyl-Hca, wherein each Ar, Het, Cak, Hca, alkyl, and haloalkyl group is optionally substituted by one or two —$R^{Z2}$ groups;
wherein each —$R^{Z2}$ is independently halogen, cyano, $C_{1-6}$alkyl, $C_{1-6}$haloalkyl, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR);
or

--- optionally substituted by one or two —$R^Z$ groups that are each independently $C_{3-8}$Cak($C_{0-6}$alkyl), Hca($C_{0-6}$alkyl), Ar($C_{0-6}$alkyl), Het($C_{0-6}$alkyl), halogen, cyano, $C_{1-6}$alkyl, $C_{1-6}$haloalkyl, —$C_1$-$C_6$alkoxy, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂, —CH₂—OP(O)(OR), —O$C_{1-6}$alkyl-OR, —O—$C_{1-6}$alkyl-SR, —O—$C_{1-6}$ alkyl-NR₂, —O—$C_{1-6}$alkyl-Hca, wherein each Ar, Het, Cak, Hca, alkyl, and haloalkyl group is optionally substituted by one or two —$R^{Z2}$ groups;
wherein each —$R^{Z2}$ is independently halogen, cyano, $C_{1-6}$alkyl, $C_{1-6}$haloalkyl, —$C_1$-$C_6$alkoxy, —OR, —SR, —NR₂, —C(O)R, —C(O)OR, —C(O)NR₂, —S(O)₂NR₂, —S(O)₂R, —OC(O)R, —N(R)C(O)R, —OC(O)OR, —OC(O)NR₂, —N(R)C(O)OR, —N(R)C(O)NR₂, —N(R)S(O)₂R, —OP(O)(OR)₂ or —CH₂—OP(O)(OR); or (b)

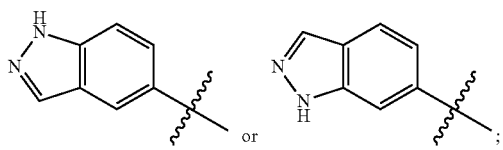 [SMILES: *c1ccc2[nH]ncc2c1 ; *c1ccc2cn[nH]c2c1]

$R^1$ is hydrogen, $C_1$-$C_6$alkyl or —C(O)OR,
wherein the alkyl is optionally substituted with 1, 2, 3, or 4 —OR groups;
each R is independently hydrogen or $C_1$-$C_6$alkyl;
each $R^2$ is independently halogen or —$C_1$-$C_6$alkyl; and
n is 0, 1, 2 or 3.

In embodiment $II_4$ of this aspect, the invention comprises compounds of embodiment $II_3$, wherein
Z is optionally substituted by one or two —$R^Z$ groups that are each independently halogen, cyano, $C_{1-6}$alkyl, $C_{1-6}$haloalkyl, $C_{1-6}$alkoxy, —O—$C_{1-6}$alkyl-OR, —O—$C_{1-6}$alkyl-SR, —O—$C_{1-6}$alkyl-NR$_2$, —O—$C_{1-6}$alkyl-Hca or Het($C_{0-6}$alkyl), wherein each alkyl, haloalkyl, alkoxy, Hca or Het group is optionally substituted by one or two —$R^{Z2}$ groups;
wherein each —$R^{Z2}$ is independently halogen, cyano, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

In embodiment $II_5$ of this aspect, the invention comprises compounds of embodiment $II_4$, wherein
Z is

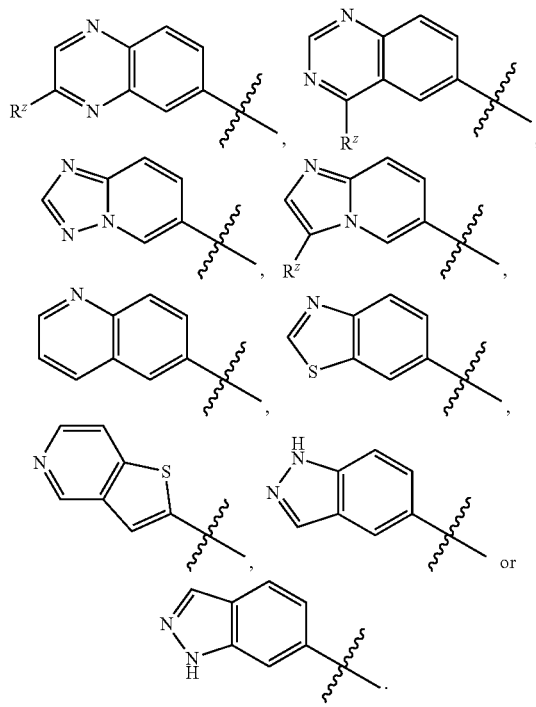

In embodiment $II_6$ of this aspect, the invention comprises compounds of any of embodiments $II_1$-$II_5$, wherein X is —CH—.

In embodiment $II_7$ of this aspect, the invention comprises compounds of any of embodiments $II_1$-$II_5$, wherein X is —N—.

In embodiment $II_8$, the compounds of the invention are one of formulae (IIa)-(IIh), wherein $R^1$, $R^2$, n, p and $R^a$ are as defined in embodiments $II_1$-$II_7$ above:

Structural Formula (II) is One of Formulae (IIa)-(IIh):

(IIa)

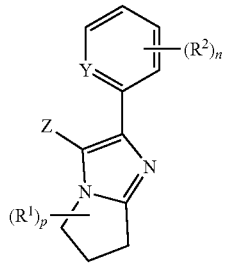

(IIb)

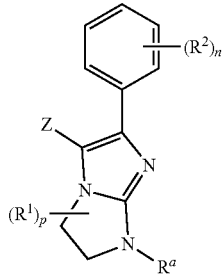

(IIc)

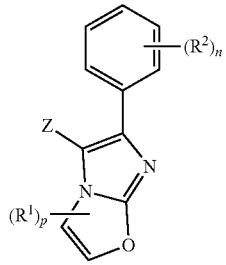

(IId)

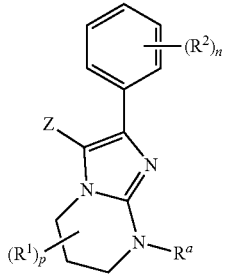

(IIe)

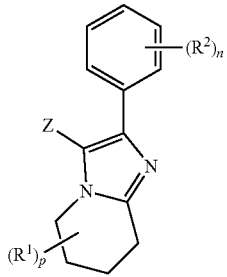

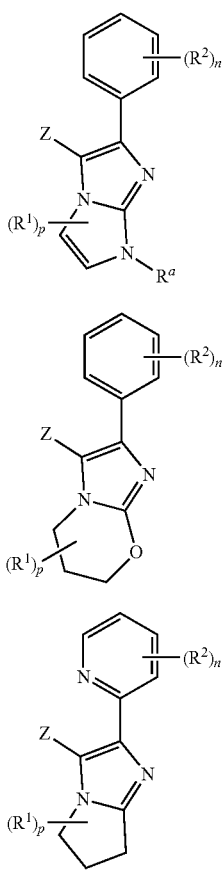

Particular embodiments of this aspect of the invention comprise compounds of any one of the formulae (II), and (IIa)-(IIh), each as defined in each of the following rows (or a pharmaceutically acceptable salt, prodrug, or N-oxide thereof, or a solvate or hydrate thereof), wherein each entry is a group number as defined above (e.g., (3y) refers to $R^1$ is C(O)OR, and a dash "—" indicates that the variable is as defined in embodiment $I_1$ or defined according to any one of the applicable variable definitions (1a)-(1y), (2a)-(2aaa) and (3a)-(3mm) [e.g., when $R^1$ is a dash, it can be either as defined in any of embodiments $II_1$-$II_4$ or any one of the applicable definitions (3a)-(3mm)]:

| | (II) | A | Z | $R^1$ |
|---|---|---|---|---|
| (2)-1 | (IIa) | (1k) | (2w) | (3q) |
| (2)-2 | (IIb) | (1m) | (2x) | (3r) |
| (2)-3 | (IIc) | (1n) | (2y) | (3s) |
| (2)-4 | (IId) | (1p) | (2z) | (3x) |
| (2)-5 | (IIe) | (1q) | (2aa) | (3y) |
| (2)-6 | (IIf) | (1k) | (2bb) | (3z) |
| (2)-7 | (IIg) | (1s) | (2w) | (3q) |
| (2)-8 | (IIa) | (1t) | (2dd) | (3r) |
| (2)-9 | (IIb) | (1k) | (2ee) | (3s) |
| (2)-10 | (IIe) | (1m) | (2ff) | (3x) |
| (2)-11 | (IId) | (1n) | (2gg) | (3y) |
| (2)-12 | (IIh) | (1ff) | (2w) | (3z) |
| (2)-13 | (IIf) | (1q) | (2ii) | (3r) |
| (2)-14 | (IIg) | (1r) | (2pp) | (3r) |
| (2)-15 | (IIa) | (1s) | (2qq) | (3r) |
| (2)-16 | (IIb) | (1t) | (2w) | (3q) |
| (2)-17 | (IIc) | (1k) | (2ss) | (3r) |
| (2)-18 | (IId) | (1m) | (2tt) | (3s) |
| (2)-19 | (IIe) | (1n) | (2uu) | (3x) |
| (2)-20 | (IIf) | (1p) | (2w) | (3y) |
| (2)-21 | (IIh) | (1ww) | (2ww) | (3z) |
| (2)-22 | (IIb) | (1r) | (2xx) | (3r) |
| (2)-23 | (IIc) | (1s) | (2ss) | (3r) |
| (2)-24 | (IIa) | (1t) | (2tt) | (3q) |
| (2)-25 | (IIb) | (1n) | (2uu) | (3r) |
| (2)-26 | (IIc) | (1p) | (2vv) | (3s) |
| (2)-27 | (IIf) | (1n) | (2ww) | (3x) |
| (2)-28 | (IIg) | (1p) | (2xx) | (3y) |
| (2)-29 | (IIa) | (1m) | (2yy) | (3z) |
| (2)-30 | (IIb) | (1n) | (2zz) | (3r) |
| (2)-31 | (IIa) | (1p) | (2aaa) | (3r) |
| (2)-32 | (IIb) | (1q) | (2w) | (3x) |
| (2)-33 | (IIc) | (1r) | (2x) | (3y) |
| (2)-34 | (IIh) | (1hh) | (2pp) | (3z) |
| (2)-35 | (IIg) | (1t) | (2w) | (3s) |
| (2)-36 | (IIa) | (1s) | (2rr) | (3x) |
| (2)-37 | (IIb) | (1t) | (2ss) | (3y) |
| (2)-38 | (IIc) | (1p) | (2tt) | (3z) |
| (2)-39 | (IId) | (1s) | (2uu) | (3s) |
| (2)-40 | (IIa) | (1t) | (2vv) | (3x) |
| (2)-41 | (IIb) | (1p) | (2ww) | (3y) |
| (2)-42 | (IIh) | (1xx) | (2xx) | (3z) |
| (2)-43 | (IIa) | (1n) | (2hh) | (3r) |
| (2)-44 | (IIb) | (1p) | (2ii) | (3r) |
| (2)-45 | (IIc) | (1q) | (2pp) | (3r) |
| (2)-46 | (IIa) | (1r) | (2qq) | (3r) |
| (2)-47 | (IIb) | (1s) | (2rr) | (3q) |
| (2)-48 | (IIc) | (1t) | (2ss) | (3r) |
| (2)-49 | (IIg) | (1s) | (2w) | (3s) |
| (2)-50 | (IIa) | (1t) | (2uu) | (3x) |
| (2)-51 | (IIb) | (1n) | (2vv) | (3y) |
| (2)-52 | (IIc) | (1p) | (2ww) | (3z) |
| (2)-53 | (IId) | (1s) | (2xx) | (3r) |
| (2)-54 | (IIe) | (1t) | (2ss) | (3q) |
| (2)-55 | (IIf) | (1n) | (2tt) | (3r) |
| (2)-56 | (IIg) | (1p) | (2uu) | (3s) |
| (2)-57 | (IIa) | (1p) | (2vv) | (3x) |
| (2)-58 | (IIb) | (1s) | (2ww) | (3y) |
| (2)-59 | (IIc) | (1t) | (2w) | (3z) |
| (2)-60 | (IId) | (1p) | (2qq) | (3q) |
| (2)-61 | (IIa) | (1m) | (2rr) | (3r) |
| (2)-62 | (IIb) | (1n) | (2ss) | (3s) |
| (2)-63 | (IIc) | (1p) | (2tt) | (3x) |
| (2)-64 | (IIa) | (1q) | (2w) | (3y) |
| (2)-65 | (IIh) | (1ff) | (2vv) | (3z) |
| (2)-66 | (IIc) | (1s) | (2ww) | (3q) |
| (2)-67 | (IId) | (1t) | (2xx) | (3r) |
| (2)-68 | (IIe) | (1k) | (2oo) | (3s) |
| (2)-69 | (IIf) | (1k) | (2pp) | (3x) |
| (2)-70 | (IIg) | (1k) | (2qq) | (3y) |
| (2)-71 | (IIa) | (1m) | (2w) | (3z) |
| (2)-72 | (IIb) | (1n) | (2ss) | (3x) |
| (2)-73 | (IIc) | (1p) | (2tt) | (3y) |
| (2)-74 | (IId) | (1q) | (2nn) | (3z) |
| (2)-75 | (IIa) | (1r) | (2oo) | (3s) |
| (2)-76 | (IIb) | (1s) | (2w) | (3x) |
| (2)-77 | (IIc) | (1t) | (2qq) | (3y) |
| (2)-78 | (IIh) | (1ff) | (2rr) | (3z) |
| (2)-79 | (IIb) | (1k) | (2ss) | (3y) |
| (2)-80 | (IIc) | (1k) | (2tt) | (3z) |
| (2)-81 | (IId) | (1k) | (2uu) | (3r) |
| (2)-82 | (IIe) | (1n) | (2vv) | (3r) |
| (2)-83 | (IIf) | (1p) | (2ww) | (3r) |
| (2)-84 | (IIg) | (1n) | (2xx) | (3q) |
| (2)-85 | (IIa) | (1p) | (2w) | (3r) |
| (2)-86 | (IIb) | (1m) | (2qq) | (3s) |
| (2)-87 | (IIc) | (1n) | (2rr) | (3x) |
| (2)-88 | (IIa) | (1p) | (2ss) | (3y) |
| (2)-89 | (IIh) | (1xx) | (2aaa) | (3z) |
| (2)-90 | (IIc) | (1r) | (2kk) | (3x) |
| (2)-91 | (IIg) | (1s) | (2w) | (3y) |
| (2)-92 | (IIa) | (1t) | (2qq) | (3z) |
| (2)-93 | (IIb) | (1s) | (2rr) | (3x) |
| (2)-94 | (IIc) | (1t) | (2ss) | (3y) |
| (2)-95 | (IIh) | (1uu) | (2tt) | (3z) |

|  | (II) | A | Z | R¹ |
|---|---|---|---|---|
| (2)-96 | (IIe) | (1k) | (2w) | (3s) |
| (2)-97 | (IIf) | (1m) | (2vv) | (3x) |
| (2)-98 | (IIa) | (1n) | (2ww) | (3x) |
| (2)-99 | (IIb) | (1p) | (2xx) | (3y) |
| (2)-100 | (IIc) | (1q) | (2qq) | (3z) |
| (2)-101 | (IIc) | (1r) | (2w) | (3r) |
| (2)-102 | (IId) | (1s) | (2ss) | (3r) |
| (2)-103 | (IIe) | (1t) | (2tt) | (3x) |
| (2)-104 | (IIa) | (1k) | (2pp) | (3y) |
| (2)-105 | (IIb) | (1k) | (2qq) | (3z) |
| (2)-106 | (IIc) | (1k) | (2rr) | (3s) |
| (2)-107 | (IIb) | (1k) | (2ss) | (3x) |
| (2)-108 | (IIc) | (1n) | (2tt) | (3y) |
| (2)-109 | (IIh) | (1mm) | (2w) | (3z) |
| (2)-110 | (IIe) | (1k) | (2vv) | (3r) |
| (2)-111 | (IIf) | (1m) | (2ww) | (3q) |
| (2)-112 | (IIa) | (1n) | (2xx) | (3r) |
| (2)-113 | (IIb) | (1p) | (2rr) | (3s) |
| (2)-114 | (IIc) | (1q) | (2w) | (3x) |
| (2)-115 | (IIa) | (1r) | (2tt) | (3y) |
| (2)-116 | (IIb) | (1s) | (2dd) | (3z) |
| (2)-117 | (IIc) | (1t) | (2ee) | (3x) |
| (2)-118 | (IIf) | (1k) | (2ff) | (3y) |
| (2)-119 | (IIh) | (1ww) | (2gg) | (3z) |
| (2)-120 | (IIb) | (1k) | (2hh) | (3q) |
| (2)-121 | (IIc) | (1k) | (2ii) | (3r) |
| (2)-122 | (IIc) | (1m) | (2jj) | (3s) |
| (2)-123 | (IId) | (1n) | (2kk) | (3x) |
| (2)-124 | (IIe) | (1p) | (2pp) | (3y) |
| (2)-125 | (IIf) | (1q) | (2qq) | (3z) |
| (2)-126 | (IIg) | (1r) | (2w) | (3x) |
| (2)-127 | (IIa) | (1s) | (2ss) | (3y) |
| (2)-128 | (IIh) | (1kk) | (2tt) | (3z) |
| (2)-129 | (IIc) | (1k) | (2uu) | (3q) |
| (2)-130 | (IIb) | (1m) | (2vv) | (3r) |
| (2)-131 | (IIc) | (1n) | (2w) | (3s) |
| (2)-132 | (IId) | (1p) | (2xx) | (3x) |
| (2)-133 | (IIe) | (1q) | (2nn) | (3y) |
| (2)-134 | (IIf) | (1r) | (2oo) | (3z) |
| (2)-135 | (IIg) | (1s) | (2pp) | (3r) |
| (2)-136 | (IIa) | (1t) | (2qq) | (3q) |
| (2)-137 | (IIb) | (1k) | (2rr) | (3r) |
| (2)-138 | (IIc) | (1p) | (2aaa) | (3s) |
| (2)-139 | (IIa) | (1q) | (2w) | (3x) |
| (2)-140 | (IIb) | (1r) | (2ll) | (3y) |
| (2)-141 | (IIh) | (1yy) | (2mm) | (3z) |
| (2)-142 | (IId) | (1t) | (2nn) | (3q) |
| (2)-143 | (IIe) | (1k) | (2oo) | (3r) |
| (2)-144 | (IIa) | (1k) | (2pp) | (3s) |
| (2)-145 | (IIb) | (1k) | (2qq) | (3x) |
| (2)-146 | (IIc) | (1m) | (2pp) | (3y) |
| (2)-147 | (IIa) | (1n) | (2qq) | (3z) |
| (2)-148 | (IIb) | (1p) | (2rr) | (3x) |
| (2)-149 | (IIc) | (1q) | (2ss) | (3y) |
| (2)-150 | (IIc) | (1r) | (2tt) | (3z) |
| (2)-151 | (IId) | (1s) | (2uu) | (3r) |
| (2)-152 | (IIe) | (1t) | (2w) | (3q) |
| (2)-153 | (IIf) | (1k) | (2ww) | (3r) |
| (2)-154 | (IIg) | (1k) | (2xx) | (3s) |
| (2)-155 | (IIa) | (1m) | (2xx) | (3x) |
| (2)-156 | (IIb) | (1n) | (2jj) | (3y) |
| (2)-157 | (IIh) | (1hh) | (2aaa) | (3z) |
| (2)-158 | (IIb) | (1q) | (2kk) | (3y) |
| (2)-159 | (IIc) | (1r) | (2w) | (3z) |
| (2)-160 | (IIb) | (1s) | (2pp) | (3r) |
| (2)-161 | (IIc) | (1t) | (2qq) | (3s) |
| (2)-162 | (IIa) | (1k) | (2rr) | (3x) |
| (2)-163 | (IIb) | (1m) | (2ss) | (3y) |
| (2)-164 | (IIh) | (1uu) | (2w) | (3z) |
| (2)-165 | (IIc) | (1p) | (2uu) | (3q) |
| (2)-166 | (IId) | (1q) | (2vv) | (3r) |
| (2)-167 | (IIe) | (1r) | (2ww) | (3s) |
| (2)-168 | (IIf) | (1s) | (2xx) | (3x) |
| (2)-169 | (IIg) | (1t) | (2ww) | (3y) |
| (2)-170 | (IIa) | (1m) | (2xx) | (3z) |
| (2)-171 | (IIb) | (1n) | (2yy) | (3r) |
| (2)-172 | (IIc) | (1p) | (2zz) | (3q) |
| (2)-173 | (IIb) | (1q) | (2w) | (3r) |
| (2)-174 | (IIc) | (1r) | (2kk) | (3s) |
| (2)-175 | (IId) | (1s) | (2pp) | (3x) |
| (2)-176 | (IIe) | (1t) | (2qq) | (3y) |
| (2)-177 | (IIh) | (1rr) | (2rr) | (3z) |
| (2)-178 | (IIa) | (1q) | (2ss) | (3r) |
| (2)-179 | (IIb) | (1r) | (2tt) | (3s) |
| (2)-180 | (IIc) | (1s) | (2uu) | (3x) |
| (2)-181 | (IIa) | (1t) | (2w) | (3y) |
| (2)-182 | (IIb) | (1k) | (2ww) | (3z) |
| (2)-183 | (IIc) | (1m) | (2xx) | (3r) |
| (2)-184 | (IIa) | (1n) | (2uu) | (3r) |
| (2)-185 | (IIb) | (1p) | (2vv) | (3q) |
| (2)-186 | (IIc) | (1q) | (2ww) | (3r) |
| (2)-187 | (IIb) | (1r) | (2xx) | (3s) |
| (2)-188 | (IIc) | (1s) | (2yy) | (3x) |
| (2)-189 | (IIa) | (1t) | (2zz) | (3y) |
| (2)-190 | (IIb) | (1k) | (2w) | (3z) |
| (2)-191 | (IIc) | (1k) | (2kk) | (3s) |
| (2)-192 | (IId) | (1k) | (2pp) | (3x) |
| (2)-193 | (IIe) | (1m) | (2qq) | (3y) |
| (2)-194 | (IIh) | (1ff) | (2rr) | (3z) |
| (2)-195 | (IIb) | (1p) | (2ss) | (3r) |
| (2)-196 | (IIc) | (1q) | (2tt) | (3s) |
| (2)-197 | (IId) | (1r) | (2w) | (3x) |
| (2)-198 | (IIe) | (1s) | (2vv) | (3y) |
| (2)-199 | (IIf) | (1t) | (2ww) | (3z) |
| (2)-200 | (IIg) | (1k) | (2xx) | (3r) |

In some embodiments, the compound of formulae (II) or (IIa)-(IIh) is one of the following compounds (or a pharmaceutically acceptable salt, prodrug, or N-oxide thereof, or a solvate or hydrate thereof):

1, 2, 3, 4, 5, 6, 7, 8, 9, 10, 11, 12, 13, 14, 15, 16, 17, 18, 32, 36, 37, 38, 39, 44, 45, 46, 49, 50, 51, 52, 53, 54, 55, 56, 57, 61, 64, 65, 66, 67, 68, 69, 73, 74, 81, 82, 83, 90, 92, 93, 94, 96, 98, 99, 100, 101, 102, 103, 105, 106, 107, 108, 109, 110, 111, 112, 113, 115, 116, 117, 118, 119, 120, 121, 122, 123, 124, 125, 126, 127, 128, 129, 130, 133, 134, 135, 136, 137, 139, 140, 141, 142, 143, 144, 145, 146, 147, 148, 149, 150, 151, 152, 154, 155, 156, 157, 158, 159, 160, 161, 162, 163, 164, 165, 166, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 199, 200, 201, 202, 203, 204, 205, 206, 207, 208, 209, 210, 211, 214, 217, 218, 219, 220, 221, 222, 224, 225, 226, 227, 228, 229, 230, 231, 232, 235, 236, 237, 238, 240, 247, 260, 261, 262, 263, 264, 265, 266, 267, 268, 269, 270, 271, 276, 280, 281, 282, 283, 288, 289, 290, 291, 293, 296, 297, 298, 299, 301, 305, 308, 309, 310, 311, 313, 316, 317, 318, 319, 328, 329, 332, 337, 338, 339, 340, 342, 343, 344, 345, 346, 347, 348, 349, 350, 353, 354, 355, 356, 357, 358, 359, 360, 362, 363, 364, 365, 366, 367, 368, 369 or 370.

In embodiment III₁ of this aspect, the invention comprises compounds having the structure of formula (III):

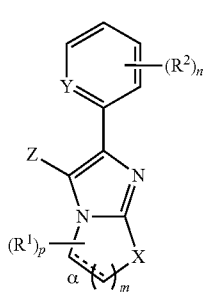

(III)

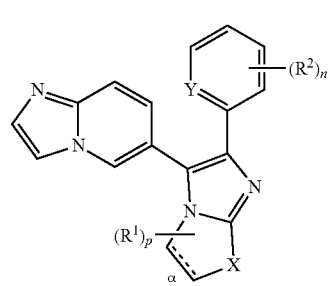

(IIIa)

or a pharmaceutically acceptable salt, prodrug or N-oxide thereof, or solvate or hydrate thereof, wherein
bond α is a single bond, X is —CH$_2$— and p is 0; or
bond α is a single bond, X is —N(R$^a$)— and p is 1, wherein R$^a$ is hydrogen or —C(O)R; or
bond α is a double bond, X is —O— and p is 0;
Y is —CH— or —N—; and
Z is

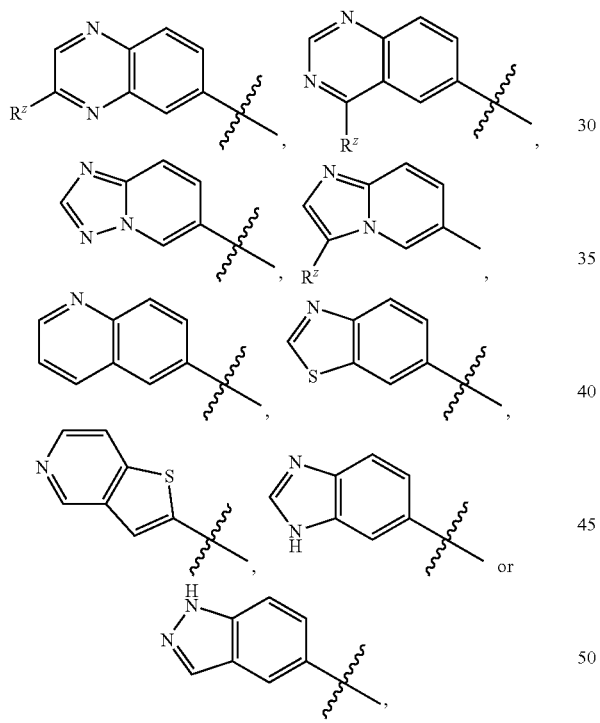

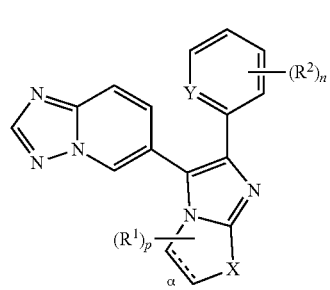

(IIIb)

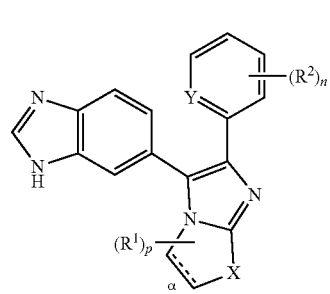

(IIIc)

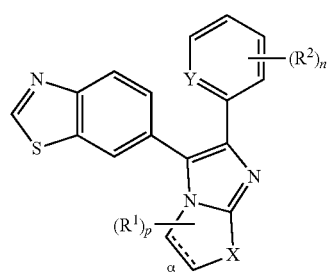

(IIId)

wherein each R$^Z$ is independently hydrogen, —NR$_2$, —OC(O)NR$_2$, —O—C$_{1-6}$alkyl-OR, Het(C$_{0-6}$alkyl) or —O—C$_{1-6}$alkyl-NR$_2$;
R$^1$ is hydrogen, C$_1$-C$_6$alkyl or —C(O)OR, wherein the alkyl is optionally substituted with 1, 2, 3, or 4 —OR groups;
each R is independently hydrogen or C$_1$-C$_6$alkyl;
each R$^2$ is independently halogen or —C$_1$-C$_6$alkyl; and
n is 0, 1, 2 or 3.

In embodiment III$_2$, the compounds of the invention are of one of formulae (IIIa)-(IIIr), wherein A, Z, and R$^1$ are as defined in embodiment III$_1$ above:

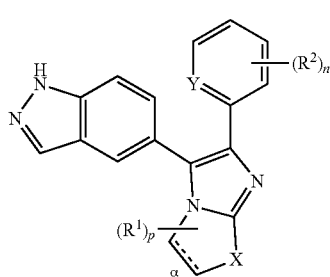

(IIIe)

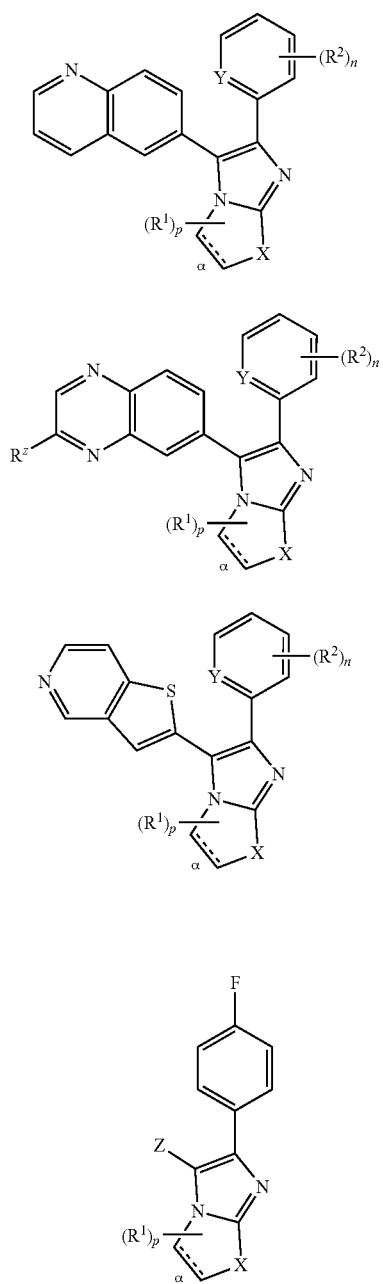
(IIIf)
(IIIg)
(IIIh)
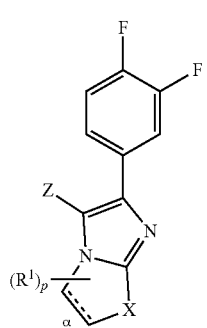
(IIIi)
(IIIj)
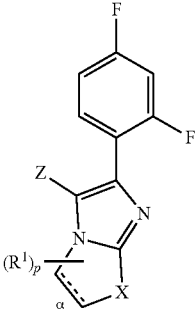
(IIIk)
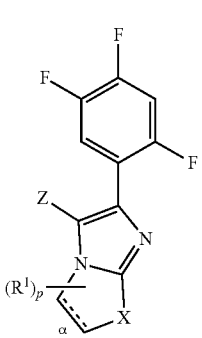
(IIIl)
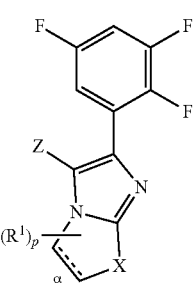
(IIIm)
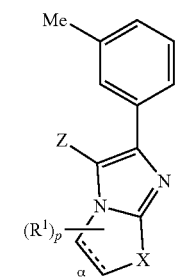
(IIIn)
(IIIo)

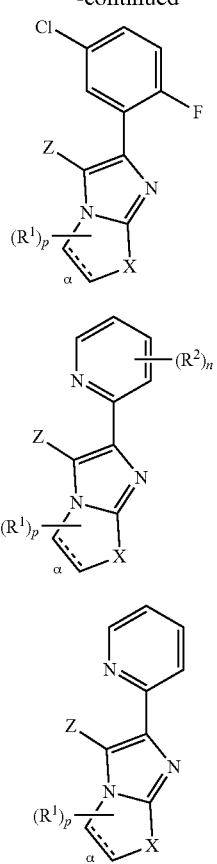

Particular embodiments of this aspect of the invention comprise compounds of any one of the formulae (III), and (IIIa)-(IIp), each as defined in each of the following rows (or a pharmaceutically acceptable salt, prodrug, or N-oxide thereof, or a solvate or hydrate thereof), wherein each entry is a group number as defined above (e.g., (3y) refers to R¹ is C(O)OR), an "X" indicates that the variable is defined by another group in the embodiment (e.g., in embodiment (3)-1 below, Z is defined in (IIIa)) and a dash "—" indicates that the variable is as defined in embodiment I₁ or defined according to any one of the applicable variable definitions (1a)-(1zz), (2a)-(2aaa) and (3a)-(3mm) [e.g., when R¹ is a dash, it can be either as defined in embodiment III₁ or any one of the applicable definitions (3a)-(3mm)]:

|  | (II) | A | Z | R¹ |
|---|---|---|---|---|
| (3)-1 | (IIIa) | (1k) | X | (3q) |
| (3)-2 | (IIIb) | (1m) | X | (3r) |
| (3)-3 | (IIIc) | (1n) | X | (3s) |
| (3)-4 | (IIId) | (1p) | X | (3x) |
| (3)-5 | (IIIe) | (1q) | X | (3y) |
| (3)-6 | (IIIf) | (1k) | X | (3z) |
| (3)-7 | (IIIg) | (1s) | X | (3q) |
| (3)-8 | (IIIh) | (1t) | X | (3r) |
| (3)-9 | (IIIa) | (1k) | X | (3s) |
| (3)-10 | (IIIb) | (1m) | X | (3x) |
| (3)-11 | (IIIc) | (1n) | X | (3y) |
| (3)-12 | (IIId) | (1k) | X | (3z) |
| (3)-13 | (IIIe) | (1q) | X | (3r) |
| (3)-14 | (IIIf) | (1r) | X | (3r) |
| (3)-15 | (IIIg) | (1s) | X | (3r) |
| (3)-16 | (IIIh) | (1t) | X | (3q) |
| (3)-17 | (IIIa) | (1k) | X | (3r) |
| (3)-18 | (IIIb) | (1m) | X | (3s) |
| (3)-19 | (IIIc) | (1n) | X | (3x) |
| (3)-20 | (IIId) | (1p) | X | (3y) |
| (3)-21 | (IIIe) | (1q) | X | (3z) |
| (3)-22 | (IIIf) | (1r) | X | (3r) |
| (3)-23 | (IIIg) | (1s) | X | (3r) |
| (3)-24 | (IIIh) | (1t) | X | (3q) |
| (3)-25 | (IIIa) | (1n) | X | (3r) |
| (3)-26 | (IIIb) | (1p) | X | (3s) |
| (3)-27 | (IIIc) | (1n) | X | (3x) |
| (3)-28 | (IIId) | (1p) | X | (3y) |
| (3)-29 | (IIIe) | (1m) | X | (3z) |
| (3)-30 | (IIIf) | (1n) | X | (3r) |
| (3)-31 | (IIIg) | (1p) | X | (3r) |
| (3)-32 | (IIIh) | (1q) | X | (3x) |
| (3)-33 | (IIIa) | (1r) | X | (3y) |
| (3)-34 | (IIIb) | (1s) | X | (3z) |
| (3)-35 | (IIIc) | (1t) | X | (3s) |
| (3)-36 | (IIId) | (1s) | X | (3x) |
| (3)-37 | (IIIe) | (1t) | X | (3y) |
| (3)-38 | (IIIf) | (1p) | X | (3z) |
| (3)-39 | (IIIg) | (1s) | X | (3s) |
| (3)-40 | (IIIh) | (1t) | X | (3x) |
| (3)-41 | (IIIa) | (1p) | X | (3y) |
| (3)-42 | (IIIb) | (1m) | X | (3z) |
| (3)-43 | (IIIc) | (1n) | X | (3r) |
| (3)-44 | (IIId) | (1p) | X | (3r) |
| (3)-45 | (IIIe) | (1q) | X | (3r) |
| (3)-46 | (IIIf) | (1r) | X | (3r) |
| (3)-47 | (IIIg) | (1s) | X | (3q) |
| (3)-48 | (IIIh) | (1t) | X | (3r) |
| (3)-49 | (IIIa) | (1s) | X | (3s) |
| (3)-50 | (IIIb) | (1t) | X | (3x) |
| (3)-51 | (IIIc) | (1n) | X | (3y) |
| (3)-52 | (IIId) | (1p) | X | (3z) |
| (3)-53 | (IIIe) | (1s) | X | (3r) |
| (3)-54 | (IIIf) | (1t) | X | (3q) |
| (3)-55 | (IIIg) | (1n) | X | (3r) |
| (3)-56 | (IIIh) | (1p) | X | (3s) |
| (3)-57 | (IIIa) | (1p) | X | (3x) |
| (3)-58 | (IIIb) | (1s) | X | (3y) |
| (3)-59 | (IIIc) | (1t) | X | (3z) |
| (3)-60 | (IIId) | (1p) | X | (3q) |
| (3)-61 | (IIIe) | (1m) | X | (3r) |
| (3)-62 | (IIIf) | (1n) | X | (3s) |
| (3)-63 | (IIIg) | (1p) | X | (3x) |
| (3)-64 | (IIIh) | (1q) | X | (3y) |
| (3)-65 | (IIIa) | (1r) | X | (3z) |
| (3)-66 | (IIIb) | (1s) | X | (3q) |
| (3)-67 | (IIIc) | (1t) | X | (3r) |
| (3)-68 | (IIId) | (1k) | X | (3s) |
| (3)-69 | (IIIe) | (1k) | X | (3x) |
| (3)-70 | (IIIf) | (1k) | X | (3y) |
| (3)-71 | (IIIr) | (1m) | X | (3z) |
| (3)-72 | (IIIh) | (1n) | X | (3x) |
| (3)-73 | (IIIa) | (1p) | X | (3y) |
| (3)-74 | (IIIb) | (1q) | X | (3z) |
| (3)-75 | (IIIc) | (1r) | X | (3s) |
| (3)-76 | (IIId) | (1s) | X | (3x) |
| (3)-77 | (IIIe) | (1t) | X | (3y) |
| (3)-78 | (IIIq) | (1k) | X | (3z) |
| (3)-79 | (IIIg) | (1k) | X | (3y) |
| (3)-80 | (IIIh) | (1k) | X | (3z) |
| (3)-81 | (IIIa) | (1k) | X | (3r) |
| (3)-82 | (IIIb) | (1n) | X | (3r) |
| (3)-83 | (IIIc) | (1p) | X | (3r) |
| (3)-84 | (IIId) | (1n) | X | (3q) |
| (3)-85 | (IIIe) | (1p) | X | (3r) |
| (3)-86 | (IIIf) | (1m) | X | (3s) |
| (3)-87 | (IIIg) | (1n) | X | (3x) |
| (3)-88 | (IIIh) | (1p) | X | (3y) |
| (3)-89 | (IIIa) | (1q) | X | (3z) |
| (3)-90 | (IIIb) | (1r) | X | (3x) |
| (3)-91 | (IIIc) | (1s) | X | (3y) |
| (3)-92 | (IIId) | (1t) | X | (3z) |
| (3)-93 | (IIIe) | (1s) | X | (3x) |

-continued

| | (II) | A | Z | R¹ |
|---|---|---|---|---|
| (3)-94 | (IIIf) | (1t) | X | (3y) |
| (3)-95 | (IIIg) | (1k) | X | (3z) |
| (3)-96 | (IIIh) | (1k) | X | (3s) |
| (3)-97 | (IIIa) | (1m) | X | (3x) |
| (3)-98 | (IIIb) | (1n) | X | (3x) |
| (3)-99 | (IIIc) | (1p) | X | (3y) |
| (3)-100 | (IIId) | (1q) | X | (3z) |
| (3)-101 | (IIIe) | (1r) | X | (3r) |
| (3)-102 | (IIIf) | (1s) | X | (3r) |
| (3)-103 | (IIIg) | (1t) | X | (3x) |
| (3)-104 | (IIIh) | (1k) | X | (3y) |
| (3)-105 | (IIIi) | X | (2bb) | (3z) |
| (3)-106 | (IIIj) | X | (2w) | (3s) |
| (3)-107 | (IIIk) | X | (2dd) | (3x) |
| (3)-108 | (IIIl) | X | (2ee) | (3y) |
| (3)-109 | (IIIq) | X | (2ff) | (3z) |
| (3)-110 | (IIIn) | X | (2gg) | (3r) |
| (3)-111 | (IIIo) | X | (2w) | (3q) |
| (3)-112 | (IIIp) | X | (2ii) | (3r) |
| (3)-113 | (IIIi) | X | (2pp) | (3s) |
| (3)-114 | (IIIj) | X | (2qq) | (3x) |
| (3)-115 | (IIIk) | X | (2w) | (3y) |
| (3)-116 | (IIIr) | X | (2ss) | (3z) |
| (3)-117 | (IIIm) | X | (2tt) | (3x) |
| (3)-118 | (IIIn) | X | (2uu) | (3y) |
| (3)-119 | (IIIo) | X | (2w) | (3z) |
| (3)-120 | (IIIp) | X | (2ww) | (3q) |
| (3)-121 | (IIIi) | X | (2xx) | (3r) |
| (3)-122 | (IIIj) | X | (2ss) | (3s) |
| (3)-123 | (IIIk) | X | (2tt) | (3x) |
| (3)-124 | (IIIl) | X | (2uu) | (3y) |
| (3)-125 | (IIIq) | X | (2vv) | (3z) |
| (3)-126 | (IIIn) | X | (2ww) | (3x) |
| (3)-127 | (IIIo) | X | (2xx) | (3y) |
| (3)-128 | (IIIp) | X | (2yy) | (3z) |
| (3)-129 | (IIIi) | X | (2zz) | (3q) |
| (3)-130 | (IIIj) | X | (2aaa) | (3r) |
| (3)-131 | (IIIk) | X | (2w) | (3s) |
| (3)-132 | (IIIl) | X | (2x) | (3x) |
| (3)-133 | (IIIm) | X | (2pp) | (3y) |
| (3)-134 | (IIIn) | X | (2w) | (3z) |
| (3)-135 | (IIIr) | X | (2rr) | (3r) |
| (3)-136 | (IIIp) | X | (2ss) | (3q) |
| (3)-137 | (IIIi) | X | (2tt) | (3r) |
| (3)-138 | (IIIj) | X | (2uu) | (3s) |
| (3)-139 | (IIIk) | X | (2vv) | (3x) |
| (3)-140 | (IIIl) | X | (2ww) | (3y) |
| (3)-141 | (IIIr) | X | (2xx) | (3z) |
| (3)-142 | (IIIn) | X | (2hh) | (3q) |
| (3)-143 | (IIIo) | X | (2ii) | (3r) |
| (3)-144 | (IIIp) | X | (2pp) | (3s) |
| (3)-145 | (IIIi) | X | (2qq) | (3x) |
| (3)-146 | (IIIj) | X | (2rr) | (3y) |
| (3)-147 | (IIIq) | X | (2ss) | (3z) |
| (3)-148 | (IIIl) | X | (2w) | (3x) |
| (3)-149 | (IIIm) | X | (2uu) | (3y) |
| (3)-150 | (IIIn) | X | (2vv) | (3z) |
| (3)-151 | (IIIo) | X | (2ww) | (3r) |
| (3)-152 | (IIIp) | X | (2xx) | (3q) |
| (3)-153 | (IIIi) | X | (2ss) | (3r) |
| (3)-154 | (IIIj) | X | (2tt) | (3s) |
| (3)-155 | (IIIk) | X | (2uu) | (3x) |
| (3)-156 | (IIIl) | X | (2vv) | (3y) |
| (3)-157 | (IIIq) | X | (2ww) | (3z) |
| (3)-158 | (IIIn) | X | (2w) | (3y) |
| (3)-159 | (IIIo) | X | (2qq) | (3z) |
| (3)-160 | (IIIp) | X | (2rr) | (3r) |
| (3)-161 | (IIIi) | X | (2ss) | (3s) |
| (3)-162 | (IIIj) | X | (2tt) | (3x) |
| (3)-163 | (IIIk) | X | (2w) | (3y) |
| (3)-164 | (IIIr) | X | (2vv) | (3z) |
| (3)-165 | (IIIm) | X | (2ww) | (3q) |
| (3)-166 | (IIIn) | X | (2xx) | (3r) |
| (3)-167 | (IIIo) | X | (2oo) | (3s) |
| (3)-168 | (IIIp) | X | (2pp) | (3x) |
| (3)-169 | (IIIi) | X | (2qq) | (3y) |
| (3)-170 | (IIIj) | X | (2w) | (3z) |
| (3)-171 | (IIIk) | X | (2ss) | (3r) |
| (3)-172 | (IIIl) | X | (2tt) | (3q) |
| (3)-173 | (IIIm) | X | (2nn) | (3r) |
| (3)-174 | (IIIn) | X | (2oo) | (3s) |
| (3)-175 | (IIIo) | X | (2w) | (3x) |
| (3)-176 | (IIIp) | X | (2qq) | (3y) |
| (3)-177 | (IIIq) | X | (2rr) | (3z) |
| (3)-178 | (IIIj) | X | (2ss) | (3r) |
| (3)-179 | (IIIk) | X | (2tt) | (3s) |
| (3)-180 | (IIIl) | X | (2uu) | (3x) |
| (3)-181 | (IIIm) | X | (2vv) | (3y) |
| (3)-182 | (IIIn) | X | (2ww) | (3z) |
| (3)-183 | (IIIo) | X | (2xx) | (3r) |
| (3)-184 | (IIIp) | X | (2w) | (3r) |
| (3)-185 | (IIIi) | X | (2qq) | (3q) |
| (3)-186 | (IIIj) | X | (2rr) | (3r) |
| (3)-187 | (IIIk) | X | (2ss) | (3s) |
| (3)-188 | (IIIl) | X | (2aaa) | (3x) |
| (3)-189 | (IIIm) | X | (2kk) | (3y) |
| (3)-190 | (IIIr) | X | (2w) | (3z) |
| (3)-191 | (IIIo) | X | (2qq) | (3s) |
| (3)-192 | (IIIp) | X | (2rr) | (3x) |
| (3)-193 | (IIIi) | X | (2ss) | (3y) |
| (3)-194 | (IIIj) | X | (2tt) | (3z) |
| (3)-195 | (IIIk) | X | (2w) | (3r) |
| (3)-196 | (IIIl) | X | (2vv) | (3s) |
| (3)-197 | (IIIm) | X | (2ww) | (3x) |
| (3)-198 | (IIIn) | X | (2xx) | (3y) |
| (3)-199 | (IIIq) | X | (2qq) | (3z) |
| (3)-200 | (IIIp) | X | (2w) | (3r) |

In some embodiments, the compound of formulae (III) or (IIIa)-(IIIr) is one of the following compounds (or a pharmaceutically acceptable salt, prodrug, or N-oxide thereof, or a solvate or hydrate thereof):

9, 12, 14, 36, 38, 39, 51, 52, 82, 83, 93, 94, 96, 102, 103, 105, 106, 107, 108, 109, 110, 111, 112, 116, 118, 119, 120, 121, 125, 126, 127, 129, 135, 137, 139, 140, 141, 142, 143, 144, 147, 148, 149, 150, 151, 152, 154, 156, 158, 159, 168, 169, 170, 172, 173, 180, 190, 191, 201, 203, 218, 219, 264, 268, 269, 270, 271, 289, 337, 338, 339, 345, 346, 348, 349, 354, 357, 360, 363, 364, 365, 366, 367, 369 or 370.

In some embodiments, the compound of formulae (III) or (IIIa)-(IIIr) is one of the following compounds (or a pharmaceutically acceptable salt, prodrug, or N-oxide thereof, or a solvate or hydrate thereof):

38, 82, 83, 94, 96, 103, 105, 106, 107, 108, 109, 110, 111, 112, 116, 118, 119, 120, 121, 127, 139, 140, 141, 142, 143, 151, 337, 338, 339, 346, 357, 360, 363. 364, 365, 367 or 370.

In another aspect, the present invention comprises pharmaceutical compositions comprising a compound according to any one of the preceding aspects of the invention or any embodiment thereof, together with a pharmaceutically acceptable excipient, diluent, or carrier.

In another aspect, the invention comprises the use of a compound described by any one of the preceding aspects of the invention or any embodiment thereof, for the preparation of a medicament for the treatment of medical diseases or conditions that benefit from the inhibition of cytokine signaling. Medical conditions contemplated in this aspect include all diseases and conditions described herein.

The compounds of formulae (I), (Ia)-(Ig), (II), (IIa)-(IIh), (III) and (IIIa)-(IIIr) described above are useful as kinase inhibitors and/or inhibitors of cytokine signaling. Exemplary kinases inhibited by the presently disclosed compounds include, without limitation, ACVR1; ACVR1B (ALK-4); ACVR1C; ACVR2A; ACVR2B; ACVRL1; BMPR1A; BMPR1B; BMPR2; TGFBR1 (ALK-5), PI3K and MAP4K4

(HGK). Exemplary cytokines, the signaling of which is inhibited by the present compounds include, without limitation, TGF-β superfamily, including Activin, Nodal, TGF-β1, and GDF-8. In one aspect the present compounds are selective for one or more kinase and/or cytokine signaling pathway. For example, exemplary compounds inhibit TGF-β1 signaling, GDF-8 signaling, or both. In one aspect the present compounds inhibit GDF-8 signaling preferentially to TGF-β1 signaling, such that GDF8 signaling is inhibited at least about 1.5-fold more potently or from about 1.1-fold to about 25-fold more potently. In one embodiment certain compounds inhibit GDF8 signaling at least about 5-fold more potently, such as from about 8-fold to about 50-fold, or at least about 10-fold more potently, such as from about 15-fold to about 300-fold more potently.

In particular, the present compounds can be use to treat disorders, such as pulmonary hypertension, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, atherosclerosis, peritoneal and sub-dermal adhesion, kidney fibrosis, lung fibrosis, including idiopathic pulmonary fibrosis, and liver fibrosis, hepatitis B, hepatitis C, alcohol-induced hepatitis, cancer, haemochromatosis, primary biliary cirrhosis, restenosis, retroperitoneal fibrosis, mesenteric fibrosis, endometriosis, keloids, cancer, abnormal bone function, inflammatory disorders, scarring and photoaging of the skin.

Particular proliferative diseases that can be treated with the present compounds include those selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, melanoma, psoriasis, prostate hyperplasia, a neoplasia, a neoplasia of epithelial character, leukemias and lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

The compounds described herein also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, $^{18}F$ etc. Thus, the disclosed compounds may be enriched in one or more of these isotopes relative to the natural abundance of such isotope. As is known to those of skill in the art, such isotopically enriched compounds are useful for a variety of purposes. For example, substitution with heavier isotopes such as deuterium ($^2H$) may afford certain therapeutic advantages that result from greater metabolic stability. Substitution with positron emitting isotopes, such as 18F can be useful in Positron Emission Tomography (PET) studies. By way of example, deuterium ($^2H$) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

In another aspect, the invention comprises combination therapies for the treatment of cancer, including both pre-malignant and malignant neoplasms. In this aspect, the invention comprises a method of treating cancer comprising administering to a subject a compound disclosed herein in conjunction with a therapeutic treatment of cancer. In some embodiments of the invention, the compounds disclosed herein are used in combination of standard of care anti-proliferative treatments of cancer. The amount of a compound disclosed herein for use in the combination therapy is an amount sufficient to inhibit signaling by members of the TGF-β superfamily, such as Nodal and Activin, which promote the survival and/or differentiation of cancer stem cells and thereby enhance the efficacy of the therapeutic treatment. Treatment with the present compounds thus blocks the ability of cancer stem cells to recapitulate a tumor destroyed by treatment with standard of care. Efficacy of treatment can be determined by any art recognized method generally employed for the particular cancer being treated and includes, for example, retardation, inhibition, or regression of tumor growth.

Reference to "combination therapy" and treatment with a compound disclosed herein "in conjunction with" another therapeutic treatment means that the compound and other therapeutic treatment can be administered simultaneously or sequentially such that the resultant treatment is more efficacious than either treatment alone.

One embodiment of treating cancer in a subject comprises administering to a subject in need thereof an amount described above of a compound disclosed herein in combination with the administration of a therapeutically effective amount of one or more chemotherapeutic agents, wherein the one or more chemotherapeutic agents is selected from the group consisting of antimetabolites, alkylating agents, coordination compounds, platinum complexes, DNA cross-linking compounds, inhibitors of transcription enzymes, tyrosine kinase inhibitors, protein kinase inhibitors, topoisomerase inhibitors, DNA minor-groove binding compounds, vinca alkyloids, taxanes, antitumor antibiotics, hormones, aromatase inhibitors, enzymes, growth factor receptors antibodies, cytokines, cell surface markers antibodies, HDAC inhibitors, HSP 90 inhibitors, BCL-2 inhibitors, B-raf inhibitors, MEK inhibitors, mTOR inhibitors, proteasome inhibitors and monoclonal antibodies.

Among the BCL-2 inhibitors useful in the invention is ABT-199.

Another embodiment of methods for treating a subject comprises administering to the subject an amount (as described above) of a compound disclosed herein in combination with the administration of a therapeutically effective amount of one or more chemotherapeutic agents, the one or more chemotherapeutic agents being independently selected from the group consisting of mechlorothamine, cyclophosphamide, ifosfamide, melphalan, chlorambucil, ethyleneimines, methylmelamines, procarbazine, dacarbazine, temozolomide, busulfan, carmustine, lomustine, methotrexate, fluorouracil, capecitabine, cytarabine, gemcitabine, cytosine arabinoside, mecaptopurine, fludarabine, cladribine, thioguanine, azathioprine, vinblastine, vincristine, paclitaxel, docetaxel, colchicine, actinomycin D, daunorubicin, bleomycin, L-asparaginase, cisplatin, carboplatin, oxaliplatin, prednisone, dexamethasone, amino glutethimide, formestane, anastrozole, hydroxyprogesterone caproate, medroxyprogesterone, tamoxifen, amsacrine, mitoxantrone, topotecan, irinotecan, camptothecin, afatinib, axitinib, bosutinib, bortezomib, carfilzomib, cabozantinib, cediranib, crizotinib, dasatinib, dabrafenib, evorolimus, ibrutinib, LDK378, LGX818, MEK162, regorafenib, ruxolitinib, selumetinib, sorafenib, trametinib, vemurafenib, erlotinib, gefitinib, imatinib, lapatinib, lestaurtinib, nilotinib, palbociclib, pazopanib, pomatinib, semaxanib, sirolimus, sunitinib, temsirolimus, vatalanib, vandetanib, anti Her2 antibodies, interferon-α, interferon-γ, interleukin 2, GM CSF, anti CTLA 4 antibodies, rituximab, anti CD33 antibodies, MGCD0103, vorinostat, 17-AAG, thalidomide, lenalidomide, rapamycin, CCI-779, doxorubicine, gemcitabine, melphalan, NPI052, gemtuzumab, alemtuzumab, cetuximab, ibritumomab tiuxaetan, tositumomab, iodine-131 tositumomab, trastuzumab, ado-trastuzumab emtansine, obinutuzumab, bevacizumab, rituximab, and anti-TRAIL death receptor antibodies.

Among the CTLA 4 antibodies that can be used in the present invention is ipilimumab, marketed as YERVOY® by Bristol-Myers Squibb.

Other chemotherapeutic agents include checkpoint pathway inhibitors, e.g., PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed TGF-β signalling inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The following table displays exemplary cancers treatable in the combination therapies of the invention and the therapeutic drug and/or other treatment for use with the compounds disclosed herein:

| Cancer | Drug or Treatment |
|---|---|
| Glioma | lomustine, temozolide and/or radiation |
| hepatocellular carcinoma | sorafenib, regorafenib |
| myelodysplastic syndromes | decitabine or azacytidine |
| pancreatic cancer | Gemcitabine |
| ovarian cancer, such as epithelial ovarian carcinoma | carboplatin, cisplatin, doxorubicin, gemcitabine, paclitaxel |
| breast cancer | Trastuzumab |
| basal and squamous skin carcinomas | 5-fluorouracil, imiquimod, photodynamic therapy (e.g. with 5-aminolevulinic acid), |
| head and neck carcinoma | bleomycin, cisplatin, cetuximab, docetaxel, fluorouracil, methotrexate |
| triple negative breast cancer | Paclitaxel |
| Prostate | abiraterone, enzalutamide |

In another aspect, the invention comprises a method of determining and measuring the ability of the compounds disclosed herein to inhibit signaling by members of the TGF-β superfamily, such as Nodal and Activin, in order to identify cancers and, more specifically, tumors. In one embodiment, neoplasms susceptible to such combination therapy can be identified by testing for Nodal and Activin signaling activity using techniques known to those skilled in the art, including, for example, assays described in Lonardo, E. et al. (2011) Cell Stem Cell 9, 433-446 (which is hereby incorporated by reference in its entirety). Optionally in this embodiment, where the tested compound is found to inhibit signalling of a member of the TGF-β superfamily, such as Nodal and Activin, in the tested neoplasm, the compound is subsequently used in a combination therapy for treatment of the neoplasm, as described herein.

Definitions

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, such as 1 to 6 carbons (i.e., inclusive of 1 and 6), 1 to 6 carbons, 1 to 3 carbons, or 1, 2, 3, 4, 5 or 6. The term "$C_m$-$C_n$alkyl" means an alkyl group having from m to n carbon atoms (i.e., inclusive of m and n). The term "$C_m$-$C_n$alkyl" means an alkyl group having from m to n carbon atoms. For example, "$C_1$-$C_6$alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$alkyl"), the group is simply a single covalent bond if it is a divalent radical or is a hydrogen atom if it is a monovalent radical. For example, the moiety "—($C_0$-$C_6$alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 6 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" or "Ar" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" or "Het" refers to an aromatic ring system containing at least one heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic ring, for example, cycloalkyl or heterocycloalkyl rings, wherein the cycloalkyl (Cak) and heterocycloalkyl (Hca) rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" or "Hca" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" or "Cak" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo (e.g., fluoro, chloro, bromo, and iodo), cyano, —($C_1$-$C_4$ fluoroalkyl), —O—($C_1$-$C_4$ fluoroalkyl), —C(O)—($C_0$-$C_4$alkyl), —C(O)O—($C_0$-$C_4$alkyl), —C(O)N($C_0$-$C_4$alkyl)($C_0$-$C_4$alkyl), —S(O)$_2$O—($C_0$-$C_4$alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below, unless specified otherwise.

Substituent groups for substituting for hydrogens on saturated carbon atoms in the specified group or radical are, unless otherwise specified, —$R^{60}$, halo, —$O^-M^+$, =O, —$OR^{70}$, —$SR^{70}$, —$S^-M^+$, =S, —$N^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —P(O)($O^-$)$_2$($M^+$)$_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —C(O)$O^-M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)$O^-M^+$, —OC(O)$OR^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{71}$, —$SR^{71}$, —$S^-M^+$, =S, —$NR^{81}R^{81}$, =$NR^{71}$, =N—$OR^{71}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{71}$, —$OSO_2R^{71}$, —$OSO_2O^-M^+$, —$OSO_2OR^{71}$, —P(O)($O^-$)$_2$($M^+$)$_2$, —P(O)($OR^{71}$)$O^-M^+$, —P(O)($OR^{71}$)$_2$, —C(O)$R^{71}$, —C(S)$R^{71}$, —C($NR^{71}$)$R^{71}$, —C(O)$O^-M^+$, —C(O)$OR^{71}$, —C(S)$OR^{71}$, —C(O)$NR^{81}R^{81}$, —C($NR^{71}$)$NR^{81}R^{81}$, —OC(O)$R^{71}$, —OC(O)$O^-M^+$, —OC(O)$OR^{71}$, —OC(S)$OR^{71}$, —$NR^{71}$C(O)$R^{71}$, —$NR^{71}$C(S)$R^{71}$, —$NR^{71}CO_2^-M^+$, —$NR^{71}CO_2R^{71}$, —$NR^{71}$C(S)$OR^{71}$, —$NR^{71}$C(O)$NR^{81}R^{81}$, —$NR^{71}$C($NR^{71}$)$R^{71}$, and —$NR^{71}$C($NR^{71}$)$NR^{81}R^{81}$. Each $R^{70}$ is independently hydrogen or $R^{60}$; each $R^{80}$ is independently $R^{70}$ or alternatively, two $R^{80}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$alkyl substitution; and each $M^+$ is a counter ion with a net single positive charge. Each $R^{71}$ is independently hydrogen or $R^{61}$, in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{72}$, —$SR^{72}$, —$S^-M^+$, =S, —$NR^{82}R^{82}$, =$NR^{72}$, =N—$OR^{72}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{72}$, —$OSO_2R^{72}$, —$OSO_2O^-M^+$, —$OSO_2OR^{72}$, —P(O)($O^-$)$_2$($M^+$)$_2$, —P(O)($OR^{72}$)$O^-M^+$, —P(O)($OR^{72}$)$_2$, —C(O)$R^{72}$, —C(S)$R^{72}$, —C($NR^{72}$)$R^{72}$, —C(O)$O^-M^+$, —C(O)$OR^{72}$, —C(S)$OR^{72}$, —C(O)$NR^{82}R^{82}$, —C($NR^{72}$)$NR^{82}R^{82}$, —OC(O)$R^{72}$, —OC(S)$R^{72}$, —OC(O)$O^-M^+$, —OC(O)$OR^{72}$, —OC(S)$OR^{72}$, —$NR^{72}$C(O)$R^{72}$, —$NR^{72}$C(S)$R^{72}$, —$NR^{72}CO_2^-M^+$, —$NR^{72}CO_2R^{72}$, —$NR^{72}$C(S)$OR^{72}$, —$NR^{72}$C(O)$NR^{82}R^{82}$, —$NR^{72}$C($NR^{72}$)$R^{72}$ and —$NR^{72}$C($NR^{72}$)$NR^{82}R^{82}$, and each $R^{81}$ is independently $R^{71}$ or alternatively, two $R^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each $R^{72}$ is independently hydrogen, ($C_1$-$C_6$alkyl) or ($C_1$-$C_6$fluoroalkyl); each $R^{82}$ is independently $R^{72}$ or alternatively, two $R^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$alkyl substitution. Each M may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ (" subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —$NR^{80}R^{80}$ is meant to include —$NH_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$—$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —$CO_2^-M^+$, —$CO_2R^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —$OCO_2^-M^+$, —$OCO_2R^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined.

Substituent groups for hydrogens on nitrogen atoms in "substituted" heteroalkyl and heterocycloalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)$—$R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain embodiments, substituent groups on "substituted" alkyl, cycloalkyl, heterocycloalkyl, aryl and heteroaryl groups are -halo, —OH, —O—($C_1$-$C_4$alkyl), —O—($C_1$-$C_4$haloalkyl), —N($C_0$-$C_4$ alkyl)($C_0$-$C_4$alkyl), —SH, —$S(O)_{0-2}$—($C_1$-$C_4$alkyl), —($C_1$-$C_4$alkyl), —($C_1$-$C_4$haloalkyl), —C(O)—($C_0$-$C_4$alkyl), —C(O)N($C_0$-$C_4$alkyl)($C_0$-$C_4$alkyl), —N($C_0$-$C_4$alkyl)C(O)($C_0$-$C_4$alkyl)($C_0$-$C_4$alkyl), —C(O)O—($C_0$-$C_4$alkyl), —OC(O)—($C_0$-$C_4$alkyl), $S(O)_2$—O($C_0$-$C_4$alkyl), and —$NO_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxoglutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}$F. Similarly, compounds may be enriched in the heavy isotopes of hydrogen: deuterium and tritium; and similarly can be enriched in a radioactive isotope of carbon, such as $^{13}$C. Such isotopic variant compounds undergo different metabolic pathways and can be useful, for example, in studying the ubiquitination pathway and its role in disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" an enzyme with a compound includes the administration of a compound described herein to an individual or patient, such as a human, as well as, for example, introducing a compound into a sample containing a cellular or purified preparation containing the enzyme.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed or otherwise susceptible to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease (including a symptom thereof); for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof; or (ii) eliciting the referenced biological effect (e.g., modulation or inhibition of GDF-8 or TGF-β1).

Manifestation of amelioration of a disease condition by inhibiting GDF-8 or TGF-β1 may require the concomitant or sequential administration of additional therapeutic agents, such as antineoplastic agents in the case of cancer, or antiretroviral agents in the case of viral diseases. For example, administration of GDF-8 and TGF-β1 inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

PHARMACEUTICAL FORMULATIONS AND DOSAGE FORMS

The compounds of structural formulae (I)-(III) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(III).

In the pharmaceutical compositions disclosed herein, one or more compounds of structural formulae (I)-(III) may be present in association with one or more pharmaceutically acceptable carriers, diluents or excipients, and, if desired, other active ingredients. The pharmaceutical compositions containing compounds of structural formulae (I)-(III) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(III) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(III) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins.

Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-3, or analogous synthetic schemes.

One of skill in the art can adapt the reaction sequences of Schemes 1 and 2 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(III) can be synthesized using different routes altogether.

Compounds suitable for use in the presently disclosed pharmaceutical compositions include compounds of Table 1, above. These compounds can be made according to the general schemes described above, for example using a procedure similar to that described below in the Examples.

The following examples are intended to further illustrate certain embodiments and are not intended to limit the scope of the presently disclosed compounds.

EXAMPLES

Example 1: Synthesis and Characterization

Scheme 1: General Synthesis of Bicyclic Imidazole

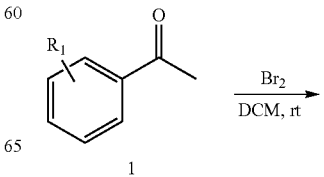

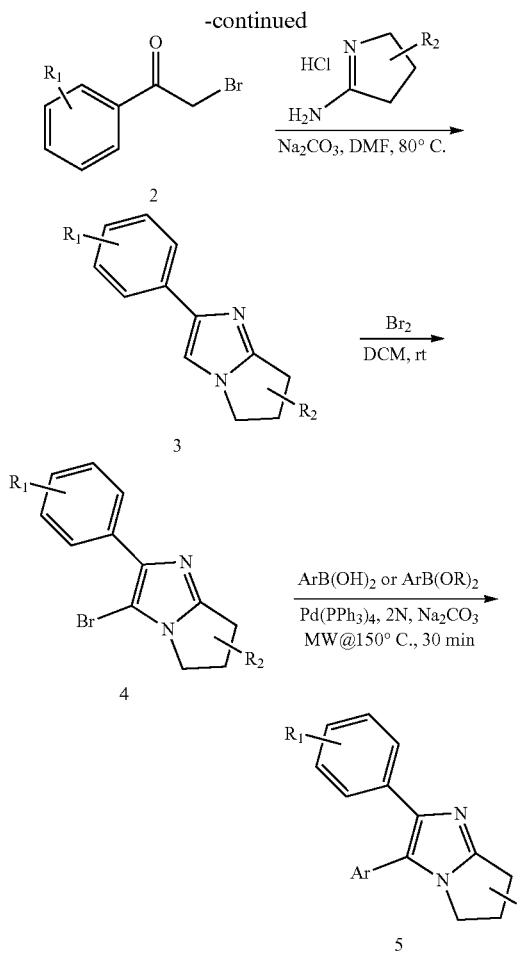

Step 1: To a solution of 2',4',5'-triifluoroacetophenone (2.4 g, 14 mmol) in dichloromethane (16 mL) at room temperature was added a solution of bromine (2.2 g, 13.9 mmol) in dichloromethane (7 mL) drop wise. Once the addition was complete, the resulting solution was stirred at room temperature for 1 h. Ice water was then added into reaction flask and the mixture was stirred for 15 min. The organic layer was separated, washed with water, dried over sodium sulfate, filtered, and concentrated under reduced pressure to give 2-bromo-1-(2,4,5-trifluorophenyl)ethan-1-one as a pale yellow oil (3.0 g, 85%).

Step 2: A mixture of 2-bromo-1-(2,4,5-trifluorophenyl)ethan-1-one (2.5 g, 10 mmol), 3,4-dihydro-2H-pyrrol-5-amine hydrochloride (3.6 g, 30 mmol) and Na$_2$CO$_3$ (5.3 g, 50 mmol) in DMF (15 mL) was stirred at 80° C. for 18 h. After cooling to room temperature, the reaction mixture was then partitioned between water and ethyl acetate. The organic layer was separated, dried over sodium sulfate, filtered, and concentrated under reduced pressure to give a residue, which was purified by chromatography eluting with ethyl acetate to provide 2-(2,4,5-trifluorophenyl)-6,7-dihydro-5H-pyrrolo[1,2-c]imidazole as a pale white solid (0.7 g, 30%).

Step 3: To a solution of 2-(2,4,5-trifluorophenyl)-6,7-dihydro-5H-pyrrolo[1,2-a]imidazole (0.7 g, 2.9 mmol) in dichloromethane (16 mL) at room temperature was added and bromine (0.5 g, 3.2 mmol). The resulting mixture was stirred at room temperature for 20 min and then quenched by saturated aqueous NaHCO$_3$. The organic layer was separated, dried over sodium sulfate, filtered, and concentrated under reduced pressure to give a residue, which was purified by chromatography eluting with ethyl acetate/hexanes (8/2) to provide 3-bromo-2-(2,4,5-trifluorophenyl)-6,7-dihydro-5H-pyrrolo[1,2-a]imidazole as a pale white solid (0.5 g, 55%).

Step 4: A mixture of 3-bromo-2-(2,4,5-trifluorophenyl)-6,7-dihydro-5H-pyrrolo[1,2-a]imidazole (0.04 g, 0.13 mmol), 6-(4,4,5,5-tetramethyl-1,3,2-dioxaborolan-2-yl)quinoxaline (0.05 g, 0.18 mmol), tetrakis(triphenylphosphine)palladium(0) (0.2 g, 0.2 mmol), and 2.0 M of aqueous Na$_2$CO$_3$ (4.0 mL) in 1,2-dimethoxyethane (1.4 mL), EtOH (0.6 mL) and water (0.4 mL) was irradiated under microwave at 150° C. for 0.5 h. The mixture was then concentrated under reduced pressure to give a residue, which was purified by chromatography eluting with ethyl acetate to provide Compound 219: 6-(2-(2,4,5-trifluorophenyl)-6,7-dihydro-5H-pyrrolo[1,2-a]imidazol-3-yl)quinoxaline as a pale white solid (0.2 g, 42%). $^1$H NMR (DMSO-d$_6$, 300 MHz) 8.05 (d, J=9.0 Hz, 1H), 7.97 (m, 1H), 7.69 (m, 1H), 7.59 (m, 3H), 7.45 (m, 1H), 4.20 (t, J=6.9 Hz, 2H), 2.90 (t, J=6.9 Hz, 2H), 2.60 (m, 2H) ppm; MS m/e: 367 (M+H)$^+$.

Compound 98: 2-(2-(2,3,5-trifluorophenyl)-6,7-dihydro-5H-pyrrolo[1,2-a]imidazol-3-yl)thieno[3,2-c]pyridine. $^1$H NMR (DMSO-d$_6$, 300 MHz) 9.06 (m, 1H), 8.35 (d, J=5.4 Hz, 1H), 7.99 (m, 1H), 7.64 (m, 1H), 7.55 (m, 1H), 7.23 (m, 1H), 4.24 (t, J=6.9 Hz, 2H), 2.90 (t, J=6.9 Hz, 2H), 2.62 (m, 2H) ppm; MS m/e: 372 (M+H)$^+$.

Compound 99: 2-(2-(2,4,5-trifluorophenyl)-6,7-dihydro-5H-pyrrolo[1,2-a]imidazol-3-yl)thieno[3,2-c]pyridine. $^1$H NMR (DMSO-d$_6$, 300 MHz) 9.04 (m, 1H), 8.37 (d, J=5.4 Hz, 1H), 7.96 (m, 1H), 7.60 (m, 3H), 4.24 (t, J=7.5 Hz, 2H), 2.89 (t, J=7.5 Hz, 2H), 2.62 (m, 2H) ppm; MS m/e: 372 (M+H)$^+$.

Compound 100: 2-(2-(2-fluorophenyl)-6,7-dihydro-5H-pyrrolo[1,2-a]imidazol-3-yl)thieno[3,2-c]pyridine. $^1$H NMR (DMSO-d$_6$, 300 MHz) 9.02 (s, 1H), 8.33 (m, 1H), 7.92 (m, 1H), 7.59 (m, 1H), 7.51 (m, 1H), 7.41 (m, 1H), 7.23 (m, 2H), 4.25 (t, J=6.9 Hz, 2H), 2.89 (t, J=6.9 Hz, 2H), 2.59 (m, 2H) ppm; MS m/e: 336 (M+H)$^+$.

Compound 101: 2-(2-(4-fluorophenyl)-6,7-dihydro-5H-pyrrolo[1,2-a]imidazol-3-yl)thieno[3,2-c]pyridine. $^1$H NMR (DMSO-d$_6$, 300 MHz) 9.07 (s, 1H), 8.39 (m, 1H), 7.99 (m, 1H), 7.67 (m, 1H), 7.53 (m, 2H), 7.15 (m, 2H), 4.09 (t, J=7.5 Hz, 2H), 2.84 (t, J=7.5 Hz, 2H), 2.55 (m, 2H) ppm; MS m/e: 336 (M+H)$^+$.

Compound 102: 2-(2-(5-chloro-2-fluorophenyl)-6,7-dihydro-5H-pyrrolo[1,2-a]imidazol-3-yl)thieno[3,2-c]pyridine. MS m/e: 370 (M+H)$^+$.

Compound 1: 6-(2-(m-tolyl)-6,7-dihydro-5H-pyrrolo[1,2-a]imidazol-3-yl)imidazo[1,2-c]pyridine. MS m/e: 315 (M+H)$^+$.

Compound 2: 6-(2-(4-fluorophenyl)-6,7-dihydro-5H-pyrrolo[1,2-c]imidazol-3-yl)imidazo[1,2-c]pyridine. MS m/e: 319 (M+H)$^+$.

Compound 3: 6-(2-(4-fluoro-3-methylphenyl)-6,7-dihydro-5H-pyrrolo[1,2-a]imidazol-3-yl)imidazo[1,2-a]pyridine. $^1$H NMR (DMSO-d$_6$, 300 MHz) 8.68 (m, 1H), 7.94 (m, 1H), 7.58 (m, 2H), 7.45 (m, 1H), 7.17 (m, 1H), 7.09 (m, 1H), 6.98 (m, 1H), 3.96 (t, J=6.9 Hz, 2H), 2.81 (t, J=6.9 Hz, 2H), 2.54 (m, 2H), 2.15 (s, 3H) ppm; MS m/e: 333 (M+H)$^+$.

Compound 4: 6-(2-(3-(trifluoromethyl)phenyl)-6,7-dihydro-5H-pyrrolo[1,2-c]imidazol-3-yl)imidazo[1,2-c]pyridine. MS m/e: 369 (M+H)$^+$.

Compound 5: 6-(2-(3-methoxyphenyl)-6,7-dihydro-5H-pyrrolo[1,2-c]imidazol-3-yl)imidazo[1,2-a]pyridine. MS m/e: 331 (M+H)$^+$.

Compound 6: 6-(2-(3-chlorophenyl)-6,7-dihydro-5H-pyrrolo[1,2-a]imidazol-3-yl)imidazo[1,2-a]pyridine. MS m/e: 335 (M+H)⁺.

Compound 7: 6-(2-(3-fluorophenyl)-6,7-dihydro-5H-pyrrolo[1,2-c]imidazol-3-yl)imidazo[1,2-c]pyridine. MS m/e: 319 (M+H)⁺.

Compound 8: 6-(2-(2-fluorophenyl)-6,7-dihydro-5H-pyrrolo[1,2-c]imidazol-3-yl)imidazo[1,2-c]pyridine. MS m/e: 319 (M+H)⁺.

Compound 9: 6-(2-(2,4-difluorophenyl)-6,7-dihydro-5H-pyrrolo[1,2-c]imidazol-3-yl)imidazo[1,2-c]pyridine. MS m/e: 337 (M+H)⁺.

Compound 10: 6-(2-(3,4-difluorophenyl)-6,7-dihydro-5H-pyrrolo[1,2-c]imidazol-3-yl)imidazo[1,2-c]pyridine. MS m/e: 337 (M+H)⁺.

Compound 11: 6-(2-(2,6-difluorophenyl)-6,7-dihydro-5H-pyrrolo[1,2-c]imidazol-3-yl)imidazo[1,2-c]pyridine. MS m/e: 337 (M+H)⁺.

Compound 12: 6-(2-(2,4,5-trifluorophenyl)-6,7-dihydro-5H-pyrrolo[1,2-c]imidazol-3-yl)imidazo[1,2-a]pyridine. ¹H NMR (DMSO-d₆, 300 MHz) 8.57 (m, 1H), 7.91 (m, 1H), 7.57 (m, 3H), 7.45 (m, 1H), 7.07 (m, 1H), 4.07 (t, J=7.5 Hz, 2H), 2.84 (t, J=7.5 Hz, 2H), 2.61 (m, 2H) ppm; MS m/e: 355 (M+H)⁺.

Compound 13: 6-(2-(3,4,5-trifluorophenyl)-6,7-dihydro-5H-pyrrolo[1,2-c]imidazol-3-yl)imidazo[1,2-c]pyridine. MS m/e: 355 (M+H)⁺.

Compound 14: 6-(2-(2,4,5-trifluorophenyl)-6,7-dihydro-5H-pyrrolo[1,2-a]imidazol-3-yl)-[1,2,4]triazolo[1,5-a]pyridine. ¹H NMR (DMSO-d₆, 300 MHz) 9.02 (m, 1H), 8.52 (s, 1H), 7.83 (m, 1H), 7.63 (m, 1H), 7.43 (m, 2H), 4.12 (t, J=6.9 Hz, 2H), 2.86 (t, J=6.9 Hz, 2H), 2.57 (m, 2H) ppm; MS m/e: 356 (M+H)⁺.

Compound 15: 6-(2-(2,3,4-trifluorophenyl)-6,7-dihydro-5H-pyrrolo[1,2-a]imidazol-3-yl)-[1,2,4]triazolo[1,5-a]pyridine. MS m/e: 356 (M+H)⁺.

Compound 16: 6-(2-(3,4,5-trifluorophenyl)-6,7-dihydro-5H-pyrrolo[1,2-a]imidazol-3-yl)-[1,2,4]triazolo[1,5-a]pyridine. ¹H NMR (DMSO-d₆, 300 MHz) 9.19 (m, 1H), 8.57 (s, 1H), 7.90 (m, 1H), 7.55 (m, 1H), 7.26 (m, 2H), 4.00 (t, J=6.9 Hz, 2H), 2.86 (t, J=6.9 Hz, 2H), 2.56 (m, 2H) ppm; MS m/e: 356 (M+H)⁺.

Compound 17: 6-(2-(2,3,5-trifluorophenyl)-6,7-dihydro-5H-pyrrolo[1,2-a]imidazol-3-yl)-[1,2,4]triazolo[1,5-a]pyridine. ¹H NMR (DMSO-d₆, 300 MHz) 9.08 (m, 1H), 8.54 (s, 1H), 7.86 (m, 1H), 7.51 (m, 1H), 7.43 (m, 1H), 7.24 (m, 1H), 4.12 (t, J=6.9 Hz, 2H), 2.89 (t, J=6.9 Hz, 2H), 2.60 (m, 2H) ppm; MS m/e: 356 (M+H)⁺.

Compound 18: 6-(2-(4-chloro-2,5-difluorophenyl)-6,7-dihydro-5H-pyrrolo[1,2-a]imidazol-3-yl)-[1,2,4]triazolo[1,5-a]pyridine. MS m/e: 372 (M+H)⁺.

Compound 19: 6-(2-(4-chloro-2,5-difluorophenyl)-6,7-dihydro-5H-pyrrolo[1,2-a]imidazol-3-yl)imidazo[1,2-a]pyridine. MS m/e: 371 (M+H)⁺.

Compound 22: 3-isopropyl-6-(2-(2,3,5-trifluorophenyl)-6,7-dihydro-5H-pyrrolo[1,2-a]imidazol-3-yl)-[1,2,4]triazolo[4,3-a]pyridine. MS m/e: 398 (M+H)⁺.

Compound 21: 3-isopropyl-6-(2-(2,4,5-trifluorophenyl)-6,7-dihydro-5H-pyrrolo[1,2-a]imidazol-3-yl)-[1,2,4]triazolo[4,3-a]pyridine. MS m/e: 398 (M+H)⁺.

Compound 20: 6-(2-(4-chloro-2,5-difluorophenyl)-6,7-dihydro-5H-pyrrolo[1,2-a]imidazol-3-yl)-3-isopropyl-[1,2,4]triazolo[4,3-a]pyridine. MS m/e: 414 (M+H)⁺.

Compound 23: 3-isopropyl-6-(2-(2,3,4-trifluorophenyl)-6,7-dihydro-5H-pyrrolo[1,2-a]imidazol-3-yl)-[1,2,4]triazolo[4,3-a]pyridine. MS m/e: 398 (M+H)⁺.

Compound 24: 6-(2-(4-chloro-3,5-dimethylphenyl)-6,7-dihydro-5H-pyrrolo[1,2-a]imidazol-3-yl)-[1,2,4]triazolo[1,5-a]pyridine. MS m/e: 364 (M+H)⁺.

Compound 25: 6-(2-(4-chloro-3,5-dimethylphenyl)-6,7-dihydro-5H-pyrrolo[1,2-a]imidazol-3-yl)imidazo[1,2-a]pyridine. MS m/e: 363 (M+H)⁺.

Compound 26: 6-(2-(2,3-difluoro-4-methylphenyl)-6,7-dihydro-5H-pyrrolo[1,2-a]imidazol-3-yl)-[1,2,4]triazolo[1,5-a]pyridine. MS m/e: 352 (M+H)⁺.

Compound 27: 6-(2-(2,3-difluoro-4-methylphenyl)-6,7-dihydro-5H-pyrrolo[1,2-c]imidazol-3-yl)imidazo[1,2-c]pyridine. MS m/e: 351 (M+H)⁺.

Compound 28: 6-(2-(4-chloro-2-fluoro-5-methylphenyl)-6,7-dihydro-5H-pyrrolo[1,2-c]imidazol-3-yl)-[1,2,4]triazolo[1,5-c]pyridine. MS m/e: 368 (M+H)⁺.

Compound 29: 6-(2-(4-chloro-2-fluoro-5-methylphenyl)-6,7-dihydro-5H-pyrrolo[1,2-c]imidazol-3-yl)imidazo[1,2-c]pyridine. MS m/e: 367 (M+H)⁺.

Compound 30: 6-(2-(4-methoxy-3,5-dimethylphenyl)-6,7-dihydro-5H-pyrrolo[1,2-a]imidazol-3-yl)-[1,2,4]triazolo[1,5-a]pyridine. MS m/e: 360 (M+H)⁺.

Compound 31: 6-(2-(4-methoxy-3,5-dimethylphenyl)-6,7-dihydro-5H-pyrrolo[1,2-c]imidazol-3-yl)imidazo[1,2-c]pyridine. MS m/e: 359 (M+H)⁺.

Compound 32: 6-(2-(4,5-difluoro-2-methylphenyl)-6,7-dihydro-5H-pyrrolo[1,2-c]imidazol-3-yl)imidazo[1,2-c]pyridine. MS m/e: 351 (M+H)⁺.

Compound 33: 3-(trifluoromethyl)-6-(2-(3,4,5-trifluorophenyl)-6,7-dihydro-5H-pyrrolo[1,2-c]imidazol-3-yl)-[1,2,4]triazolo[4,3-c]pyridine. MS m/e: 424 (M+H)⁺.

Compound 34: 3-(trifluoromethyl)-6-(2-(2,4,5-trifluorophenyl)-6,7-dihydro-5H-pyrrolo[1,2-c]imidazol-3-yl)-[1,2,4]triazolo[4,3-c]pyridine. MS m/e: 424 (M+H)⁺.

Compound 35: 3-(trifluoromethyl)-6-(2-(2,3,4-trifluorophenyl)-6,7-dihydro-5H-pyrrolo[1,2-c]imidazol-3-yl)-[1,2,4]triazolo[4,3-c]pyridine. MS m/e: 424 (M+H)⁺.

Compound 36: 6-(2-(3-chloro-4-fluorophenyl)-6,7-dihydro-5H-pyrrolo[1,2-a]imidazol-3-yl)-[1,2,4]triazolo[1,5-a]pyridine. MS m/e: 354 (M+H)⁺.

Compound 37: 6-(2-(3-chloro-4-fluorophenyl)-6,7-dihydro-5H-pyrrolo[1,2-c]imidazol-3-yl)imidazo[1,2-c]pyridine. ¹H NMR (DMSO-d₆, 300 MHz) 8.72 (m, 1H), 7.95 (m, 1H), 7.63 (m, 1H), 7.30 (m, 2H), 7.13 (m, 1H), 3.96 (t, J=7.2 Hz, 2H), 2.85 (t, J=7.2 Hz, 2H), 2.54 (m, 2H) ppm; MS m/e: 353 (M+H)⁺.

Compound 38: 6-(2-(2,4-difluoro-5-methylphenyl)-6,7-dihydro-5H-pyrrolo[1,2-a]imidazol-3-yl)-[1,2,4]triazolo[1,5-a]pyridine. ¹H NMR (DMSO-d₆, 300 MHz) 8.96 (m, 1H), 8.51 (s, 1H), 7.81 (m, 1H), 7.53 (m, 1H), 7.43 (m, 1H), 7.06 (m, 1H), 4.13 (t, J=7.2 Hz, 2H), 2.87 (t, J=7.2 Hz, 2H), 2.57 (m, 2H), 2.21 (s, 3H) ppm; MS m/e: 352 (M+H)⁺.

Compound 39: 6-(2-(2,4-difluoro-5-methylphenyl)-6,7-dihydro-5H-pyrrolo[1,2-a]imidazol-3-yl)imidazo[1,2-c]pyridine. ¹H NMR (DMSO-d₆, 300 MHz) 8.54 (m, 1H), 7.91 (m, 1H), 7.53 (m, 3H), 7.04 (m, 2H), 4.07 (t, J=7.2 Hz, 2H), 2.86 (t, J=7.2 Hz, 2H), 2.54 (m, 2H), 2.20 (s, 3H) ppm; MS m/e: 351 (M+H)⁺.

Compound 40: 6-(2-(3-chloro-4-fluoro-5-methylphenyl)-6,7-dihydro-5H-pyrrolo[1,2-c]imidazol-3-yl)-[1,2,4]triazolo[1,5-c]pyridine. MS m/e: 368 (M+H)⁺.

Compound 41: 6-(2-(3-chloro-4-fluoro-5-methylphenyl)-6,7-dihydro-5H-pyrrolo[1,2-c]imidazol-3-yl)imidazo[1,2-c]pyridine. ¹H NMR (DMSO-d₆, 300 MHz) 8.73 (m, 1H), 7.95 (m, 1H), 7.61 (m, 1H), 7.34 (m, 2H), 7.11 (m, 1H), 3.97 (t, J=6.6 Hz, 2H), 2.84 (t, J=6.6 Hz, 2H), 2.54 (m, 2H), 2.16 (s, 3H) ppm; MS m/e: 367 (M+H)⁺.

Compound 42: 6-(2-(4-fluoro-3,5-dimethylphenyl)-6,7-dihydro-5H-pyrrolo[1,2-a]imidazol-3-yl)-[1,2,4]triazolo[1,5-a]pyridine. MS m/e: 348 (M+H)$^+$.

Compound 43: 6-(2-(4-fluoro-3,5-dimethylphenyl)-6,7-dihydro-5H-pyrrolo[1,2-a]imidazol-3-yl)imidazo[1,2-c]pyridine. MS m/e: 347 (M+H)$^+$.

Compound 44: 6-(2-(3,4-difluoro-2-methylphenyl)-6,7-dihydro-5H-pyrrolo[1,2-a]imidazol-3-yl)-[1,2,4]triazolo[1,5-a]pyridine. MS m/e: 352 (M+H)$^+$.

Compound 45: 6-(2-(2,4-difluoro-3-methylphenyl)-6,7-dihydro-5H-pyrrolo[1,2-a]imidazol-3-yl)-[1,2,4]triazolo[1,5-a]pyridine. $^1$H NMR (DMSO-d$_6$, 300 MHz) 8.99 (s, 1H), 8.51 (s, 1H), 7.80 (m, 1H), 7.39 (m, 2H), 7.06 (m, 2H), 4.14 (t, J=6.9 Hz, 2H), 2.87 (t, J=6.9 Hz, 2H), 2.54 (m, 2H), 2.03 (s, 3H) ppm; MS m/e: 352 (M+H)$^+$.

Compound 46: 6-(2-(2,4-difluoro-3-methylphenyl)-6,7-dihydro-5H-pyrrolo[1,2-a]imidazol-3-yl)imidazo[1,2-a]pyridine. $^1$H NMR (DMSO-d$_6$, 300 MHz) 8.58 (m, 1H), 7.92 (m, 1H), 7.52 (m, 2H), 7.35 (m, 1H), 7.01 (m, 2H), 4.08 (t, J=7.2 Hz, 2H), 2.88 (t, J=7.2 Hz, 2H), 2.56 (m, 2H), 2.03 (s, 3H) ppm; MS m/e: 351 (M+H)$^+$.

Compound 47: 6-(2-(2,5-difluoro-4-methylphenyl)-6,7-dihydro-5H-pyrrolo[1,2-a]imidazol-3-yl)-[1,2,4]triazolo[1,5-a]pyridine. MS m/e: 352 (M+H)$^+$.

Compound 48: 6-(2-(2,5-difluoro-4-methylphenyl)-6,7-dihydro-5H-pyrrolo[1,2-a]imidazol-3-yl)imidazo[1,2-c]pyridine. $^1$H NMR (DMSO-d$_6$, 300 MHz) 8.56 (m, 1H), 7.91 (m, 1H), 7.56 (m, 1H), 7.53 (m, 1H), 7.28 (m, 1H), 7.04 (m, 2H), 4.06 (t, J=6.9 Hz, 2H), 2.86 (t, J=6.9 Hz, 2H), 2.56 (m, 2H), 2.20 (s, 3H) ppm; MS m/e: 351 (M+H)$^+$.

Compound 49: 6-(2-(2-chloro-4,5-difluorophenyl)-6,7-dihydro-5H-pyrrolo[1,2-a]imidazol-3-yl)-[1,2,4]triazolo[1,5-a]pyridine. MS m/e: 372 (M+H)$^+$.

Compound 50: 6-(2-(2-chloro-4,5-difluorophenyl)-6,7-dihydro-5H-pyrrolo[1,2-c]imidazol-3-yl)imidazo[1,2-c]pyridine. MS m/e: 371 (M+H)$^+$.

Compound 51: 6-(2-(3-chloro-4-fluorophenyl)-6,7-dihydro-5H-pyrrolo[1,2-c]imidazol-3-yl)imidazo[1,2-c]pyridine-3-carboxamide. $^1$H NMR (DMSO-d$_6$, 300 MHz) 9.55 (m, 1H), 8.36 (s, 1H), 7.96 (bs, 1H), 7.78 (m, 1H), 7.64 (m, 1H), 7.32 (m, 4H), 3.94 (t, J=6.9 Hz, 2H), 2.85 (t, J=6.9 Hz, 2H), 2.55 (m, 2H) ppm; MS m/e: 396 (M+H)$^+$.

Compound 52: 6-(2-(4,5-difluoro-2-methylphenyl)-6,7-dihydro-5H-pyrrolo[1,2-c]imidazol-3-yl)imidazo[1,2-c]pyridine-3-carboxamide. $^1$H NMR (DMSO-d$_6$, 300 MHz) 9.55 (m, 1H), 8.36 (m, 1H), 8.00 (bs, 1H), 7.78 (m, 1H), 7.64 (m, 1H), 7.33 (m, 3H), 3.94 (t, J=7.5 Hz, 2H), 2.83 (t, J=7.5 Hz, 2H), 2.52 (m, 2H) ppm; MS m/e: 394 (M+H)$^+$.

Compound 53: 6-(2-(3,4,5-trifluorophenyl)-6,7-dihydro-5H-pyrrolo[1,2-c]imidazol-3-yl)imidazo[1,2-a]pyridine-3-carboxamide. $^1$H NMR (DMSO-d$_6$, 300 MHz) 9.56 (s, 1H), 8.38 (s, 1H), 8.00 (bs, 1H), 7.79 (d, J=9.3 Hz, 1H), 7.41 (m, 2H), 7.26 (m, 2H), 3.94 (t, J=6.9 Hz, 2H), 3.30 (s, 3H), 2.86 (t, J=6.9 Hz, 2H), 2.55 (m, 2H) ppm; MS m/e: 398 (M+H)$^+$.

Compound 54: 6-(2-(4-fluoro-2-methylphenyl)-6,7-dihydro-5H-pyrrolo[1,2-a]imidazol-3-yl)-[1,2,4]triazolo[1,5-a]pyridine. MS m/e: 334 (M+H)$^+$.

Compound 55: 6-(2-(4-fluoro-2-methylphenyl)-6,7-dihydro-5H-pyrrolo[1,2-c]imidazol-3-yl)imidazo[1,2-c]pyridine. MS m/e: 333 (M+H)$^+$.

Compound 58: 6-(2-(5-fluoro-2-methylphenyl)-6,7-dihydro-5H-pyrrolo[1,2-a]imidazol-3-yl)-[1,2,4]triazolo[1,5-a]pyridine. MS m/e: 334 (M+H)$^+$.

Compound 59: 6-(2-(5-fluoro-2-methylphenyl)-6,7-dihydro-5H-pyrrolo[1,2-c]imidazol-3-yl)imidazo[1,2-c]pyridine. MS m/e: 333 (M+H)$^+$.

Compound 62: 6-(2-(2-methylphenyl)-6,7-dihydro-5H-pyrrolo[1,2-c]imidazol-3-yl)-[1,2,4]triazolo[1,5-a]pyridine. MS m/e: 316 (M+H)$^+$.

Compound 63: 6-(2-(2-methylphenyl)-6,7-dihydro-5H-pyrrolo[1,2-c]imidazol-3-yl)imidazo[1,2-c]pyridine. MS m/e: 315 (M+H)$^+$.

Compound 61: 6-(2-(3-chloro-4-fluorophenyl)-6,7-dihydro-5H-pyrrolo[1,2-c]imidazol-3-yl)imidazo[1,2-c]pyridine-3-carbonitrile. MS m/e: 378 (M+H)$^+$.

Compound 56: 6-(2-(5-chloro-4-fluoro-2-methylphenyl)-6,7-dihydro-5H-pyrrolo[1,2-a]imidazol-3-yl)-[1,2,4]triazolo[1,5-a]pyridine. $^1$H NMR (DMSO-d$_6$, 300 MHz) 8.93 (m, 1H), 8.51 (m, 1H), 7.79 (m, 1H), 7.31 (m, 3H), 4.16 (t, J=6.9 Hz, 2H), 2.87 (t, J=6.9 Hz, 2H), 2.58 (m, 2H), 2.07 (s, 3H) ppm; MS m/e: 368 (M+H)$^+$.

Compound 57: 6-(2-(5-chloro-4-fluoro-2-methylphenyl)-6,7-dihydro-5H-pyrrolo[1,2-c]imidazol-3-yl)imidazo[1,2-c]pyridine. $^1$H NMR (DMSO-d$_6$, 300 MHz) 8.54 (m, 1H), 7.92 (s, 1H), 7.56 (m, 1H), 7.50 (m, 1H), 7.28 (m, 2H), 6.89 (m, 1H), 4.11 (t, J=7.2 Hz, 2H), 2.86 (t, J=7.2 Hz, 2H), 2.58 (m, 2H), 2.06 (s, 3H) ppm; MS m/e: 367 (M+H)$^+$.

Compound 311: 6-(2-(4-fluoro-2,5-dimethylphenyl)-6,7-dihydro-5H-pyrrolo[1,2-a]imidazol-3-yl)quinoline. $^1$H NMR (DMSO-d$_6$, 300 MHz) 8.82 (m, 1H), 8.27 (m, 1H), 7.86 (m, 2H), 7.49 (m, 1H), 7.37 (m, 1H), 7.11 (m, 1H), 6.95 (m, 1H), 4.21 (t, J=6.6 Hz, 2H), 2.87 (t, J=6.6 Hz, 2H), 2.60 (m, 2H), 2.11 (s, 3H), 1.93 (s, 3H) ppm; MS m/e: 358 (M+H)$^+$.

Compound 64: 6-(2-(4-fluoro-2,5-dimethylphenyl)-6,7-dihydro-5H-pyrrolo[1,2-a]imidazol-3-yl)-[1,2,4]triazolo[1,5-a]pyridine. MS m/e: 347 (M+H)$^+$.

Compound 65: 6-(2-(4-fluoro-2,5-dimethylphenyl)-6,7-dihydro-5H-pyrrolo[1,2-c]imidazol-3-yl)imidazo[1,2-c]pyridine Compound 66: 6-(2-(2-chloro-4-fluoro-3-methylphenyl)-6,7-dihydro-5H-pyrrolo[1,2-a]imidazol-3-yl)-[1,2,4]triazolo[1,5-a]pyridine. $^1$H NMR (DMSO-d$_6$, 300 MHz) 8.86 (m, 1H), 8.49 (m, 1H), 7.77 (m, 1H), 7.30 (m, 2H), 7.19 (m, 1H), 4.19 (t, J=6.9 Hz, 2H), 2.88 (t, J=6.9 Hz, 2H), 2.58 (m, 2H), 2.21 (s, 3H) ppm; MS m/e: 368 (M+H)$^+$.

Compound 67: 6-(2-(2-chloro-4-fluoro-3-methylphenyl)-6,7-dihydro-5H-pyrrolo[1,2-c]imidazol-3-yl)imidazo[1,2-c]pyridine. $^1$H NMR (DMSO-d$_6$, 300 MHz) 8.52 (m, 1H), 7.91 (s, 1H), 7.54 (m, 1H), 7.47 (m, 1H), 7.28 (m, 1H), 7.17 (m, 1H), 6.85 (m, 1H), 4.13 (t, J=6.6 Hz, 2H), 2.86 (t, J=6.6 Hz, 2H), 2.58 (m, 2H), 2.22 (s, 3H) ppm; MS m/e: 367 (M+H)$^+$.

Compound 68: 6-(2-(2-chloro-4-fluoro-5-methylphenyl)-6,7-dihydro-5H-pyrrolo[1,2-c]imidazol-3-yl)imidazo[1,2-c]pyridine. MS m/e: 367 (M+H)$^+$.

Compound 69: 6-(2-(2-chloro-4-fluoro-5-methylphenyl)-6,7-dihydro-5H-pyrrolo[1,2-a]imidazol-3-yl)-[1,2,4]triazolo[1,5-a]pyridine. $^1$H NMR (DMSO-d$_6$, 300 MHz) 8.86 (m, 1H), 8.49 (m, 1H), 7.79 (m, 1H), 7.45 (m, 1H), 7.32 (m, 2H), 4.19 (t, J=6.6 Hz, 2H), 2.88 (t, J=6.6 Hz, 2H), 2.58 (m, 2H), 2.21 (s, 3H) ppm; MS m/e: 368 (M+H)$^+$.

Compound 70: 2-fluoro-N-(3-(3-(imidazo[1,2-c]pyridin-6-yl)-6,7-dihydro-5H-pyrrolo[1,2-c]imidazol-2-yl)phenyl)benzenesulfonamide. MS m/e: 474 (M+H)$^+$.

Compound 71: 3'-([1,2,4]triazolo[1,5-a]pyridin-6-yl)-2'-(4-fluorophenyl)-5'H,7'H-spiro[cyclopentane-1,6'-pyrrolo[1,2-c]imidazole]. MS m/e: 374 (M+H)$^+$.

Compound 72: 2'-(4-fluorophenyl)-3'-(imidazo[1,2-c]pyridin-6-yl)-5'H,7'H-spiro[cyclopentane-1,6'-pyrrolo[1,2-c]imidazole]. MS m/e: 373 (M+H)$^+$.

Compound 73: 6-(2-(4-fluoro-2,3-dimethylphenyl)-6,7-dihydro-5H-pyrrolo[1,2-c]imidazol-3-yl)-[1,2,4]triazolo[1,5-a]pyridine. MS m/e: 368 (M+H)⁺.

Compound 74: 6-(2-(4-fluoro-2,3-dimethylphenyl)-6,7-dihydro-5H-pyrrolo[1,2-c]imidazol-3-yl)imidazo[1,2-c]pyridine. MS m/e: 367 (M+H)⁺.

Compound 75: (3'-([1,2,4]triazolo[1,5-a]pyridin-6-yl)-2'-(4-fluorophenyl)-5'H,7'H-spiro[cyclohexane-1,6'-pyrrolo[1,2-c]imidazol]-4-yl)methanol. MS m/e: 418 (M+H)⁺.

Compound 76: 3'-([1,2,4]triazolo[1,5-a]pyridin-6-yl)-2'-(4-fluorophenyl)-5'H,7'H-spiro[cyclohexane-1,6'-pyrrolo[1,2-c]imidazole]-4-carboxylic acid. MS m/e: 432 (M+H)⁺.

Compound 77: Ethyl 3'-([1,2,4]triazolo[1,5-a]pyridin-6-yl)-2'-(4-fluorophenyl)-5'H,7'H-spiro[cyclohexane-1,6'-pyrrolo[1,2-c]imidazole]-4-carboxylate. MS m/e: 460 (M+H)⁺.

Compound 81: 6-(2-(3-chloro-2,4-difluorophenyl)-6,7-dihydro-5H-pyrrolo[1,2-c]imidazol-3-yl)-[1,2,4]triazolo[1,5-a]pyridine. MS m/e: 372 (M+H)⁺.

Compound 78: 3'-([1,2,4]triazolo[1,5-a]pyridin-6-yl)-2'-(4-fluorophenyl)-N-methyl-5'H,7'H-spiro[cyclohexane-1,6'-pyrrolo[1,2-c]imidazole]-4-carboxamide. MS m/e: 445 (M+H)⁺.

Compound 79: 3'-([1,2,4]triazolo[1,5-a]pyridin-6-yl)-2'-(4-fluorophenyl)-N,N-dimethyl-5'H,7'H-spiro[cyclohexane-1,6'-pyrrolo[1,2-c]imidazole]-4-carboxamide. MS m/e: 459 (M+H)⁺.

Compound 80: 3'-([1,2,4]triazolo[1,5-a]pyridin-6-yl)-2'-(4-fluorophenyl)-5'H,7'H-spiro[cyclohexane-1,6'-pyrrolo[1,2-c]imidazole]-4-carboxamide. MS m/e: 431 (M+H)⁺.

Compound 82: 6-(2-(5-chloro-2-fluoro)-6,7-dihydro-5H-pyrrolo[1,2-c]imidazol-3-yl)-[1,2,4]triazolo[1,5-a]pyridine. ¹H NMR (DMSO-d₆, 300 MHz) 9.02 (m, 1H), 8.52 (m, 1H), 7.83 (m, 1H), 7.64 (m, 1H), 7.49 (m, 1H), 7.36 (m, 1H), 7.14 (m, 1H), 4.12 (t, J=6.9 Hz, 2H), 2.89 (t, J=6.9 Hz, 2H), 2.57 (m, 2H) ppm; MS m/e: 354 (M+H)⁺.

Compound 83: 6-(2-(5-chloro-2-fluoro)-6,7-dihydro-5H-pyrrolo[1,2-c]imidazol-3-yl)imidazo[1,2-a]pyridine. ¹H NMR (DMSO-d₆, 300 MHz) 8.60 (m, 1H), 7.93 (m, 1H), 7.60 (m, 3H), 7.34 (m, 1H), 7.13 (m, 2H), 4.08 (t, J=6.9 Hz, 2H), 2.88 (t, J=6.9 Hz, 2H), 2.57 (m, 2H) ppm; MS m/e: 353 (M+H)⁺.

Compound 88: benzyl 3-([1,2,4]triazolo[1,5-a]pyridin-6-yl)-2-(4-fluorophenyl)-5,5a,6,7,9,9a-hexahydro-8H-imidazo[1',2':1,2]pyrrolo[3,4-c]pyridine-8-carboxylate. MS m/e: 509 (M+H)⁺.

Compound 89: 3-([1,2,4]triazolo[1,5-a]pyridin-6-yl)-2-(4-fluorophenyl)-8-methyl-5a,6,7,8,9,9a-hexahydro-5H-imidazo[1',2':1,2]pyrrolo[3,4-c]pyridine. ¹H NMR (DMSO-d₆, 300 MHz) 9.12 (m, 1H), 8.54 (s, 1H), 7.86 (m, 1H), 7.48 (m, 3H), 7.08 (m, 2H), 4.01 (m, 1H), 3.76 (m, 1H), 3.21 (m, 1H), 2.84 (m, 1H), 2.71 (m, 1H), 2.39 (m, 1H), 2.25 (m, 4H), 1.83 (m, 1H), 1.55 (m, 1H), 1.22 (m, 1H) ppm; MS m/e: 389 (M+H)⁺.

Compound 84: (3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)methyl methanesulfonate. MS m/e: 496 (M+H)⁺.

Compound 85: 3'-([1,2,4]triazolo[1,5-a]pyridin-6-yl)-4-(azidomethyl)-2'-(4-fluorophenyl)-5'H,7'H-spiro[cyclohexane-1,6'-pyrrolo[1,2-a]imidazole]. MS m/e: 443 (M+H)⁺.

Compound 86: 1-(3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)-N-methylmethanamine. MS m/e: 431 (M+H)⁺.

Compound 87: 1-(3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)-N,N-dimethylmethanamine. MS m/e: 445 (M+H)⁺.

Compound 90: 6-(2-(5-chloro-2-methyl)-6,7-dihydro-5H-pyrrolo[1,2-a]imidazol-3-yl)-[1,2,4]triazolo[1,5-a]pyridine. ¹H NMR (DMSO-d₆, 300 MHz) 8.91 (m, 1H), 8.50 (s, 1H), 7.79 (m, 1H), 7.25 (m, 4H), 4.17 (t, J=6.6 Hz, 2H), 2.88 (t, J=6.6 Hz, 2H), 2.58 (m, 2H), 2.05 (s, 3H) ppm; MS m/e: 350 (M+H)⁺.

Compound 91: 6-(2-(5-([1,2,4]triazolo[1,5-a]pyridin-6-yl)-2-methylphenyl)-6,7-dihydro-5H-pyrrolo[1,2-a]imidazol-3-yl)-[1,2,4]triazolo[1,5-a]pyridine. ¹H NMR (DMSO-d₆, 300 MHz) 9.16 (m, 1H), 8.92 (m, 1H), 8.48 (s, 2H), 7.82 (m, 3H), 7.66 (m, 2H), 7.36 (m, 2H), 4.20 (t, J=6.9 Hz, 2H), 2.90 (t, J=6.9 Hz, 2H), 2.60 (m, 2H), 2.11 (s, 3H) ppm; MS m/e: 433 (M+H)⁺.

Compound 92: 6-(2-(2,5-dichlorophenyl)-6,7-dihydro-5H-pyrrolo[1,2-c]imidazol-3-yl)-[1,2,4]triazolo[1,5-a]pyridine. ¹H NMR (DMSO-d₆, 300 MHz) 8.90 (m, 1H), 8.50 (m, 1H), 7.81 (m, 1H), 7.55 (m, 1H), 7.41 (m, 3H), 4.18 (t, J=6.6 Hz, 2H), 2.89 (t, J=6.6 Hz, 2H), 2.59 (m, 2H) ppm; MS m/e: 370 (M+H)⁺.

Compound 94: 6-(2-(5-chloro-2,4-difluoro)-6,7-dihydro-5H-pyrrolo[1,2-c]imidazol-3-yl)-[1,2,4]triazolo[1,5-c]pyridine. MS m/e: 372 (M+H)⁺.

Compound 93: 6-(2-(2,5-dichlorophenyl)-6,7-dihydro-5H-pyrrolo[1,2-c]imidazol-3-yl)imidazo[1,2-a]pyridine. ¹H NMR (DMSO-d₆, 300 MHz) 8.52 (m, 1H), 7.92 (m, 1H), 7.54 (m, 3H), 7.41 (m, 2H), 6.96 (m, 1H), 4.13 (t, J=6.6 Hz, 2H), 2.88 (t, J=6.6 Hz, 2H), 2.59 (m, 2H) ppm; MS m/e: 369 (M+H)⁺.

Compound 95: 6-(2-(4-methoxyphenyl)-6,7-dihydro-5H-pyrrolo[1,2-c]imidazol-3-yl)-[1,2,4]triazolo[1,5-a]pyridine. MS m/e: 332 (M+H)⁺.

Compound 96: 6-(2-(2-fluoro-5-methylphenyl)-6,7-dihydro-5H-pyrrolo[1,2-a]imidazol-3-yl)-[1,2,4]triazolo[1,5-a]pyridine. ¹H NMR (DMSO-d₆, 300 MHz) 8.93 (m, 1H), 8.50 (s, 1H), 7.81 (m, 1H), 7.42 (m, 2H), 7.09 (m, 1H), 6.94 (m, 1H), 4.13 (t, J=6.9 Hz, 2H), 2.87 (t, J=6.9 Hz, 2H), 2.54 (m, 2H), 2.28 (s, 3H) ppm; MS m/e: 334 (M+H)⁺.

Compound 168: 5-(2-(m-tolyl)-6,7-dihydro-5H-pyrrolo[1,2-a]imidazol-3-yl)-1H-indazole. MS m/e: 315 (M+H)⁺.

Compound 169: 6-(2-(m-tolyl)-6,7-dihydro-5H-pyrrolo[1,2-a]imidazol-3-yl)-1H-indazole. MS m/e: 315 (M+H)⁺.

Compound 170: 6-(2-(m-tolyl)-6,7-dihydro-5H-pyrrolo[1,2-a]imidazol-3-yl)benzo[d]thiazole. ¹H NMR (DMSO-d₆, 300 MHz) 9.40 (s, 1H), 8.22 (m, 1H), 8.07 (m, 1H), 7.47 (m, 1H), 7.34 (s, 1H), 7.08 (m, 2H), 6.95 (m, 1H), 3.96 (t, J=7.2 Hz, 2H), 2.84 (t, J=7.2 Hz, 2H), 2.53 (m, 2H), 2.18 (s, 3H) ppm; MS m/e: 332 (M+H)⁺.

Compound 171: 5-(2-(m-tolyl)-6,7-dihydro-5H-pyrrolo[1,2-a]imidazol-3-yl)-1H-benzo[d]imidazole. MS m/e: 315 (M+H)⁺.

Compound 180: 6-(2-(m-tolyl)-6,7-dihydro-5H-pyrrolo[1,2-a]imidazol-3-yl)quinoxaline. ¹H NMR (DMSO-d₆, 300 MHz) 8.93 (m, 2H), 8.10 (m, 1H), 8.05 (d, J=9.0 Hz, 1H), 7.75 (m, 1H), 7.35 (m, 1H), 7.12 (m, 2H), 7.00 (m, 1H), 4.09 (t, J=7.2 Hz, 2H), 2.87 (t, J=7.2 Hz, 2H), 2.57 (m, 2H), 2.20 (s, 3H) ppm; MS m/e: 327 (M+H)⁺.

Compound 172: 5-(2-(4-fluoro-3-methylphenyl)-6,7-dihydro-5H-pyrrolo[1,2-c]imidazol-3-yl)-1H-indazole. MS m/e: 333 (M+H)⁺.

Compound 177: 6-(2-(4-fluoro-3-methylphenyl)-6,7-dihydro-5H-pyrrolo[1,2-a]imidazol-3-yl)-1H-indazole. ¹H NMR (DMSO-d₆, 300 MHz) 13.1 (s, 1H), 8.07 (m, 1H), 7.77 (m, 1H), 7.51 (s, 1H), 7.75 (m, 1H), 7.42 (m, 1H), 7.10

(m, 2H), 6.93 (m, 1H), 3.94 (t, J=6.9 Hz, 2H), 2.83 (t, J=6.9 Hz, 2H), 2.53 (m, 2H), 2.12 (s, 3H) ppm; MS m/e: 333 (M+H)$^+$.

Compound 173: 6-(2-(4-fluoro-3-methylphenyl)-6,7-dihydro-5H-pyrrolo[1,2-a]imidazol-3-yl)benzo[d]thiazole. $^1$H NMR (DMSO-d$_6$, 300 MHz) 9.41 (s, 1H), 8.23 (m, 1H), 8.07 (m, 1H), 7.47 (m, 1H), 7.41 (m, 1H), 7.12 (m, 1H), 6.94 (m, 1H), 3.96 (t, J=6.9 Hz, 2H), 2.84 (t, J=6.9 Hz, 2H), 2.54 (m, 2H), 2.12 (s, 3H) ppm; MS m/e: 350 (M+H)$^+$.

Compound 174: 6-(2-(4-fluorophenyl)-6,7-dihydro-5H-pyrrolo[1,2-c]imidazol-3-yl)benzo[d]thiazole. $^1$H NMR (DMSO-d$_6$, 300 MHz) 9.41 (s, 1H), 8.23 (m, 1H), 8.09 (m, 1H), 7.43 (m, 3H), 7.05 (m, 2H), 3.95 (t, J=6.9 Hz, 2H), 2.85 (t, J=6.9 Hz, 2H), 2.53 (m, 2H) ppm; MS m/e: 336 (M+H)$^+$.

Compound 175: 5-(2-(4-fluorophenyl)-6,7-dihydro-5H-pyrrolo[1,2-c]imidazol-3-yl)-1H-indazole. MS m/e: 319 (M+H)$^+$.

Compound 176: 6-(2-(4-fluorophenyl)-6,7-dihydro-5H-pyrrolo[1,2-c]imidazol-3-yl)-1H-indazole. MS m/e: 319 (M+H)$^+$.

Compound 178: 6-(2-(4-fluorophenyl)-6,7-dihydro-5H-pyrrolo[1,2-c]imidazol-3-yl)quinoxaline. MS m/e: 331 (M+H)$^+$.

Compound 179: 6-(2-(4-fluoro-3-methylphenyl)-6,7-dihydro-5H-pyrrolo[1,2-a]imidazol-3-yl)quinoxaline. $^1$H NMR (DMSO-d$_6$, 300 MHz) 8.93 (m, 2H), 8.09 (m, 1H), 8.06 (m, 1H), 7.74 (m, 1H), 7.43 (m, 1H), 7.15 (m, 1H), 6.98 (m, 1H), 4.08 (t, J=7.2 Hz, 2H), 2.87 (t, J=7.2 Hz, 2H), 2.59 (m, 2H), 2.15 (s, 3H) ppm; MS m/e: 345 (M+H)$^+$.

Compound 181: 5-(2-(3-trifluoromethyl)-6,7-dihydro-5H-pyrrolo[1,2-a]imidazol-3-yl)-1H-indazole. MS m/e: 369 (M+H)$^+$.

Compound 182: 6-(2-(3-trifluoromethyl)-6,7-dihydro-5H-pyrrolo[1,2-a]imidazol-3-yl)-1H-indazole. MS m/e: 369 (M+H)$^+$.

Compound 183: 6-(2-(3-trifluoromethyl)-6,7-dihydro-5H-pyrrolo[1,2-a]imidazol-3-yl)benzo[d]thiazole. MS m/e: 386 (M+H)$^+$.

Compound 184: 6-(2-(3-trifluoromethyl)-6,7-dihydro-5H-pyrrolo[1,2-c]imidazol-3-yl)quinoxaline. MS m/e: 381 (M+H)$^+$.

Compound 185: 5-(2-(3-methoxyphenyl)-6,7-dihydro-5H-pyrrolo[1,2-c]imidazol-3-yl)-1H-indazole. MS m/e: 331 (M+H)$^+$.

Compound 186: 6-(2-(3-methoxyphenyl)-6,7-dihydro-5H-pyrrolo[1,2-c]imidazol-3-yl)-1H-indazole. MS m/e: 331 (M+H)$^+$.

Compound 187: 6-(2-(3-methoxyphenyl)-6,7-dihydro-5H-pyrrolo[1,2-c]imidazol-3-yl)benzo[d]thiazole. MS m/e: 348 (M+H)$^+$.

Compound 188: 6-(2-(3-methoxyphenyl)-6,7-dihydro-5H-pyrrolo[1,2-c]imidazol-3-yl)quinoxaline. MS m/e: 347 (M+H)$^+$.

Compound 189: 5-(2-(3-chlorophenyl)-6,7-dihydro-5H-pyrrolo[1,2-c]imidazol-3-yl)-1H-indazole. $^1$H NMR (DMSO-d$_6$, 300 MHz) 13.2 (s, 1H), 8.10 (m, 1H), 7.83 (m, 1H), 7.59 (m, 1H), 7.47 (m, 1H), 7.30 (m, 2H), 7.17 (m, 2H), 3.89 (t, J=7.5 Hz, 2H), 2.84 (t, J=7.5 Hz, 2H), 2.52 (m, 2H) ppm; MS m/e: 335 (M+H)$^+$.

Compound 190: 6-(2-(3-chlorophenyl)-6,7-dihydro-5H-pyrrolo[1,2-c]imidazol-3-yl)-1H-indazole. $^1$H NMR (DMSO-d$_6$, 300 MHz) 13.1 (s, 1H), 8.10 (m, 1H), 8.10 (m, 1H), 7.81 (m, 1H), 7.56 (m, 1H), 7.48 (m, 1H), 7.31 (m, 1H), 7.16 (m, 3H), 3.93 (t, J=7.2 Hz, 2H), 2.85 (t, J=7.2 Hz, 2H), 2.53 (m, 2H) ppm; MS m/e: 335 (M+H)$^+$.

Compound 191: 6-(2-(3-chlorophenyl)-6,7-dihydro-5H-pyrrolo[1,2-c]imidazol-3-yl)benzo[d]thiazole. MS m/e: 352 (M+H)$^+$.

Compound 192: 6-(2-(3-chlorophenyl)-6,7-dihydro-5H-pyrrolo[1,2-c]imidazol-3-yl)quinoxaline. MS m/e: 351 (M+H)$^+$.

Compound 193: 5-(2-(3-fluorophenyl)-6,7-dihydro-5H-pyrrolo[1,2-c]imidazol-3-yl)-1H-indazole. MS m/e: 319 (M+H)$^+$.

Compound 194: 6-(2-(3-fluorophenyl)-6,7-dihydro-5H-pyrrolo[1,2-c]imidazol-3-yl)-1H-indazole. MS m/e: 319 (M+H)$^+$.

Compound 195: 6-(2-(3-fluorophenyl)-6,7-dihydro-5H-pyrrolo[1,2-c]imidazol-3-yl)benzo[d]thiazole. MS m/e: 336 (M+H)$^+$.

Compound 196: 6-(2-(3-fluorophenyl)-6,7-dihydro-5H-pyrrolo[1,2-c]imidazol-3-yl)quinoxaline. MS m/e: 331 (M+H)$^+$.

Compound 197: 5-(2-(2-fluorophenyl)-6,7-dihydro-5H-pyrrolo[1,2-a]imidazol-3-yl)-1H-indazole. MS m/e: 319 (M+H)$^+$.

Compound 198: 6-(2-(2-fluorophenyl)-6,7-dihydro-5H-pyrrolo[1,2-a]imidazol-3-yl)-1H-indazole. MS m/e: 319 (M+H)$^+$.

Compound 199: 6-(2-(2-fluorophenyl)-6,7-dihydro-5H-pyrrolo[1,2-a]imidazol-3-yl)benzo[d]thiazole. MS m/e: 336 (M+H)$^+$.

Compound 200: 6-(2-(2-fluorophenyl)-6,7-dihydro-5H-pyrrolo[1,2-a]imidazol-3-yl)quinoxaline. MS m/e: 331 (M+H)$^+$.

Compound 201: 5-(2-(2,4-difluorophenyl)-6,7-dihydro-5H-pyrrolo[1,2-a]imidazol-3-yl)-1H-indazole. MS m/e: 337 (M+H)$^+$.

Compound 202: 6-(2-(2,4-difluorophenyl)-6,7-dihydro-5H-pyrrolo[1,2-a]imidazol-3-yl)-1H-indazole. MS m/e: 337 (M+H)$^+$.

Compound 203: 6-(2-(2,4-difluorophenyl)-6,7-dihydro-5H-pyrrolo[1,2-a]imidazol-3-yl)benzo[d]thiazole. $^1$H NMR (DMSO-d$_6$, 300 MHz) 9.36 (s, 1H), 8.12 (m, 1H), 8.01 (m, 1H), 7.55 (m, 1H), 7.32 (m, 1H), 7.11 (m, 2H), 4.10 (t, J=6.9 Hz, 2H), 2.87 (t, J=6.9 Hz, 2H), 2.56 (m, 2H) ppm; MS m/e: 354 (M+H)$^+$.

Compound 204: 6-(2-(2,4-difluorophenyl)-6,7-dihydro-5H-pyrrolo[1,2-a]imidazol-3-yl)quinoxaline. MS m/e: 349 (M+H)$^+$.

Compound 205: 5-(2-(3,4-difluorophenyl)-6,7-dihydro-5H-pyrrolo[1,2-a]imidazol-3-yl)-1H-indazole. MS m/e: 337 (M+H)$^+$.

Compound 206: 6-(2-(3,4-difluorophenyl)-6,7-dihydro-5H-pyrrolo[1,2-a]imidazol-3-yl)-1H-indazole. MS m/e: 337 (M+H)$^+$.

Compound 207: 6-(2-(3,4-difluorophenyl)-6,7-dihydro-5H-pyrrolo[1,2-a]imidazol-3-yl)benzo[d]thiazole. MS m/e: 354 (M+H)$^+$.

Compound 208: 6-(2-(3,4-difluorophenyl)-6,7-dihydro-5H-pyrrolo[1,2-a]imidazol-3-yl)quinoxaline. MS m/e: 349 (M+H)$^+$.

Compound 209: 6-(2-(3-fluorophenyl)-6,7-dihydro-5H-pyrrolo[1,2-a]imidazol-3-yl)quinoline. MS m/e: 330 (M+H)$^+$.

Compound 210: 6-(2-(2-fluorophenyl)-6,7-dihydro-5H-pyrrolo[1,2-a]imidazol-3-yl)quinoline. MS m/e: 330 (M+H)$^+$.

Compound 211: 6-(2-(2,4-difluorophenyl)-6,7-dihydro-5H-pyrrolo[1,2-a]imidazol-3-yl)quinoline. MS m/e: 348 (M+H)$^+$.

Compound 212: 5-(2-(2,6-difluorophenyl)-6,7-dihydro-5H-pyrrolo[1,2-a]imidazol-3-yl)-1H-indazole. MS m/e: 337 (M+H)$^+$.

Compound 213: 6-(2-(2,6-difluorophenyl)-6,7-dihydro-5H-pyrrolo[1,2-a]imidazol-3-yl)-1H-indazole. MS m/e: 337 (M+H)$^+$.

Compound 214: 6-(2-(2,6-difluorophenyl)-6,7-dihydro-5H-pyrrolo[1,2-a]imidazol-3-yl)benzo[d]thiazole. MS m/e: 354 (M+H)$^+$.

Compound 215: 6-(2-(2,6-difluorophenyl)-6,7-dihydro-5H-pyrrolo[1,2-a]imidazol-3-yl)quinoxaline. MS m/e: 349 (M+H)$^+$.

Compound 216: 6-(2-(2,6-difluorophenyl)-6,7-dihydro-5H-pyrrolo[1,2-a]imidazol-3-yl)quinoline. MS m/e: 348 (M+H)$^+$.

Compound 220: 5-(2-(2,4,5-trifluorophenyl)-6,7-dihydro-5H-pyrrolo[1,2-a]imidazol-3-yl)-1H-indazole. $^1$H NMR (DMSO-d$_6$, 300 MHz) 13.1 (s, 1H), 8.04 (s, 1H), 7.68 (m, 1H), 7.523 (m, 2H), 7.37 (m, 1H), 7.19 (m, 1H), 4.04 (t, J=6.9 Hz, 2H), 2.85 (t, J=6.9 Hz, 2H), 2.55 (m, 2H) ppm; MS m/e: 355 (M+H)$^+$.

Compound 217: 6-(2-(2,4,5-trifluorophenyl)-6,7-dihydro-5H-pyrrolo[1,2-a]imidazol-3-yl)-1H-indazole. $^1$H NMR (DMSO-d$_6$, 300 MHz) 13.0 (s, 1H), 8.04 (m, 1H), 7.72 (m, 1H), 7.53 (m, 1H), 7.41 (m, 2H), 6.99 (m, 1H), 4.07 (t, J=6.9 Hz, 2H), 2.86 (t, J=6.9 Hz, 2H), 2.56 (m, 2H) ppm; MS m/e: 355 (M+H)$^+$.

Compound 218: 6-(2-(2,4,5-trifluorophenyl)-6,7-dihydro-5H-pyrrolo[1,2-a]imidazol-3-yl)benzo[d]thiazole. $^1$H NMR (DMSO-d$_6$, 300 MHz) 9.38 (m, 1H), 8.15 (m, 1H), 8.02 (m, 1H), 7.56 (m, 1H), 7.39 (m, 2H), 4.10 (t, J=7.2 Hz, 2H), 2.87 (t, J=7.2 Hz, 2H), 2.56 (m, 2H) ppm; MS m/e: 372 (M+H)$^+$.

Compound 221: 5-(2-(2,3,6-trifluorophenyl)-6,7-dihydro-5H-pyrrolo[1,2-a]imidazol-3-yl)-1H-indazole. MS m/e: 355 (M+H)$^+$.

Compound 222: 6-(2-(2,3,6-trifluorophenyl)-6,7-dihydro-5H-pyrrolo[1,2-a]imidazol-3-yl)benzo[d]thiazole. MS m/e: 372 (M+H)$^+$.

Compound 223: 3-(benzo[d][1,3]dioxol-5-yl)-2-(3-fluorophenyl)-6,7-dihydro-5H-pyrrolo[1,2-a]imidazole. MS m/e: 323 (M+H)$^+$.

Compound 224: 6-(2-(2,3,4-trifluorophenyl)-6,7-dihydro-5H-pyrrolo[1,2-a]imidazol-3-yl)quinoxaline. $^1$H NMR (DMSO-d$_6$, 300 MHz) 8.97 (m, 2H), 8.15 (m, 1H), 8.13 (m, 1H), 7.81 (m, 1H), 7.23 (m, 2H), 4.05 (t, J=6.9 Hz, 2H), 2.85 (t, J=6.9 Hz, 2H), 2.56 (m, 2H) ppm; MS m/e: 367 (M+H)$^+$.

Compound 225: 5-(2-(2,3,4-trifluorophenyl)-6,7-dihydro-5H-pyrrolo[1,2-c]imidazol-3-yl)-1H-indazole. MS m/e: 355 (M+H)$^+$.

Compound 226: 6-(2-(2,3,4-trifluorophenyl)-6,7-dihydro-5H-pyrrolo[1,2-c]imidazol-3-yl)benzo[d]thiazole. MS m/e: 372 (M+H)$^+$.

Compound 227: 6-(2-(3,4,5-trifluorophenyl)-6,7-dihydro-5H-pyrrolo[1,2-a]imidazol-3-yl)quinoxaline. $^1$H NMR (DMSO-d$_6$, 300 MHz) 8.97 (m, 2H), 8.16 (m, 1H), 8.13 (m, 1H), 7.81 (m, 1H), 7.23 (m, 2H), 4.06 (t, J=6.9 Hz, 2H), 2.85 (t, J=6.9 Hz, 2H), 2.54 (m, 2H) ppm; MS m/e: 367 (M+H)$^+$.

Compound 228: 5-(2-(3,4,5-trifluorophenyl)-6,7-dihydro-5H-pyrrolo[1,2-c]imidazol-3-yl)-1H-indazole. MS m/e: 355 (M+H)$^+$.

Compound 229: 6-(2-(3,4,5-trifluorophenyl)-6,7-dihydro-5H-pyrrolo[1,2-c]imidazol-3-yl)benzo[d]thiazole. MS m/e: 372 (M+H)$^+$.

Compound 230: 5-(2-(3,5-difluorophenyl)-6,7-dihydro-5H-pyrrolo[1,2-c]imidazol-3-yl)-1H-indazole. MS m/e: 337 (M+H)$^+$.

Compound 231: 6-(2-(3,5-difluorophenyl)-6,7-dihydro-5H-pyrrolo[1,2-c]imidazol-3-yl)-1H-indazole. MS m/e: 337 (M+H)$^+$.

Compound 232: 6-(2-(3,5-difluorophenyl)-6,7-dihydro-5H-pyrrolo[1,2-c]imidazol-3-yl)benzo[d]thiazole. MS m/e: 354 (M+H)$^+$.

Compound 233: 6-(2-(3,5-difluorophenyl)-6,7-dihydro-5H-pyrrolo[1,2-c]imidazol-3-yl)quinoxaline. MS m/e: 349 (M+H)$^+$.

Compound 234: 6-(2-(3,5-difluorophenyl)-6,7-dihydro-5H-pyrrolo[1,2-c]imidazol-3-yl)quinoline. MS m/e: 348 (M+H)$^+$.

Compound 235: 6-(2-(2,3,5-trifluorophenyl)-6,7-dihydro-5H-pyrrolo[1,2-c]imidazol-3-yl)benzo[d]thiazole. MS m/e: 372 (M+H)$^+$.

Compound 236: 5-(2-(2,3,5-trifluorophenyl)-6,7-dihydro-5H-pyrrolo[1,2-c]imidazol-3-yl)-1H-indazole. MS m/e: 355 (M+H)$^+$.

Compound 237: 6-(2-(2,3,5-trifluorophenyl)-6,7-dihydro-5H-pyrrolo[1,2-a]imidazol-3-yl)quinoline. MS m/e: 366 (M+H)$^+$.

Compound 238: 6-(2-(2,3,5-trifluorophenyl)-6,7-dihydro-5H-pyrrolo[1,2-a]imidazol-3-yl)quinoxaline. MS m/e: 367 (M+H)$^+$.

Compound 239: 5-(2-(4-chloro-2,5-difluorophenyl)-6,7-dihydro-5H-pyrrolo[1,2-a]imidazol-3-yl)-1H-indazole. MS m/e: 371 (M+H)$^+$.

Compound 240: 6-(2-(4-chloro-2,5-difluorophenyl)-6,7-dihydro-5H-pyrrolo[1,2-a]imidazol-3-yl)benzo[d]thiazole. MS m/e: 388 (M+H)$^+$.

Compound 241: 6-(2-(4-chloro-2,5-difluorophenyl)-6,7-dihydro-5H-pyrrolo[1,2-a]imidazol-3-yl)quinoxaline. MS m/e: 383 (M+H)$^+$.

Compound 242: 6-(2-(4-chloro-2,5-difluorophenyl)-6,7-dihydro-5H-pyrrolo[1,2-a]imidazol-3-yl)quinoline. MS m/e: 382 (M+H)$^+$.

Compound 243: 5-(2-(4-chloro-3,5-dimethylphenyl)-6,7-dihydro-5H-pyrrolo[1,2-a]imidazol-3-yl)-1H-indazole. MS m/e: 363 (M+H)$^+$.

Compound 244: 6-(2-(4-chloro-3,5-dimethylphenyl)-6,7-dihydro-5H-pyrrolo[1,2-a]imidazol-3-yl)benzo[d]thiazole. MS m/e: 380 (M+H)$^+$.

Compound 245: 6-(2-(4-chloro-3,5-dimethylphenyl)-6,7-dihydro-5H-pyrrolo[1,2-a]imidazol-3-yl)quinoxaline. MS m/e: 375 (M+H)$^+$.

Compound 246: 6-(2-(4-chloro-3,5-dimethylphenyl)-6,7-dihydro-5H-pyrrolo[1,2-a]imidazol-3-yl)quinoline. MS m/e: 376 (M+H)$^+$.

Compound 247: 6-(2-(3,4,5-trifluorophenyl)-6,7-dihydro-5H-pyrrolo[1,2-a]imidazol-3-yl)quinoline. MS m/e: 366 (M+H)$^+$.

Compound 248: 5-(2-(2,3-difluoro-4-methylphenyl)-6,7-dihydro-5H-pyrrolo[1,2-a]imidazol-3-yl)-1H-indazole. MS m/e: 351 (M+H)$^+$.

Compound 249: 6-(2-(2,3-difluoro-4-methylphenyl)-6,7-dihydro-5H-pyrrolo[1,2-a]imidazol-3-yl)benzo[d]thiazole. MS m/e: 368 (M+H)$^+$.

Compound 250: 6-(2-(2,3-difluoro-4-methylphenyl)-6,7-dihydro-5H-pyrrolo[1,2-a]imidazol-3-yl)quinoxaline. MS m/e: 363 (M+H)$^+$.

Compound 251: 6-(2-(2,3-difluoro-4-methylphenyl)-6,7-dihydro-5H-pyrrolo[1,2-a]imidazol-3-yl)quinoline. MS m/e: 362 (M+H)$^+$.

Compound 252: 6-(2-(4-chloro-2-fluoro-5-methylphenyl)-6,7-dihydro-5H-pyrrolo[1,2-a]imidazol-3-yl)-1H-indazole. MS m/e: 367 (M+H)⁺.

Compound 253: 6-(2-(4-chloro-2-fluoro-5-methylpheny)-6,7-dihydro-5H-pyrrolo[1,2-a]imidazol-3-yl)benzo[d]thiazole. MS m/e: 384 (M+H)⁺.

Compound 254: 6-(2-(4-chloro-2-fluoro-5-methylpheny)-6,7-dihydro-5H-pyrrolo[1,2-c]imidazol-3-yl)quinoxaline. MS m/e: 379 (M+H)⁺.

Compound 255: 6-(2-(4-chloro-2-fluoro-5-methylphenyl)-6,7-dihydro-5H-pyrrolo[1,2-c]imidazol-3-yl)quinoline. MS m/e: 378 (M+H)⁺.

Compound 256: 6-(2-(4-methoxy-3,5-dimethylphenyl)-6,7-dihydro-5H-pyrrolo[1,2-c]imidazol-3-yl)-1H-indazole. MS m/e: 359 (M+H)⁺.

Compound 257: 6-(2-(4-methoxy-3,5-dimethylphenyl)-6,7-dihydro-5H-pyrrolo[1,2-a]imidazol-3-yl)benzo[d]thiazole. MS m/e: 376 (M+H)⁺.

Compound 258: 6-(2-(4-methoxy-3,5-dimethylphenyl)-6,7-dihydro-5H-pyrrolo[1,2-a]imidazol-3-yl)quinoxaline. MS m/e: 388 (M+H)⁺.

Compound 259: 6-(2-(4-methoxy-3,5-dimethylphenyl)-6,7-dihydro-5H-pyrrolo[1,2-a]imidazol-3-yl)quinoline. MS m/e: 390 (M+H)⁺.

Compound 260: 5-(2-(3,4-difluoro-2-methylphenyl)-6,7-dihydro-5H-pyrrolo[1,2-c]imidazol-3-yl)-1H-indazole. MS m/e: 351 (M+H)⁺.

Compound 261: 6-(2-(3,4-difluoro-2-methylphenyl)-6,7-dihydro-5H-pyrrolo[1,2-a]imidazol-3-yl)benzo[d]thiazole. MS m/e: 368 (M+H)⁺.

Compound 262: 6-(2-(3,4-difluoro-2-methylphenyl)-6,7-dihydro-5H-pyrrolo[1,2-a]imidazol-3-yl)quinoxaline. ¹H NMR (DMSO-d₆, 300 MHz) 8.89 (m, 2H), 8.00 (m, 1H), 7.89 (m, 1H), 7.57 (m, 1H), 7.30 (m, 1H), 7.18 (m, 1H), 4.25 (t, J=6.3 Hz, 2H), 2.92 (t, J=6.3 Hz, 2H), 2.61 (m, 2H), 2.00 (s, 3H) ppm; MS m/e: 363 (M+H)⁺.

Compound 263: 6-(2-(3,4-difluoro-2-methylphenyl)-6,7-dihydro-5H-pyrrolo[1,2-a]imidazol-3-yl)quinoline. MS m/e: 362 (M+H)⁺.

Compound 264: 5-(2-(3-chloro-4-fluoropheny)-6,7-dihydro-5H-pyrrolo[1,2-a]imidazol-3-yl)-1H-indazole. ¹H NMR (DMSO-d₆, 300 MHz) 13.2 (s, 1H), 8.10 (s, 1H), 7.83 (m, 1H), 7.57 (m, 1H), 7.51 (m, 1H), 7.25 (m, 3H), 3.89 (t, J=6.9 Hz, 2H), 2.84 (t, J=6.9 Hz, 2H), 2.54 (m, 2H) ppm; MS m/e: 353 (M+H)⁺.

Compound 265: 6-(2-(3-chloro-4-fluorophenyl)-6,7-dihydro-5H-pyrrolo[1,2-a]imidazol-3-yl)benzo[d]thiazole. ¹H NMR (DMSO-d₆, 300 MHz) 9.43 (s, 1H), 8.27 (s, 1H), 8.12 (d, J=8.4 Hz, 1H), 7.58 (m, 1H), 7.51 (m, 1H), 7.25 (m, 2H), 3.95 (t, J=6.9 Hz, 2H), 2.85 (t, J=6.9 Hz, 2H), 2.56 (m, 2H) ppm; MS m/e: 370 (M+H)⁺.

Compound 266: 6-(2-(3-chloro-4-fluorophenyl)-6,7-dihydro-5H-pyrrolo[1,2-a]imidazol-3-yl)quinoxaline. ¹H NMR (DMSO-d₆, 300 MHz) 8.95 (m, 2H), 8.13 (m, 1H), 8.11 (m, 1H), 7.78 (m, 1H), 7.61 (m, 1H), 7.29 (m, 2H), 4.07 (t, J=7.2 Hz, 2H), 2.88 (t, J=7.2 Hz, 2H), 2.56 (m, 2H) ppm; MS m/e: 365 (M+H)⁺.

Compound 267: 6-(2-(3-chloro-4-fluoropheny)-6,7-dihydro-5H-pyrrolo[1,2-a]imidazol-3-yl)quinoline. ¹H NMR (DMSO-d₆, 300 MHz) 8.91 (m, 1H), 8.37 (m, 1H), 8.08 (m, 1H), 8.03 (m, 1H), 7.69 (m, 1H), 7.58 (m, 2H), 7.29 (m, 2H), 4.01 (t, J=6.9 Hz, 2H), 2.87 (t, J=6.9 Hz, 2H), 2.53 (m, 2H) ppm; MS m/e: 364 (M+H)⁺.

Compound 268: 5-(2-(2,4-difluoro-5-methylphenyl)-6,7-dihydro-5H-pyrrolo[1,2-a]imidazol-3-yl)-1H-indazole. ¹H NMR (DMSO-d₆, 300 MHz) 13.2 (s, 1H), 8.03 (m, 1H), 7.65 (m, 1H), 7.46 (m, 2H), 7.16 (m, 1H), 6.98 (m, 1H), 4.04 (t, J=6.9 Hz, 2H), 2.84 (t, J=6.9 Hz, 2H), 2.55 (m, 2H) ppm; MS m/e: 351 (M+H)⁺.

Compound 269: 6-(2-(2,4-difluoro-5-methylphenyl)-6,7-dihydro-5H-pyrrolo[1,2-a]imidazol-3-yl)benzo[d]thiazole. ¹H NMR (DMSO-d₆, 300 MHz) 9.36 (m, 1H), 8.12 (m, 1H), 8.00 (m, 1H), 7.48 (m, 1H), 7.31 (m, 1H), 7.01 (m, 1H), 4.10 (t, J=6.9 Hz, 2H), 2.86 (t, J=6.9 Hz, 2H), 2.56 (m, 2H), 2.20 (s, 3H) ppm; MS m/e: 368 (M+H)⁺.

Compound 270: 6-(2-(2,4-difluoro-5-methylphenyl)-6,7-dihydro-5H-pyrrolo[1,2-a]imidazol-3-yl)quinoxaline. ¹H NMR (DMSO-d₆, 300 MHz) 8.90 (m, 2H), 8.02 (m, 1H), 7.94 (m, 1H), 7.67 (m, 1H), 7.53 (m, 1H), 7.06 (m, 1H), 4.21 (t, J=7.2 Hz, 2H), 2.89 (t, J=7.2 Hz, 2H), 2.59 (m, 2H), 2.20 (s, 3H) ppm; MS m/e: 363 (M+H)⁺.

Compound 271: 6-(2-(2,4-difluoro-5-methylphenyl)-6,7-dihydro-5H-pyrrolo[1,2-a]imidazol-3-yl)quinoline. ¹H NMR (DMSO-d₆, 300 MHz) 8.85 (m, 1H), 8.30 (m, 1H), 7.92 (m, 2H), 7.51 (m, 3H), 7.02 (m, 1H), 4.16 (t, J=6.9 Hz, 2H), 2.88 (t, J=6.9 Hz, 2H), 2.59 (m, 2H), 2.21 (s, 3H) ppm; MS m/e: 362 (M+H)⁺.

Compound 272: 5-(2-(3-chloro-4-fluoro-5-methylphenyl)-6,7-dihydro-5H-pyrrolo[1,2-a]imidazol-3-yl)-1H-indazole. MS m/e: 367 (M+H)⁺.

Compound 273: 6-(2-(3-chloro-4-fluoro-5-methylpheny)-6,7-dihydro-5H-pyrrolo[1,2-a]imidazol-3-yl)benzo[d]thiazole. ¹H NMR (DMSO-d₆, 300 MHz) 9.43 (s, 1H), 8.27 (m, 1H), 8.11 (m, 1H), 7.49 (m, 1H), 7.29 (m, 2H), 3.96 (t, J=6.9 Hz, 2H), 2.85 (t, J=6.9 Hz, 2H), 2.53 (m, 2H), 2.14 (s, 3H) ppm; MS m/e: 384 (M+H)⁺.

Compound 274: 6-(2-(3-chloro-4-fluoro-5-methylpheny)-6,7-dihydro-5H-pyrrolo[1,2-a]imidazol-3-yl)quinoxaline. ¹H NMR (DMSO-d₆, 300 MHz) 8.94 (m, 2H), 8.12 (m, 1H), 8.08 (m, 1H), 7.77 (m, 1H), 7.32 (m, 2H), 4.08 (t, J=6.9 Hz, 2H), 2.87 (t, J=6.9 Hz, 2H), 2.58 (m, 2H), 2.15 (s, 3H) ppm; MS m/e: 379 (M+H)⁺.

Compound 275: 6-(2-(3-chloro-4-fluoro-5-methylpheny)-6,7-dihydro-5H-pyrrolo[1,2-a]imidazol-3-yl)quinoline. ¹H NMR (DMSO-d₆, 300 MHz) 8.91 (m, 1H), 8.37 (m, 1H), 8.08 (m, 1H), 8.02 (m, 1H), 7.67 (m, 1H), 7.55 (m, 1H), 7.31 (m, 2H), 4.02 (t, J=6.9 Hz, 2H), 2.86 (t, J=6.9 Hz, 2H), 2.55 (m, 2H), 2.14 (s, 3H) ppm; MS m/e: 378 (M+H)⁺.

Compound 276: 5-(2-(4-fluoro-3,5-dimethylphenyl)-6,7-dihydro-5H-pyrrolo[1,2-a]imidazol-3-yl)-1H-indazole. MS m/e: 347 (M+H)⁺.

Compound 277: 6-(2-(4-fluoro-3,5-dimethylphenyl)-6,7-dihydro-5H-pyrrolo[1,2-a]imidazol-3-yl)benzo[d]thiazole. MS m/e: 364 (M+H)⁺.

Compound 278: 6-(2-(4-fluoro-3,5-dimethylphenyl)-6,7-dihydro-5H-pyrrolo[1,2-a]imidazol-3-yl)quinoxaline. MS m/e: 359 (M+H)⁺.

Compound 279: 6-(4-fluoro-3,5-dimethylphenyl)-6,7-dihydro-5H-pyrrolo[1,2-a]imidazol-3-yl)quinoline. MS m/e: 358 (M+H)⁺.

Compound 280: 5-(2-(2,4-difluoro-3-methylphenyl)-6,7-dihydro-5H-pyrrolo[1,2-a]imidazol-3-yl)-1H-indazole. ¹H NMR (DMSO-d₆, 300 MHz) 13.1 (s, 1H), 8.03 (m, 1H), 7.67 (m, 1H), 7.47 (m, 1H), 7.28 (m, 1H), 7.13 (m, 1H), 6.99 (m, 1H), 4.05 (t, J=6.9 Hz, 2H), 2.84 (t, J=6.9 Hz, 2H), 2.52 (m, 2H), 2.01 (s, 3H) ppm; MS m/e: 347 (M+H)⁺.

Compound 281: 6-(2-(2,4-difluoro-3-methylphenyl)-6,7-dihydro-5H-pyrrolo[1,2-a]imidazol-3-yl)benzo[d]thiazole. ¹H NMR (DMSO-d₆, 300 MHz) 9.36 (s, 1H), 8.14 (m, 1H), 7.99 (m, 1H), 7.31 (m, 2H), 7.03 (m, 1H), 4.11 (t, J=7.2 Hz, 2H), 2.86 (t, J=7.2 Hz, 2H), 2.57 (m, 2H), 2.02 (s, 3H) ppm; MS m/e: 364 (M+H)⁺.

Compound 282: 6-(2-(2,4-difluoro-3-methylphenyl)-6,7-dihydro-5H-pyrrolo[1,2-a]imidazol-3-yl)quinoxaline. $^1$H NMR (DMSO-d$_6$, 300 MHz) 8.86 (m, 1H), 8.31 (m, 1H), 7.93 (m, 2H), 7.51 (m, 2H), 7.35 (m, 1H), 7.04 (m, 1H), 4.18 (t, J=6.6 Hz, 2H), 2.88 (t, J=6.6 Hz, 2H), 2.59 (m, 2H), 2.01 (s, 3H) ppm; MS m/e: 359 (M+H)$^+$.

Compound 283: 6-(2-(2,4-difluoro-3-methylphenyl)-6,7-dihydro-5H-pyrrolo[1,2-a]imidazol-3-yl)quinoline. $^1$H NMR (DMSO-d$_6$, 300 MHz) 8.90 (m, 2H), 8.01 (m, 1H), 7.96 (m, 1H), 7.65 (m, 1H), 7.38 (m, 1H), 7.07 (m, 1H), 4.22 (t, J=7.2 Hz, 2H), 2.89 (t, J=7.2 Hz, 2H), 2.60 (m, 2H), 2.02 (s, 3H) ppm; MS m/e: 358 (M+H)$^+$.

Compound 284: 5-(2-(2,5-difluoro-4-methylphenyl)-6,7-dihydro-5H-pyrrolo[1,2-c]imidazol-3-yl)-1H-indazole. MS m/e: 347 (M+H)$^+$.

Compound 285: 6-(2-(2,5-difluoro-4-methylphenyl)-6,7-dihydro-5H-pyrrolo[1,2-a]imidazol-3-yl)benzo[d]thiazole. MS m/e: 364 (M+H)$^+$.

Compound 286: 6-(2-(2,5-difluoro-4-methylphenyl)-6,7-dihydro-5H-pyrrolo[1,2-c]imidazol-3-yl)quinoxaline. MS m/e: 359 (M+H)$^+$.

Compound 287: 6-(2-(2,5-difluoro-4-methylphenyl)-6,7-dihydro-5H-pyrrolo[1,2-c]imidazol-3-yl)quinoline. MS m/e: 358 (M+H)$^+$.

Compound 288: 5-(2-(2-chloro-4,5-difluorophenyl)-6,7-dihydro-5H-pyrrolo[1,2-c]imidazol-3-yl)-1H-indazole. MS m/e: 371 (M+H)$^+$.

Compound 289: 6-(2-(2-chloro-4,5-difluorophenyl)-6,7-dihydro-5H-pyrrolo[1,2-a]imidazol-3-yl)benzo[d]thiazole. MS m/e: 388 (M+H)$^+$.

Compound 290: 6-(2-(2-chloro-4,5-difluorophenyl)-6,7-dihydro-5H-pyrrolo[1,2-a]imidazol-3-yl)quinoline. MS m/e: 382 (M+H)$^+$.

Compound 291: 6-(2-(2-chloro-4,5-difluorophenyl)-6,7-dihydro-5H-pyrrolo[1,2-a]imidazol-3-yl)quinoxaline. MS m/e: 383 (M+H)$^+$.

Compound 292: 5-(2-(4-fluoro-2-methylphenyl)-6,7-dihydro-5H-pyrrolo[1,2-c]imidazol-3-yl)-1H-indazole. MS m/e: 333 (M+H)$^+$.

Compound 293: 6-(2-(4-fluoro-2-methylphenyl)-6,7-dihydro-5H-pyrrolo[1,2-c]imidazol-3-yl)benzo[d]thiazole. MS m/e: 350 (M+H)$^+$.

Compound 294: 6-(2-(4-fluoro-2-methylphenyl)-6,7-dihydro-5H-pyrrolo[1,2-c]imidazol-3-yl)quinoxaline. MS m/e: 345 (M+H)$^+$.

Compound 295: 6-(2-(4-fluoro-2-methylphenyl)-6,7-dihydro-5H-pyrrolo[1,2-a]imidazol-3-yl)quinoline. MS m/e: 344 (M+H)$^+$.

Compound 296: 5-(2-(5-chloro-4-fluoro-2-methylphenyl)-6,7-dihydro-5H-pyrrolo[1,2-a]imidazol-3-yl)-1H-indazole. $^1$H NMR (DMSO-d$_6$, 300 MHz) 13.1 (s, 1H), 8.03 (m, 1H), 7.64 (m, 1H), 7.48 (m, 1H), 7.25 (m, 2H), 7.07 (m, 1H), 4.08 (t, J=6.9 Hz, 2H), 2.85 (t, J=6.9 Hz, 2H), 2.56 (m, 2H), 1.95 (s, 3H) ppm; MS m/e: 367 (M+H)$^+$.

Compound 297: 6-(2-(5-chloro-4-fluoro-2-methylphenyl)-6,7-dihydro-5H-pyrrolo[1,2-a]imidazol-3-yl)benzo[d]thiazole. $^1$H NMR (DMSO-d$_6$, 300 MHz) 9.36 (s, 1H), 8.13 (m, 1H), 7.98 (m, 1H), 7.25 (m, 3H), 4.14 (t, J=6.9 Hz, 2H), 2.87 (t, J=6.9 Hz, 2H), 2.59 (m, 2H), 1.97 (s, 3H) ppm; MS m/e: 384 (M+H)$^+$.

Compound 298: 6-(2-(5-chloro-4-fluoro-2-methylphenyl)-6,7-dihydro-5H-pyrrolo[1,2-c]imidazol-3-yl)quinoxaline. $^1$H NMR (DMSO-d$_6$, 300 MHz) 8.89 (m, 2H), 8.01 (m, 1H), 7.89 (m, 1H), 7.57 (m, 1H), 7.32 (m, 2H), 4.25 (t, J=6.3 Hz, 2H), 2.87 (t, J=6.3 Hz, 2H), 2.61 (m, 2H), 2.01 (s, 3H) ppm; MS m/e: 379 (M+H)$^+$.

Compound 299: 6-(2-(5-chloro-4-fluoro-2-methylphenyl)-6,7-dihydro-5H-pyrrolo[1,2-c]imidazol-3-yl)quinoline. $^1$H NMR (DMSO-d$_6$, 300 MHz) 8.84 (m, 1H), 8.30 (m, 1H), 7.89 (m, 2H), 7.51 (m, 1H), 7.41 (m, 1H), 7.28 (m, 2H), 4.20 (t, J=6.9 Hz, 2H), 2.86 (t, J=6.9 Hz, 2H), 2.60 (m, 2H), 1.97 (s, 3H) ppm; MS m/e: 378 (M+H)$^+$.

Compound 300: 5-(2-(5-fluoro-2-methylphenyl)-6,7-dihydro-5H-pyrrolo[1,2-c]imidazol-3-yl)-1H-indazole. MS m/e: 333 (M+H)$^+$.

Compound 301: 6-(2-(5-fluoro-2-methylphenyl)-6,7-dihydro-5H-pyrrolo[1,2-c]imidazol-3-yl)benzo[d]thiazole. MS m/e: 350 (M+H)$^+$.

Compound 302: 6-(2-(5-fluoro-2-methylphenyl)-6,7-dihydro-5H-pyrrolo[1,2-c]imidazol-3-yl)quinoxaline. MS m/e: 345 (M+H)$^+$.

Compound 303: 6-(5-fluoro-2-methylphenyl)-6,7-dihydro-5H-pyrrolo[1,2-a]imidazol-3-yl)quinoline. MS m/e: 344 (M+H)$^+$.

Compound 304: 5-(2-(o-tolyl)-6,7-dihydro-5H-pyrrolo[1,2-a]imidazol-3-yl)-1H-indazole. MS m/e: 315 (M+H)$^+$.

Compound 305: 6-(2-(o-tolyl)-6,7-dihydro-5H-pyrrolo[1,2-a]imidazol-3-yl)benzo[d]thiazole. MS m/e: 332 (M+H)$^+$.

Compound 306: 6-(2-(o-tolyl)-6,7-dihydro-5H-pyrrolo[1,2-a]imidazol-3-yl)quinoxaline. MS m/e: 327 (M+H)$^+$.

Compound 307: 6-(2-(o-tolyl)-6,7-dihydro-5H-pyrrolo[1,2-a]imidazol-3-yl)quinoline. MS m/e: 326 (M+H)$^+$.

Compound 308: 5-(2-(4-fluoro-2,5-dimethylphenyl)-6,7-dihydro-5H-pyrrolo[1,2-c]imidazol-3-yl)-1H-indazole. MS m/e: 347 (M+H)$^+$.

Compound 309: 6-(2-(4-fluoro-2,5-dimethylphenyl)-6,7-dihydro-5H-pyrrolo[1,2-c]imidazol-3-yl)benzo[d]thiazole. MS m/e: 364 (M+H)$^+$.

Compound 310: 6-(2-(4-fluoro-2,5-dimethylphenyl)-6,7-dihydro-5H-pyrrolo[1,2-c]imidazol-3-yl)quinoxaline. MS m/e: 359 (M+H)$^+$.

Compound 311: 6-(4-fluoro-2,5-dimethylphenyl)-6,7-dihydro-5H-pyrrolo[1,2-c]imidazol-3-yl)quinoline. MS m/e: 358 (M+H)$^+$.

Compound 312: 5-(2-(2-chloro-4-fluoro-3-methylphenyl)-6,7-dihydro-5H-pyrrolo[1,2-c]imidazol-3-yl)-1H-indazole. MS m/e: 367 (M+H)$^+$.

Compound 313: 6-(2-(2-chloro-4-fluoro-3-methylphenyl)-6,7-dihydro-5H-pyrrolo[1,2-c]imidazol-3-yl)benzo[d]thiazole. MS m/e: 384 (M+H)$^+$.

Compound 314: 6-(2-(2-chloro-4-fluoro-3-methylphenyl)-6,7-dihydro-5H-pyrrolo[1,2-a]imidazol-3-yl)quinoxaline. $^1$H NMR (DMSO-d$_6$, 300 MHz) 8.87 (m, 2H), 7.99 (m, 1H), 7.86 (m, 1H), 7.57 (m, 1H), 7.31 (m, 1H), 7.20 (m, 1H), 4.28 (t, J=7.2 Hz, 2H), 2.88 (t, J=7.2 Hz, 2H), 2.62 (m, 2H), 2.22 (s, 3H) ppm; MS m/e: 379 (M+H)$^+$.

Compound 315: 6-(2-(2-chloro-4-fluoro-3-methylphenyl)-6,7-dihydro-5H-pyrrolo[1,2-c]imidazol-3-yl)quinoline. MS m/e: 378 (M+H)$^+$.

Compound 316: 5-(2-(2-chloro-4-fluoro-5-methylphenyl)-6,7-dihydro-5H-pyrrolo[1,2-c]imidazol-3-yl)-1H-indazole. MS m/e: 367 (M+H)$^+$.

Compound 317: 6-(2-(2-chloro-4-fluoro-5-methylphenyl)-6,7-dihydro-5H-pyrrolo[1,2-c]imidazol-3-yl)benzo[d]thiazole. MS m/e: 384 (M+H)$^+$.

Compound 318: 6-(2-(2-chloro-4-fluoro-5-methylphenyl)-6,7-dihydro-5H-pyrrolo[1,2-c]imidazol-3-yl)quinoxaline. $^1$H NMR (DMSO-d$_6$, 300 MHz) 8.88 (m, 2H), 8.00 (m, 1H), 7.85 (m, 1H), 7.59 (m, 1H), 7.45 (m, 1H), 7.31 (m, 1H), 4.26 (t, J=6.9 Hz, 2H), 2.89 (t, J=6.9 Hz, 2H), 2.59 (m, 2H), 2.22 (s, 3H) ppm; MS m/e: 379 (M+H)$^+$.

Compound 319: 6-(2-(2-chloro-4-fluoro-5-methylphenyl)-6,7-dihydro-5H-pyrrolo[1,2-c]imidazol-3-yl)quinoline. MS m/e: 378 (M+H)+.

Compound 320: N-(3-(3-(1H-indazol-5-yl)-6,7-dihydro-5H-pyrrolo[1,2-c]imidazol-2-yl)phenyl)-2-fluorobenzenesulfonamide. MS m/e: 474 (M+H)+.

Compound 321: 6-(2-(2-chloro-4-fluoro-5-methylphenyl)-6,7-dihydro-5H-pyrrolo[1,2-c]imidazol-3-yl)quinoxaline. MS m/e: 486 (M+H)+.

Compound 322: 6-(2-(2-chloro-4-fluoro-5-methylphenyl)-6,7-dihydro-5H-pyrrolo[1,2-c]imidazol-3-yl)quinoline. MS m/e: 485 (M+H)+.

Compound 323: 6-(2-(2-chloro-4-fluoro-5-methylphenyl)-6,7-dihydro-5H-pyrrolo[1,2-c]imidazol-3-yl)benzo[d]thiazole. MS m/e: 491 (M+H)+.

Compound 324: 2'-(4-fluorophenyl)-3'-(1H-indazol-5-yl)-5'H,7'H-spiro[cyclopentane-1,6'-pyrrolo[1,2-c]imidazole]. MS m/e: 373 (M+H)+.

Compound 325: 6-(2'-(4-fluorophenyl)-5'H,7'H-spiro[cyclopentane-1,6'-pyrrolo[1,2-c]imidazol]-3'-yl)benzo[d]thiazole. MS m/e: 390 (M+H)+.

Compound 326: 2'-(4-fluorophenyl)-3'-(quinoxalin-6-yl)-5'H,7'H-spiro[cyclopentane-1,6'-pyrrolo[1,2-c]imidazole]. MS m/e: 385 (M+H)+.

Compound 327: 2'-(4-fluorophenyl)-3'-(quinolin-6-yl)-5'H,7'H-spiro[cyclopentane-1,6'-pyrrolo[1,2-c]imidazole]. MS m/e: 384 (M+H)+.

Compound 328: 5-(2-(4-fluoro-2,3-dimethylphenyl)-6,7-dihydro-5H-pyrrolo[1,2-c]imidazol-3-yl)-1H-indazole. MS m/e: 347 (M+H)+.

Compound 329: 6-(2-(4-fluoro-2,3-dimethylphenyl)-6,7-dihydro-5H-pyrrolo[1,2-c]imidazol-3-yl)benzo[d]thiazole. MS m/e: 364 (M+H)+.

Compound 330: 6-(2-(4-fluoro-2,3-dimethylphenyl)-6,7-dihydro-5H-pyrrolo[1,2-c]imidazol-3-yl)quinoxaline. MS m/e: 359 (M+H)+.

Compound 331: 6-(2-(4-fluoro-2,3-dimethylphenyl)-6,7-dihydro-5H-pyrrolo[1,2-c]imidazol-3-yl)quinoline. MS m/e: 358 (M+H)+.

Compound 332: 3'-(benzo[d]thiazol-6-yl)-2'-(4-fluorophenyl)-5'H,7'H-spiro[cyclohexane-1,6'-pyrrolo[1,2-c]imidazole]-4-carboxylic acid. MS m/e: 448 (M+H)+.

Compound 335: (3'-(benzo[d]thiazol-6-yl)-2'-(4-fluorophenyl)-5'H,7'H-spiro[cyclohexane-1,6'-pyrrolo[1,2-c]imidazol]-4-yl)methanol. MS m/e: 434 (M+H)+.

Compound 336: (2'-(4-fluorophenyl)-3'-(quinoxalin-6-yl)-5'H,7'H-spiro[cyclohexane-1,6'-pyrrolo[1,2-c]imidazol]-4-yl)methanol. MS m/e: 429 (M+H)+.

Compound 333: Ethyl 2'-(4-fluorophenyl)-3'-(quinoxalin-6-yl)-5'H,7'H-spiro[cyclohexane-1,6'-pyrrolo[1,2-c]imidazole]-4-carboxylate. MS m/e: 471 (M+H)+.

Compound 334: 2'-(4-fluorophenyl)-3'-(quinoxalin-6-yl)-5'H,7'H-spiro[cyclohexane-1,6'-pyrrolo[1,2-c]imidazole]-4-carboxylic acid. MS m/e: 443 (M+H)+.

Compound 337: 6-(2-(5-chloro-2-fluoropheny)-6,7-dihydro-5H-pyrrolo[1,2-a]imidazol-3-yl)quinoxaline. $^1$H NMR (DMSO-$d_6$, 300 MHz) 8.91 (m, 2H), 8.04 (m, 1H), 7.97 (m, 1H), 7.71 (m, 1H), 7.62 (m, 1H), 7.39 (m, 1H), 7.14 (m, 1H), 4.02 (t, J=6.9 Hz, 2H), 2.88 (t, J=6.9 Hz, 2H), 2.60 (m, 2H) ppm; MS m/e: 365 (M+H)+.

Compound 338: 6-(2-(5-chloro-2-fluoropheny)-6,7-dihydro-5H-pyrrolo[1,2-a]imidazol-3-yl)quinoline. $^1$H NMR (DMSO-$d_6$, 300 MHz) 8.87 (m, 1H), 8.31 (m, 1H), 7.95 (m, 2H), 7.57 (m, 3H), 7.34 (m, 1H), 7.11 (m, 1H), 4.15 (t, J=7.5 Hz, 2H), 2.89 (t, J=7.5 Hz, 2H), 2.59 (m, 2H) ppm; MS m/e: 364 (M+H)+.

Compound 339: 6-(2-(5-chloro-2-fluoropheny)-6,7-dihydro-5H-pyrrolo[1,2-c]imidazol-3-yl)benzo[d]thiazole. $^1$H NMR (DMSO-$d_6$, 300 MHz) 9.38 (m, 1H), 8.15 (m, 1H), 8.02 (m, 1H), 7.58 (m, 1H), 7.34 (m, 2H), 7.11 (m, 1H), 4.09 (t, J=6.9 Hz, 2H), 2.88 (t, J=6.9 Hz, 2H), 2.59 (m, 2H) ppm; MS m/e: 370 (M+H)+.

Compound 340: 6-(2-(5-chloro-2-methylpheny)-6,7-dihydro-5H-pyrrolo[1,2-a]imidazol-3-yl)quinoline. $^1$H NMR (DMSO-$d_6$, 300 MHz) 8.85 (m, 1H), 8.29 (m, 1H), 7.88 (m, 2H), 7.50 (m, 1H), 7.39 (m, 1H), 7.21 (m, 13H), 4.21 (t, J=6.3 Hz, 2H), 2.89 (t, J=6.3 Hz, 2H), 2.60 (m, 2H), 1.98 (s, 3H) ppm; MS m/e: 360 (M+H)+.

Compound 341: 6-(4-methyl-3-(3-(quinoxalin-6-yl)-6,7-dihydro-5H-pyrrolo[1,2-c]imidazol-2-yl)phenyl)quinoxaline. $^1$H NMR (DMSO-$d_6$, 300 MHz) 8.88 (m, 4H), 8.08 (m, 3H), 7.99 (m, 2H), 7.71 (m, 3H), 7.40 (m, 1H), 4.29 (t, J=7.2 Hz, 2H), 2.93 (t, J=7.2 Hz, 2H), 2.64 (m, 2H), 2.13 (s, 3H) ppm; MS m/e: 455 (M+H)+.

Compound 342: 6-(2-(5-chloro-2-methylpheny)-6,7-dihydro-5H-pyrrolo[1,2-c]imidazol-3-yl)quinoxaline. MS m/e: 361 (M+H)+.

Compound 343: 6-(2-(2,5-dichlorophenyl)-6,7-dihydro-5H-pyrrolo[1,2-c]imidazol-3-yl)quinoline. MS m/e: 380 (M+H)+.

Compound 344: 6-(2-(2,3,5-trifluorophenyl)-6,7-dihydro-5H-pyrrolo[1,2-a]imidazol-3-yl)quinazolin-4-amine. $^1$H NMR (DMSO-$d_6$, 300 MHz) 8.37 (s, 1H), 8.16 (m, 1H), 7.81 (bs, 2H), 7.61 (m, 1H), 7.53 (m, 1H), 7.40 (m, 1H), 7.19 (m, 1H), 4.14 (t, J=7.5 Hz, 2H), 2.92 (t, J=7.5 Hz, 2H), 2.58 (m, 2H) ppm; MS m/e: 382 (M+H)+.

Compound 345: 6-(2-(2,4,5-trifluorophenyl)-6,7-dihydro-5H-pyrrolo[1,2-a]imidazol-3-yl)quinazolin-4-amine. $^1$H NMR (DMSO-$d_6$, 300 MHz) 8.37 (s, 1H), 8.13 (m, 1H), 7.82 (bs, 2H), 7.59 (m, 3H), 7.40 (m, 1H), 4.14 (t, J=6.9 Hz, 2H), 2.89 (t, J=6.9 Hz, 2H), 2.55 (m, 2H) ppm; MS m/e: 382 (M+H)+.

Compound 346: 6-(2-(5-chloro-2-fluorophenyl)-6,7-dihydro-5H-pyrrolo[1,2-a]imidazol-3-yl)quinazolin-4-amine. $^1$H NMR (DMSO-$d_6$, 300 MHz) 8.36 (s, 1H), 8.15 (m, 1H), 7.79 (bs, 2H), 7.60 (m, 1H), 7.56 (s, 1H), 7.48 (m, 1H), 7.33 (m, 1H), 7.10 (m, 1H), 4.14 (t, J=6.9 Hz, 2H), 2.89 (t, J=6.9 Hz, 2H), 2.60 (m, 2H) ppm; MS m/e: 380 (M+H)+.

Compound 347: 6-(2-(3-chloro-4-fluorophenyl)-6,7-dihydro-5H-pyrrolo[1,2-a]imidazol-3-yl)quinazolin-4-amine. $^1$H NMR (DMSO-$d_6$, 300 MHz) 8.39 (s, 1H), 8.28 (m, 1H), 7.82 (bs, 2H), 7.66 (s, 2H), 7.60 (m, 1H), 7.25 (m, 2H), 4.00 (t, J=6.9 Hz, 2H), 2.87 (t, J=6.9 Hz, 2H), 2.55 (m, 2H) ppm; MS m/e: 380 (M+H)+.

Compound 348: 6-(2-(2,5-dichloropheny)-6,7-dihydro-5H-pyrrolo[1,2-a]imidazol-3-yl)quinoxaline. MS m/e: 381 (M+H)+.

Compound 349: 6-(2-(2,5-dichlorophenyl)-6,7-dihydro-5H-pyrrolo[1,2-c]imidazol-3-yl)benzo[d]thiazole. $^1$H NMR (DMSO-$d_6$, 300 MHz) 9.36 (s, 1H), 8.09 (m, 1H), 7.99 (m, 1H), 7.49 (m, 1H), 7.40 (m, 2H), 7.24 (m, 1H), 4.16 (t, J=7.2 Hz, 2H), 2.88 (t, J=7.2 Hz, 2H), 2.59 (m, 2H) ppm; MS m/e: 386 (M+H)+.

Compound 350: 6-(2-(5-chloro-2-methylphenyl)-6,7-dihydro-5H-pyrrolo[1,2-c]imidazol-3-yl)benzo[d]thiazole. MS m/e: 366 (M+H)+.

Compound 351: 6-(2-(4-methoxyphenyl)-6,7-dihydro-5H-pyrrolo[1,2-c]imidazol-3-yl)quinoxaline. MS m/e: 343 (M+H)+.

Compound 352: 6-(2-(4-methoxyphenyl)-6,7-dihydro-5H-pyrrolo[1,2-c]imidazol-3-yl)quinoline. MS m/e: 342 (M+H)+.

Compound 353: 2-(2-methoxyethoxy)-7-(2-(2,4,5-trifluorophenyl)-6,7-dihydro-5H-pyrrolo[1,2-a]imidazol-3-yl)quinoxaline. $^1$H NMR (DMSO-d$_6$, 300 MHz) 8.57 (s, 1H), 7.94 (m, 1H), 7.69 (m, 1H), 7.61 (m, 1H), 7.43 (m, 2H), 4.53 (m, 2H), 4.16 (m, 2H), 3.72 (m, 2H), 3.29 (s, 3H), 2.89 (m, 2H), 2.58 (m, 2H) ppm; MS m/e: 441 (M+H)$^+$.

Compound 117: 2-(2-methoxyethoxy)-7-(2-(2,3,5-trifluorophenyl)-5,6-dihydro-7λ$^2$-imidazo[3,2-c]imidazol-3-yl)quinoxaline. $^1$H NMR (DMSO-d$_6$, 300 MHz) 8.59 (s, 1H), 7.97 (m, 1H), 7.73 (m, 1H), 7.47 (m, 1H), 7.24 (m, 1H), 4.54 (m, 2H), 4.16 (m, 2H), 3.72 (m, 2H), 3.29 (s, 3H), 2.90 (m, 2H), 2.59 (m, 2H) ppm; MS m/e: 441 (M+H)$^+$.

Compound 354: 7-(2-(5-chloro-2-fluorophenyl)-6,7-dihydro-5H-pyrrolo[1,2-c]imidazol-3-yl)-2-(2-methoxyethoxy)quinoxaline. $^1$H NMR (DMSO-d$_6$, 300 MHz) 8.57 (s, 1H), 7.94 (d, J=8.4 Hz, 1H), 7.68 (m, 1H), 7.61 (m, 1H), 7.47 (m, 1H), 7.37 (m, 1H), 7.13 (t, J=9.6 Hz, 1H), 4.52 (m, 2H), 4.15 (m, 2H), 3.71 (m, 2H), 3.29 (s, 3H), 2.89 (m, 2H), 2.68 (m, 2H) ppm; MS m/e: 439 (M+H)$^+$.

Compound 355: 7-(2-(3-chloro-4-fluorophenyl)-6,7-dihydro-5H-pyrrolo[1,2-c]imidazol-3-yl)-2-(2-methoxyethoxy)quinoxaline. MS m/e: 439 (M+H)$^+$.

Compound 356: 6-(2-(2-fluoro-5-methylphenyl)-6,7-dihydro-5H-pyrrolo[1,2-a]imidazol-3-yl)quinoline. $^1$H NMR (DMSO-d$_6$, 300 MHz) 8.85 (m, 1H), 8.29 (m, 1H), 7.90 (m, 2H), 7.52 (m, 2H), 7.40 (m, 1H), 7.09 (m, 1H), 6.92 (m, 1H), 4.16 (t, J=6.6 Hz, 2H), 2.88 (t, J=6.6 Hz, 2H), 2.61 (m, 2H), 2.28 (s, 3H) ppm; MS m/e: 344 (M+H)$^+$.

Compound 358: 7-(2-(2-fluoro-5-methylphenyl)-6,7-dihydro-5H-pyrrolo[1,2-c]imidazol-3-yl)-2-(2-methoxyethoxy)quinoxaline. $^1$H NMR (DMSO-d$_6$, 300 MHz) 8.54 (m, 1H), 7.91 (m, 1H), 7.66 (m, 1H), 7.42 (m, 2H), 7.11 (m, 1H), 6.94 (m, 1H), 4.51 (m, 2H), 4.17 (t, J=6.6 Hz, 2H), 3.71 (m, 2H),), 3.29 (s, 3H), 2.88 (t, J=6.6 Hz, 2H), 2.48 (m, 2H), 2.29 (s, 3H) ppm; MS m/e: 419 (M+H)$^+$.

Compound 357: 6-(2-(2-fluoro-5-methylphenyl)-6,7-dihydro-5H-pyrrolo[1,2-a]imidazol-3-yl)quinoxaline. $^1$H NMR (DMSO-d$_6$, 300 MHz) 8.89 (m, 2H), 8.01 (m, 1H), 7.93 (m, 1H), 7.67 (m, 1H), 7.43 (m, 1H), 7.11 (m, 1H), 6.94 (m, 1H), 4.21 (t, J=6.9 Hz, 2H), 2.89 (t, J=6.9 Hz, 2H), 2.60 (m, 2H), 2.29 (s, 3H) ppm; MS m/e: 345 (M+H)$^+$.

Compound 359: 2-(1H-imidazol-1-yl)-7-(2-(2,3,5-trifluorophenyl)-6,7-dihydro-5H-pyrrolo[1,2-c]imidazol-3-yl)quinoxaline. MS m/e: 433 (M+H)$^+$.

Compound 360: 7-(2-(5-chloro-2-fluorophenyl)-6,7-dihydro-5H-pyrrolo[1,2-c]imidazol-3-yl)-2-(1H-imidazol-1-yl)quinoxaline. MS m/e: 431 (M+H)$^+$.

Compound 361: N,N-dimethyl-2-((7-(2-(2,3,5-trifluorophenyl)-6,7-dihydro-5H-pyrrolo[1,2-c]imidazol-3-yl)quinoxalin-2-yl)oxy)ethan-1-amine. $^1$H NMR (DMSO-d$_6$, 300 MHz) 8.56 (s, 1H), 8.01 (m, 1H), 7.95 (m, 1H), 7.72 (m, 1H), 7.44 (m, 2H), 7.22 (m, 1H), 4.49 (m, 2H), 4.16 (m, 2H), 2.90 (m, 2H), 2.67 (m, 2H), 2.59 (m, 2H), 2.20 (s, 6H) ppm; MS m/e: 454 (M+H)$^+$.

Compound 362: N,N-dimethyl-2-((7-(2-(2,4,5-trifluorophenyl)-6,7-dihydro-5H-pyrrolo[1,2-c]imidazol-3-yl)quinoxalin-2-yl)oxy)ethan-1-amine. $^1$H NMR (DMSO-d$_6$, 300 MHz) 8.54 (s, 1H), 7.94 (m, 1H), 7.68 (m, 1H), 7.61 (m, 1H), 7.43 (m, 2H), 4.49 (m, 2H), 4.16 (m, 2H), 2.89 (m, 2H), 2.66 (m, 2H), 2.58 (m, 2H), 2.20 (s, 6H) ppm; MS m/e: 454 (M+H)$^+$.

Compound 363: 2-((7-(2-(5-chloro-2-fluorophenyl)-6,7-dihydro-5H-pyrrolo[1,2-a]imidazol-3-yl)quinoxalin-2-yl)oxy)-N,N-dimethylethan-1-amine. $^1$H NMR (DMSO-d$_6$, 300 MHz) 8.54 (s, 1H), 7.93 (d, J=8.4 Hz, 1H), 7.68 (m, 1H), 7.61 (m, 1H), 7.46 (m, 1H), 7.37 (m, 1H), 7.13 (t, J=9.3 Hz, 1H), 4.48 (t, J=5.7 Hz, 2H), 4.16 (t, J=6.9 Hz, 2H), 2.89 (t, J=6.9 Hz, 2H), 2.66 (t, J=5.7 Hz, 2H), 2.58 (m, 2H), 2.20 (s, 6H) ppm; MS m/e: 452 (M+H)$^+$.

Scheme 2: General Synthesis of Bicyclic Imidazo[2,1-b]oxazoles

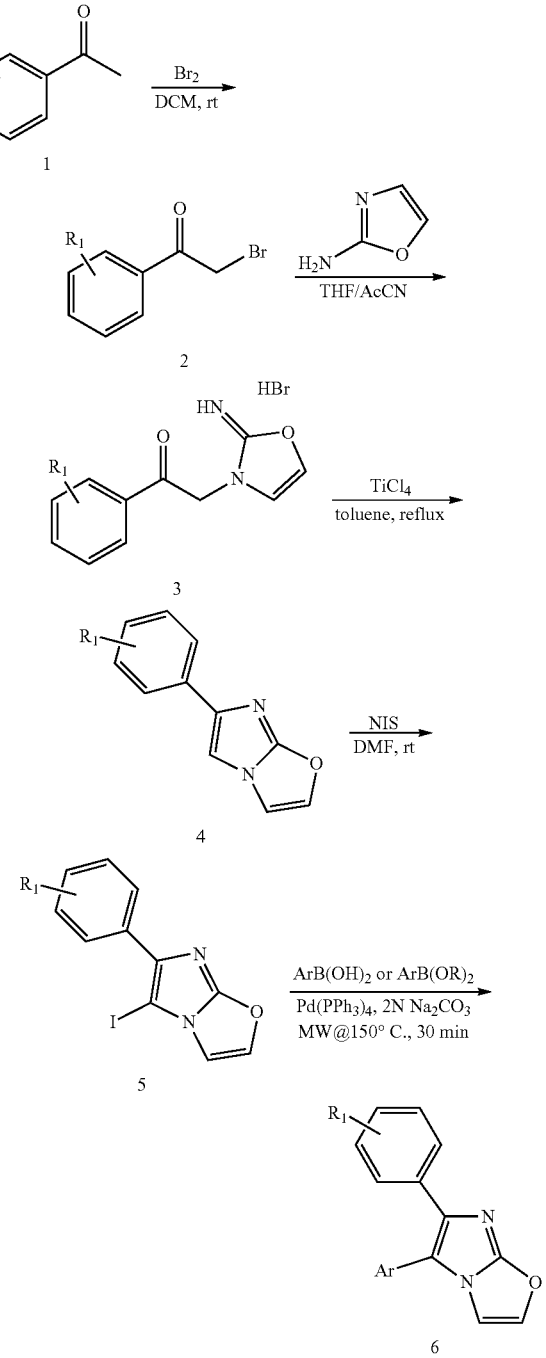

Step 1: To a solution of 2',4'-difluoroacetophenone (8.0 g, 51.3 mmol) in dichloromethane (60 mL) at room temperature was added a solution of bromine (8.1 g, 50.9 mmol) in dichloromethane (25 mL) drop wise. Once the addition was complete, the resulting solution was stirred at room temperature for 1 h. Ice water was then added into reaction flask and the mixture was stirred for 15 min. The organic layer was separated, washed with water, dried over sodium sulfate, filtered, and concentrated under reduced pressure to give 2-bromo-1-(2,4-difluorophenyl)ethan-1-one as a pale yellow oil (10.2 g, 85%).

Step 2: A mixture of 2-bromo-1-(2,4-difluorophenyl)ethan-1-one (8.4 g, 35.7 mmol) and oxazole-2-amine (2.0 g, 23.8 mmol) in THF (36 mL) and acetonitrile (60 mL) was stirred at room temperature for 20 h. The resulting precipitate was collected by filtration, washed with acetonitrile, and dried under vacuum to 1-(2,4-difluorophenyl)-2-(2-iminooxazol-3(2H)-yl)ethan-1-one hydrobromide as a white solid (5.4 g, 71%).

Step 3: To a mixture of 1-(2,4-difluorophenyl)-2-(2-iminooxazol-3(2H)-yl)ethan-1-one hydrobromide (5.4 g, 16.9 mmol) in toluene (40 mL) at 0° C. was added a 1.0 M solution of $TiCl_4$ in toluene (44 mL) drop wise. Once the addition was complete, the resulting mixture was stirred at 0° C. for 0.5 h and then heated to 100° C. for 3 h. The mixture was cooled to room temperature. After the toluene was decanted off, ice was added into reaction flask. The mixture was adjusted to pH 8 with the addition of $Na_2CO_3$, followed by the addition of ethyl acetate. The mixture was stirred for 1 h and then filtered through a pad of diatomaceous earth. The filtrate was separated, dried over sodium sulfate, filtered, and concentrated under reduced pressure to give a residue, which was purified by chromatography eluting with ethyl acetate/Hexanes (1/1) to provide 6-(2,4-difluorophenyl)imidazo[2,1-b]oxazole as a pale white solid (3.0 g, 80%).

Step 4: A mixture of 6-(2,4-difluorophenyl)imidazo[2,1-b]oxazole (3.0 g, 13.6 mmol) and NIS (3.2 g, 14.0 mmol) in DMF (35 mL) was stirred at room temperature for 1 h. The mixture was then partitioned between water and dichloromethane. The organic layer was separated, washed with saturated aqueous $NaHCO_3$, dried over sodium sulfate, filtered, and concentrated under reduced pressure to give a residue, which was purified by chromatography eluting with ethyl acetate/Hexanes (2/3) to provide 6-(2,4-difluorophenyl)-5-iodoimidazo[2,1-b]oxazole as a white solid (4.2 g, 83%).

Step 5: A mixture of 6-(2,4-difluorophenyl)-5-iodoimidazo[2,1-b]oxazole (1.1 g, 3.2 mmol), 6-(4,4,5,5-tetramethyl-1,3,2-dioxaborolan-2-yl)quinoline (1.1 g, 4.4 mmol), tetrakis(triphenylphosphine)palladium(0) (0.2 g, 0.2 mmol), and 2.0 M of aqueous $Na_2CO_3$ (4.0 mL) in 1,2-dimethoxyethane (21 mL), EtOH (9 mL) and water (6 mL) was irradiated under microwave at 150° C. for 0.5 h. The mixture was then partitioned between water and ethyl acetate. The organic layer was separated, dried over sodium sulfate, filtered, and concentrated under reduced pressure to give a residue, which was purified by chromatography eluting with ethyl acetate to provide Compound 158: 5-(quinolin-6-yl)-6-(2,4-difluorophenyl)imidazo[2,1-b]oxazole as a white solid (0.8 g, 73%). $^1$H NMR (DMSO-$d_6$, 300 MHz) 8.88 (m, 1H), 8.37 (m, 2H), 8.14 (m, 1H), 8.03 (m, 1H), 7.95 (m, 1H), 7.65 (m, 1H), 7.54 (m, 2H), 7.20 (m, 2H) ppm; MS m/e: 348 (M+H)$^+$.

Compound 126: 6-(4-fluorophenyl)-5-(1H-indazol-5-yl)imidazo[2,1-b]oxazole. $^1$H NMR (DMSO-$d_6$, 300 MHz) 13.2 (s, 1H), 8.10 (m, 1H), 7.99 (m, 2H), 7.90 (m, 1H), 7.60 (m, 1H), 7.50 (m, 2H), 7.32 (m, 1H), 7.09 (m, 2H) ppm; MS m/e: 319 (M+H)$^+$.

Compound 127: 5-(benzo[d]thiazol-6-yl)-6-(4-fluorophenyl)imidazo[2,1-b]oxazole. $^1$H NMR (DMSO-$d_6$, 300 MHz) 8.42 (m, 1H), 8.31 (m, 1H), 8.10 (m, 1H), 8.04 (m, 1H), 7.51 (m, 3H), 7.13 (m, 2H) ppm; MS m/e: 336 (M+H)$^+$.

Compound 128: 6-(4-fluorophenyl)-5-(1H-indazol-6-yl)imidazo[2,1-b]oxazole. $^1$H NMR (DMSO-$d_6$, 300 MHz) 13.1 (s, 1H), 8.10 (m, 1H), 8.04 (m, 2H), 7.82 (m, 1H), 7.56 (m, 3H), 7.12 (m, 3H) ppm; MS m/e: 319 (M+H)$^+$.

Compound 129: 6-(4-fluorophenyl)-5-(imidazo[1,2-a]pyridin-6-yl)imidazo[2,1-b]oxazole. $^1$H NMR (DMSO-$d_6$, 300 MHz) 8.80 (m, 1H), 8.12 (m, 1H), 8.03 (m, 1H), 7.96 (m, 1H), 7.57 (m, 4H), 7.14 (m, 3H) ppm; MS m/e: 319 (M+H)$^+$.

Compound 130: 6-(4-fluorophenyl)-5-(quinoxalin-6-yl)imidazo[2,1-b]oxazole. MS m/e: 331 (M+H)$^+$.

Compound 133: 6-(3,4-difluorophenyl)-5-(1H-indazol-5-yl)imidazo[2,1-b]oxazole. $^1$H NMR (DMSO-$d_6$, 300 MHz) 13.2 (s, 1H), 8.12 (m, 1H), 8.00 (m, 2H), 7.93 (m, 1H), 7.58 (m, 2H), 7.36 (m, 3H) ppm; MS m/e: 337 (M+H)$^+$.

Compound 134: 6-(3,4-difluorophenyl)-5-(1H-indazol-6-yl)imidazo[2,1-b]oxazole. $^1$H NMR (DMSO-$d_6$, 300 MHz) 13.2 (s, 1H), 8.12 (m, 1H), 8.04 (m, 2H), 7.85 (m, 1H), 7.63 (m, 1H), 7.47 (m, 1H), 7.32 (m, 2H), 7.15 (m, 1H) ppm; MS m/e: 337 (M+H)$^+$.

Compound 135: 5-(benzo[d]thiazol-6-yl)-6-(3,4-difluorophenyl)imidazo[2,1-b]oxazole. $^1$H NMR (DMSO-$d_6$, 300 MHz) 9.44 (m, 1H), 8.36 (m, 1H), 8.14 (m, 2H), 8.06 (m, 1H), 7.51 (m, 2H), 7.31 (m, 2H) ppm; MS m/e: 354 (M+H)$^+$.

Compound 136: 6-(3,4-difluorophenyl)-5-(quinoxalin-6-yl)imidazo[2,1-b]oxazole. $^1$H NMR (DMSO-$d_6$, 300 MHz) 8.96 (m, 2H), 8.24 (m, 1H), 8.18 (m, 1H), 8.11 (m, 2H), 7.85 (m, 1H), 7.52 (m, 1H), 7.34 (m, 2H) ppm; MS m/e: 349 (M+H)$^+$.

Compound 137: 6-(3,4-difluorophenyl)-5-(imidazo[1,2-a]pyridin-6-yl)imidazo[2,1-b]oxazole. $^1$H NMR (DMSO-$d_6$, 300 MHz) 8.82 (m, 1H), 8.13 (m, 1H), 8.05 (m, 1H), 7.97 (m, 1H), 7.64 (m, 2H), 7.54 (m, 1H), 7.36 (m, 2H), 7.16 (m, 1H) ppm; MS m/e: 337 (M+H)$^+$.

Compound 139: 6-(m-tolyl)-5-(1H-indazol-5-yl)imidazo[2,1-b]oxazole. $^1$H NMR (DMSO-$d_6$, 300 MHz) 13.2 (s, 1H), 7.98 (m, 2H), 7.57 (m, 3H), 7.36 (m, 2H), 7.20 (m, 1H), 7.10 (m, 1H), 7.00 (m, 1H) ppm; MS m/e: 315 (M+H)$^+$.

Compound 140: 6-(m-tolyl)-5-(1H-indazol-6-yl)imidazo[2,1-b]oxazole. $^1$H NMR (DMSO-$d_6$, 300 MHz) 13.1 (s, 1H), 8.05 (m, 2H), 7.80 (m, 1H), 7.59 (m, 1H), 7.40 (m, 1H), 7.22 (m, 1H), 7.12 (m, 2H), 7.03 (m, 2H) ppm; MS m/e: 315 (M+H)$^+$.

Compound 141: 5-(benzo[d]thiazol-6-yl)-6-(m-tolyl)imidazo[2,1-b]oxazole. $^1$H NMR (DMSO-$d_6$, 300 MHz) 9.42 (s, 1H), 8.31 (m, 1H), 8.12 (m, 1H), 8.07 (d, J=8.4 Hz, 1H), 8.03 (m, 1H), 7.51 (m, 1H), 7.39 (m, 1H), 7.22 (m, 1H), 7.14 (m, 1H), 7.05 (m, 1H) ppm; MS m/e: 332 (M+H)$^+$.

Compound 142: 5-(quinoxalin-6-yl)-6-(m-tolyl)imidazo[2,1-b]oxazole. $^1$H NMR (DMSO-$d_6$, 300 MHz) 8.95 (m, 1H), 8.25 (m, 1H), 8.15 (m, 1H), 8.08 (m, 1H), 8.03 (m, 2H), 7.81 (m, 1H), 7.42 (s, 1H), 7.20 (m, 3H) ppm; MS m/e: 327 (M+H)$^+$.

Compound 143: 6-(m-tolyl)-5-(imidazo[1,2-a]pyridin-6-yl)imidazo[2,1-b]oxazole. MS m/e: 315 (M+H)$^+$.

Compound 144: 5-(quinolin-6-yl)-6-(m-tolyl)imidazo[2,1-b]oxazole. $^1$H NMR (DMSO-$d_6$, 300 MHz) 8.90 (m, 1H), 8.38 (m, 1H), 8.21 (m, 1H), 8.13 (m, 1H), 8.037 (m, 1H), 7.99 (m, 1H), 7.68 (m, 1H), 7.56 (m, 1H), 7.42 (s, 1H), 7.25 (m, 1H), 7.16 (m, 1H), 7.08 (m, 1H) ppm; MS m/e: 326 (M+H)$^+$.

Compound 145: 5-(quinolin-6-yl)-6-(3,4-difluorophenyl)imidazo[2,1-b]oxazole. $^1$H NMR (DMSO-$d_6$, 300 MHz) 8.93 (m, 1H), 8.40 (m, 1H), 8.18 (m, 2H), 8.06 (m, 2H), 7.67 (m, 1H), 7.56 (m, 2H), 7.34 (m, 2H) ppm; MS m/e: 348 (M+H)$^+$.

Compound 146: 5-(quinolin-6-yl)-6-(4-fluorophenyl)imidazo[2,1-b]oxazole. $^1$H NMR (DMSO-$d_6$, 300 MHz) 8.90

(m, 1H), 8.38 (m, 1H), 8.20 (m, 1H), 8.13 (m, 1H), 8.08 (m, 1H), 8.01 (m, 1H), 7.57 (m, 3H), 7.16 (m, 3H) ppm; MS m/e: 330 (M+H)⁺.

Compound 147: 6-(2,4,5-trifluorophenyl)-5-(1H-indazol-6-yl)imidazo[2,1-b]oxazole. ¹H NMR (DMSO-d₆, 300 MHz) 13.0 (s, 1H), 8.23 (m, 1H), 8.08 (m, 2H), 7.77 (d, J=8.4 Hz, 1H), 7.55 (m, 3H), 7.07 (m, 1H) ppm; MS m/e: 355 (M+H)⁺.

Compound 148: 6-(2,4,5-trifluorophenyl)-5-(imidazo[1,2-a]pyridin-6-yl)imidazo[2,1-b]oxazole. ¹H NMR (DMSO-d₆, 300 MHz) 8.74 (m, 1H), 8.26 (m, 1H), 8.12 (m, 1H), 7.96 (m, 1H), 7.60 (m, 4H), 7.12 (m, 1H) ppm; MS m/e: 355 (M+H)⁺.

Compound 149: 5-(quinoxalin-6-yl)-6-(2,4,5-trifluorophenyl)imidazo[2,1-b]oxazole. ¹H NMR (DMSO-d₆, 300 MHz) 8.93 (m, 2H), 8.40 (m, 1H), 8.16 (m, 1H), 8.08 (d, J=9.0 Hz, 1H), 8.03 (m, 1H), 7.78 (m, 1H), 7.70 (m, 1H), 7.57 (m, 1H) ppm; MS m/e: 367 (M+H)⁺.

Compound 150: 5-(quinolin-6-yl)-6-(2,4,5-trifluorophenyl)imidazo[2,1-b]oxazole. ¹H NMR (DMSO-d₆, 300 MHz) 8.88 (m, 1H), 8.37 (m, 2H), 8.16 (m, 1H), 8.04 (m, 1H), 7.97 (m, 1H), 7.69 (m, 1H), 7.57 (m, 3H) ppm; MS m/e: 366 (M+H)⁺.

Compound 151: 5-(benzo[d]thiazol-6-yl)-6-(2,4,5-trifluorophenyl)imidazo[2,1-b]oxazole. MS m/e: 372 (M+H)⁺.

Compound 152: 6-(2,4,5-trifluorophenyl)-5-(1H-indazol-5-yl)imidazo[2,1-b]oxazole. ¹H NMR (DMSO-d₆, 300 MHz) 13.2 (s, 1H), 8.19 (m, 1H), 8.07 (m, 2H), 7.80 (m, 1H), 7.57 (m, 3H), 7.23 (m, 1H) ppm; MS m/e: 355 (M+H)⁺.

Compound 154: 6-(2,4-difluorophenyl)-5-(1H-indazol-5-yl)imidazo[2,1-b]oxazole. ¹H NMR (DMSO-d₆, 300 MHz) 13.1 (s, 1H), 8.18 (m, 1H), 8.06 (m, 2H), 7.77 (s, 1H), 7.55 (m, 2H), 7.16 (m, 3H) ppm; MS m/e: 337 (M+H)⁺.

Compound 155: 6-(2,4-difluorophenyl)-5-(1H-indazol-6-yl)imidazo[2,1-b]oxazole. ¹H NMR (DMSO-d₆, 300 MHz) 13.0 (s, 1H), 8.22 (m, 1H), 8.07 (m, 2H), 7.72 (d, J=8.7 Hz, 1H), 7.59 (m, 2H), 7.19 (m, 2H), 7.05 (m, 1H) ppm; MS m/e: 337(M+H)⁺.

Compound 156: 5-(benzo[d]thiazol-6-yl)-6-(2,4-difluorophenyl)imidazo[2,1-b]oxazole. ¹H NMR (DMSO-d₆, 300 MHz) 9.39 (m, 1H), 8.30 (m, 1H), 8.23 (m, 1H), 8.11 (m, 1H), 8.02 (d, J=8.4 Hz, 1H), 7.61 (m, 1H), 7.35 (m, 1H), 7.21 (m, 2H) ppm; MS m/e: 354 (M+H)⁺.

Compound 157: 6-(2,4-difluorophenyl)-5-(quinoxalin-6-yl)imidazo[2,1-b]oxazole. ¹H NMR (DMSO-d₆, 300 MHz) 8.91 (m, 2H), 8.40 (m, 1H), 8.15 (m, 1H), 8.07 (d, J=8.7 Hz, 1H), 7.99 (m, 1H), 7.75 (m, 1H), 7.65 (m, 1H), 7.24 (m, 2H) ppm; MS m/e: 349 (M+H)⁺.

Compound 159: 6-(2,4-difluorophenyl)-5-(imidazo[1,2-a]pyridin-6-yl)imidazo[2,1-b]oxazole. ¹H NMR (DMSO-d₆, 300 MHz) 8.70 (m, 1H), 8.25 (m, 1H), 8.17 (s, 1H), 8.09 (m, 1H), 7.92 (s, 1H), 7.58 (m, 3H), 7.19 (m, 2H) ppm; MS m/e: 337 (M+H)⁺.

Compound 160: 6-(2,3,4-trifluorophenyl)-5-(1H-indazol-5-yl)imidazo[2,1-b]oxazole. ¹H NMR (DMSO-d₆, 300 MHz) 13.2 (s, 1H), 8.20 (m, 1H), 8.08 (m, 2H), 7.82 (m, 1H), 7.59 (m, 1H), 7.35 (m, 2H), 2.23 (m, 1H) ppm; MS m/e: 355 (M+H)⁺.

Compound 161: 5-(benzo[d]thiazol-6-yl)-6-(2,3,4-trifluorophenyl)imidazo[2,1-b]oxazole. ¹H NMR (DMSO-d₆, 300 MHz) 9.40 (s, 1H), 8.31 (m, 1H), 8.27 (m, 1H), 8.13 (m, 1H), 8.05 (d, J=8.4 Hz, 1H), 7.39 (m, 3H) ppm; MS m/e: 372 (M+H)⁺.

Compound 162: 5-(quinolin-6-yl)-6-(2,3,4-trifluorophenyl)imidazo[2,1-b]oxazole. ¹H NMR (DMSO-d₆, 300 MHz) 8.88 (m, 1H), 8.38 (m, 2H), 8.16 (m, 1H), 8.06 (m, 1H), 7.97 (d, J=8.7 Hz, 1H), 7.58 (m, 2H), 7.40 (m, 2H) ppm; MS m/e: 366 (M+H)⁺.

Compound 163: 5-(imidazo[1,2-a]pyridin-6-yl)-6-(2,3,4-trifluorophenyl)imidazo[2,1-b]oxazole. MS m/e: 355 (M+H)⁺.

Compound 164: 5-(quinoxalin-6-yl)-6-(2,3,4-trifluorophenyl)imidazo[2,1-b]oxazole. ¹H NMR (DMSO-d₆, 300 MHz) 9.94 (m, 2H), 8.41 (m, 1H), 8.17 (m, 1H), 8.08 (m, 1H), 8.05 (m, 1H), 7.76 (m, 1H), 7.43 (m, 2H) ppm; MS m/e: 367 (M+H)⁺.

Scheme 3: General Synthesis of Pyrrolodinoimidazole

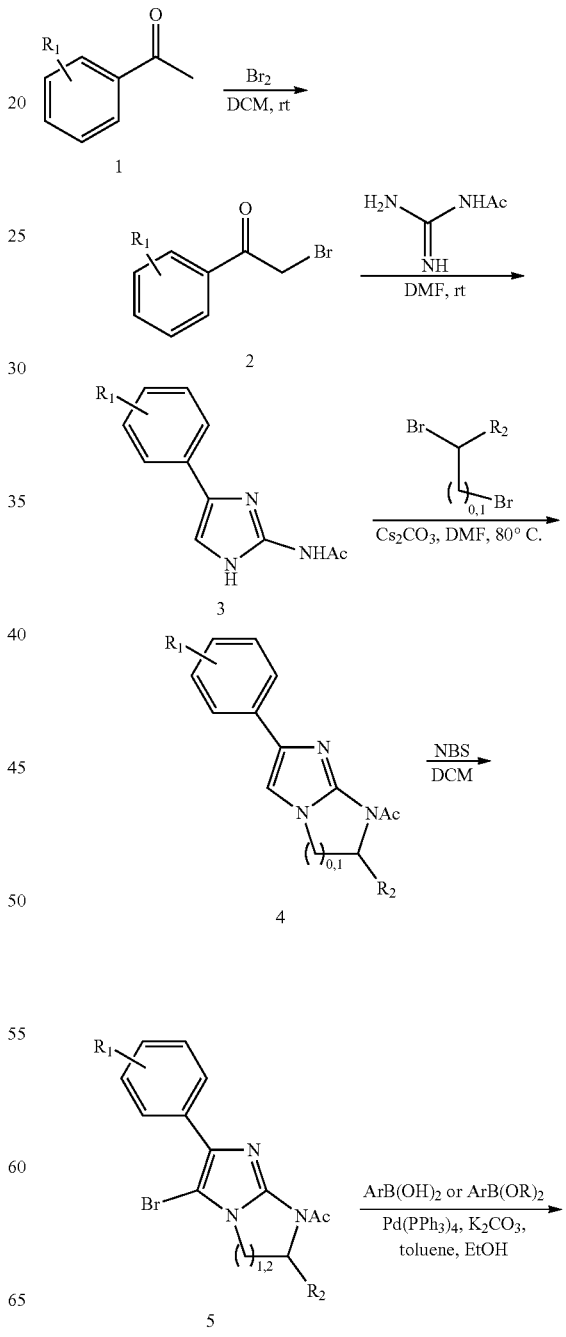

-continued

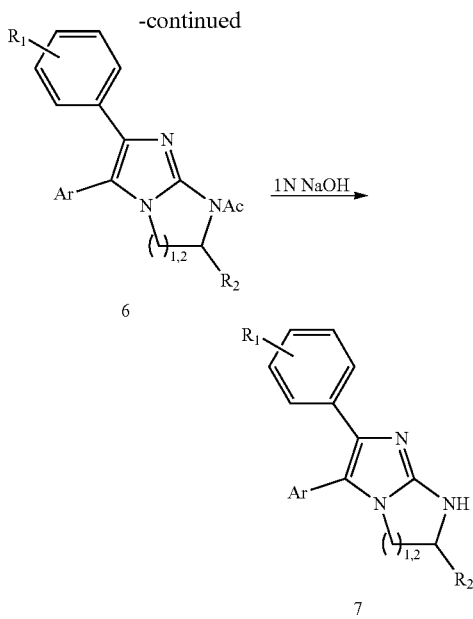

Step 1: To a solution of 2',3',5'-triifluoroacetophenone (8.9 g, 51.3 mmol) in dichloromethane (60 mL) at room temperature was added a solution of bromine (8.1 g, 50.9 mmol) in dichloromethane (25 mL) drop wise. Once the addition was complete, the resulting solution was stirred at room temperature for 1 h. Ice water was then added into reaction flask and the mixture was stirred for 15 min. The organic layer was separated, washed with water, dried over sodium sulfate, filtered, and concentrated under reduced pressure to give 2-bromo-1-(2,3,5-trifluorophenyl)ethan-1-one as a pale yellow oil (10.6 g, 82%).

Step 2: A mixture of 2-bromo-1-(2,3,5-trifluorophenyl) ethan-1-one (9.0 g, 35.6 mmol) and 1-acetylguanidine (10.8 g, 107.1 mmol) in DMF (100 mL) was stirred at room temperature for 48 h. The reaction mixture was then concentrated under reduced pressure to give a residue, which was purified by chromatography eluting with ethyl acetate to provide N-(4-(2,3,5-trifluorophenyl)-1H-imidazol-2-yl)acetamide as a pale white solid (2.9 g, 32%).

Step 3: A mixture of N-(4-(2,3,5-trifluorophenyl)-1H-imidazol-2-yl)acetamide (0.3 g, 1.2 mmol), 1,2-dibromoethane (0.7 g, 3.6 mmol), Cs$_2$CO$_3$ (1.9 g, 5.8 mmol) in DMF (15 mL) was stirred at 80° C. for 5 h. After cooling to room temperature, the reaction mixture was then partitioned between water and dichloromethane. The organic layers was separated, dried over sodium sulfate, filtered, and concentrated under reduced pressure to give a residue, which was purified by chromatography eluting with ethyl acetate to provide 1-(6-(2,3,5-trifluorophenyl)-2,3-dihydro-1H-imidazo[1,2-a]imidazol-1-yl)ethan-1-one as a pale white solid (0.2 g, 59%).

Step 4: To a solution of 1-(6-(2,3,5-trifluorophenyl)-2,3-dihydro-1H-imidazo[1,2-a]imidazol-1-yl)ethan-1-one (0.2 g, 0.7 mmol) in dichloromethane (10 mL) at 0° C. was added N-bromosuccinimide (0.1 g, 0.7 mmol). The resulting mixture was stirred at room temperature for 20 min and then partitioned between water and dichloromethane. The organic layer was separated, dried over sodium sulfate, filtered, and concentrated under reduced pressure to give a residue, which was purified by chromatography eluting with ethyl acetate/hexanes (1/1) to provide 1-(5-bromo-6-(2,3,5-trifluorophenyl)-2,3-dihydro-1H-imidazo[1,2-a]imidazol-1-yl)ethan-1-one as a pale white solid (0.2 g, 79%).

Step 5: A mixture of 1-(5-bromo-6-(2,3,5-trifluorophenyl)-2,3-dihydro-1H-imidazo[1,2-a]imidazol-1-yl)ethan-1-one (0.1 g, 0.3 mmol), 6-(4,4,5,5-tetramethyl-1,3,2-dioxaborolan-2-yl)quinoxaline (0.1 g, 0.4 mmol), tetrakis(triphenylphosphine)palladium(0) (0.2 g, 0.02 mmol), and K$_2$CO$_3$ (0.07 g, 0.5 mmol) in toluene (5 mL) and EtOH (0.2 mL) was stirred at 100° C. for 18 h. The mixture was then concentrated under reduced pressure to give a residue, which was purified by chromatography eluting with ethyl acetate/hexanes (8/2) to provide 1-(5-(quinoxalin-6-yl)-6-(2,3,5-trifluorophenyl)-2,3-dihydro-1H-imidazo[1,2-a]imidazol-1-yl)ethan-1-one as a pale white solid (0.05 g, 41%).

Step 6: A mixture of 1-(5-(quinoxalin-6-yl)-6-(2,3,5-trifluorophenyl)-2,3-dihydro-1H-imidazo[1,2-a]imidazol-1-yl) ethan-1-one (0.05 g, 0.1 mmol) and 1.0 M of aqueous NaOH (0.15 mL) in EtOH (5 mL) was stirred at 60° C. for 2 h. The mixture was then concentrated under reduced pressure to give a residue, which was purified by chromatography eluting with dichloromethane/MeOH (10/0.5) to provide Compound 111: 6-(6-(2,3,5-trifluorophenyl)-2,3-dihydro-1H-imidazo[1,2-a]imidazol-5-yl)quinoxaline as a pale white solid (0.03 g, 61%). $^1$H NMR (DMSO-d$_6$, 300 MHz) 8.88 (m, 2H), 8.01 (d, J=8.7 Hz, 1H), 7.92 (s, 1H), 7.67 (d, J=8.7 Hz, 1H), 7.43 (m, 1H), 7.20 (m, 1H), 4.28 (m, 2H), 3.91 (m, 2H) ppm; MS m/e: 368 (M+H)$^+$ Compound 103: 6-(6-(2,4,5-trifluorophenyl)-2,3-dihydro-1H-imidazo[1,2-a]imidazol-5-yl)benzo[d]thiazole. MS m/e: 373 (M+H)$^+$.

Compound 104: 1-(5-([1,2,4]triazolo[1,5-a]pyridin-6-yl)-6-(2,4,5-trifluorophenyl)-2,3-dihydro-1H-imidazo[1,2-a]imidazol-1-yl)ethan-1-one. $^1$H NMR (DMSO-d$_6$, 300 MHz) 9.05 (m, 1H), 8.54 (s, 1H), 7.85 (m, 1H), 7.66 (m, 1H), 7.50 (m, 2H), 4.33 (m, 4H), 2.49 (s, 3H) ppm; MS m/e: 399 (M+H)$^+$.

Compound 105: 6-(6-(2,4,5-trifluorophenyl)-2,3-dihydro-1H-imidazo[1,2-a]imidazol-5-yl)-[1,2,4]triazolo[1,5-a]pyridine. MS m/e: 357 (M+H)$^+$.

Compound 106: 6-(6-(2,4,5-trifluorophenyl)-2,3-dihydro-1H-imidazo[1,2-a]imidazol-5-yl)quinoxaline. MS m/e: 368 (M+H)$^+$.

Compound 107: 6-(6-(2,4,5-trifluorophenyl)-2,3-dihydro-1H-imidazo[1,2-a]imidazol-5-yl)quinoline. MS m/e: 367 (M+H)$^+$.

Compound 108: 6-(6-(2,4,5-trifluorophenyl)-2,3-dihydro-1H-imidazo[1,2-a]imidazol-5-yl)imidazo[1,2-a]pyridine. MS m/e: 356 (M+H)$^+$.

Compound 109: 1-(5-([1,2,4]triazolo[1,5-a]pyridin-6-yl)-6-(2,3,5-trifluorophenyl)-2,3-dihydro-1H-imidazo[1,2-a]imidazol-1-yl)ethan-1-one. $^1$H NMR (DMSO-d$_6$, 300 MHz) 8.99 (m, 1H), 8.51 (s, 1H), 7.81 (m, 1H), 7.47 (m, 1H), 7.39 (m, 1H), 7.19 (m, 1H), 6.40 (s, 1H), 4.20 (t, J=7.5 Hz, 2H), 3.87 (t, J=7.5 Hz, 2H) ppm; MS m/e: 399 (M+H)$^+$.

Compound 110: 6-(6-(2,3,5-trifluorophenyl)-2,3-dihydro-1H-imidazo[1,2-a]imidazol-5-yl)quinoline. MS m/e: 367 (M+H)$^+$.

Compound 112: 2-(6-(2,3,5-trifluorophenyl)-2,3-dihydro-1H-imidazo[1,2-a]imidazol-5-yl)thieno[3,2-c]pyridine. $^1$H NMR (DMSO-d$_6$, 300 MHz) 9.00 (m, 1H), 8.92 (m, 1H), 8.32 (m, 1H), 7.93 (m, 1H), 7.57 (m, 1H), 7.20 (m, 1H), 4.31 (t, J=8.1 Hz, 2H), 3.93 (t, J=8.1 Hz, 2H) ppm; MS m/e: 373 (M+H)$^+$.

Compound 113: 6-(6-(2,3,5-trifluorophenyl)-2,3-dihydro-1H-imidazo[1,2-a]imidazol-5-yl)quinazolin-4-amine. $^1$H NMR (DMSO-d$_6$, 300 MHz) 8.35 (s, 1H), 8.09 (m, 1H), 7.77 (bs, 1H), 7.56 (m, 1H), 7.49 (m, 1H), 7.35 (m, 1H), 7.14

(m, 1H), 6.36 (m, 1H), 4.22 (t, J=7.5 Hz, 2H), 3.88 (t, J=7.5 Hz, 2H) ppm; MS m/e: 383 (M+H)⁺.

Compound 116: 2-(6-(2,4,5-trifluorophenyl)-2,3-dihydro-1H-imidazo[1,2-a]imidazol-5-yl)thieno[3,2-c]pyridine. ¹H NMR (DMSO-d₆, 300 MHz) 8.98 (m, 1H), 8.30 (m, 1H), 7.90 (m, 1H), 7.57 (m, 2H), 7.45 (s, 1H), 6.50 (m, 1H), 4.31 (t, J=7.5 Hz, 2H), 3.93 (t, J=7.5 Hz, 2H) ppm; MS m/e: 373 (M+H)⁺.

Compound 114: 1-(5-(3-(2-methoxyethoxy)quinoxalin-6-yl)-6-(2,4,5-trifluorophenyl)-2,3-dihydro-1H-imidazo[1,2-a]imidazol-1-yl)ethan-1-one. MS m/e: 484 (M+H)⁺.

Compound 115: 2-(2-methoxyethoxy)-7-(6-(2,4,5-trifluorophenyl)-2,3-dihydro-1H-imidazo[1,2-a]imidazol-5-yl)quinoxaline. ¹H NMR (DMSO-d₆, 300 MHz) 8.52 (m, 1H), 7.87 (m, 1H), 7.61 (m, 1H), 7.48 (m, 3H), 6.38 (m, 1H), 4.52 (m, 2H), 4.24 (m, 2H), 3.89 (m, 2H), 3.72 (m, 2H), 3.30 (s, 3H) ppm; MS m/e: 442 (M+H)⁺.

Compound 118: 5-([1,2,4]triazolo[1,5-a]pyridin-6-yl)-6-(2,3,5-trifluorophenyl)-2,3-dihydro-1H-imidazo[1,2-a]imidazole-2-carboxylic acid. MS m/e: 401 (M+H)⁺.

Compound 119: 5-([1,2,4]triazolo[1,5-a]pyridin-6-yl)-1-acetyl-6-(2,3,5-trifluorophenyl)-2,3-dihydro-1H-imidazo[1,2-a]imidazole-2-carboxylic acid. MS m/e: 443 (M+H)⁺.

Compound 120: N,N-dimethyl-2-((7-(6-(2,4,5-trifluorophenyl)-2,3-dihydro-1H-imidazo[1,2-a]imidazol-5-yl)quinoxalin-2-yl)oxy)ethan-1-amine. ¹H NMR (DMSO-d₆, 300 MHz) 8.48 (m, 1H), 7.87 (m, 1H), 7.60 (m, 1H), 7.55 (m, 1H), 7.45 (m, 2H), 6.37 (m, 1H), 4.48 (t, J=6.0 Hz, 2H), 4.24 (t, J=7.5 Hz, 2H), 3.89 (t, J=7.5 Hz, 2H), 2.66 (t, J=6.0 Hz, 2H), 2.20 (s, 6H) ppm; MS m/e: 455 (M+H)⁺.

Compound 121: (5-([1,2,4]triazolo[1,5-a]pyridin-6-yl)-6-(2,3,5-trifluorophenyl)-2,3-dihydro-1H-imidazo[1,2-a]imidazol-2-yl)methanol. ¹H NMR (DMSO-d₆, 300 MHz) 8.99 (m, 1H), 8.51 (m, 1H), 7.81 (m, 1H), 7.46 (m, 1H), 7.39 (m, 1H), 7.19 (m, 1H), 4.97 (m, 1H), 4.30 (m, 2H), 3.95 (m, 1H), 3.53 (m, 2H) ppm; MS m/e: 387 (M+H)⁺.

Compound 122: 4-(2-((7-(6-(2,4,5-trifluorophenyl)-2,3-dihydro-1H-imidazo[1,2-a]imidazol-5-yl)quinoxalin-2-yl)oxy)ethyl)morpholine. ¹H NMR (DMSO-d₆, 300 MHz) 8.61 (m, 1H), 8.02 (d, J=8.4 Hz, 1H), 7.79 (m, 1H), 7.65 (m, 3H), 7.52 (m, 1H), 4.76 (m, 2H), 4.40 (m, 2H), 4.12 (m, 4H), 3.91 (m, 2H), 3.72 (m, 2H), 3.64 (m, 4H) ppm; MS m/e: MS m/e: 497 (M+H)⁺.

Compound 123: (5-(quinolin-6-yl)-6-(2,3,5-trifluorophenyl)-2,3-dihydro-1H-imidazo[1,2-a]imidazol-2-yl)methanol. ¹H NMR (DMSO-d₆, 300 MHz) 8.84 (m, 1H), 8.31 (m, 1H), 7.91 (m, 2H), 7.53 (m, 2H), 7.39 (m, 1H), 7.16 (m, 1H), 6.55 (m, 1H), 4.99 (m, 1H), 4.33 (m, 2H), 3.98 (m, 1H), 3.54 (m, 2H) ppm; MS m/e: MS m/e: 397 (M+H)⁺.

Compound 124: (5-(quinoxalin-6-yl)-6-(2,3,5-trifluorophenyl)-2,3-dihydro-1H-imidazo[1,2-a]imidazol-2-yl)methanol. ¹H NMR (DMSO-d₆, 300 MHz) 8.88 (m, 2H), 8.01 (d, J=9.0 Hz 1H), 7.91 (m, 1H), 7.66 (m, 1H), 7.43 (m, 1H), 7.20 (m, 1H), 6.64 (m, 1H), 5.01 (m, 1H), 4.36 (m, 2H), 4.04 (m, 1H), 3.55 (m, 2H) ppm; MS m/e: 398 (M+H)⁺.

Compound 125: 5-(quinoxalin-6-yl)-6-(2,3,5-trifluorophenyl)-2,3-dihydro-1H-imidazo[1,2-a]imidazole-2-carboxylic acid. MS m/e: 412 (M+H)⁺.

Compound 165: 6-(2-(2,3,5-trifluorophenyl)-5,6,7,8-tetrahydroimidazo[1,2-a]pyrimidin-3-yl)quinoline. ¹H NMR (DMSO-d₆, 300 MHz) 8.87 (m, 1H), 8.30 (m, 1H), 7.95 (m, 1H), 7.84 (m, 1H), 7.57 (m, 1H), 7.52 (m, 1H), 7.30 (m, 1H), 7.10 (m, 1H), 6.73 (m, 1H), 3.84 (m, 2H), 3.27 (m, 2H), 1.93 (m, 2H) ppm; MS m/e: 381 (M+H)⁺.

Compound 166: 6-(2-(2,3,5-trifluorophenyl)-5,6,7,8-tetrahydroimidazo[1,2-a]pyrimidin-3-yl)-[1,2,4]triazolo[1,5-a]pyridine. ¹H NMR (DMSO-d₆, 300 MHz) 8.92 (m, 1H), 8.51 (m, 1H), 7.83 (m, 1H), 7.53 (m, 1H), 7.32 (m, 1H), 7.16 (m, 1H), 6.76 (m, 1H), 3.81 (m, 2H), 3.26 (m, 2H), 1.93 (m, 2H) ppm; MS m/e: 371 (M+H)⁺.

Compound 167: 2-(2-methoxyethoxy)-7-(2-(2,3,5-trifluorophenyl)-5,6,7,8-tetrahydroimidazo[1,2-a]pyrimidin-3-yl)quinoxaline. ¹H NMR (DMSO-d₆, 300 MHz) 8.56 (m, 1H), 7.92 (m, 1H), 7.62 (m, 1H), 7.42 (m, 1H), 7.33 (m, 1H), 7.11 (m, 1H), 6.77 (m, 1H), 4.53 (m, 2H), 3.87 (m, 2H), 3.81 (m, 2H), 3.30 (m, 5H), 1.92 (m, 2H) ppm; MS m/e: 456 (M+H)⁺.

Scheme 4: General synthesis of 2-(pyridin-2-yl)-6,7-dihydro-5H-pyrrolo[1,2-a]imidazoles

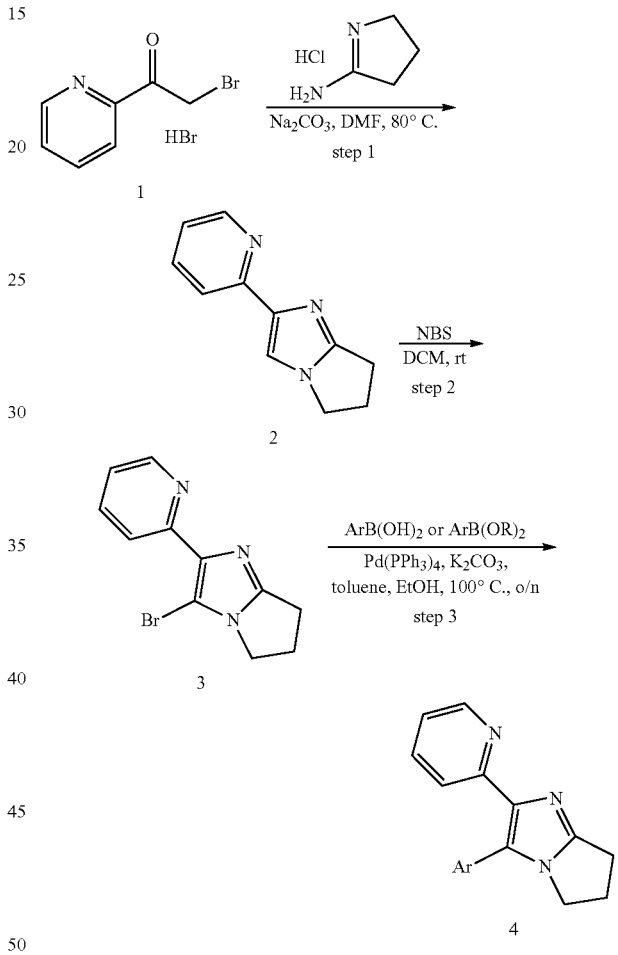

Step 1: A mixture of 2-bromo-1-(pyridin-2-yl)ethan-1-one hydrobromide (1.4 g, 5.0 mmol), 3,4-dihydro-2H-pyrrol-5-amine hydrochloride (2.5 g, 20 mmol) and Na₂CO₃ (3.2 g, 30 mmol) in DMF (20 mL) was stirred at 80° C. for 18 h. After cooling to room temperature, the reaction mixture was then partitioned between water and dichloromethane. The organic layer was separated, dried over sodium sulfate, filtered, and concentrated under reduced pressure to give a residue, which was purified by chromatography eluting with dichloromethane/methanol/ammonium hydroxide (15/1/0.05) to provide 2-(pyridin-2-yl)-6,7-dihydro-5H-pyrrolo[1,2-a]imidazole as a brown oil (0.8 g, 86%).

Step 2. To a solution of 2-(pyridin-2-yl)-6,7-dihydro-5H-pyrrolo[1,2-a]imidazole (0.8 g, 4.3 mmol) in dichloromethane (40 mL) was added N-bromosuccinimide (0.8 g, 4.3 mmol) at room temperature. The mixture was stirred at room temperature for 20 min and then quenched by saturated aqueous NaHCO₃. The organic layer was separated and aqueous layer was extracted with dichloromethane. The combined organic layers were dried over sodium sulfate, filtered, and concentrated under reduced pressure to give a residue, which was triturated with ethyl acetate to provide 3-bromo-2-(pyridin-2-yl)-6,7-dihydro-5H-pyrrolo[1,2-a] imidazole as a pale white solid (1.0 g, 88%).

Step 3. A mixture of 3-bromo-2-(pyridin-2-yl)-6,7-dihydro-5H-pyrrolo[1,2-a]imidazole (0.13 g, 0.5 mmol), 6-(4,4,5,5-tetramethyl-1,3,2-dioxaborolan-2-yl)quinoline (0.15 g, 0.6 mmol), tetrakis(triphenylphosphine)palladium(0) (0.03 g, 0.025 mmol), and K₂CO₃ (0.14 g, 1 mmol) in toluene (4.5 mL) and EtOH (0.25 mL) was stirred at 100° C. for 18 h. The mixture was then concentrated under reduced pressure to give a residue, which was purified by chromatography eluting with dichloromethane/methanol/ammonium hydroxide (7/1/0.05) to provide 6-(2-(pyridin-2-yl)-6, 7-dihydro-5H-pyrrolo[1,2-a]imidazol-3-yl)quinoline as a white solid (0.11 g, 71%).

Compound 364: 6-(2-(6-methylpyridin-2-yl)-6,7-dihydro-5H-pyrrolo[1,2-c]imidazol-3-yl)benzo[d]thiazole. $^1$H NMR (CD₃OD, 300 MHz) 9.27 (s, 1H), 8.19 (d, J=1.2 Hz, 1H), 8.05 (d, J=8.5 Hz, 1H), 7.61 (t, J=7.8 Hz, 1H), 7.55 (dd, J=8.5, 1.7 Hz, 1H), 7.38 (d, J=7.8 Hz, 1H), 7.09 (d, J=7.9 Hz, 1H), 4.12 (t, J=7.2 Hz, 2H), 3.00 (t, J=7.6 Hz, 2H), 2.70 (p, J=7.3 Hz, 2H), 2.33 (s, 3H). MS m/e: 333 (M+H)⁺.

Compound 365: 5-(2-(pyridin-2-yl)-3a,4,5,6-tetrahydro-cyclopenta[b]pyrrol-3-yl)-1H-indazole. $^1$H NMR (CD3OD, 300 MHz) 8.36 (m, 1H), 8.05 (m, 1H), 7.82 (m, 1H), 7.69 (m, 1H), 7.52 (m, 2H), 7.32 (m, 1H), 7.19 (m, 1H), 4.05 (t, J=6.9 Hz, 2H), 2.99 (t, J=6.9 Hz, 2H), 2.67 (m, 2H) ppm; MS m/e: 301 (M+H)⁺.

Compound 366: 6-(2-(pyridin-2-yl)-3a,4,5,6-tetrahydro-cyclopenta[b]pyrrol-3-yl)-1H-indazole. $^1$H NMR (CD3OD, 300 MHz) 8.39 (m, 1H), 8.05 (m, 1H), 7.75 (m, 2H), 7.54 (m, 2H), 7.22 (m, 1H), 7.11 (m, 1H), 4.10 (t, J=7.2 Hz, 2H), 3.00 (t, J=7.2 Hz, 2H), 2.66 (m, 2H) ppm; MS m/e: 301 (M+H)⁺.

Compound 367: 6-(2-(pyridin-2-yl)-6,7-dihydro-5H-pyrrolo[1,2-a]imidazol-3-yl)benzo[d]thiazole. $^1$H NMR (CD3OD, 300 MHz) 9.26 (m, 1H), 8.35 (m, 1H), 8.13 (m, 1H), 8.04 (m, 1H), 7.74 (m, 1H), 7.60 (m, 1H), 7.52 (m, 1H), 7.22 (m, 1H), 4.10 (t, J=7.5 Hz, 2H), 2.99 (t, J=7.5 Hz, 2H), 2.69 (m, 2H) ppm; MS m/e: 319 (M+H)⁺.

Compound 368: 6-(2-(pyridin-2-yl)-6,7-dihydro-5H-pyrrolo[1,2-a]imidazol-3-yl)quinoxaline. $^1$H NMR (CD3OD, 300 MHz) 8.86 (m, 2H), 8.32 (m, 1H), 8.14 (m, 1H), 8.04 (m, 1H), 7.81 (m, 2H), 7.72 (m, 1H), 7.25 (m, 1H), 4.19 (t, J=7.5 Hz, 2H), 3.03 (t, J=7.5 Hz, 2H), 2.72 (m, 2H) ppm; MS m/e: 314 (M+H)⁺.

Compound 369: 6-(2-(pyridin-2-yl)-6,7-dihydro-5H-pyrrolo[1,2-a]imidazol-3-yl)quinoline. $^1$H NMR (DMSO-d₆, 300 MHz) 8.88 (m, 1H), 8.34 (m, 1H), 8.22 (m, 1H), 8.10 (m, 1H), 7.94 (m, 1H), 7.87 (m, 1H), 7.76 (m, 2H), 7.53 (m, 1H), 7.12 (m, 1H), 4.04 (t, J=6.9 Hz, 2H), 2.89 (t, J=6.9 Hz, 2H), 2.56 (m, 2H) ppm; MS m/e: 313 (M+H)⁺.

Compound 370: 6-(2-(pyridin-2-yl)-6,7-dihydro-5H-pyrrolo[1,2-a]imidazol-3-yl)imidazo[1,2-a]pyridine. MS m/e: 302 (M+H)⁺.

Example 2: AlphaScreen® SureFire® SMAD3 (p-Ser423/425) Assay

The p-SMAD-3 (Ser423/425) SureFire® assay has been designed to measure the phosphorylation of endogenous cellular p-SMAD-3 (Ser423/425) in cell lysates and is a system for the screening of both modulators of receptor activation (e.g. agonists and antagonists) as well as agents acting intracellularly, such as small molecule inhibitors of upstream events. The assay will measure p-SMAD-3 (Ser423/425) activation by either cloned or endogenous receptors, and can be applied to primary cells.

P-SMAD-3 (Ser423/425) SureFire® Assay Protocols

Step A: Preparation of Buffers

1× Lysis buffer: 1 ml of 5× Lysis buffer was diluted with 4 ml of sterile water. After dilution, excess 1× Lysis buffer can be frozen and thawed up to 5 times without loss in activity.

Activation buffer: The buffer was warmed slowly to 37° C. and gently mixed to re-suspend. Activation buffer can be stored at room temperature with noloss in activity.

Reaction buffer: The buffer was kept at 4° C. while in use.

AlphaScreen® Protein A IgG Kit: The kit was stored at 4° C. in the dark.

Reaction buffer+Activation buffer+AlphaScreen® Acceptor beads: Reaction buffer (40 parts), Activation Buffer (10 parts) and Acceptor beads (1 part) were mixed and the mixture was stored at room temperature and used the same day. Mixture was added to 384-well plates; excess mixture-was discarded.

Dilution buffer+AlphaScreen® Donor beads: Dilution buffer (20 parts) and Donor beads (1 part) were mixed and the mixture was stored at room temperature and used the same day. Excess mixture was discarded.

Assay control samples: After reconstitution in 250 μl of water, lysates were at −20° C. in single use aliquots.

Step B: Preparation of Samples and Cells 96-well Assay Protocol for 293FT and RMS13 adherent cells can be carried out manually or in high throughput with liquid handling robots.

The cells (80 μL of cells for 96 well plates) were plated in collagen coated tissue culture plates in RPMI or FreeStyle medium (Invitrogen) and incubated overnight. For manual analysis, 6 plates for GDF8, 6 plates for TGFβ, and optionally 6 plates for Alk5ca(ALK5 constitutively active) were used.

The compound dilution plates were prepared as follows: 12 μL of DMSO was transferred into first column of 96-well plate, and 16 μL of DMSO was transferred into columns 2-12 of the 96-well plate. 12 μL of compound solution was transferred into first column of the DMSO-containing 96-well plate. Three-fold dilution was performed up to column 10 of the DMSO-containing 96-well plate.

Step C: Treatment and Analysis

The plate containing cells were treated with compounds for about 10 minutes, and then ligand was added. GDF8 or TGFb was added to plates to stimulate. 293FL cells were stimulatedfor 90 minutes at 37° C.; and RMS13 cells were stimulated for 60 minutes at 37° C. The medium was then removed from the cells, and 1× Lysis Buffer (about 25 μL) was added and the plate was gently agitated on plate shaker for 5-10 minutes.

The lysate (5 μL) was then placed into 384-well shallow plates avoiding the generation of bubbles. To this, the Reaction Buffer+Activation Buffer+AlphaScreen® Acceptor beadsmixture (5 μL) was added. The plate was sealed with adhesive cover and shielded from light (e.g., with metal foil), and agitated gently on plate shaker for 2 hours at room temperature.

Dilution buffer+AlphaScreen® Donor beads (2 μL) was then added, and the plate was intubated on the plate shaker for an additional 1½ hours. After completion, the plate was read on Synergy-4 or Enspire plate reader, using AlphaScreen® pSMAD3® settings.

Representative results for inhibition of GDF8 (data=GDF pSMAD (MPC11) (μM)) and TGF-β (data=TGF-β pSMAD (MPC-11) (μM)) signaling are shown in Table 1(A=<0.05 μM, B=0.05–<0.1 μM, C=0.1–<1.0 μM, D=>1.0 μM):

| No. | GDF8 | TGF-β |
|---|---|---|
| 1 | B | C |
| 2 | C | C |
| 3 | B | C |
| 4 | C | C |
| 5 | C | C |
| 6 | C | C |
| 7 | C | D |
| 8 | C | C |
| 9 | A | C |
| 10 | C | D |
| 11 | C | D |
| 12 | A | C |
| 13 | C | D |
| 14 | A | C |
| 15 | C | D |
| 16 | C | D |
| 17 | C | D |
| 18 | C | D |
| 19 | D | D |
| 20 | D | D |
| 21 | D | D |
| 22 | D | D |
| 23 | D | D |
| 24 | D | D |
| 25 | D | D |
| 26 | D | D |
| 27 | D | D |
| 28 | D | D |
| 29 | D | D |
| 30 | D | D |
| 31 | D | D |
| 32 | C | D |
| 33 | D | D |
| 34 | D | D |
| 35 | D | D |
| 36 | A | C |
| 37 | B | C |
| 38 | A | A |
| 39 | A | B |
| 40 | D | D |
| 41 | D | D |
| 42 | D | D |
| 43 | D | D |
| 44 | C | D |
| 45 | C | C |
| 46 | C | C |
| 47 | D | D |
| 48 | D | D |
| 49 | C | C |
| 50 | B | C |
| 51 | A | B |
| 52 | A | B |
| 53 | B | B |
| 54 | C | D |
| 55 | C | D |
| 56 | C | C |
| 57 | C | C |
| 58 | D | D |
| 59 | D | D |
| 60 | D | D |
| 61 | C | C |
| 62 | D | D |
| 63 | D | D |
| 64 | C | D |
| 65 | C | D |
| 66 | C | D |
| 67 | C | D |
| 68 | B | C |
| 69 | B | C |
| 70 | D | D |
| 71 | D | D |
| 72 | D | D |
| 73 | C | D |
| 74 | C | D |
| 75 | D | D |
| 76 | D | D |
| 77 | D | D |
| 78 | D | D |
| 79 | D | D |
| 80 | D | D |
| 81 | C | C |
| 82 | A | A |
| 83 | A | A |
| 84 | D | D |
| 85 | D | D |
| 86 | D | D |
| 87 | D | D |
| 88 | D | D |
| 89 | D | D |
| 90 | C | C |
| 91 | D | D |
| 92 | B | C |
| 93 | A | B |
| 94 | A | A |
| 95 | D | D |
| 96 | A | A |
| 97 | D | D |
| 98 | C | C |
| 99 | B | C |
| 100 | C | D |
| 101 | C | C |
| 102 | A | B |
| 103 | A | A |
| 104 | D | D |
| 105 | A | A |
| 106 | A | A |
| 107 | A | A |
| 108 | A | A |
| 109 | A | A |
| 110 | A | A |
| 111 | A | A |
| 112 | A | A |
| 113 | B | B |
| 114 | D | D |
| 115 | C | C |
| 116 | A | A |
| 117 | C | D |
| 118 | A | A |
| 119 | A | A |
| 120 | A | A |
| 121 | A | A |
| 122 | B | C |
| 123 | B | C |
| 124 | C | C |
| 125 | B | A |
| 126 | A | B |
| 127 | A | A |
| 128 | C | C |
| 129 | A | B |
| 130 | C | C |
| 131 | D | D |
| 132 | D | D |
| 133 | B | B |
| 134 | B | C |
| 135 | A | B |
| 136 | C | C |
| 137 | A | B |
| 138 | D | D |
| 139 | A | A |
| 140 | A | A |
| 141 | A | A |
| 142 | A | A |
| 143 | A | A |
| 144 | A | B |
| 145 | B | C |
| 146 | C | C |
| 147 | A | B |

| No. | GDF8 | TGF-β |
|---|---|---|
| 148 | A | B |
| 149 | A | B |
| 150 | A | B |
| 151 | A | A |
| 152 | A | B |
| 153 | D | D |
| 154 | A | C |
| 155 | B | C |
| 156 | A | B |
| 157 | C | C |
| 158 | A | B |
| 159 | A | B |
| 160 | B | C |
| 161 | B | C |
| 162 | B | C |
| 163 | B | C |
| 164 | C | C |
| 165 | D | C |
| 166 | B | B |
| 167 | D | D |
| 168 | A | B |
| 169 | A | B |
| 170 | A | B |
| 171 | B | C |
| 172 | A | B |
| 173 | A | B |
| 174 | B | C |
| 175 | C | C |
| 176 | C | D |
| 177 | B | C |
| 178 | C | D |
| 179 | B | C |
| 180 | A | C |
| 181 | B | C |
| 182 | B | C |
| 183 | B | C |
| 184 | B | C |
| 185 | C | C |
| 186 | B | C |
| 187 | B | C |
| 188 | C | C |
| 189 | B | C |
| 190 | A | B |
| 191 | A | C |
| 192 | B | C |
| 193 | C | D |
| 194 | C | D |
| 195 | C | C |
| 196 | C | D |
| 197 | C | D |
| 198 | D | D |
| 199 | C | C |
| 200 | C | D |
| 201 | A | C |
| 202 | B | C |
| 203 | A | C |
| 204 | C | C |
| 205 | C | C |
| 206 | C | D |
| 207 | C | C |
| 208 | C | D |
| 209 | C | D |
| 210 | C | D |
| 211 | C | C |
| 212 | D | D |
| 213 | D | D |
| 214 | C | C |
| 215 | D | D |
| 216 | D | D |
| 217 | C | C |
| 218 | A | B |
| 219 | A | C |
| 220 | B | C |
| 221 | C | D |
| 222 | C | C |
| 223 | D | D |
| 224 | C | D |
| 225 | C | C |
| 226 | C | C |
| 227 | C | D |
| 228 | C | C |
| 229 | C | D |
| 230 | C | D |
| 231 | C | D |
| 232 | C | D |
| 233 | D | D |
| 234 | D | D |
| 235 | C | C |
| 236 | C | D |
| 237 | C | D |
| 238 | C | C |
| 239 | D | D |
| 240 | C | D |
| 241 | D | D |
| 242 | D | D |
| 243 | D | D |
| 244 | D | D |
| 245 | D | D |
| 246 | D | D |
| 247 | C | D |
| 248 | D | D |
| 249 | D | D |
| 250 | D | D |
| 251 | D | D |
| 252 | D | D |
| 253 | D | D |
| 254 | D | D |
| 255 | D | D |
| 256 | D | D |
| 257 | D | D |
| 258 | D | D |
| 259 | D | D |
| 260 | C | D |
| 261 | C | D |
| 262 | C | D |
| 263 | C | D |
| 264 | A | C |
| 265 | B | C |
| 266 | B | C |
| 267 | C | C |
| 268 | A | B |
| 269 | A | B |
| 270 | A | B |
| 271 | A | C |
| 272 | D | D |
| 273 | D | D |
| 274 | D | D |
| 275 | D | D |
| 276 | C | D |
| 277 | D | D |
| 278 | D | D |
| 279 | D | D |
| 280 | B | C |
| 281 | B | C |
| 282 | C | C |
| 283 | C | D |
| 284 | D | D |
| 285 | D | D |
| 286 | D | D |
| 287 | D | D |
| 288 | C | D |
| 289 | A | C |
| 290 | C | D |
| 291 | B | C |
| 292 | D | D |
| 293 | C | C |
| 294 | D | D |
| 295 | D | D |
| 296 | C | D |
| 297 | C | C |
| 298 | C | D |
| 299 | C | D |
| 300 | D | D |
| 301 | C | D |

243
-continued

| No. | GDF8 | TGF-β |
|---|---|---|
| 302 | D | D |
| 303 | D | D |
| 304 | D | D |
| 305 | C | D |
| 306 | D | D |
| 307 | D | D |
| 308 | C | D |
| 309 | C | C |
| 310 | C | D |
| 311 | C | D |
| 312 | D | D |
| 313 | C | C |
| 314 | D | D |
| 315 | D | D |
| 316 | C | C |
| 317 | B | C |
| 318 | B | C |
| 319 | C | D |
| 320 | D | D |
| 321 | D | D |
| 322 | D | D |
| 323 | D | D |
| 324 | D | D |
| 325 | D | D |
| 326 | D | D |
| 327 | D | D |
| 328 | C | D |
| 329 | C | D |
| 330 | D | D |
| 331 | D | D |
| 332 | C | D |
| 333 | D | D |
| 334 | D | D |
| 335 | D | D |
| 336 | D | D |
| 337 | A | A |
| 338 | A | A |
| 339 | A | A |
| 340 | C | C |
| 341 | D | D |
| 342 | C | C |
| 343 | C | C |
| 344 | C | C |
| 345 | A | B |
| 346 | A | A |
| 347 | B | B |
| 348 | A | B |
| 349 | A | B |
| 350 | B | C |
| 351 | D | D |
| 352 | D | D |
| 353 | C | C |
| 354 | B | A |
| 355 | C | C |
| 356 | B | C |
| 357 | A | A |
| 358 | C | C |
| 359 | B | C |
| 360 | A | A |
| 361 | D | D |
| 362 | C | C |
| 363 | A | A |
| 364 | — | A |
| 365 | A | A |
| 366 | A | B |
| 367 | A | A |
| 368 | B | B |
| 369 | A | B |
| 370 | A | A |

244

What is claimed:

1. A compound having the structure of formula (I):

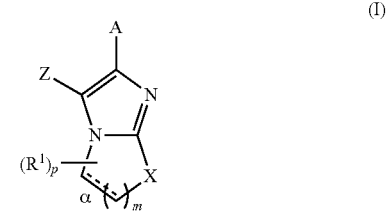

or a pharmaceutically acceptable salt, or solvate or hydrate thereof, wherein bond α is a single or double bond;

X is $CH_2$, —$CH(R^x)$—, or —$N(R^a)$—;
  wherein $R^a$ is hydrogen, —$C_1$-$C_6$alkyl, —$C_1$-$C_6$haloalkyl, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R or —N(R)S(O)$_2$R, and
  wherein when X is —$CH(R^x)$—, p≥1, and $R^x$ combines with an $R^1$ group bound to the carbon adjacent to X to form a 5- or 6-membered heterocyclyl with an annular —$N(R^a)$—;

m is 1 or 2;

A is phenyl, optionally substituted with one to five $R^2$ groups, wherein each $R^2$ is independently halogen, —$C_1$-$C_6$alkyl, —$C_1$-$C_6$haloalkyl, —$C_1$-$C_6$alkoxy, $C_{3-8}$Cak($C_{0-6}$alkyl), Hca($C_{0-6}$alkyl), Ar($C_{0-6}$alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, —$NO_2$ or —CN, wherein the Ar, Het, Cak, Hca, alkyl, and haloalkyl are optionally substituted with 1, 2, 3, or 4 groups that are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, or $C_1$-$C_6$haloalkyl;

Z is a fused bicyclic ring of the formula,

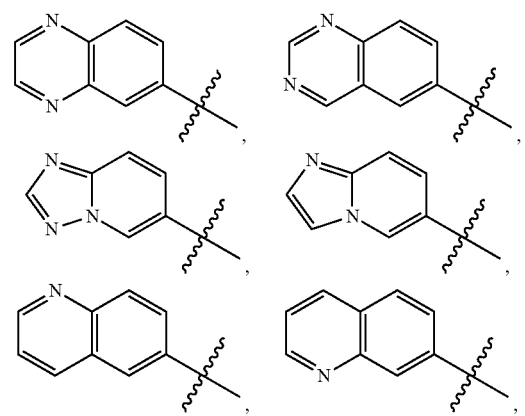

245

-continued

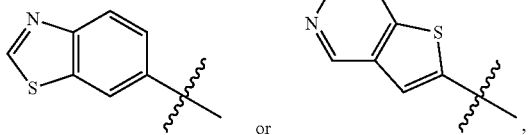

or wherein

Z is optionally substituted by one or two —$R^Z$ groups that are each independently $C_{3-8}$Cak($C_{0-6}$alkyl), Hca($C_{0-6}$alkyl), Ar($C_{0-6}$alkyl), Het($C_{0-6}$alkyl), halogen, cyano, $C_{1-6}$alkyl, $C_{1-6}$haloalkyl, —$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), —O—$C_{1-6}$alkyl-OR, —O—$C_{1-6}$alkyl-SR, —O—$C_{1-6}$alkyl-$NR_2$, —O—$C_{1-6}$alkyl-Hca, wherein each Ar, Het, Cak, Hca, alkyl, and haloalkyl group is optionally substituted by one or two —$R^{Z2}$ groups;

wherein each —$R^{Z2}$ is independently halogen, cyano, $C_{1-6}$alkyl, $C_{1-6}$haloalkyl, —$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR);

each optionally substituted as described above, or

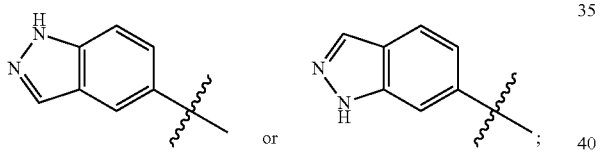

each $R^1$ is independently hydrogen, halogen, $C_1$-$C_6$alkyl, $C_1$-$C_6$haloalkyl, —$C_1$-$C_6$alkoxy, $C_3$-Cak($C_{0-6}$alkyl), Hca($C_{0-6}$alkyl), Ar($C_{0-6}$alkyl), Het($C_{0-6}$alkyl), —O—($C_{0-6}$alkyl)-Ar, —O—($C_0$-$C_6$alkyl)-Het, —O—($C_0$-$C_6$alkyl)-Cak, —O—($C_0$-$C_6$alkyl)-Hca, —C(O)OR, —$NO_2$ or —CN, wherein the Ar, Het, Cak, Hca, alkyl, and haloalkyl are optionally substituted with 1, 2, 3, or 4 groups that are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, —$C_1$-$C_6$alkoxy or $C_1$-$C_6$haloalkyl;

or, when α is a single bond, two $R^1$ groups taken together, when attached to the same carbon atom, form a spirocycle, wherein the spirocycle is $C_3$-$C_8$Cak, or $C_3$-$C_8$Hca, and the Cak and Hca are optionally substituted with 1, 2, 3, or 4 groups which are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR,

246

—N(R)C(O)$NR_2$, —N(R)S(O)R, —N(R)S(O)$_2$R, $C_1$-$C_6$alkyl, —$C_1$-$C_6$alkoxy, or $C_1$-$C_6$haloalkyl;

p is 0, 1, 2, 3, 4, 5 or 6;

each R is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;

wherein "Cak" represents cycloalkyl and "Hca" represents heterocycloalkyl;

provided that the compound is not
1-isopropylsulfonyl-2-amino-6-(2-(phenyl)-imidazo[1,2-a]pyridin-3-yl) benzimidazole dimethanesulfonate,
1-isopropylsulfonyl-2-amino-6-(8-(methyl)-2-(phenyl)-imidazo[1,2-a]pyridin-3-yl)-benzimidazole dimethanesulfonate,
1-isopropylsulfonyl-2-amino-6-(2-(phenyl)-6,7-dihydro-5H-pyrrolo[1,2-a]imidazol-3-yl)-benzimidazole dimethanesulfonate,
1-isopropylsulfonyl-2-amino-6-(2-(4-fluorophenyl)-6,7-dihydro-5H-pyrrolo[1,2-a]imidazole-3-yl)benzimidazole methanesulfonate, or
1-isopropylsulfonyl-2-amino-6-(2-(phenyl)-5,6,7,8-tetrahydro-imidazo[1,2-a]pyridin-3-yl)-benzimidazole.

2. The compound of claim 1, wherein the compound has the structure

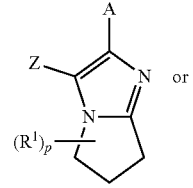
(Ia)

or

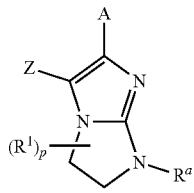
(Ib)

3. A compound that is:
6-(2-(m-tolyl)-6,7-dihydro-5H-pyrrolo[1,2-a]imidazol-3-yl)imidazo[1,2-a]pyridine
6-(2-(4-fluorophenyl)-6,7-dihydro-5H-pyrrolo[1,2-a]imidazol-3-yl)imidazo[1,2-a]pyridine
6-(2-(4-fluoro-3-methylphenyl)-6,7-dihydro-5H-pyrrolo[1,2-a]imidazol-3-yl)imidazo[1,2-a]pyridine
6-(2-(3-(trifluoromethyl)phenyl)-6,7-dihydro-5H-pyrrolo[1,2-a]imidazol-3-yl)imidazo[1,2-a]pyridine
6-(2-(3-methoxyphenyl)-6,7-dihydro-5H-pyrrolo[1,2-a]imidazol-3-yl)imidazo[1,2-a]pyridine
6-(2-(3-chlorophenyl)-6,7-dihydro-5H-pyrrolo[1,2-a]imidazol-3-yl)imidazo[1,2-a]pyridine
6-(2-(3-fluorophenyl)-6,7-dihydro-5H-pyrrolo[1,2-a]imidazol-3-yl)imidazo[1,2-a]pyridine
6-(2-(2-fluorophenyl)-6,7-dihydro-5H-pyrrolo[1,2-a]imidazol-3-yl)imidazo[1,2-a]pyridine 6-(2-(2,4-difluorophenyl)-6,7-dihydro-5H-pyrrolo[1,2-a]imidazol-3-yl)imidazo[1,2-a]pyridine
6-(2-(3,4-difluorophenyl)-6,7-dihydro-5H-pyrrolo[1,2-a]imidazol-3-yl)imidazo[1,2-a]pyridin
6-(2-(2,6-difluorophenyl)-6,7-dihydro-5H-pyrrolo[1,2-a]imidazol-3-yl)imidazo[1,2-a]pyridine
6-(2-(2,4,5-trifluorophenyl)-6,7-dihydro-5H-pyrrolo[1,2-a]imidazol-3-yl)imidazo[1,2-a]pyridine
6-(2-(3,4,5-trifluorophenyl)-6,7-dihydro-5H-pyrrolo[1,2-a]imidazol-3-yl)imidazo[1,2-a]pyridine
6-(2-(2,4,5-trifluorophenyl)-6,7-dihydro-5H-pyrrolo[1,2-a]imidazol-3-yl)-[1,2,4]triazolo[1,5-a]pyridine
6-(2-(2,3,4-trifluorophenyl)-6,7-dihydro-5H-pyrrolo[1,2-a]imidazol-3-yl)-[1,2,4]triazolo[1,5-a]pyridine
6-(2-(3,4,5-trifluorophenyl)-6,7-dihydro-5H-pyrrolo[1,2-a]imidazol-3-yl)-[1,2,4]triazolo[1,5-a]pyridine
6-(2-(2,3,5-trifluorophenyl)-6,7-dihydro-5H-pyrrolo[1,2-a]imidazol-3-yl)-[1,2,4]triazolo[1,5-a]pyridine
6-(2-(4-chloro-2,5-difluorophenyl)-6,7-dihydro-5H-pyrrolo[1,2-a]imidazol-3-yl)-[1,2,4]triazolo[1,5-a]pyridine
6-(2-(4-chloro-2,5-difluorophenyl)-6,7-dihydro-5H-pyrrolo[1,2-a]imidazol-3-yl)imidazo[1,2-a]pyridine
6-(2-(4-chloro-2,5-difluorophenyl)-6,7-dihydro-5H-pyrrolo[1,2-a]imidazol-3-yl)-3-isopropyl-[1,2,4]triazolo[4,3-a]pyridine
3-isopropyl-6-(2-(2,4,5-trifluorophenyl)-6,7-dihydro-5H-pyrrolo[1,2-a]imidazol-3-yl)-[1,2,4]triazolo[4,3-a]pyridine
3-isopropyl-6-(2-(2,3,5-trifluorophenyl)-6,7-dihydro-5H-pyrrolo[1,2-a]imidazol-3-yl)-[1,2,4]triazolo[4,3-a]pyridine
3-isopropyl-6-(2-(2,3,4-trifluorophenyl)-6,7-dihydro-5H-pyrrolo[1,2-a]imidazol-3-yl)-[1,2,4]triazolo[4,3-a]pyridine
6-(2-(4-chloro-3,5-dimethylphenyl)-6,7-dihydro-5H-pyrrolo[1,2-a]imidazol-3-yl)-[1,2,4]triazolo[1,5-a]pyridine
6-(2-(4-chloro-3,5-dimethylphenyl)-6,7-dihydro-5H-pyrrolo[1,2-a]imidazol-3-yl)imidazo[1,2-a]pyridine
6-(2-(2,3-difluoro-4-methylphenyl)-6,7-dihydro-5H-pyrrolo[1,2-a]imidazol-3-yl)-[1,2,4]triazolo[1,5-a]pyridine
6-(2-(2,3-difluoro-4-methylphenyl)-6,7-dihydro-5H-pyrrolo[1,2-a]imidazol-3-yl)imidazo[1,2-a]pyridine
6-(2-(4-chloro-2-fluoro-5-methylphenyl)-6,7-dihydro-5H-pyrrolo[1,2-a]imidazol-3-yl)-[1,2,4]triazolo[1,5-a]pyridine
6-(2-(4-chloro-2-fluoro-5-methylphenyl)-6,7-dihydro-5H-pyrrolo[1,2-a]imidazol-3-yl)imidazo[1,2-a]pyridine
6-(2-(4-methoxy-3,5-dimethylphenyl)-6,7-dihydro-5H-pyrrolo[1,2-a]imidazol-3-yl)-[1,2,4]triazolo[1,5-a]pyridine
6-(2-(4-methoxy-3,5-dimethylphenyl)-6,7-dihydro-5H-pyrrolo[1,2-a]imidazol-3-yl)imidazo[1,2-a]pyridine
6-(2-(4,5-difluoro-2-methylphenyl)-6,7-dihydro-5H-pyrrolo[1,2-a]imidazol-3-yl)imidazo[1,2-a]pyridine
3-(trifluoromethyl)-6-(2-(3,4,5-trifluorophenyl)-6,7-dihydro-5H-pyrrolo[1,2-a]imidazol-3-yl)-[1,2,4]triazolo[4,3-a]pyridine
3-(trifluoromethyl)-6-(2-(2,4,5-trifluorophenyl)-6,7-dihydro-5H-pyrrolo[1,2-a]imidazol-3-yl)-[1,2,4]triazolo[4,3-a]pyridine
3-(trifluoromethyl)-6-(2-(2,3,4-trifluorophenyl)-6,7-dihydro-5H-pyrrolo[1,2-a]imidazol-3-yl)-[1,2,4]triazolo[4,3-a]pyridine
6-(2-(3-chloro-4-fluorophenyl)-6,7-dihydro-5H-pyrrolo[1,2-a]imidazol-3-yl)-[1,2,4]triazolo[1,5-a]pyridine
6-(2-(3-chloro-4-fluorophenyl)-6,7-dihydro-5H-pyrrolo[1,2-a]imidazol-3-yl)imidazo[1,2-a]pyridine
6-(2-(2,4-difluoro-5-methylphenyl)-6,7-dihydro-5H-pyrrolo[1,2-a]imidazol-3-yl)-[1,2,4]triazolo[1,5-a]pyridine
6-(2-(2,4-difluoro-5-methylphenyl)-6,7-dihydro-5H-pyrrolo[1,2-a]imidazol-3-yl)imidazo[1,2-a]pyridine
6-(2-(3-chloro-4-fluoro-5-methylphenyl)-6,7-dihydro-5H-pyrrolo[1,2-a]imidazol-3-yl)-[1,2,4]triazolo[1,5-a]pyridine
6-(2-(3-chloro-4-fluoro-5-methylphenyl)-6,7-dihydro-5H-pyrrolo[1,2-a]imidazol-3-yl)imidazo[1,2-a]pyridine
6-(2-(4-fluoro-3,5-dimethylphenyl)-6,7-dihydro-5H-pyrrolo[1,2-a]imidazol-3-yl)-[1,2,4]triazolo[1,5-a]pyridine
6-(2-(4-fluoro-3,5-dimethylphenyl)-6,7-dihydro-5H-pyrrolo[1,2-a]imidazol-3-yl)imidazo[1,2-a]pyridine
6-(2-(3,4-difluoro-2-methylphenyl)-6,7-dihydro-5H-pyrrolo[1,2-a]imidazol-3-yl)-[1,2,4]triazolo[1,5-a]pyridine
6-(2-(2,4-difluoro-3-methylphenyl)-6,7-dihydro-5H-pyrrolo[1,2-a]imidazol-3-yl)-[1,2,4]triazolo[1,5-a]pyridine
6-(2-(2,4-difluoro-3-methylphenyl)-6,7-dihydro-5H-pyrrolo[1,2-a]imidazol-3-yl)imidazo[1,2-a]pyridine
6-(2-(2,5-difluoro-4-methylphenyl)-6,7-dihydro-5H-pyrrolo[1,2-a]imidazol-3-yl)-[1,2,4]triazolo[1,5-a]pyridine
6-(2-(2,5-difluoro-4-methylphenyl)-6,7-dihydro-5H-pyrrolo[1,2-a]imidazol-3-yl)imidazo[1,2-a]pyridine
6-(2-(2-chloro-4,5-difluorophenyl)-6,7-dihydro-5H-pyrrolo[1,2-a]imidazol-3-yl)-[1,2,4]triazolo[1,5-a]pyridine
6-(2-(2-chloro-4,5-difluorophenyl)-6,7-dihydro-5H-pyrrolo[1,2-a]imidazol-3-yl)imidazo[1,2-a]pyridine
6-(2-(3-chloro-4-fluorophenyl)-6,7-dihydro-5H-pyrrolo[1,2-a]imidazol-3-yl)imidazo[1,2-a]pyridine-3-carboxamide
6-(2-(4,5-difluoro-2-methylphenyl)-6,7-dihydro-5H-pyrrolo[1,2-a]imidazol-3-yl)imidazo[1,2-a]pyridine-3-carboxamide
6-(2-(3,4,5-trifluorophenyl)-6,7-dihydro-5H-pyrrolo[1,2-a]imidazol-3-yl)imidazo[1,2-a]pyridine-3-carboxamide
6-(2-(4-fluoro-2-methylphenyl)-6,7-dihydro-5H-pyrrolo[1,2-a]imidazol-3-yl)-[1,2,4]triazolo[1,5-a]pyridine
6-(2-(4-fluoro-2-methylphenyl)-6,7-dihydro-5H-pyrrolo[1,2-a]imidazol-3-yl)imidazo[1,2-a]pyridine
6-(2-(5-chloro-4-fluoro-2-methylphenyl)-6,7-dihydro-5H-pyrrolo[1,2-a]imidazol-3-yl)-[1,2,4]triazolo[1,5-a]pyridine
6-(2-(5-chloro-4-fluoro-2-methylphenyl)-6,7-dihydro-5H-pyrrolo[1,2-a]imidazol-3-yl)imidazo[1,2-a]pyridine
6-(2-(5-fluoro-2-methylphenyl)-6,7-dihydro-5H-pyrrolo[1,2-a]imidazol-3-yl)-[1,2,4]triazolo[1,5-a]pyridine
6-(2-(5-fluoro-2-methylphenyl)-6,7-dihydro-5H-pyrrolo[1,2-a]imidazol-3-yl)imidazo[1,2-a]pyridine
6-(2-(3-chloro-4-fluorophenyl)-6,7-dihydro-5H-pyrrolo[1,2-a]imidazol-3-yl)imidazo[1,2-a]pyridine-3-carbonitrile
6-(2-(2-methylphenyl)-6,7-dihydro-5H-pyrrolo[1,2-a]imidazol-3-yl)-[1,2,4]triazolo[1,5-a]pyridine 6-(2-(2-methylphenyl)-6,7-dihydro-5H-pyrrolo[1,2-a]
  imidazol-3-yl)imidazo[1,2-a]pyridine
6-(2-(4-fluoro-2,5-dimethylphenyl)-6,7-dihydro-5H-pyrrolo[1,2-a]imidazol-3-yl)-[1,2,4]triazolo[1,5-a]pyridine
6-(2-(4-fluoro-2,5-dimethylphenyl)-6,7-dihydro-5H-pyrrolo[1,2-a]imidazol-3-yl)imidazo[1,2-a]pyridine
6-(2-(2-chloro-4-fluoro-3-methylphenyl)-6,7-dihydro-5H-pyrrolo[1,2-a]imidazol-3-yl)-[1,2,4]triazolo[1,5-a]pyridine
6-(2-(2-chloro-4-fluoro-3-methylphenyl)-6,7-dihydro-5H-pyrrolo[1,2-a]imidazol-3-yl)imidazo[1,2-a]pyridine
6-(2-(2-chloro-4-fluoro-5-methylphenyl)-6,7-dihydro-5H-pyrrolo[1,2-a]imidazol-3-yl)imidazo[1,2-a]pyridine
6-(2-(2-chloro-4-fluoro-5-methylphenyl)-6,7-dihydro-5H-pyrrolo[1,2-a]imidazol-3-yl)-[1,2,4]triazolo[1,5-a]pyridine
2-fluoro-N-(3-(3-(imidazo[1,2-a]pyridin-6-yl)-6,7-dihydro-5H-pyrrolo[1,2-a]imidazol-2-yl)phenyl)benzenesulfonamide
3'-([1,2,4]triazolo[1,5-a]pyridin-6-yl)-2'-(4-fluorophenyl)-5'H,7'H-spiro[cyclopentane-1,6'-pyrrolo[1,2-a]imidazole]
2'-(4-fluorophenyl)-3'-(imidazo[1,2-a]pyridin-6-yl)-5'H,7'H-spiro[cyclopentane-1,6'-pyrrolo[1,2-a]imidazole]
6-(2-(4-fluoro-2,3-dimethylphenyl)-6,7-dihydro-5H-pyrrolo[1,2-a]imidazol-3-yl)-[1,2,4]triazolo[1,5-a]pyridine
6-(2-(4-fluoro-2,3-dimethylphenyl)-6,7-dihydro-5H-pyrrolo[1,2-a]imidazol-3-yl)imidazo[1,2-a]pyridine
(3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)methanol
3'-([1,2,4]triazolo[1,5-a]pyridin-6-yl)-2'-(4-fluorophenyl)-5'H,7'H-spiro[cyclohexane-1,6'-pyrrolo[1,2-a]imidazole]-4-carboxylic acid
ethyl 3'-([1,2,4]triazolo[1,5-a]pyridin-6-yl)-2'-(4-fluorophenyl)-5'H,7'H-spiro[cyclohexane-1,6'-pyrrolo[1,2-a]imidazole]-4-carboxylate
3'-([1,2,4]triazolo[1,5-a]pyridin-6-yl)-2'-(4-fluorophenyl)-N-methyl-5'H,7'H-spiro[cyclohexane-1,6'-pyrrolo[1,2-a]imidazole]-4-carboxamide
3'-([1,2,4]triazolo[1,5-a]pyridin-6-yl)-2'-(4-fluorophenyl)-N,N-dimethyl-5'H,7'H-spiro[cyclohexane-1,6'-pyrrolo[1,2-a]imidazole]-4-carboxamide
3'-([1,2,4]triazolo[1,5-a]pyridin-6-yl)-2'-(4-fluorophenyl)-5'H,7'H-spiro[cyclohexane-1,6'-pyrrolo[1,2-a]imidazole]-4-carboxamide
6-(2-(3-chloro-2,4-difluorophenyl)-6,7-dihydro-5H-pyrrolo[1,2-a]imidazol-3-yl)-[1,2,4]triazolo[1,5-a]pyridine
6-(2-(5-chloro-2-fluoro)-6,7-dihydro-5H-pyrrolo[1,2-a]imidazol-3-yl)-[1,2,4]triazolo[1,5-a]pyridine
6-(2-(5-chloro-2-fluoro)-6,7-dihydro-5H-pyrrolo[1,2-a]imidazol-3-yl)imidazo[1,2-a]pyridine
(3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)methyl methanesulfonate
3'-([1,2,4]triazolo[1,5-a]pyridin-6-yl)-4-(azidomethyl)-2'-(4-fluorophenyl)-5'H,7'H-spiro[cyclohexane-1,6'-pyrrolo[1,2-a]imidazole]
1-(3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)-N-methylmethanamine
1-(3'-([1,2,4]triazolo[1,5-a]pyridin-6-yl)-2'-(4-fluorophenyl)-5'H,7'H-spiro[cyclohexane-1,6'-pyrrolo[1,2-a]imidazol]-4-yl)-N,N-dimethylmethanamine
benzyl 3-([1,2,4]triazolo[1,5-a]pyridin-6-yl)-2-(4-fluorophenyl)-5,5a,6,7,9,9a-hexahydro-8H-imidazo[1',2':1,2]pyrrolo[3,4-c]pyridine-8-carboxylate
3-([1,2,4]triazolo[1,5-a]pyridin-6-yl)-2-(4-fluorophenyl)-8-methyl-5a,6,7,8,9,9a-hexahydro-5H-imidazo[1',2':1,2]pyrrolo[3,4-c]pyridine
6-(2-(5-chloro-2-methyl)-6,7-dihydro-5H-pyrrolo[1,2-a]imidazol-3-yl)-[1,2,4]triazolo[1,5-a]pyridine
6-(2-(5-([1,2,4]triazolo[1,5-a]pyridin-6-yl)-2-methylphenyl)-6,7-dihydro-5H-pyrrolo[1,2-a]imidazol-3-yl)-[1,2,4]triazolo[1,5-a]pyridine
6-(2-(2,5-dichlorophenyl)-6,7-dihydro-5H-pyrrolo[1,2-a]imidazol-3-yl)-[1,2,4]triazolo[1,5-a]pyridine
6-(2-(2,5-dichlorophenyl)-6,7-dihydro-5H-pyrrolo[1,2-a]imidazol-3-yl)imidazo[1,2-a]pyridine
6-(2-(5-chloro-2,4-difluoro)-6,7-dihydro-5H-pyrrolo[1,2-a]imidazol-3-yl)-[1,2,4]triazolo[1,5-a]pyridine
6-(2-(4-methoxyphenyl)-6,7-dihydro-5H-pyrrolo[1,2-a]imidazol-3-yl)-[1,2,4]triazolo[1,5-a]pyridine
6-(2-(2-fluoro-5-methylphenyl)-6,7-dihydro-5H-pyrrolo[1,2-a]imidazol-3-yl)-[1,2,4]triazolo[1,5-a]pyridine
2-(2-(2,3-trifluorophenyl)-6,7-dihydro-5H-pyrrolo[1,2-a]imidazol-3-yl)thieno[3,2-c]pyridine
2-(2-(2,4,5-trifluorophenyl)-6,7-dihydro-5H-pyrrolo[1,2-a]imidazol-3-yl)thieno[3,2-c]pyridine
2-(2-(2-fluorophenyl)-6,7-dihydro-5H-pyrrolo[1,2-a]imidazol-3-yl)thieno[3,2-c]pyridine
2-(2-(4-fluorophenyl)-6,7-dihydro-5H-pyrrolo[1,2-a]imidazol-3-yl)thieno[3,2-c]pyridine
2-(2-(5-chloro-2-fluorophenyl)-6,7-dihydro-5H-pyrrolo[1,2-a]imidazol-3-yl)thieno[3,2-c]pyridine
6-(6-(2,4,5-trifluorophenyl)-2,3-dihydro-1H-imidazo[1,2-a]imidazol-5-yl)benzo[d]thiazole
1-(5-([1,2,4]triazolo[1,5-a]pyridin-6-yl)-6-(2,4,5-trifluorophenyl)-2,3-dihydro-1H-imidazo[1,2-a]imidazol-1-yl)ethan-1-one
6-(6-(2,4,5-trifluorophenyl)-2,3-dihydro-1H-imidazo[1,2-a]imidazol-5-yl)-[1,2,4]triazolo[1,5-a]pyridine
6-(6-(2,4,5-trifluorophenyl)-2,3-dihydro-1H-imidazo[1,2-a]imidazol-5-yl)quinoxaline
6-(6-(2,4,5-trifluorophenyl)-2,3-dihydro-1H-imidazo[1,2-a]imidazol-5-yl)quinoline
6-(6-(2,4,5-trifluorophenyl)-2,3-dihydro-1H-imidazo[1,2-a]imidazol-5-yl)imidazo[1,2-a]pyridine
1-(5-([1,2,4]triazolo[1,5-a]pyridin-6-yl)-6-(2,3,5-trifluorophenyl)-2,3-dihydro-1H-imidazo[1,2-a]imidazol-1-yl)ethan-1-one
6-(6-(2,3,5-trifluorophenyl)-2,3-dihydro-1H-imidazo[1,2-a]imidazol-5-yl)quinoline
6-(6-(2,3,5-trifluorophenyl)-2,3-dihydro-1H-imidazo[1,2-a]imidazol-5-yl)quinoxaline
2-(6-(2,3,5-trifluorophenyl)-2,3-dihydro-1H-imidazo[1,2-a]imidazol-5-yl)thieno[3,2-c]pyridine
6-(6-(2,3,5-trifluorophenyl)-2,3-dihydro-1H-imidazo[1,2-a]imidazol-5-yl)quinazolin-4-amine
1-(5-(3-(2-methoxyethoxy)quinoxalin-6-yl)-6-(2,4,5-trifluorophenyl)-2,3-dihydro-1H-imidazo[1,2-a]imidazol-1-yl)ethan-1-one
2-(2-methoxyethoxy)-7-(6-(2,4,5-trifluorophenyl)-2,3-dihydro-1H-imidazo[1,2-a]imidazol-5-yl)quinoxaline
2-(6-(2,4,5-trifluorophenyl)-2,3-dihydro-1H-imidazo[1,2-a]imidazol-5-yl)thieno[3,2-c]pyridine
2-(2-methoxyethoxy)-7-(2-(2,3,5-trifluorophenyl)-5,6-dihydro-7$\lambda^2$-imidazo[3,2-a]imidazol-3-yl)quinoxaline 5-([1,2,4]triazolo[1,5-a]pyridin-6-yl)-6-(2,3,5-trifluorophenyl)-2,3-dihydro-1H-imidazo[1,2-a]imidazole-2-carboxylic acid
5-([1,2,4]triazolo[1,5-a]pyridin-6-yl)-1-acetyl-6-(2,3,5-trifluorophenyl)-2,3-dihydro-1H-imidazo[1,2-a]imidazole-2-carboxylic acid
N,N-dimethyl-2-((7-(6-(2,4,5-trifluorophenyl)-2,3-dihydro-1H-imidazo[1,2-a]imidazol-5-yl)quinoxalin-2-yl)oxy)ethan-1-amine
(5-([1,2,4]triazolo[1,5-a]pyridin-6-yl)-6-(2,3,5-trifluorophenyl)-2,3-dihydro-1H-imidazo[1,2-a]imidazol-2-yl)methanol
4-(2-((7-(6-(2,4,5-trifluorophenyl)-2,3-dihydro-1H-imidazo[1,2-a]imidazol-5-yl)quinoxalin-2-yl)oxy)ethyl)morpholine
(5-(quinolin-6-yl)-6-(2,3,5-trifluorophenyl)-2,3-dihydro-1H-imidazo[1,2-a]imidazol-2-yl)methanol
(5-(quinoxalin-6-yl)-6-(2,3,5-trifluorophenyl)-2,3-dihydro-1H-imidazo[1,2-a]imidazol-2-yl)methanol
5-(quinoxalin-6-yl)-6-(2,3,5-trifluorophenyl)-2,3-dihydro-1H-imidazo[1,2-a]imidazole-2-carboxylic acid
6-(4-fluorophenyl)-5-(1H-indazol-5-yl)imidazo[2,1-b]oxazole
5-(benzo[d]thiazol-6-yl)-6-(4-fluorophenyl)imidazo[2,1-b]oxazole
6-(4-fluorophenyl)-5-(1H-indazol-6-yl)imidazo[2,1-b]oxazole
6-(4-fluorophenyl)-5-(imidazo[1,2-a]pyridin-6-yl)imidazo[2,1-b]oxazole
6-(4-fluorophenyl)-5-(quinoxalin-6-yl)imidazo[2,1-b]oxazole
6-(3,4-difluorophenyl)imidazo[2,1-b]oxazole
6-(3,4-difluorophenyl)-5-iodoimidazo[2,1-b]oxazole
6-(3,4-difluorophenyl)-5-(1H-indazol-5-yl)imidazo[2,1-b]oxazole
6-(3,4-difluorophenyl)-5-(1H-indazol-6-yl)imidazo[2,1-b]oxazole
5-(benzo[d]thiazol-6-yl)-6-(3,4-difluorophenyl)imidazo[2,1-b]oxazole
6-(3,4-difluorophenyl)-5-(quinoxalin-6-yl)imidazo[2,1-b]oxazole
6-(3,4-difluorophenyl)-5-(imidazo[1,2-a]pyridin-6-yl)imidazo[2,1-b]oxazole
5-iodo-6-(m-tolyl)imidazo[2,1-b]oxazole
6-(m-tolyl)-5-(1H-indazol-5-yl)imidazo[2,1-b]oxazole
6-(m-tolyl)-5-(1H-indazol-6-yl)imidazo[2,1-b]oxazole
5-(benzo[d]thiazol-6-yl)-6-(m-tolyl)imidazo[2,1-b]oxazole
5-(quinoxalin-6-yl)-6-(m-tolyl)imidazo[2,1-b]oxazole
6-(m-tolyl)-5-(imidazo[1,2-a]pyridin-6-yl)imidazo[2,1-b]oxazole
5-(quinolin-6-yl)-6-(m-tolyl)imidazo[2,1-b]oxazole
5-(quinolin-6-yl)-6-(3,4-difluorophenyl)imidazo[2,1-b]oxazole
5-(quinolin-6-yl)-6-(4-fluorophenyl)imidazo[2,1-b]oxazole
6-(2,4,5-trifluorophenyl)-5-(1H-indazol-5-yl)imidazo[2,1-b]oxazole
6-(2,4,5-trifluorophenyl)-5-(imidazo[1,2-a]pyridin-6-yl)imidazo[2,1-b]oxazole
5-(quinoxalin-6-yl)-6-(2,4,5-trifluorophenyl)imidazo[2,1-b]oxazole
5-(quinolin-6-yl)-6-(2,4,5-trifluorophenyl)imidazo[2,1-b]oxazole
5-(benzo[d]thiazol-6-yl)-6-(2,4,5-trifluorophenyl)imidazo[2,1-b]oxazole
6-(2,4,5-trifluorophenyl)-5-(1H-indazol-5-yl)imidazo[2,1-b]oxazole
5-bromo-6-(2-fluoro-4-methylphenyl)imidazo[2,1-b]oxazole
6-(2,4-difluorophenyl)-5-(1H-indazol-5-yl)imidazo[2,1-b]oxazole
6-(2,4-difluorophenyl)-5-(1H-indazol-6-yl)imidazo[2,1-b]oxazole
5-(benzo[d]thiazol-6-yl)-6-(2,4-difluorophenyl)imidazo[2,1-b]oxazole
6-(2,4-difluorophenyl)-5-(quinoxalin-6-yl)imidazo[2,1-b]oxazole
5-(quinolin-6-yl)-6-(2,4-difluorophenyl)imidazo[2,1-b]oxazole
6-(2,4-difluorophenyl)-5-(imidazo[1,2-a]pyridin-6-yl)imidazo[2,1-b]oxazole
6-(2,3,4-trifluorophenyl)-5-(1H-indazol-5-yl)imidazo[2,1-b]oxazole
5-(benzo[d]thiazol-6-yl)-6-(2,3,4-trifluorophenyl)imidazo[2,1-b]oxazole
5-(quinolin-6-yl)-6-(2,3,4-trifluorophenyl)imidazo[2,1-b]oxazole
5-(imidazo[1,2-a]pyridin-6-yl)-6-(2,3,4-trifluorophenyl)imidazo[2,1-b]oxazole
5-(quinoxalin-6-yl)-6-(2,3,4-trifluorophenyl)imidazo[2,1-b]oxazole
6-(2-(2,3,5-trifluorophenyl)-5,6,7,8-tetrahydroimidazo[1,2-a]pyrimidin-3-yl)quinoline
6-(2-(2,3,5-trifluorophenyl)-5,6,7,8-tetrahydroimidazo[1,2-a]pyrimidin-3-yl)-[1,2,4]triazolo[1,5-a]pyridine
2-(2-methoxyethoxy)-7-(2-(2,3,5-trifluorophenyl)-5,6,7,8-tetrahydroimidazo[1,2-a]pyrimidin-3-yl)quinoxaline
5-(2-(m-tolyl)-6,7-dihydro-5H-pyrrolo[1,2-a]imidazol-3-yl)-1H-indazole
6-(2-(m-tolyl)-6,7-dihydro-5H-pyrrolo[1,2-a]imidazol-3-yl)-1H-indazole
6-(2-(m-tolyl)-6,7-dihydro-5H-pyrrolo[1,2-a]imidazol-3-yl)benzo[d]thiazole
5-(2-(m-tolyl)-6,7-dihydro-5H-pyrrolo[1,2-a]imidazol-3-yl)-1H-benzo[d]imidazole
5-(2-(4-fluoro-3-methylphenyl)-6,7-dihydro-5H-pyrrolo[1,2-a]imidazol-3-yl)-1H-indazole
6-(2-(4-fluoro-3-methylphenyl)-6,7-dihydro-5H-pyrrolo[1,2-a]imidazol-3-yl)benzo[d]thiazole
6-(2-(4-fluorophenyl)-6,7-dihydro-5H-pyrrolo[1,2-a]imidazol-3-yl)benzo[d]thiazole
5-(2-(4-fluorophenyl)-6,7-dihydro-5H-pyrrolo[1,2-a]imidazol-3-yl)-1H-indazole
6-(2-(4-fluorophenyl)-6,7-dihydro-5H-pyrrolo[1,2-a]imidazol-3-yl)-1H-indazole
6-(2-(4-fluoro-3-methylphenyl)-6,7-dihydro-5H-pyrrolo[1,2-a]imidazol-3-yl)-1H-indazole
6-(2-(4-fluorophenyl)-6,7-dihydro-5H-pyrrolo[1,2-a]imidazol-3-yl)quinoxaline
6-(2-(4-fluoro-3-methylphenyl)-6,7-dihydro-5H-pyrrolo[1,2-a]imidazol-3-yl)quinoxaline
6-(2-(m-tolyl)-6,7-dihydro-5H-pyrrolo[1,2-a]imidazol-3-yl)quinoxaline
5-(2-(3-(trifluoromethyl)phenyl)-6,7-dihydro-5H-pyrrolo[1,2-a]imidazol-3-yl)-1H-indazole
6-(2-(3-(trifluoromethyl)phenyl)-6,7-dihydro-5H-pyrrolo[1,2-a]imidazol-3-yl)-1H-indazole
6-(2-(3-(trifluoromethyl)phenyl)-6,7-dihydro-5H-pyrrolo[1,2-a]imidazol-3-yl)benzo[d]thiazole
6-(2-(3-(trifluoromethyl)phenyl)-6,7-dihydro-5H-pyrrolo[1,2-a]imidazol-3-yl)quinoxaline 5-(2-(3-methoxyphenyl)-6,7-dihydro-5H-pyrrolo[1,2-a]imidazol-3-yl)-1H-indazole 6-(2-(3-methoxyphenyl)-6,7-dihydro-5H-pyrrolo[1,2-a]imidazol-3-yl)-1H-indazole 6-(2-(3-methoxyphenyl)-6,7-dihydro-5H-pyrrolo[1,2-a]imidazol-3-yl)benzo[d]thiazole 6-(2-(3-methoxyphenyl)-6,7-dihydro-5H-pyrrolo[1,2-a]imidazol-3-yl)quinoxaline 5-(2-(3-chlorophenyl)-6,7-dihydro-5H-pyrrolo[1,2-a]imidazol-3-yl)-1H-indazole 6-(2-(3-chlorophenyl)-6,7-dihydro-5H-pyrrolo[1,2-a]imidazol-3-yl)-1H-indazole 6-(2-(3-chlorophenyl)-6,7-dihydro-5H-pyrrolo[1,2-a]imidazol-3-yl)benzo[d]thiazole 6-(2-(3-chlorophenyl)-6,7-dihydro-5H-pyrrolo[1,2-a]imidazol-3-yl)quinoxaline 5-(2-(3-fluorophenyl)-6,7-dihydro-5H-pyrrolo[1,2-a]imidazol-3-yl)-1H-indazole 6-(2-(3-fluorophenyl)-6,7-dihydro-5H-pyrrolo[1,2-a]imidazol-3-yl)-1H-indazole 6-(2-(3-fluorophenyl)-6,7-dihydro-5H-pyrrolo[1,2-a]imidazol-3-yl)benzo[d]thiazole 6-(2-(3-fluorophenyl)-6,7-dihydro-5H-pyrrolo[1,2-a]imidazol-3-yl)quinoxaline 5-(2-(2-fluorophenyl)-6,7-dihydro-5H-pyrrolo[1,2-a]imidazol-3-yl)-1H-indazole 6-(2-(2-fluorophenyl)-6,7-dihydro-5H-pyrrolo[1,2-a]imidazol-3-yl)-1H-indazole 6-(2-(2-fluorophenyl)-6,7-dihydro-5H-pyrrolo[1,2-a]imidazol-3-yl)benzo[d]thiazole 6-(2-(2-fluorophenyl)-6,7-dihydro-5H-pyrrolo[1,2-a]imidazol-3-yl)quinoxaline 5-(2-(2,4-difluorophenyl)-6,7-dihydro-5H-pyrrolo[1,2-a]imidazol-3-yl)-1H-indazole 6-(2-(2,4-difluorophenyl)-6,7-dihydro-5H-pyrrolo[1,2-a]imidazol-3-yl)-1H-indazole 6-(2-(2,4-difluorophenyl)-6,7-dihydro-5H-pyrrolo[1,2-a]imidazol-3-yl)benzo[d]thiazole 6-(2-(2,4-difluorophenyl)-6,7-dihydro-5H-pyrrolo[1,2-a]imidazol-3-yl)quinoxaline 5-(2-(3,4-difluorophenyl)-6,7-dihydro-5H-pyrrolo[1,2-a]imidazol-3-yl)-1H-indazole 6-(2-(3,4-difluorophenyl)-6,7-dihydro-5H-pyrrolo[1,2-a]imidazol-3-yl)-1H-indazole 6-(2-(3,4-difluorophenyl)-6,7-dihydro-5H-pyrrolo[1,2-a]imidazol-3-yl)benzo[d]thiazole 6-(2-(3,4-difluorophenyl)-6,7-dihydro-5H-pyrrolo[1,2-a]imidazol-3-yl)quinoxaline 6-(2-(3-fluorophenyl)-6,7-dihydro-5H-pyrrolo[1,2-a]imidazol-3-yl)quinoline 6-(2-(2-fluorophenyl)-6,7-dihydro-5H-pyrrolo[1,2-a]imidazol-3-yl)quinoline 6-(2-(2,4-difluorophenyl)-6,7-dihydro-5H-pyrrolo[1,2-a]imidazol-3-yl)quinoline 5-(2-(2,6-difluorophenyl)-6,7-dihydro-5H-pyrrolo[1,2-a]imidazol-3-yl)-1H-indazole 6-(2-(2,6-difluorophenyl)-6,7-dihydro-5H-pyrrolo[1,2-a]imidazol-3-yl)-1H-indazole 6-(2-(2,6-difluorophenyl)-6,7-dihydro-5H-pyrrolo[1,2-a]imidazol-3-yl)benzo[d]thiazole 6-(2-(2,6-difluorophenyl)-6,7-dihydro-5H-pyrrolo[1,2-a]imidazol-3-yl)quinoxaline 6-(2-(2,6-difluorophenyl)-6,7-dihydro-5H-pyrrolo[1,2-a]imidazol-3-yl)quinoline 6-(2-(2,4,5-tifluorophenyl)-6,7-dihydro-5H-pyrrolo[1,2-a]imidazol-3-yl)-1H-indazole 6-(2-(2,4,5-tifluorophenyl)-6,7-dihydro-5H-pyrrolo[1,2-a]imidazol-3-yl)benzo[d]thiazole 6-(2-(2,4,5-tifluorophenyl)-6,7-dihydro-5H-pyrrolo[1,2-a]imidazol-3-yl)quinoxaline 5-(2-(2,4,5-tifluorophenyl)-6,7-dihydro-5H-pyrrolo[1,2-a]imidazol-3-yl)-1H-indazole 5-(2-(2,3,6-tifluorophenyl)-6,7-dihydro-5H-pyrrolo[1,2-a]imidazol-3-yl)-1H-indazole 6-(2-(2,3,6-tifluorophenyl)-6,7-dihydro-5H-pyrrolo[1,2-a]imidazol-3-yl)benzo[d]thiazole 3-(benzo[d][1,3]dioxol-5-yl)-2-(3-fluorophenyl)-6,7-dihydro-5H-pyrrolol[1,2-a]imidazole 6-(2-(2,3,4-tifluorophenyl)-6,7-dihydro-5H-pyrrolo[1,2-a]imidazol-3-yl)quinoxaline 5-(2-(2,3,4-tifluorophenyl)-6,7-dihydro-5H-pyrrolo[1,2-a]imidazol-3-yl)-1H-indazole 6-(2-(2,3,4-tifluorophenyl)-6,7-dihydro-5H-pyrrolo[1,2-a]imidazol-3-yl)benzo[d]thiazole 6-(2-(3,4,5-tifluorophenyl)-6,7-dihydro-5H-pyrrolo[1,2-a]imidazol-3-yl)quinoxaline 5-(2-(3,4,5-tifluorophenyl)-6,7-dihydro-5H-pyrrolo[1,2-a]imidazol-3-yl)-1H-indazole 6-(2-(3,4,5-tifluorophenyl)-6,7-dihydro-5H-pyrrolo[1,2-a]imidazol-3-yl)benzo[d]thiazole 5-(2-(3,5-difluorophenyl)-6,7-dihydro-5H-pyrrolo[1,2-a]imidazol-3-yl)-1H-indazole 6-(2-(3,5-difluorophenyl)-6,7-dihydro-5H-pyrrolo[1,2-a]imidazol-3-yl)-1H-indazole 6-(2-(3,5-difluorophenyl)-6,7-dihydro-5H-pyrrolo[1,2-a]imidazol-3-yl)benzo[d]thiazole 6-(2-(3,5-difluorophenyl)-6,7-dihydro-5H-pyrrolo[1,2-a]imidazol-3-yl)quinoxaline 6-(2-(3,5-difluorophenyl)-6,7-dihydro-5H-pyrrolo[1,2-a]imidazol-3-yl)quinoline 6-(2-(2,3,5-trifluorophenyl)-6,7-dihydro-5H-pyrrolo[1,2-a]imidazol-3-yl)benzo[d]thiazole 5-(2-(2,3,5-trifluorophenyl)-6,7-dihydro-5H-pyrrolo[1,2-a]imidazol-3-yl)-1H-indazole 6-(2-(2,3,5-trifluorophenyl)-6,7-dihydro-5H-pyrrolo[1,2-a]imidazol-3-yl)quinoline 6-(2-(2,3,5-trifluorophenyl)-6,7-dihydro-5H-pyrrolo[1,2-a]imidazol-3-yl)quinoxaline 5-(2-(4-chloro-2,5-difluorophenyl)-6,7-dihydro-5H-pyrrolo[1,2-a]imidazol-3-yl)-1H-indazole 6-(2-(4-chloro-2,5-difluorophenyl)-6,7-dihydro-5H-pyrrolo[1,2-a]imidazol-3-yl)benzo[d]thiazole 6-(2-(4-chloro-2,5-difluorophenyl)-6,7-dihydro-5H-pyrrolo[1,2-a]imidazol-3-yl)quinoxaline 6-(2-(4-chloro-2,5-difluorophenyl)-6,7-dihydro-5H-pyrrolo[1,2-a]imidazol-3-yl)quinoline 5-(2-(4-chloro-3,5-dimethylphenyl)-6,7-dihydro-5H-pyrrolo[1,2-a]imidazol-3-yl)-1H-indazole 6-(2-(4-chloro-3,5-dimethylphenyl)-6,7-dihydro-5H-pyrrolo[1,2-a]imidazol-3-yl)benzo[d]thiazole 6-(2-(4-chloro-3,5-dimethylphenyl)-6,7-dihydro-5H-pyrrolo[1,2-a]imidazol-3-yl)quinoxaline 6-(2-(4-chloro-3,5-dimethylphenyl)-6,7-dihydro-5H-pyrrolo[1,2-a]imidazol-3-yl)quinoline 6-(2-(3,4,5-trifluorophenyl)-6,7-dihydro-5H-pyrrolo[1,2-a]imidazol-3-yl)quinoline 5-(2-(2,3-difluoro-4-methylphenyl)-6,7-dihydro-5H-pyrrolo[1,2-a]imidazol-3-yl)-1H-indazole 6-(2-(2,3-difluoro-4-methylphenyl)-6,7-dihydro-5H-pyrrolo[1,2-a]imidazol-3-yl)benzo[d]thiazole 6-(2-(2,3-difluoro-4-methylphenyl)-6,7-dihydro-5H-pyrrolo[1,2-a]imidazol-3-yl)quinoxaline 6-(2-(2,3-difluoro-4-methylphenyl)-6,7-dihydro-5H-pyrrolo[1,2-a]imidazol-3-yl)quinoline
6-(2-(4-chloro-2-fluoro-5-methylphenyl)-6,7-dihydro-5H-pyrrolo[1,2-a]imidazol-3-yl)-1H-indazole
6-(2-(4-chloro-2-fluoro-5-methylpheny)-6,7-dihydro-5H-pyrrolo[1,2-a]imidazol-3-yl)benzo[d]thiazole
6-(2-(4-chloro-2-fluoro-5-methylpheny)-6,7-dihydro-5H-pyrrolo[1,2-a]imidazol-3-yl)quinoxaline
6-(2-(4-chloro-2-fluoro-5-methylpheny)-6,7-dihydro-5H-pyrrolo[1,2-a]imidazol-3-yl)quinoline
6-(2-(4-methoxy-3,5-dimethylphenyl)-6,7-dihydro-5H-pyrrolo[1,2-a]imidazol-3-yl)-1H-indazole
6-(2-(4-methoxy-3,5-dimethylphenyl)-6,7-dihydro-5H-pyrrolo[1,2-a]imidazol-3-yl)benzo[d]thiazole
6-(2-(4-methoxy-3,5-dimethylphenyl)-6,7-dihydro-5H-pyrrolo[1,2-a]imidazol-3-yl)quinoxaline
6-(2-(4-methoxy-3,5-dimethylphenyl)-6,7-dihydro-5H-pyrrolo[1,2-a]imidazol-3-yl)quinoline
5-(2-(3,4-difluoro-2-methylphenyl)-6,7-dihydro-5H-pyrrolo[1,2-a]imidazol-3-yl)-1H-indazole
6-(2-(3,4-difluoro-2-methylphenyl)-6,7-dihydro-5H-pyrrolo[1,2-a]imidazol-3-yl)benzo[d]thiazole
6-(2-(3,4-difluoro-2-methylphenyl)-6,7-dihydro-5H-pyrrolo[1,2-a]imidazol-3-yl)quinoxaline
6-(2-(3,4-difluoro-2-methylphenyl)-6,7-dihydro-5H-pyrrolo[1,2-a]imidazol-3-yl)quinoline
5-(2-(3-chloro-4-fluoropheny)-6,7-dihydro-5H-pyrrolo[1,2-a]imidazol-3-yl)-1H-indazole
6-(2-(3-chloro-4-fluoropheny)-6,7-dihydro-5H-pyrrolo[1,2-a]imidazol-3-yl)benzo[d]thiazole
6-(2-(3-chloro-4-fluoropheny)-6,7-dihydro-5H-pyrrolo[1,2-a]imidazol-3-yl)quinoxaline
6-(2-(3-chloro-4-fluoropheny)-6,7-dihydro-5H-pyrrolo[1,2-a]imidazol-3-yl)quinoline
5-(2-(2,4-difluoro-5-methylphenyl)-6,7-dihydro-5H-pyrrolo[1,2-a]imidazol-3-yl)-1H-indazole
6-(2-(2,4-difluoro-5-methylphenyl)-6,7-dihydro-5H-pyrrolo[1,2-a]imidazol-3-yl)benzo[d]thiazole
6-(2-(2,4-difluoro-5-methylphenyl)-6,7-dihydro-5H-pyrrolo[1,2-a]imidazol-3-yl)quinoxaline
6-(2-(2,4-difluoro-5-methylphenyl)-6,7-dihydro-5H-pyrrolo[1,2-a]imidazol-3-yl)quinoline
5-(2-(3-chloro-4-fluoro-5-methylphenyl)-6,7-dihydro-5H-pyrrolo[1,2-a]imidazol-3-yl)-1H-indazole
6-(2-(3-chloro-4-fluoro-5-methylpheny)-6,7-dihydro-5H-pyrrolo[1,2-a]imidazol-3-yl)benzo[d]thiazole
6-(2-(3-chloro-4-fluoro-5-methylpheny)-6,7-dihydro-5H-pyrrolo[1,2-a]imidazol-3-yl)quinoxaline
6-(2-(3-chloro-4-fluoro-5-methylpheny)-6,7-dihydro-5H-pyrrolo[1,2-a]imidazol-3-yl)quinoline
5-(2-(4-fluoro-3,5-dimethylphenyl)-6,7-dihydro-5H-pyrrolo[1,2-a]imidazol-3-yl)-1H-indazole
6-(2-(4-fluoro-3,5-dimethylphenyl)-6,7-dihydro-5H-pyrrolo[1,2-a]imidazol-3-yl)benzo[d]thiazole
6-(2-(4-fluoro-3,5-dimethylphenyl)-6,7-dihydro-5H-pyrrolo[1,2-a]imidazol-3-yl)quinoxaline
6-(4-fluoro-3,5-dimethylphenyl)-6,7-dihydro-5H-pyrrolo[1,2-a]imidazol-3-yl)quinoline
5-(2-(2,4-difluoro-3-methylphenyl)-6,7-dihydro-5H-pyrrolo[1,2-a]imidazol-3-yl)-1H-indazole
6-(2-(2,4-difluoro-3-methylphenyl)-6,7-dihydro-5H-pyrrolo[1,2-a]imidazol-3-yl)benzo[d]thiazole
6-(2-(2,4-difluoro-3-methylphenyl)-6,7-dihydro-5H-pyrrolo[1,2-a]imidazol-3-yl)quinoxaline
6-(2-(2,4-difluoro-3-methylphenyl)-6,7-dihydro-5H-pyrrolo[1,2-a]imidazol-3-yl)quinoline
5-(2-(2,5-difluoro-4-methylphenyl)-6,7-dihydro-5H-pyrrolo[1,2-a]imidazol-3-yl)-1H-indazole
6-(2-(2,5-difluoro-4-methylphenyl)-6,7-dihydro-5H-pyrrolo[1,2-a]imidazol-3-yl)benzo[d]thiazole
6-(2-(2,5-difluoro-4-methylphenyl)-6,7-dihydro-5H-pyrrolo[1,2-a]imidazol-3-yl)quinoxaline
6-(2-(2,5-difluoro-4-methylphenyl)-6,7-dihydro-5H-pyrrolo[1,2-a]imidazol-3-yl)quinoline
5-(2-(2-chloro-4,5-difluorophenyl)-6,7-dihydro-5H-pyrrolo[1,2-a]imidazol-3-yl)-1H-indazole
6-(2-(2-chloro-4,5-difluorophenyl)-6,7-dihydro-5H-pyrrolo[1,2-a]imidazol-3-yl)benzo[d]thiazole
6-(2-(2-chloro-4,5-difluorophenyl)-6,7-dihydro-5H-pyrrolo[1,2-a]imidazol-3-yl)quinoline
6-(2-(2-chloro-4,5-difluorophenyl)-6,7-dihydro-5H-pyrrolo[1,2-a]imidazol-3-yl)quinoxaline
5-(2-(4-fluoro-2-methylphenyl)-6,7-dihydro-5H-pyrrolo[1,2-a]imidazol-3-yl)-1H-indazole
6-(2-(4-fluoro-2-methylphenyl)-6,7-dihydro-5H-pyrrolo[1,2-a]imidazol-3-yl)benzo[d]thiazole
6-(2-(4-fluoro-2-methylphenyl)-6,7-dihydro-5H-pyrrolo[1,2-a]imidazol-3-yl)quinoxaline
6-(2-(4-fluoro-2-methylphenyl)-6,7-dihydro-5H-pyrrolo[1,2-a]imidazol-3-yl)quinoline
5-(2-(5-chloro-4-fluoro-2-methylphenyl)-6,7-dihydro-5H-pyrrolo[1,2-a]imidazol-3-yl)-1H-indazole
6-(2-(5-chloro-4-fluoro-2-methylphenyl)-6,7-dihydro-5H-pyrrolo[1,2-a]imidazol-3-yl)benzo[d]thiazole
6-(2-(5-chloro-4-fluoro-2-methylphenyl)-6,7-dihydro-5H-pyrrolo[1,2-a]imidazol-3-yl)quinoxaline
6-(2-(5-chloro-4-fluoro-2-methylphenyl)-6,7-dihydro-5H-pyrrolo[1,2-a]imidazol-3-yl)quinoline
5-(2-(5-fluoro-2-methylphenyl)-6,7-dihydro-5H-pyrrolo[1,2-a]imidazol-3-yl)-1H-indazole
6-(2-(5-fluoro-2-methylphenyl)-6,7-dihydro-5H-pyrrolo[1,2-a]imidazol-3-yl)benzo[d]thiazole
6-(2-(5-fluoro-2-methylphenyl)-6,7-dihydro-5H-pyrrolo[1,2-a]imidazol-3-yl)quinoxaline
6-(5-fluoro-2-methylphenyl)-6,7-dihydro-5H-pyrrolo[1,2-a]imidazol-3-yl)quinoline
5-(2-(o-tolyl)-6,7-dihydro-5H-pyrrolo[1,2-a]imidazol-3-yl)-1H-indazole
6-(2-(o-tolyl)-6,7-dihydro-5H-pyrrolo[1,2-a]imidazol-3-yl)benzo[d]thiazole
6-(2-(o-tolyl)-6,7-dihydro-5H-pyrrolo[1,2-a]imidazol-3-yl)quinoxaline
6-(2-(o-tolyl)-6,7-dihydro-5H-pyrrolo[1,2-a]imidazol-3-yl)quinoline
5-(2-(4-fluoro-2,5-dimethylphenyl)-6,7-dihydro-5H-pyrrolo[1,2-a]imidazol-3-yl)-1H-indazole
6-(2-(4-fluoro-2,5-dimethylphenyl)-6,7-dihydro-5H-pyrrolo[1,2-a]imidazol-3-yl)benzo[d]thiazole
6-(2-(4-fluoro-2,5-dimethylphenyl)-6,7-dihydro-5H-pyrrolo[1,2-a]imidazol-3-yl)quinoxaline
6-(4-fluoro-2,5-dimethylphenyl)-6,7-dihydro-5H-pyrrolo[1,2-a]imidazol-3-yl)quinoline
5-(2-(2-chloro-4-fluoro-3-methylphenyl)-6,7-dihydro-5H-pyrrolo[1,2-a]imidazol-3-yl)-1H-indazole
6-(2-(2-chloro-4-fluoro-3-methylphenyl)-6,7-dihydro-5H-pyrrolo[1,2-a]imidazol-3-yl)benzo[d]thiazole
6-(2-(2-chloro-4-fluoro-3-methylphenyl)-6,7-dihydro-5H-pyrrolo[1,2-a]imidazol-3-yl)quinoxaline
6-(2-(2-chloro-4-fluoro-3-methylphenyl)-6,7-dihydro-5H-pyrrolo[1,2-a]imidazol-3-yl)quinoline
5-(2-(2-chloro-4-fluoro-5-methylphenyl)-6,7-dihydro-5H-pyrrolo[1,2-a]imidazol-3-yl)-1H-indazole 6-(2-(2-chloro-4-fluoro-5-methylphenyl)-6,7-dihydro-5H-pyrrolo[1,2-a]imidazol-3-yl)benzo[d]thiazole
6-(2-(2-chloro-4-fluoro-5-methylphenyl)-6,7-dihydro-5H-pyrrolo[1,2-a]imidazol-3-yl)quinoxaline
6-(2-(2-chloro-4-fluoro-5-methylphenyl)-6,7-dihydro-5H-pyrrolo[1,2-a]imidazol-3-yl)quinoline
N-(3-(3-(1H-indazol-5-yl)-6,7-dihydro-5H-pyrrolo[1,2-a]imidazol-2-yl)phenyl)-2-fluorobenzenesulfonamide
6-(2-(2-chloro-4-fluoro-5-methylphenyl)-6,7-dihydro-5H-pyrrolo[1,2-a]imidazol-3-yl)quinoxaline
6-(2-(2-chloro-4-fluoro-5-methylphenyl)-6,7-dihydro-5H-pyrrolo[1,2-a]imidazol-3-yl)quinoline
6-(2-(2-chloro-4-fluoro-5-methylphenyl)-6,7-dihydro-5H-pyrrolo[1,2-a]imidazol-3-yl)benzo[d]thiazole
2'-(4-fluorophenyl)-3'-(1H-indazol-5-yl)-5'H,7'H-spiro[cyclopentane-1,6'-pyrrolo[1,2-a]imidazole]
6-(2'-(4-fluorophenyl)-5'H,7'H-spiro[cyclopentane-1,6'-pyrrolo[1,2-a]imidazol]-3'-yl)benzo[d]thiazole
2'-(4-fluorophenyl)-3'-(quinoxalin-6-yl)-5'H,7'H-spiro[cyclopentane-1,6'-pyrrolo[1,2-a]imidazole]
2'-(4-fluorophenyl)-3'-(quinolin-6-yl)-5'H,7'H-spiro[cyclopentane-1,6'-pyrrolo[1,2-a]imidazole]
5-(2-(4-fluoro-2,3-dimethylphenyl)-6,7-dihydro-5H-pyrrolo[1,2-a]imidazol-3-yl)-1H-indazole
6-(2-(4-fluoro-2,3-dimethylphenyl)-6,7-dihydro-5H-pyrrolo[1,2-a]imidazol-3-yl)benzo[d]thiazole
6-(2-(4-fluoro-2,3-dimethylphenyl)-6,7-dihydro-5H-pyrrolo[1,2-a]imidazol-3-yl)quinoxaline
6-(2-(4-fluoro-2,3-dimethylphenyl)-6,7-dihydro-5H-pyrrolo[1,2-a]imidazol-3-yl)quinoline
3'-(benzo[d]thiazol-6-yl)-2'-(4-fluorophenyl)-5'H,7'H-spiro[cyclohexane-1,6'-pyrrolo[1,2-a]imidazole]-4-carboxylic acid
Ethyl 2'-(4-fluorophenyl)-3'-(quinoxalin-6-yl)-5'H,7'H-spiro[cyclohexane-1,6'-pyrrolo[1,2-a]imidazole]-4-carboxylate
2'-(4-fluorophenyl)-3'-(quinoxalin-6-yl)-5'H,7'H-spiro[cyclohexane-1,6'-pyrrolo[1,2-a]imidazole]-4-carboxylic acid
(3'-(benzo[d]thiazol-6-yl)-2'-(4-fluorophenyl)-5'H,7'H-spiro[cyclohexane-1,6'-pyrrolo[1,2-a]imidazol]-4-yl)methanol
(2'-(4-fluorophenyl)-3'-(quinoxalin-6-yl)-5'H,7'H-spiro[cyclohexane-1,6'-pyrrolo[1,2-a]imidazol]-4-yl)methanol
6-(2-(5-chloro-2-fluoropheny)-6,7-dihydro-5H-pyrrolo[1,2-a]imidazol-3-yl)quinoxaline
6-(2-(5-chloro-2-fluoropheny)-6,7-dihydro-5H-pyrrolo[1,2-a]imidazol-3-yl)quinoline
6-(2-(5-chloro-2-fluoropheny)-6,7-dihydro-5H-pyrrolo[1,2-a]imidazol-3-yl)benzo[d]thiazole
6-(2-(5-chloro-2-methylpheny)-6,7-dihydro-5H-pyrrolo[1,2-a]imidazol-3-yl)quinoline
6-(4-methyl-3-(3-(quinoxalin-6-yl)-6,7-dihydro-5H-pyrrolo[1,2-a]imidazol-2-yl)phenyl)quinoxaline
6-(2-(5-chloro-2-methylpheny)-6,7-dihydro-5H-pyrrolo[1,2-a]imidazol-3-yl)quinoxaline
6-(2-(2,5-dichlorophenyl)-6,7-dihydro-5H-pyrrolo[1,2-a]imidazol-3-yl)quinoline
6-(2-(2,3,5-trifluorophenyl)-6,7-dihydro-5H-pyrrolo[1,2-a]imidazol-3-yl)quinazolin-4-amine
6-(2-(2,4,5-trifluorophenyl)-6,7-dihydro-5H-pyrrolo[1,2-a]imidazol-3-yl)quinazolin-4-amine
6-(2-(5-chloro-2-fluorophenyl)-6,7-dihydro-5H-pyrrolo[1,2-a]imidazol-3-yl)quinazolin-4-amine
6-(2-(3-chloro-4-fluorophenyl)-6,7-dihydro-5H-pyrrolo[1,2-a]imidazol-3-yl)quinazolin-4-amine
6-(2-(2,5-dichloropheny)-6,7-dihydro-5H-pyrrolo[1,2-a]imidazol-3-yl)quinoxaline
6-(2-(2,5-dichlorophenyl)-6,7-dihydro-5H-pyrrolo[1,2-a]imidazol-3-yl)benzo[d]thiazole
6-(2-(5-chloro-2-methylphenyl)-6,7-dihydro-5H-pyrrolo[1,2-a]imidazol-3-yl)benzo[d]thiazole
6-(2-(4-methoxyphenyl)-6,7-dihydro-5H-pyrrolo[1,2-a]imidazol-3-yl)quinoxaline
6-(2-(4-methoxyphenyl)-6,7-dihydro-5H-pyrrolo[1,2-a]imidazol-3-yl)quinoline
2-(2-methoxyethoxy)-7-(2-(2,4,5-trifluorophenyl)-6,7-dihydro-5H-pyrrolo[1,2-a]imidazol-3-yl)quinoxaline
7-(2-(5-chloro-2-fluorophenyl)-6,7-dihydro-5H-pyrrolo[1,2-a]imidazol-3-yl)-2-(2-methoxyethoxy)quinoxaline
7-(2-(3-chloro-4-fluorophenyl)-6,7-dihydro-5H-pyrrolo[1,2-a]imidazol-3-yl)-2-(2-methoxyethoxy)quinoxaline
6-(2-(2-fluoro-5-methylphenyl)-6,7-dihydro-5H-pyrrolo[1,2-a]imidazol-3-yl)quinoline
6-(2-(2-fluoro-5-methylphenyl)-6,7-dihydro-5H-pyrrolo[1,2-a]imidazol-3-yl)quinoxaline
7-(2-(2-fluoro-5-methylphenyl)-6,7-dihydro-5H-pyrrolo[1,2-a]imidazol-3-yl)-2-(2-methoxyethoxy)quinoxaline
2-(1H-imidazol-1-yl)-7-(2-(2,3,5-trifluorophenyl)-6,7-dihydro-5H-pyrrolo[1,2-a]imidazol-3-yl)quinoxaline
7-(2-(5-chloro-2-fluorophenyl)-6,7-dihydro-5H-pyrrolo[1,2-a]imidazol-3-yl)-2-(1H-imidazol-1-yl)quinoxaline
N,N-dimethyl-2-((7-(2-(2,3,5-trifluorophenyl)-6,7-dihydro-5H-pyrrolo[1,2-a]imidazol-3-yl)quinoxalin-2-yl)oxy)ethan-1-amine
N,N-dimethyl-2-((7-(2-(2,4,5-trifluorophenyl)-6,7-dihydro-5H-pyrrolo[1,2-a]imidazol-3-yl)quinoxalin-2-yl)oxy)ethan-1-amine
2-((7-(2-(5-chloro-2-fluorophenyl)-6,7-dihydro-5H-pyrrolo[1,2-a]imidazol-3-yl)quinoxalin-2-yl)oxy)-N,N-dimethylethan-1-amine
6-(2-(6-methylpyridin-2-yl)-6,7-dihydro-5H-pyrrolo[1,2-a]imidazol-3-yl)benzo[d]thiazole
5-(2-(pyridin-2-yl)-3a,4,5,6-tetrahydrocyclopenta[b]pyrrol-3-yl)-1H-indazole
6-(2-(pyridin-2-yl)-3a,4,5,6-tetrahydrocyclopenta[b]pyrrol-3-yl)-1H-indazole
6-(2-(pyridin-2-yl)-6,7-dihydro-5H-pyrrolo[1,2-a]imidazol-3-yl)benzo[d]thiazole
6-(2-(pyridin-2-yl)-6,7-dihydro-5H-pyrrolo[1,2-a]imidazol-3-yl)quinoxaline
6-(2-(pyridin-2-yl)-6,7-dihydro-5H-pyrrolo[1,2-a]imidazol-3-yl)quinoline
6-(2-(pyridin-2-yl)-6,7-dihydro-5H-pyrrolo[1,2-a]imidazol-3-yl)imidazo[1,2-a]pyridine or a pharmaceutically acceptable salt, or solvate or hydrate thereof.

4. The compound of claim 1, wherein the compound has the structure, (IIb)
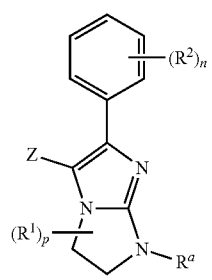
(IIe)
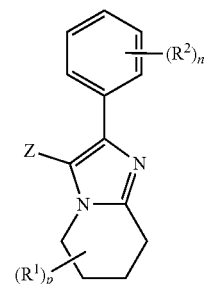
(IIf)
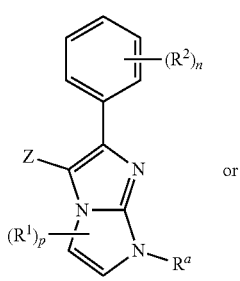
or
(IIg)
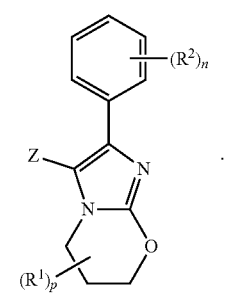
5. The compound of claim 1, wherein the compound has the structure,
(IIIa)
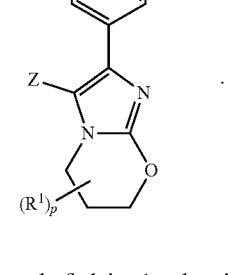
(IIIb)
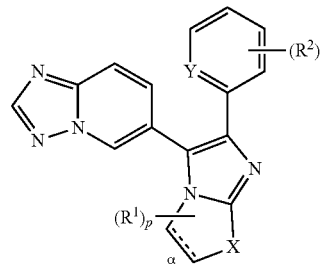
(IIIc)
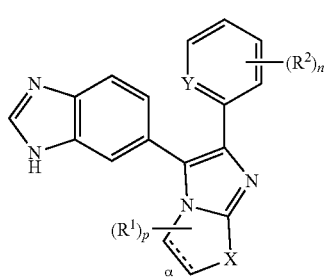
(IIId)
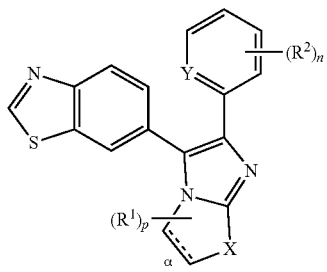
(IIIe)
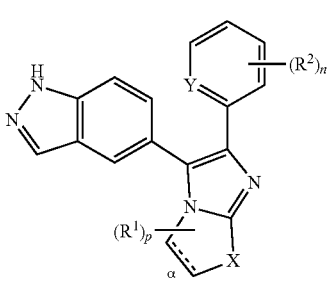
(IIIf)
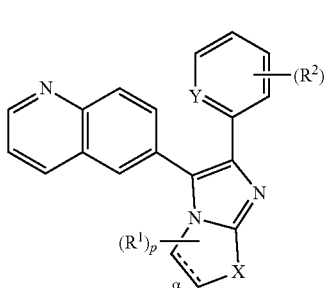

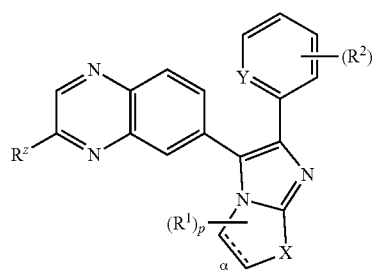 (IIIg)
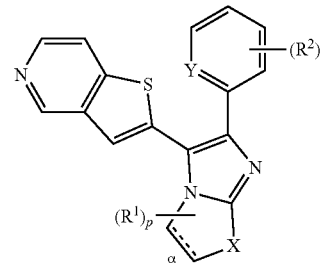 (IIIh)
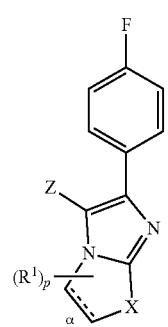 (IIIi)
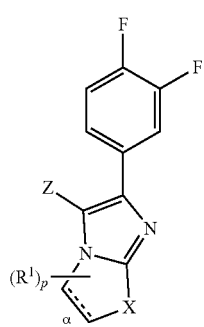 (IIIj)
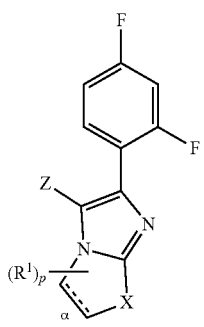 (IIIk)
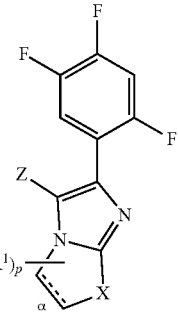 (IIIl)
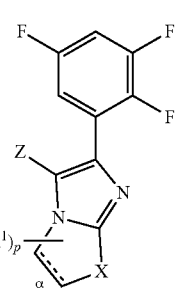 (IIIm)
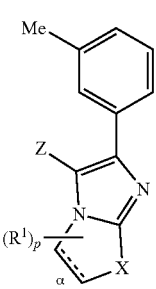 (IIIn)
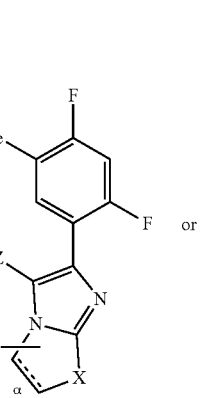 (IIIo)
or
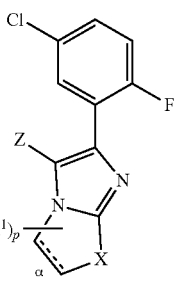 (IIIp)

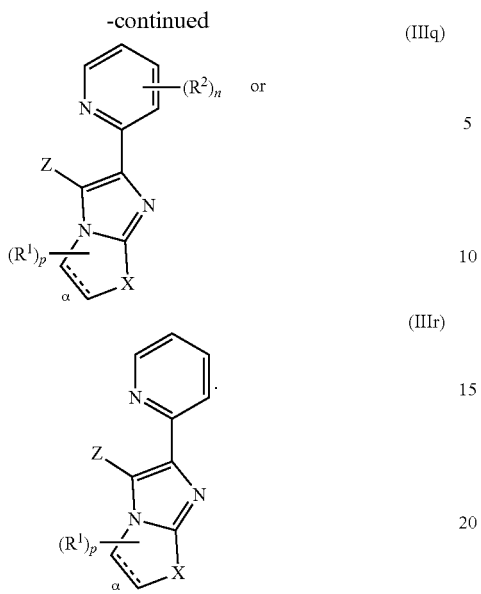

(IIIq)

(IIIr)

6. A pharmaceutical composition comprising a pharmaceutically acceptable diluent, carrier, or excipient and a compound according to claim 1.

7. A method for treating rheumatoid arthritis in a subject in need thereof, the method comprising administering to the subject an effective amount of a compound of formula (I):

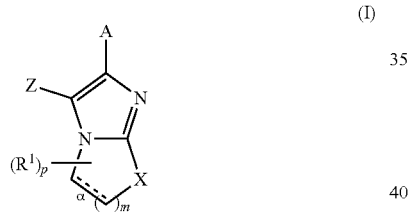

(I)

or a pharmaceutically acceptable salt, or solvate or hydrate thereof,
wherein
bond α is a single or double bond;
X is —$CH_2$—, —CH($R^x$)—, —N($R^a$)— or —O—,
wherein $R^a$ is hydrogen, —$C_1$-$C_6$alkyl, —$C_1$-$C_6$haloalkyl, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R or —N(R)S(O)$_2$R, and
wherein when X is —CH($R^x$)—, p≥1, and $R^x$ combines with an $R^1$ group bound to the carbon adjacent to X to form a 5- or 6-membered heterocyclyl with an annular —N($R^a$)—;
m is 1 or 2;
A is phenyl or pyridyl, each optionally substituted with one to five $R^2$ groups, wherein
each $R^2$ is independently halogen, —$C_1$-$C_6$alkyl, —$C_1$-$C_6$haloalkyl, —$C_1$-$C_6$alkoxy, $C_{3-8}$Cak($C_{0-6}$alkyl), Hca($C_{0-6}$alkyl), Ar($C_{0-6}$alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, —$NO_2$ or —CN, wherein the Ar, Het, Cak, Hca, alkyl, and haloalkyl are optionally substituted with 1, 2, 3, or 4 groups that are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, or $C_1$-$C_6$haloalkyl;

Z is
a fused bicyclic ring of the formula,

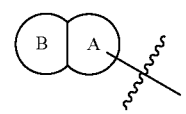

wherein
ring A is Ar or 5- or 6-membered Het,
ring B is 5- or 6-membered Het,
wherein
Z is optionally substituted by one or two —$R^Z$ groups that are each independently $C_{3-8}$Cak($C_{0-6}$alkyl), Hca($C_{0-6}$alkyl), Ar($C_{0-6}$alkyl), Het($C_{0-6}$alkyl), halogen, cyano, $C_{1-6}$alkyl, $C_{1-6}$haloalkyl, —$C_1$-$C_6$alkoxy, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), —O—$C_{1-6}$alkyl-OR, —O—$C_{1-6}$alkyl-SR, —O—$C_{1-6}$alkyl-$NR_2$, —O—$C_{1-6}$alkyl-Hca, wherein each Ar, Het, Cak, Hca, alkyl, and haloalkyl group is optionally substituted by one or two —$R^{Z2}$ groups;
wherein each —$R^{Z2}$ is independently halogen, cyano, $C_{1-6}$alkyl, $C_{1-6}$haloalkyl, —$C_1$-$C_6$alkoxy, —OR, —SR, —$NR_2$, —C(O)R, —C(O)OR, —C(O)$NR_2$, —S(O)$_2NR_2$, —S(O)$_2$ R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR);
each $R^1$ is independently hydrogen, $C_1$-$C_6$alkyl, $C_1$-$C_6$haloalkyl, —$C_1$-$C_6$alkoxy, $C_{3-8}$Cak($C_{0-6}$alkyl), Hca($C_{0-6}$alkyl), Ar($C_{0-6}$alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, —C(O)OR, —$NO_2$ or —CN, wherein the Ar, Het, Cak, Hca, alkyl, and haloalkyl are optionally substituted with 1, 2, 3, or 4 groups that are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, or $C_1$-$C_6$haloalkyl;
or, when α is a single bond, two $R^2$ groups taken together, when attached to the same carbon atom, form a spirocycle, wherein the spirocycle is $C_3$-$C_8$Cak, or $C_3$-$C_8$Hca, and the Cak and Hca are optionally substituted with 1, 2, 3, or 4 groups which are each independently halogen, cyano, nitro, —OR, —SR, —$NR_2$, —C(O)OR, —C(O)$NR_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, —C$_1$-C$_6$alkoxy or C$_1$-C$_6$haloalkyl;

p is 0, 1, 2, 3, 4, 5 or 6; and each R is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano and wherein Cak is cycloalkyl and Hca is heterocycloalkyl.

8. A pharmaceutical composition comprising a pharmaceutically acceptable diluent, carrier, or excipient and a compound according to claim 4.

9. A pharmaceutical composition comprising a pharmaceutically acceptable diluent, carrier, or excipient and a compound according to claim 5.

\* \* \* \* \*